US012577259B2

(12) United States Patent
Josien et al.

(10) Patent No.: US 12,577,259 B2
(45) Date of Patent: Mar. 17, 2026

(54) PCSK9 ANTAGONIST COMPOUNDS

(71) Applicant: MERCK SHARP & DOHME LLC, Rahway, NJ (US)

(72) Inventors: Hubert Josien, Jersey City, NJ (US); Jian Liu, Edison, NJ (US); Thomas Joseph Tucker, North Wales, PA (US); Abbas M. Walji, Lansdale, PA (US); Harold B. Wood, Westfield, NJ (US)

(73) Assignee: MERCK SHARP & DOHME LLC, Rahway, NJ (US)

(*) Notice: Subject to any disclaimer, the term of this patent is extended or adjusted under 35 U.S.C. 154(b) by 880 days.

(21) Appl. No.: 17/757,622

(22) PCT Filed: Dec. 18, 2020

(86) PCT No.: PCT/US2020/066046
§ 371 (c)(1),
(2) Date: Jun. 17, 2022

(87) PCT Pub. No.: WO2021/127460
PCT Pub. Date: Jun. 24, 2021

(65) Prior Publication Data

US 2023/0144324 A1 May 11, 2023

Related U.S. Application Data

(60) Provisional application No. 62/951,802, filed on Dec. 20, 2019.

(51) Int. Cl.
*C07D 498/22* (2006.01)
*C07K 7/64* (2006.01)

(52) U.S. Cl.
CPC .............. *C07D 498/22* (2013.01); *C07K 7/64* (2013.01)

(58) Field of Classification Search
CPC ...... C07D 498/22; C07K 7/64; A61K 47/542; A61K 38/00; A61P 3/06
See application file for complete search history.

(56) References Cited

U.S. PATENT DOCUMENTS

| | | | |
|---|---|---|---|
| 4,393,046 | A | 7/1983 | Baylis et al. |
| 4,656,269 | A | 4/1987 | Iizuka et al. |
| 5,104,869 | A | 4/1992 | Albright et al. |
| 11,427,616 | B2 | 8/2022 | Wood et al. |
| 11,484,565 | B2 | 11/2022 | Josien et al. |
| 11,530,244 | B2 | 12/2022 | Ricardo et al. |
| 2009/0275504 | A1 | 11/2009 | Mayne et al. |
| 2010/0041102 | A1 | 2/2010 | Sitlani et al. |
| 2011/0301079 | A1 | 12/2011 | Marsh et al. |
| 2012/0219558 | A1 | 8/2012 | Ni et al. |
| 2013/0158021 | A1 | 6/2013 | Dong et al. |
| 2013/0281366 | A1 | 10/2013 | Pingali et al. |
| 2017/0081383 | A1 | 3/2017 | Gruber |
| 2017/0189470 | A1 | 7/2017 | Wang et al. |
| 2018/0023071 | A1 | 1/2018 | Basak |
| 2019/0177366 | A1 | 6/2019 | Beresini et al. |

(Continued)

FOREIGN PATENT DOCUMENTS

| | | | |
|---|---|---|---|
| CN | 107158002 | A | 9/2017 |
| EP | 3 055 333 | | 8/2016 |

(Continued)

OTHER PUBLICATIONS

Xu et al. Small molecules as inhibitors of PCSK9: Current status and future challenges, European Journal of Medicinal Chemistry, vol. 162, 2019 pp. 212-233, https://doi.org/10.1016/j.ejmech.2018.11.011. (Year: 2019).*

Identification of a Small Peptide That Inhibits PCSK9 Protein Binding to the Low Density Lipoprotein Receptor Zhang, Yingnan et al. Journal of Biological Chemistry, vol. 289, Issue 2, 942-955 2014 (Year: 2014).*

Xu, Shengtao, et al. "Small molecules as inhibitors of PCSK9: Current status and future challenges." European journal of medicinal chemistry 162 (2019): 212-233. (Year: 2019).*

Zhang, Yingnan, et al. "Identification of a small peptide that inhibits PCSK9 protein binding to the low density lipoprotein receptor." Journal of Biological Chemistry 289.2 (2014): 942-955. (Year: 2014).*

(Continued)

*Primary Examiner* — Lianko G Garyu
*Assistant Examiner* — David Paul Bowles
(74) *Attorney, Agent, or Firm* — LATHROP GPM LLP; Brian C. Trinque

(57) ABSTRACT

Disclosed are compounds of Formula (I), or a pharmaceutically acceptable salt thereof: (I) wherein A, $A^1$, $A^2$, $R^1$, $R^2$ and $R^3$ are as defined herein, which compounds have properties for antagonizing PCSK9. Also described are pharmaceutical formulations comprising the compounds of Formula I or their salts, and methods of treating cardiovascular disease and conditions related to PCSK9 activity, e.g. atherosclerosis, hypercholesterolemia, coronary heart disease, metabolic syndrome, acute coronary syndrome, or related cardiovascular disease and cardiometabolic conditions.

Formula (I)

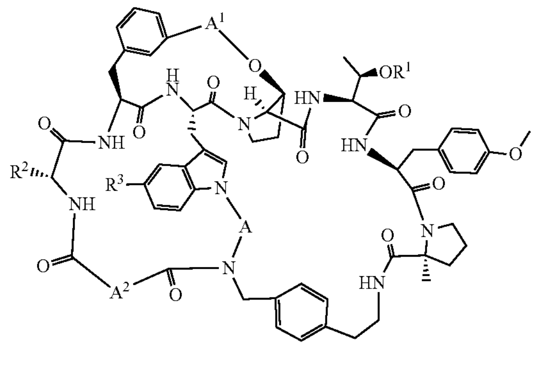

19 Claims, No Drawings

(56) References Cited

U.S. PATENT DOCUMENTS

| | | | |
|---|---|---|---|
| 2019/0389909 A1 | 12/2019 | Wood et al. |
| 2021/0069288 A1 | 3/2021 | Josien et al. |
| 2021/0163538 A1 | 6/2021 | Ricardo et al. |
| 2021/0214395 A1 | 7/2021 | Xiong et al. |
| 2021/0284694 A1 | 9/2021 | Ricardo et al. |
| 2022/0089640 A1 | 3/2022 | Ricardo et al. |

FOREIGN PATENT DOCUMENTS

| | | |
|---|---|---|
| WO | WO 2009/148605 A2 | 12/2009 |
| WO | WO 2010/144038 A1 | 12/2010 |
| WO | WO 2012/040259 A2 | 3/2012 |
| WO | WO 2012/131504 A1 | 10/2012 |
| WO | WO 2012/177741 A1 | 12/2012 |
| WO | WO 2013/041678 A1 | 3/2013 |
| WO | WO 2014/009025 A1 | 1/2014 |
| WO | WO 2014/140210 A1 | 9/2014 |
| WO | WO 2014/150326 A1 | 9/2014 |
| WO | WO 2015/191951 A2 | 12/2015 |
| WO | WO 2016/119067 A1 | 8/2016 |
| WO | WO 2017/121850 A1 | 7/2017 |
| WO | WO 2017/167202 A1 | 10/2017 |
| WO | WO 2017/181061 A1 | 10/2017 |
| WO | WO 2017/220701 A1 | 12/2017 |
| WO | WO 2018/053517 A1 | 3/2018 |
| WO | WO 2018/192492 A1 | 10/2018 |
| WO | WO 2019/246349 A1 | 12/2019 |
| WO | WO 2019/246352 A1 | 12/2019 |
| WO | WO 2019/246386 A1 | 12/2019 |
| WO | WO 2019/246387 A1 | 12/2019 |
| WO | WO 2019/246405 A1 | 12/2019 |
| WO | WO 2020/009805 A3 | 1/2020 |
| WO | WO 2021/041770 A1 | 3/2021 |
| WO | WO 2021/127460 A1 | 6/2021 |

OTHER PUBLICATIONS

Chaudhary et al., "PCSK9 inhibitors: A new era of lipid lowering therapy", World Journal of Cardiology, Feb. 26, 2017, vol. 9, No. 2, pp. 76-91.

He et al. "Lowering serum lipids via PcSK9-targeting drugs: current advances and future perspectives", ACTA Pharmacologica Sinica, Jan. 23, 2017, vol. 38, pp. 301-311.

International Search Report and Written Opinion in related PCT Application No. PCT/US2020/048342, mailed Nov. 18, 2020, 11 pages.

International Search Report and Written Opinion in related PCT Application No. PCT/US2019/038220, mailed Nov. 5, 2019, 11 pages.

International Search Report and Written Opinion in related PCT Application No. PCT/US2019/038155, mailed Nov. 15, 2019, 6 pages.

International Search Report and Written Opinion in related PCT Application No. PCT/US2019/038221, mailed Nov. 18, 2019, 12 pages.

International Search Report and Written Opinion in related PCT Application No. PCT/US2019/038247, mailed Apr. 20, 2020, 13 pages.

International Search Report and Written Opinion in related PCT Application No. PCT/US2019/038250, mailed Sep. 17, 2019, 7 pages.

International Search Report and Written Opinion in related PCT Application No. PCT/US2019/038158, mailed Dec. 26, 2019, 7 pages.

Umemura et al., Characterization of the biosynthetic gene cluster for the ribosomally synthesized cyclic peptide ustiloxin B in*Aspergillus flavus*, Fungal Genetics and Biology, 2014, vol. 68, pp. 23-30.

Zhang et al., "Identification of a Small Peptide That Inhibits PCSK9 Protein Binding to the Low Density Lipoprotein Receptor", The Journal of Biological Chemistry, Jan. 10, 2014, vol. 289, No. 2, pp. 942-955.

U.S. Appl. No. 17/253,764, filed Dec. 18, 2020, Alonso Ricardo.

PCT/US2019/038220 WO 2019/246386, Jun. 20, 2019 Dec. 26, 2019, Alonso Ricardo.

U.S. Appl. No. 17/253,774, filed Dec. 18, 2020, Alonso Ricardo.

PCT/US2019/038221 WO 2019/246387, Jun. 20, 2019 Dec. 26, 2019, Alonso Ricardo.

U.S. Appl. No. 17/253,783 2021/0163538, filed Dec. 18, 2020 Jun. 3, 2021, Alonso Ricardo.

PCT/US2019/038247 WO 2020/009805, Jun. 20, 2019 Apr. 2, 2019, Alonso Ricardo.

U.S. Appl. No. 17/253,864 2021/0284694, filed Dec. 18, 2020 Sep. 16, 2021, Alosno Ricardo.

PCT/US2019/038250 WO 2019/246405, Jun. 20, 2019 Dec. 26, 2019, Alonso Ricardo.

U.S. Appl. No. 16/446,940 2019/0389909, filed Jun. 20, 2019 Dec. 26, 2019, Harold B. Wood.

PCT/US2019/038155 WO 2019/246349, Jun. 20, 2019 Dec. 26, 2019, Harold B.Wood.

U.S. Appl. No. 17/253,815 2021/0214395, filed Dec. 18, 2020 Jul. 15, 2021, Yusheng Xiong.

PCT/US2019/038158 WO 2019/246352, Jun. 20, 2019 Dec. 26, 2019, Harold B. Wood.

U.S. Appl. No. 17/005,686 2021/0069288, filed Aug. 28, 2020, Hubert Josien.

PCT/US2020/048342 WO 2021/1041770, Aug. 28, 2020, Hubert Josien.

PCT/US2020/066046 WO 2021/127460, Dec. 18, 2020, Hubert Josien.

Alleyne et al., "Series of Novel and Highly Potent Cyclic Peptide PCSK9 Inhibitors Derived from an mRNA Display Screen and Optimized via Structure-Based Design", *Journal of Medicinal Chemistry* 63(22):13796-13824 (2020).

Callmann et al., "Antitumor Activity of 1,18-Octadecanedioic Acid-Paclitaxel Complexed with Human Serum Albumin", *Journal of the American Chemical Society* 141(30):11765-11769 (2019).

Extended European Search Report for Application No. 20901412.5 dated Dec. 14, 2023, 8 pages.

Tucker et al., "A Series of Novel, Highly Potent, and Orally Bioavailable Next-Generation Tricyclic Peptide PCSK9 Inhibitors", *Journal of Medicinal Chemistry* 64(22):16770-16800 (2021).

Abifadel et al., "Mutations in PSCK9 cause autosomal dominant hypercholesterolemia", *Nature Genetics* 34(2):154-156 (2003).

Arias et al., "Recombinant expression, antimicrobial activity and mechanism of action of tritrpticin analogs containing fluoro-tryptophan residues", *Biochimica et Biophysica Acta* 1858(5):1012-1023 (2015).

Benjannet et al., "NARC-1/PSCK9 and Its Natural Mutants", *The Journal of Biological Chemistry* 279(47):48865-48875 (2004).

Benjannet et al., "Loss- and Gain-of-function PCSK9 Variants", *The Journal of Biological Chemistry* 287:33745-33755 (2012).

Cohen et al., "Sequence Variations in PSCK9, Low LDL, and Protection against Coronary Heart Disease", *The New England Journal of Medicine* 354(12):1264-1272 (2006).

Dadu et al., "Lipid lowering with PCSK9 inhibitors", *Nature Reviews Cardiology* 11:563-575 (2014).

Dubuc et al., "Statins Upregulate PCSK9, the Gene Encoding the Proprotein Convertase Neural Apoptosis-Regulated Convertase-1 Implicated in Familial Hypercholesterolemia", *Arteriosclerosis, Thrombosis and Vascular Biology* 24:1454-1459 (2004).

Elbitar et al., "Proprotein convertase subtilisin/kexin 9 (PCSK9) inhibitors and the future of dyslipidemia therapy: an updated patent review (2011-2015)", *Expert Opinion on Therapeutics Patents* 26(12):1377-1392(2016), https://doi.org/10.1080/13543776.2016.1206080.

Graham et al., "Antisense inhibition of proprotein convertase subtilisin/kexin type 9 reduces serum LDL in hyperlipidemic mice", *Journal of Lipid Research* 48(4):763-767 (2007).

International Search Report and Written Opinion for International Application No. PCT/US2022/040747 mailed Nov. 25, 2022, 7 pages.

International Search Report and Written Opinion for Internaional Application No. PCT/US2023/072326 mailed Jan. 9, 2024, 8 pages.

(56) References Cited

OTHER PUBLICATIONS

Josephson et al., "mRNA display: from basic principles to macrocycle drug discovery", *Drug Discovery Today* 19(4):388-399 (2014).
Lalanne et al., "Wild-type PCSK9 inhibits LDL clearance but does not affect apoB-containing lipprotein production in mouse and cultured cells", *Journal of Lipid Research* 46:1312-1319 (2005).
Law et al., "Quantifying effect of statins on low density lipoprotein cholesterol, ischaemic heart disease, and stroke: systematic review and meta-analysis", *British Medical Journal* 326:1423-1427 (2003).
Leren, "Mutations in the PSCK9 gene in Norwegian subjects with autosomal dominant hypercholesterolemia", *Clinical Genetics* 65(5):419-422 (2004).
Maxwell et al., "Novel putative SREBP and LXR target genes identified by microarray analysis in liver of cholesterol-fed mice", *Journal of Lipid Research* 44:2109-2119 (2003).
Maxwell et al., "Adenoviral-mediated expression of Pcsk9 in mice results in a low-density lipoprotein receptor knockout phenotype", *PNAS* 101(18):7100-7105 (2004).
Naureckiene et al., "Functional characterization of Narc 1, a novel proteinase related to proteinase K", *Archives of Biochemistry and Biophysics* 420:55-67 (2003).
Ougurram et al., "Apolioprotein B100 Metabolism in Autosomal-Dominant Hypercholesterolemia Related to Mutations in PSCK9", *Arteriosclerosis, Thrombosis, and Vascular Biology* 24(8):1448-1453 (2004).
Park et al., "Post-transcriptional Regulation of Low Density Lipoprotein Receptor Protein by Proprotein Convertase Subtilisin/Kexin Type 9a in Mouse Liver", *The Journal of Biological Chemistry* 279(48):50630-50638 (2004).
Rashid et al., "Decreased plasma cholesterol and hypersensitivity to stains in mice lacking Pcsk9", *PNAS* 102(15):5374-5379 (2005).
Seidah et al., "The secretory proprotein convertase neural apoptosis-regulated convertase 1 (NARC-1): Liver regeneration and neuronal differentiation", *PNAS USA* 100(3):928-933 (2003).
Seidah et al., "The biology and therapeutic targeting of the proprotein convertases", *Nature Reviews Drug Discovery* 11(5):367-383 (2012).
Timms et al., "A mutation in PSCK9 causing autosomal-dominant hypercholesterolemia in a Utah pedigree", *Human Genetics* 114(4):349-353 (2004).
Zhang et al., "Discovery of a cryptic peptide-binding site on PSCK9 and design of antagonists", *Nature Structure & Molecular Biology* 24(10):848-856 (2017).

* cited by examiner

PCSK9 ANTAGONIST COMPOUNDS

CROSS REFERENCE TO RELATED APPLICATIONS

This application is a 35 U.S.C. § 371 filing of International Patent Application No. PCT/US2020/066046, filed Dec. 18, 2020, which claims the benefit of U.S. Provisional Patent Application No. 62/951,802, filed Dec. 20, 2019, the disclosures of which are incorporated herein by reference in their entireties.

BACKGROUND OF THE INVENTION

The identification of compounds and/or agents effective in the treatment of cardiovascular affliction is highly desirable. In clinical trials, reductions in LDL cholesterol levels have been directly related to the rate of coronary events; Law et al., 2003 *BMJ* 326:1423-1427. The moderate lifelong reduction in plasma LDL cholesterol levels was found to correlate with a substantial reduction in the incidence of coronary events; Cohen et al., 2006 *N. Engl. J. Med.* 354:1264-1272. This was the case even in populations with a high prevalence of non-lipid-related cardiovascular risk factors; supra. Accordingly, there is great benefit to be reaped from the managed control of LDL cholesterol levels.

Proprotein convertase subtilisin-kexin type 9 (hereinafter called "PCSK9"), also known as neural apoptosis-regulated convertase 1 ("NARC-1"), is a proteinase K-like subtilase identified as the 9$^{th}$ member of the secretory subtilase family; see Seidah et al., 2003 *PNAS* 100:928-933. PCSK9 belongs to the mammalian proprotein convertase family of serine proteases and contains an N-terminal signal sequence, prodomain, catalytic domain, and C-terminal domain; see Seidah et al., 2012 *Nat. Rev. Drug Discov.* 11:367-383. A study of PCSK9 transcriptional regulation demonstrated that it is regulated by sterol regulatory element-binding proteins ("SREBP"), as seen with other genes involved in cholesterol metabolism; Maxwell et al., 2003 *J. Lipid Res.* 44:2109-2119, as is typical of other genes implicated in lipoprotein metabolism; Dubuc et al., 2004 *Arterioscler. Thromb. Vasc. Biol.* 24:1454-1459. Statins have been shown to upregulate PCSK9 expression in a manner attributed to the cholesterol-lowering effects of the drugs; supra. Moreover, it has been shown that PCSK9 promoters possess two conserved sites involved in cholesterol regulation, a sterol regulatory element and an Sp1 site; supra.

While in the endoplasmic reticulum, PCSK9 performs as its only catalytic activity an autocleavage between residues Gln-152 and Ser-153; see Naureckiene et al., 2003 Arch. *Biochem. Biophys.* 420:55-67; Seidah et al., 2003 *Proc. Natl. Acad. Sci. U.S.A* 100:928-933. The prodomain remains tightly associated with the catalytic domain during subsequent trafficking through the trans-Golgi network. The maturation via autocleavage has been demonstrated to be critical for PCSK9 secretion and subsequent extracellular function (see Benjannet et al., 2012 *J. Biol. Chem.* 287:33745-33755). Accordingly, several lines of evidence demonstrate that PCSK9, in particular, lowers the amount of hepatic LDLR protein and thus compromises the liver's ability to remove LDL cholesterol from the circulation.

Adenovirus-mediated overexpression of PCSK9 in the livers of mice results in the accumulation of circulating LDL-C due to a dramatic loss of hepatic LDLR protein, with no effect on LDLR mRNA levels; Benjannet et al., 2004 *J. Biol. Chem.* 279:48865-48875; Maxwell & Breslow, 2004 *PNAS* 101:7100-7105; Park et al., 2004 *J. Biol. Chem.* 279:50630-50638; and Lalanne et al., 2005 *J. Lipid Res.* 46:1312-1319. The effect of PCSK9 overexpression on raising circulating LDL-C levels in mice is completely dependent on the expression of LDLR, again, indicating that the regulation of LDL-C by PCSK9 is mediated through downregulation of LDLR protein. In agreement with these findings, mice lacking PCSK9 or in which PCSK9 mRNA has been lowered by antisense oligonucleotide inhibitors have higher levels of hepatic LDLR protein and a greater ability to clear circulating LDL-C; Rashid et al., 2005 *PNAS* 102:5374-5379; and Graham et al., 2007 *J. Lipid Res.* 48(4):763-767. In addition, lowering PCSK9 levels in cultured human hepatocytes by siRNA also results in higher LDLR protein levels and an increased ability to take up LDL-C; Benjannet et al., 2004 *J. Biol. Chem.* 279:48865-48875; and Lalanne et al., 2005 *J. Lipid Res.* 46:1312-1319. Together, these data indicate that PCSK9 action leads to increased LDL-C by lowering LDLR protein levels.

A number of mutations in the gene PCSK9 have also been conclusively associated with autosomal dominant hypercholesterolemia ("ADH"), an inherited metabolism disorder characterized by marked elevations of low density lipoprotein ("LDL") particles in the plasma which can lead to premature cardiovascular failure; see Abifadel et al., 2003 *Nature Genetics* 34:154-156; Timms et al., 2004 *Hum. Genet.* 114:349-353; Leren, 2004 *Clin. Genet.* 65:419-422. A later-published study on the S127R mutation of Abifadel et al., supra, reported that patients carrying such a mutation exhibited higher total cholesterol and apoB100 in the plasma attributed to (1) an overproduction of apoB100-containing lipoproteins, such as low density lipoprotein ("LDL"), very low density lipoprotein ("VLDL") and intermediate density lipoprotein ("IDL"), and (2) an associated reduction in clearance or conversion of said lipoproteins; Ouguerram et al., 2004 Arterioscler. Thromb. Vasc. Biol. 24:1448-1453.

Accordingly, there can be no doubt that PCSK9 plays a role in the regulation of LDL. The expression or upregulation of PCSK9 is associated with increased plasma levels of LDL cholesterol, and the corresponding inhibition or lack of expression of PCSK9 is associated with reduced LDL cholesterol plasma levels. Decreased levels of LDL cholesterol associated with sequence variations in PCSK9 have been found to confer protection against coronary heart disease; Cohen, 2006 *N. Engl. J. Med.* 354:1264-1272.

Thus, identification of compounds and/or agents effective in the treatment of cardiovascular affliction is highly desirable, including antagonism of PCSK9's role in LDL regulation, however, in general, because PCSK9 circulates in blood and has modest binding affinity to cell surface LDL receptors prior attempts to utilize this mechanism in treatment of diseases related to high serum LDL levels have been focused on the use of large biomolecules, for example, antibodies. Accordingly, there is scant publication reflecting activity toward this target using small peptides or small molecules to inhibit PCSK9, see for example, Zhang et al., 2014 J. Biol. Chemistry, 289(2): 942-955. Moreover, there is a paucity of compounds which are amenable to formulation into a dosage form for utilizing an oral administration route of dosing such compounds, a route which would be highly desirable for the provision of therapy for conditions in which regulation of the activities of PCSK9 could play a role.

The present invention advances these interests by providing antagonists of PCSK9 which are believed to be of use for inhibiting the activities of PCSK9 and the corresponding role PCSK9 plays in various conditions for which the administration of a PCSK9 antagonist provides therapy. Compounds of the instant invention have a favorable pharmacokinetic profile and prolonged pharmaceutical action.

SUMMARY OF THE INVENTION

In one aspect the invention provides a compound of Formula I:

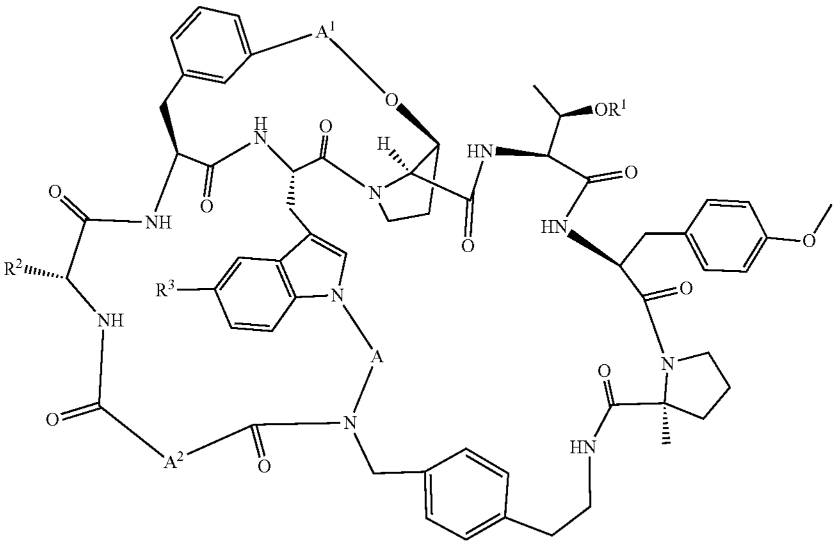

wherein:

A is selected from $C_{2-6}$ alkyl, $C_{2-6}$ alkenyl or $—(CR_2)_nR^x(CR_2)_n—$;

$A^1$ is selected from

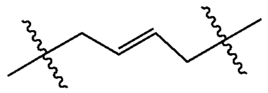

or

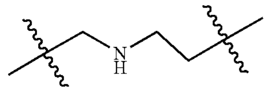

;

$A^2$ is selected from $—(CR_2)_nX(CR_2)_n—$ or $—(CR_2)_nNRC(O)(CR_2)_n—$;

X is O or $CR_2$;

R is independently selected from H or $C_{1-6}$ alkyl;

$R^a$ is independently selected from H, $—CR_2—S(O)_2OR^9$, or $—C(O)OR^9$;

$R^b$ is independently selected from H, $C_{1-6}$ alkyl, or $C_{1-6}$ alkyl-$N^+(CH_3)_2$;

$R^x$ is tetrazolyl;

$R^d$ is independently selected from H or $—C(O)OR^9$;

$R^1$ is selected from:

(a) H, (b) $—(CR_2)_z—R^x—(CR_2)_zNR_3$, (c) $—(CR_2)_z—R^x—(CR_2)_z NR—C(O)—(CR_2)_z[O(CR_2)_n]_r—N^+(CH_3)_3$, and (d) $—(CR_2)_z—R^x—(CR_2)_z—NR^b—C(O)R^{10}$;

$R^2$ is selected from:

(a) $—(CR_2)_z—NR^b—C(O)R^{10}$, and (b) $—(CR_2)_z—NR—C(O)—(CR_2)_z[O(CR_2)_n]_r—N^+(CH_3)_3$;

$R^3$ is H or F;

$R^4$ is

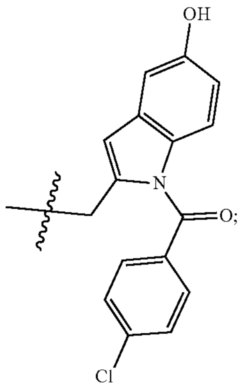 [SMILES: *Cc1cc2cc(O)ccc2n1C(=O)c1ccc(Cl)cc1]

$R^5$ is independently selected from $—(CR^a_2)_x—$, $—(CR^a_2)_x O(CR^a_2)_x—$, and $C_{1-8}$ alkyl;

$R^6$ is independently selected from $—(CR^a_2)_xNRC(O)—$, $—(CR_2)_xNRS(O)_2—$, and $—(CR^a_2)_nO(CR^a_2)_qNRC(O)—$;

$R^9$ is independently selected from H or $C_{1-6}$ alkyl;

$R^{10}$ is independently selected from:

a) $—(R^5—N^+(CH_3)_2—R^6)_u—(R^{20})_n—(R^6)_m—R^{12}$, b) $—(R^{20})_n—(R^6)_m—R^5—N^+(CH_3)_2—R^6—R^{12}$, c) $—(R^{20})_n—R^5—N^+(CH_3)_2—(R^{20})_s—(R^6)_q—R^{12}$, d) $—R^6—R^{20}—N^+(CH_3)_2—(R^{20})_n—(R^6)_m—R^{12}$, e) $—R^{20}—N^+(CH_3)_2—(R^6)_m—(R^{20})_n—(R^6)_q—R^{12}$, f) $—(R^{20})_n—(R^6)_m—R^{12}$, g) $—R^5—N^+(CH_3)_2—(R^{20})_n—(R^6)_m—R^5—[NRC(O)—R^5]q$, h) $—R^{20}—N^+(CH_3)_2—(R^6)_m—R^5$, i) $—R^5—N^+(CH_3)_2—(R^{20})_n—(R^6)_m—R^5$, j) $—R^5—N^+(CH_3)_2—(R^{20})_n—(R^6)_m—R^{12}$, k) $—(R^{20})_n—N^+(CH_3)_2—(R^{20})_n—(R^6)_q—R^{12}$, l) $-R^6-R^5-N^+(CH_3)_2-(R^{20})_n-(R^6)_q-R^{12}$, m) $-(R^{20})_n-N^+(CH_3)_2-(R^6)_q-R^{12}$, n) $-(R^{20})_n-(R^6)_m-R^{20}-N^+(CH_3)_2-(R^{20})_s-(R^6)_q-R^{12}$, o) $-R^{20}-N^+(CH_3)_2-(R^6)_m-R^4$, p) $-(R^{20})_n-N^+(CH_3)_2-(R^6)_q-(R^{20})_n-(R^6)_m-R^{12}$, q) $-R^{20}-N^+(CH_3)_2-(R^6)_m-(R^{20})_n-N^+(CH_3)_2-(R^{20})_n-(R^6)_q-R^{12}$, r) $-R^5-N^+(CH_3)_2-(R^6)_m-R^5-N^+(CH_3)_2-(R^{20})_n-(R^6)_q-R^{12}$, and s) $-CR^b_2-(R^{20})_n-(R^6)_m-R^{12}$;

$R^{12}$ is independently selected from $-C_{1-20}$ alkyl-$R^d$, $-(CR_2)_x-O-(CR_2)_x-R^d$, $-C_{11-20}$ alkyl-C(O)NR$-(CR^d_2)_2H$, and $C_{2-16}$ alkenyl;

$R^{20}$ is independently selected from a) $-(CR^a_2)_tO(CR^a_2)_qO-(CR^a_2)_t-$, b) $-(CR^a_2)_tO(CR^a_2)_qO-(CR^a_2)_t-NRC(O)-$, c) $-(CR^a_2)_tO(CR^a_2)_q-NRC(O)-(CR^a_2)_nO(CR^a_2)_nO-$, d) $-(CR^a_2)_t-NRC(O)-(CR^a_2)_qO(CR^a_2)_qO-(CR^a_2)_t-$, e) $-(CR^a_2)_tO(CR^a_2)_qO-(CR^a_2)_t-$, and f) $-(CR^a_2)_t-O-(CR^a_2)_qO(CR^a_2)_qO-(CR^a_2)_t-$;

m is independently selected from 0, 1, 2, 3 or 4;

n is independently selected from 1, 2 or 3;

q is independently selected from 1, 2, 3 or 4;

r is independently selected from 0, 1, 2, 3 or 4;

s is independently selected from 0, 1, 2 or 3;

t is independently selected from 0, 1, 2 or 3;

u is 1 or 2;

x is independently selected from 1, 2, 3, 4, 5, 6, 7, or 8;

z is independently selected from 1, 2, 3, 4, 5 or 6;

provided that if $A^1$ is

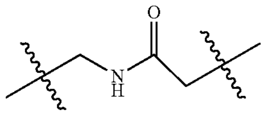 [SMILES: *CNC(=O)C*]

and $R^1$ is H, then $A^2$ is $-(CR_2)_nX(CR_2)_n-$;

or a pharmaceutically acceptable salt of any thereof.

In a further embodiment, the invention provides a compound of Formula I, wherein $R^3$ is F, or a pharmaceutically acceptable salt of any thereof.

In another embodiment, the invention provides compounds of Formula I, wherein:

A is selected from $C_{2-6}$ alkyl, $C_{2-6}$ alkenyl or $-(CR_2)_nR^x(CR_2)_n-$;

$A^1$ is selected from

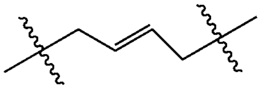

or

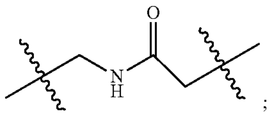

;

$A^2$ is selected from $-(CR_2)_nX(CR_2)_n-$ or $-(CR_2)_nNRC(O)(CR_2)_n-$;

X is O or $CR_2$;

R is independently selected from H or $C_{1-6}$ alkyl;

$R^a$ is independently selected from H, $-CR_2-S(O)_2OR^9$, or $-C(O)OR^9$;

$R^b$ is independently selected from H, $C_{1-6}$ alkyl, or $C_{1-6}$ alkyl-$N^+(CH_3)_2$;

$R^x$ is tetrazolyl;

$R^d$ is independently selected from H or $-C(O)OR^9$;

$R^1$ is selected from:

(a) H, (b) $-(CR_2)_z-R^x-(CR_2)_zNR_3$, (c) $-(CR_2)_z-R^x-(CR_2)_z\ NR-C(O)-(CR_2)_z[O(CR_2)_n]_r-N^+(CH_3)_3$, and (d) $-(CR_2)_z-R^x-(CR_2)_z-NR^b-C(O)R^{10}$;

$R^2$ is selected from:

(a) $-(CR_2)_z-NR^b-C(O)R^{10}$, and (b) $-(CR_2)_z-NR-C(O)-(CR_2)_z[O(CR_2)_n]_r-N^+(CH_3)_3$;

$R^3$ is F;

$R^5$ is independently selected from $-(CR^a_2)_x-$, $-(CR^a_2)_xO(CR^a_2)_x-$, and $C_{1-8}$ alkyl;

$R^6$ is independently selected from $-(CR^a_2)_xNRC(O)-$, $-(CR_2)_xNRS(O)_2-$, and $-(CR^a_2)_nO(CR^a_2)_qNRC(O)-$;

$R^9$ is independently selected from H or $C_{1-6}$ alkyl;

$R^{10}$ is independently selected from:

a) $-(R^{20})_n-(R^6)_m-R^5-N^+(CH_3)_2-R^6-R^{12}$, b) $-R^6-R^{20}-N^+(CH_3)_2-(R^{20})_n-(R^6)_m-R^{12}$, c) $-R^{20}-N^+(CH_3)_2-(R^6)_m-(R^{20})_n-(R^6)_q-R^{12}$, d) $-(R^{20})_n-(R^6)_m-R^{12}$, e) $-(R^{20})_n-N^+(CH_3)_2-(R^{20})_n-(R^6)_q-R^{12}$, f) $-R^6-R^5-N^+(CH_3)_2-(R^{20})_n-(R^6)_q-R^{12}$, g) $-(R^{20})_n-N^+(CH_3)_2-(R^6)_q-R^{12}$, h) $-(R^{20})_n-(R^6)_m-R^{20}-N^+(CH_3)_2-(R^{20})_s-(R^6)_q-R^{12}$, and i) $-(R^{20})_n-N^+(CH_3)_2-(R^6)_q-(R^{20})_n-(R^6)_m-R^{12}$;

$R^{12}$ is independently selected from $-C_{1-20}$ alkyl-$R^d$, $-(CR_2)_x-O-(CR_2)_x-R^d$, $-C_{11-20}$ alkyl-C(O)NR$-(CR^d_2)_2H$, and $C_{2-16}$ alkenyl;

$R^{20}$ is independently selected from a) $-(CR^a_2)_tO(CR^a_2)_qO-(CR^a_2)_t-$, b) $-(CR^a_2)_tO(CR^a_2)_qO-(CR^a_2)_t-NRC(O)-$, and c) $-(CR^a_2)_t-NRC(O)-(CR^a_2)_qO(CR^a_2)_qO-(CR^a_2)_t-$;

m is independently selected from 0, 1, 2, 3 or 4;

n is independently selected from 1, 2 or 3;

q is independently selected from 1, 2, 3 or 4;

r is independently selected from 0, 1, 2, 3 or 4;

s is independently selected from 0, 1, 2 or 3;

t is independently selected from 0, 1, 2 or 3;

u is 1 or 2;

x is independently selected from 1, 2, 3, 4, 5, 6, 7, or 8;

z is independently selected from 1, 2, 3, 4, 5 or 6;

provided that if $A^1$ is

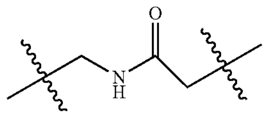 [SMILES: *CNC(=O)C*]

and $R^1$ is H, then $A^2$ is $-(CR_2)_nX(CR_2)_n-$;

or a pharmaceutically acceptable salt of any thereof.

In one embodiment the present invention provides pharmaceutical compositions comprising a compound of the invention, for example, a compound of Formula I, and at least one pharmaceutical excipient, preferably a composition directed to oral administration.

In one aspect the present invention provides a method of antagonizing PCSK9 in the provision of therapy for disease states related to PCSK9 activity, for example, atherosclerosis, hypercholesterolemia, coronary heart disease, metabolic syndrome, acute coronary syndrome, or related cardiovascular disease and cardiometabolic conditions, by administering to a subject in need thereof a therapeutically effective amount of a compound of Formula I, or a salt thereof, preferably in the form of a pharmaceutical composition.

DETAILED DESCRIPTION OF THE INVENTION

In the description that follows conventional structural representation is employed and includes conventional stereochemical notation for certain asymmetric carbon centers.

Thus, structural representation of compounds of the invention includes conventional stereochemical notation for some asymmetric carbon centers shown in the example compounds. Accordingly, in such instances, solid black "wedge" bonds represent bonds projecting from the plane of the reproduction medium, "hashed wedge" bonds representing descending bonds into the plane of the reproduction medium, and a "wavy" line appended to a carbon bearing a double bond indicates both possible cis and trans orientations are included. As is conventional, plain solid lines represent all spatial configurations for the depicted bonding. Accordingly, where no specific stereochemical notation is supplied, the representation contemplates all stereochemical and spatial orientations of the structural features.

As is shown in the examples of the invention, and mentioned above, particular asymmetric carbon centers are structurally represented using conventional "Solid Wedge" and "Hash Wedge" bonding representation. For the most part, absolute configuration has not been determined for the example compounds, but has been assigned by analogy to specific example compounds of known stereochemical configurations (determined by X-ray crystallography) prepared using the same or analogous reaction conditions and starting reagents and isolated under the same chromatographic conditions. Accordingly, specific assignment of the configurations structurally represented herein is meant to identify the specific compounds prepared has having an excess of one particular stereoisomer and is not put forth herein necessarily as being a statement of the absolute determination of the stereochemical structure of said compound unless otherwise noted in the data presented.

It will be appreciated that where isomeric mixtures are obtained, the preparation of individual stereoisomers in significant percentages of enantiomeric excess can be carried out, if desired, by separation of the mixture using customary methods, for example by chromatography or crystallization, or by the use of stereochemically uniform starting materials for the synthesis described, or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product.

Where indicated herein, absolute stereochemistry is determined by X-ray crystallography of crystalline products or crystalline intermediates which are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates) and solvated salts of such racemates, enantiomers, diastereomers and mixtures thereof.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. The present invention is meant to include all suitable isotopic variations of the compounds of Formula I.

Examples of isotopes that can be preferentially incorporated into compounds of the invention include isotopes of hydrogen, carbon, nitrogen, oxygen, phosphorus, iodine, fluorine and chlorine, for example, but not limited to: $^{2}H$, $^{3}H$, C, $^{13}C$, $^{14}C$, $^{13}N$, $^{15}N$, $^{15}O$, $^{17}O$, $^{18}O$ $^{31}P$, $^{32}P$, $^{35}S$, $^{18}F$, and $^{36}Cl$, $^{123}I$, and $^{125}I$. It will be appreciated that other isotopes may be incorporated by known means also.

In particular, certain isotopically-labeled compounds of the invention (e.g., those labeled with $^{3}H$, $^{11}C$, and $^{14}C$) are recognized as being particularly useful in compound and/or substrate tissue distribution assays using a variety of known techniques. Additionally, compounds of the invention contemplate isotopic substitution include different isotopic forms of hydrogen (H), including protium ($^{1}H$) and deuterium ($^{2}H$ or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

Where a wavy line terminates a conventional bond (as opposed to connecting two atoms within a structure) it indicates a point of bonding to a structure, e.g.:

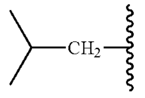

indicates a the secondary-butyl moiety is bonded via the methylene group via the bond terminated with the wavy line. Where an alphabetical notation is used to depict a substituent moiety, a dash is employed to indicate the point of bonding to the indicated substrate, e.g.: $—CH_2—C(O)—CH_2Cl$ indicates the acetyl chloride moiety is bonded via the methylene portion of the moiety.

When any variable (e.g., n, R, $R^a$, $R^6$, etc.) occurs more than one time in any constituent or in Formula I, its definition on each occurrence is independent of its definition at every other occurrence unless otherwise specified at the point of definition. One of ordinary skill in the art will recognize that choice of combinations of the various substituents defined in a structural representation, i.e. R, $R^6$, $R^{20}$, etc., are to be chosen in conformity with well-known principles of chemical structure connectivity and stability, and combinations of substituents and/or variables are permissible only if such combinations result in stable compounds. For example, if $R^{10}$ is defined as "$—R^5—N^+(CH_3)_2—(R^{20})_n—(R^6)_m—R^{12}$", integer n can be selected from 1, 2 or 3 and integer m can be selected from 0, 1, 2, 3, or 4. If integer n in this example is 3 and integer m is 4, then each of the three $R^{20}$ substitutions and each of the four $R^6$ substitutions is independently selected from the list of definitions provided herein.

A "stable" compound is a compound which can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by Formula I.

Where any variable or moiety is expressed in the form of a range, e.g. $(—CH_2—)_{0-4}$, both of the extremes of the specified range are included (i.e. 0 and 4 in the example) as well as all of the whole number values in between (i.e. 1, 2 and 3 in the example).

The term "halogen" includes fluorine, chlorine, bromine and iodine unless specified otherwise at the point of use.

As the term is used herein, "subjects" (alternatively "patients") refers to an animal, preferably a mammal, and in particular a human or a non-human animal including livestock animals and domestic animals including, but not limited to, cattle, horses, sheep, swine, goats, rabbits, cats, dogs, and other mammals in need of treatment. In some embodiments the subject is preferably a human. As used herein, the term "administration" and variants thereof (e.g., "administering" a compound) in reference to a compound of Formula I means providing the compound, or a pharmaceutically acceptable salt thereof, to a subject in need of treatment.

As mentioned above, in one aspect the present invention includes the provision of compounds of Formula I, or a pharmaceutically acceptable salt thereof, which have properties that antagonize PCSK9 function.

In another embodiment of the invention, Formula I comprises a compound of Formula Ia:

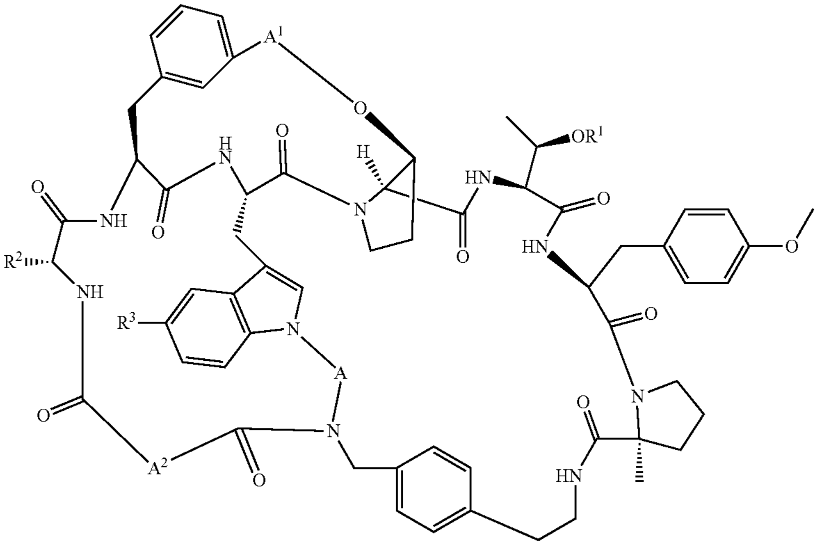

wherein:

A is $C_{2-6}$ alkyl;

$A^1$ is

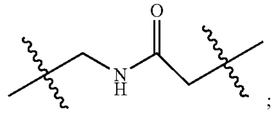

;

$A^2$ is $—(CR_2)_nX(CR_2)_n—$;

X is O or $CR_2$;

R is independently selected from H or $C_{1-6}$ alkyl;

$R^a$ is independently selected from H or $—C(O)OR^9$;

$R^b$ is independently selected from H, $C_{1-6}$ alkyl, or $C_{1-6}$ alkyl-$N^+(CH_3)_2$;

$R^d$ is independently selected from H or $—C(O)OR^9$;

$R^x$ is tetrazolyl;

$R^1$ is H;

$R^2$ is selected from:

(a) $—(CR_2)_z—NR^b—C(O)R^{10}$, and (b) $—(CR_2)_z—NR—C(O)—(CR_2)_z[O(CR_2)_n]_r—N^+(CH_3)_3$;

$R^3$ is F;

$R^4$ is

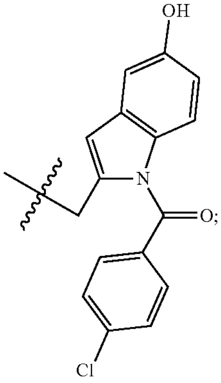 [SMILES: *Cc1cc2cc(O)ccc2n1C(=O)c1ccc(Cl)cc1]

;

$R^5$ is independently selected from $—(CR^a_2)_x—$, $—(CR^a_2)_x\,O(CR^a_2)_x—$, and $C_{1-8}$ alkyl;

$R^{6}$ is independently selected from $-(CR^{a}_{2})_{x}NRC(O)-$, $-(CR_{2})_{x}NRS(O)_{2}-$, and $-(CR^{a}_{2})_{n}O(CR^{a}_{2})_{q}NRC(O)-$;

$R^{9}$ is independently selected from H or $C_{1-6}$ alkyl;

$R^{10}$ is independently selected from:

a) $-(R^{5}-N^{+}(CH_{3})_{2}-R^{6})_{u}-(R^{20})_{n}-(R^{6})_{m}-R^{12}$,
b) $-(R^{20})_{n}-(R^{6})_{m}-R^{5}-N^{+}(CH_{3})_{2}-R^{6}-R^{12}$,
c) $-(R^{20})_{n}-R^{5}-N^{+}(CH_{3})_{2}-(R^{20})_{s}-(R^{6})_{q}-R^{12}$,
d) $-R^{6}-R^{20}-N^{+}(CH_{3})_{2}-(R^{20})_{n}-(R^{6})_{m}-R^{12}$,
e) $-R^{20}-N^{+}(CH_{3})_{2}-(R^{6})_{m}-(R^{20})_{n}-(R^{6})_{q}-R^{12}$,
f) $-(R^{20})_{n}-(R^{6})_{m}-R^{12}$,
g) $-R^{5}-N^{+}(CH_{3})_{2}-(R^{20})_{n}-(R^{6})_{m}-R^{5}-[NRC(O)-R^{5}]q$,
h) $-R^{20}-N^{+}(CH_{3})_{2}-(R^{6})_{m}-R^{5}$,
i) $-R^{5}-N^{+}(CH_{3})_{2}-(R^{20})_{n}-(R^{6})_{m}-R^{5}$,
j) $-R^{5}-N^{+}(CH_{3})_{2}-(R^{20})_{n}-(R^{6})_{m}-R^{12}$,
k) $-(R^{20})_{n}-N^{+}(CH_{3})_{2}-(R^{20})_{n}-(R^{6})_{q}-R^{12}$,
l) $-R^{6}-R^{5}-N^{+}(CH_{3})_{2}-(R^{20})_{n}-(R^{6})_{q}-R^{12}$,
m) $-(R^{20})_{n}-N^{+}(CH_{3})_{2}-(R^{6})_{q}-R^{12}$,
n) $-(R^{20})_{n}-(R^{6})_{m}-R^{20}-N^{+}(CH_{3})_{2}-(R^{20})_{s}-(R^{6})_{q}-R^{12}$,
o) $-R^{20}-N^{+}(CH_{3})_{2}-(R^{6})_{m}-R^{4}$,
p) $-(R^{20})_{n}-N^{+}(CH_{3})_{2}-(R^{6})_{q}-(R^{20})_{n}-(R^{6})_{m}-R^{12}$,
q) $-R^{20}-N^{+}(CH_{3})_{2}-(R^{6})_{m}-(R^{20})_{n}-N^{+}(CH_{3})_{2}-(R^{20})_{n}-(R^{6})_{q}-R^{12}$,
r) $-R^{5}-N^{+}(CH_{3})_{2}-(R^{6})_{m}-R^{5}-N^{+}(CH_{3})_{2}-(R^{20})_{n}-(R^{6})_{q}-R^{12}$, and
s) $-CR^{b}_{2}-(R^{20})_{n}-(R^{6})_{m}-R^{12}$;

$R^{12}$ is independently selected from $-C_{1-20}$ alkyl-$R^{d}$, $-(CR_{2})_{x}-O-(CR_{2})_{x}-R^{d}$, $-C_{11-20}$ alkyl-C(O)NR$-(CR^{d}_{2})_{2}H$, and $C_{2-16}$ alkenyl;

$R^{20}$ is independently selected from a) $-(CR^{a}_{2})_{t}O(CR^{a}_{2})_{q}O-(CR^{a}_{2})_{t}-$,
b) $-(CR^{a}_{2})_{t}O(CR^{a}_{2})_{q}O-(CR^{a}_{2})_{t}-NRC(O)-$,
c) $-(CR^{a}_{2})_{t}O(CR^{a}_{2})_{q}-NRC(O)-(CR^{a}_{2})_{n}O(CR^{a}_{2})_{n}O-$,
d) $-(CR^{a}_{2})_{t}-NRC(O)-(CR^{a}_{2})_{q}O(CR^{a}_{2})_{q}O-(CR^{a}_{2})_{t}-$,
e) $-(CR^{a}_{2})_{t}O(CR^{a}_{2})_{q}O-(CR^{a}_{2})_{t}-$, and
f) $-(CR^{a}_{2})_{t}-O-(CR^{a}_{2})_{q}O(CR^{a}_{2})_{q}O-(CR^{a}_{2})_{t}-$;

m is independently selected from 0, 1, 2, 3 or 4;
n is independently selected from 1, 2 or 3;
q is independently selected from 1, 2, 3 or 4;
r is independently selected from 0, 1, 2, 3 or 4;
s is independently selected from 0, 1, 2 or 3;
t is independently selected from 0, 1, 2 or 3;
u is 1 or 2;
x is independently selected from 1, 2, 3, 4, 5, 6, 7, or 8;
z is independently selected from 1, 2, 3, 4, 5 or 6;
or a pharmaceutically acceptable salt of any thereof.

In another embodiment, the present invention comprises compound of Formula I, wherein:

A is selected from $C_{2-6}$ alkyl or $-(CR_{2})_{n}R^{x}(CR_{2})_{n}-$;

$A^{1}$ is

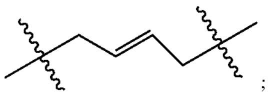
;

$A^{2}$ is $-(CR_{2})_{n}X(CR_{2})_{n}$;

X is O or $CR_{2}$;

R is independently selected from H or $C_{1-6}$ alkyl;

$R^{a}$ is independently selected from H or $-C(O)OR^{9}$;

$R^{b}$ is independently selected from H, $C_{1-6}$ alkyl, or $C_{1-6}$ alkyl-$N^{+}(CH_{3})_{2}$;

$R^{x}$ is tetrazolyl;

$R^{d}$ is independently selected from H or $-C(O)OR^{9}$;

$R^{1}$ is H;

$R^{2}$ is selected from:

(a) $-(CR_{2})_{z}-NR^{b}-C(O)R^{10}$, and
(b) $-(CR_{2})_{z}-NR-C(O)-(CR_{2})_{z}[O(CR_{2})_{n}]_{r}-N^{+}(CH_{3})_{3}$;

$R^{3}$ is F;

$R^{4}$ is

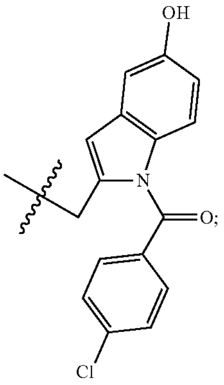 [SMILES: *Cc1cc2cc(O)ccc2n1C(=O)c1ccc(Cl)cc1]

$R^{5}$ is independently selected from $-(CR^{a}_{2})_{x}-$, $-(CR^{a}_{2})_{x}O(CR^{a}_{2})_{x}-$, and $C_{1-8}$ alkyl;

$R^{6}$ is independently selected from $-(CR^{a}_{2})_{x}NRC(O)-$, $-(CR_{2})_{x}NRS(O)_{2}-$, and $-(CR^{a}_{2})_{n}O(CR^{a}_{2})_{q}NRC(O)-$;

$R^{9}$ is independently selected from H or $C_{1-6}$ alkyl;

$R^{10}$ is independently selected from:

a) $-(R^{5}-N^{+}(CH_{3})_{2}-R^{6})_{u}-(R^{20})_{n}-(R^{6})_{m}-R^{12}$,
b) $-(R^{20})_{n}-(R^{6})_{m}-R^{5}-N^{+}(CH_{3})_{2}-R^{6}-R^{12}$,
c) $-(R^{20})_{n}-R^{5}-N^{+}(CH_{3})_{2}-(R^{20})_{s}-(R^{6})_{q}-R^{12}$,
d) $-R^{6}-R^{20}-N^{+}(CH_{3})_{2}-(R^{20})_{n}-(R^{6})_{m}-R^{12}$,
e) $-R^{20}-N^{+}(CH_{3})_{2}-(R^{6})_{m}-(R^{20})_{n}-(R^{6})_{q}-R^{12}$,
f) $-(R^{20})_{n}-(R^{6})_{m}-R^{12}$,
g) $-R^{5}-N^{+}(CH_{3})_{2}-(R^{20})_{n}-(R^{6})_{m}-R^{5}-[NRC(O)-R^{5}]q$,
h) $-R^{20}-N^{+}(CH_{3})_{2}-(R^{6})_{m}-R^{5}$,
i) $-R^{5}-N^{+}(CH_{3})_{2}-(R^{20})_{n}-(R^{6})_{m}-R^{5}$,
j) $-R^{5}-N^{+}(CH_{3})_{2}-(R^{20})_{n}-(R^{6})_{m}-R^{12}$,
k) $-(R^{20})_{n}-N^{+}(CH_{3})_{2}-(R^{20})_{n}-(R^{6})_{q}-R^{12}$,
l) $-R^{6}-R^{5}-N^{+}(CH_{3})_{2}-(R^{20})_{n}-(R^{6})_{q}-R^{12}$,
m) $-(R^{20})_{n}-N^{+}(CH_{3})_{2}-(R^{6})_{q}-R^{12}$,
n) $-(R^{20})_{n}-(R^{6})_{m}-R^{20}-N^{+}(CH_{3})_{2}-(R^{20})_{s}-(R^{6})_{q}-R^{12}$,
o) $-R^{20}-N^{+}(CH_{3})_{2}-(R^{6})_{m}-R^{4}$,
p) $-(R^{20})_{n}-N^{+}(CH_{3})_{2}-(R^{6})_{q}-(R^{20})_{n}-(R^{6})_{m}-R^{12}$,
q) $-R^{20}-N^{+}(CH_{3})_{2}-(R^{6})_{m}-(R^{20})_{n}-N^{+}(CH_{3})_{2}-(R^{20})_{n}-(R^{6})_{q}-R^{12}$,
r) $-R_{5}-N^{+}(CH_{3})_{2}-(R^{6})_{m}-R^{5}-N^{+}(CH_{3})_{2}-(R^{20})_{n}-(R^{6})_{q}-R^{12}$, and
s) $-CR^{b}_{2}-(R^{20})_{n}-(R^{6})_{m}-R^{12}$;

$R^{12}$ is independently selected from $-C_{1-20}$ alkyl-$R^{d}$, $-(CR_{2})_{x}-O-(CR_{2})_{x}-R^{d}$, $-C_{11-20}$ alkyl-C(O)NR$-(CR^{d}_{2})_{2}H$, and $C_{2-16}$ alkenyl;

$R^{20}$ is independently selected from a) $-(CR^{a}_{2})_{t}O(CR^{a}_{2})_{q}O-(CR^{a}_{2})_{t}-$,
b) $-(CR^{a}_{2})_{t}O(CR^{a}_{2})_{q}O-(CR^{a}_{2})_{t}-NRC(O)-$, c) $-(CR^a_2)_tO(CR^a_2)_q-NRC(O)-(CR^a_2)_nO(CR^a_2)_nO-$, d) $-(CR^a_2)_t-NRC(O)-(CR^a_2)_qO(CR^a_2)_qO-(CR^a_2)_t-$, e) $-(CR^a_2)_tO(CR^a_2)_qO-(CR^a_2)_t-$, and f) $-(CR^a_2)_t-O-(CR^a_2)_qO(CR^a_2)_qO-(CR^a_2)_t-$;

m is independently selected from 0, 1, 2, 3 or 4;

n is independently selected from 1, 2 or 3;

q is independently selected from 1, 2, 3 or 4;

r is independently selected from 0, 1, 2, 3 or 4;

s is independently selected from 0, 1, 2 or 3;

t is independently selected from 0, 1, 2 or 3;

u is 1 or 2;

x is independently selected from 1, 2, 3, 4, 5, 6, 7, or 8;

z is independently selected from 1, 2, 3, 4, 5 or 6;

or a pharmaceutically acceptable salt of any thereof.

In another embodiment, the present invention comprises compounds of Formula I, wherein:

A is $C_{2-6}$ alkyl;

$A^1$ is

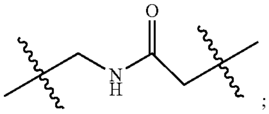 [SMILES: *CNC(=O)C*]

;

$A^2$ is $-(CR_2)_nNRC(O)(CR_2)_n-$;

R is independently selected from H or $C_{1-6}$ alkyl;

$R^a$ is independently selected from H or $-C(O)OR^9$;

$R^b$ is independently selected from H, $C_{1-6}$ alkyl, or $C_{1-6}$ alkyl-$N^+(CH_3)_2$;

$R^x$ is tetrazolyl;

$R^d$ is independently selected from H or $-C(O)OR^9$;

$R^1$ is selected from:

(a) $-(CR_2)_z-R^x-(CR_2)_zNR_2$, (b) $-(CR_2)_z-R^x-(CR_2)_z$ $NR-C(O)-(CR_2)_z[O(CR_2)_n]_r-N^+(CH_3)_3$, and (c) $-(CR_2)_z-R^x-(CR_2)_z-NR^b-C(O)R^{10}$;

$R^2$ is selected from:

(a) $-(CR_2)_z-NR^b-C(O)R^{10}$, and (b) $-(CR_2)_z-NR-C(O)-(CR_2)_z[O(CR_2)_n]_r-N^+(CH_3)_3$;

$R^3$ is F;

$R^4$ is

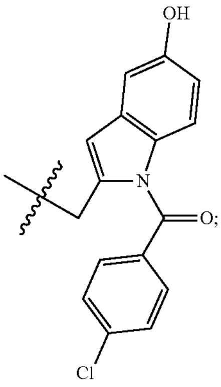 [SMILES: *Cc1cc2cc(O)ccc2n1C(=O)c1ccc(Cl)cc1]

;

$R^5$ is independently selected from $-(CR^a_2)_x-$, $-(CR^a_2)_xO(CR^a_2)_x-$, and $C_{1-8}$ alkyl;

$R^6$ is independently selected from $-(CR^a_2)_xNRC(O)-$, $-(CR_2)_xNRS(O)_2-$, and $-(CR^a_2)_nO(CR^a_2)_qNRC(O)-$;

$R^9$ is independently selected from H or $C_{1-6}$ alkyl;

$R^{10}$ is independently selected from:

a) $-(R^5-N^+(CH_3)_2-R^6)_u-(R^{20})_n-(R^6)_m-R^{12}$, b) $-(R^{20})_n-(R^6)_m-R^5-N^+(CH_3)_2-R^6-R^{12}$, c) $-(R^{20})_n-R^5-N^+(CH_3)_2-(R^{20})_s-(R^6)_q-R^{12}$, d) $-R^6-R^{20}-N^+(CH_3)_2-(R^{20})_n-(R^6)_m-R^{12}$, e) $-R^{20}-N^+(CH_3)_2-(R^6)_m-(R^{20})_n-(R^6)_q-R^{12}$, f) $-(R^{20})_n-(R^6)_m-R^{12}$, g) $-R^5-N^+(CH_3)_2-(R^{20})_n-(R^6)_m-R^5-[NRC(O)-R^5]q$, h) $-R^{20}-N^+(CH_3)_2-(R^6)_m-R^5$, i) $-R^5-N^+(CH_3)_2-(R^{20})_n-(R^6)_m-R^5$, j) $-R^5-N^+(CH_3)_2-(R^{20})_n-(R^6)_m-R^{12}$, k) $-(R^{20})_n-N^+(CH_3)_2-(R^{20})_n-(R^6)_q-R^{12}$, l) $-R^6-R^5-N^+(CH_3)_2-(R^{20})_n-(R^6)_q-R^{12}$, m) $-(R^{20})_n-N^+(CH_3)_2-(R^6)_q-R^{12}$, n) $-(R^{20})_n-(R^6)_m-R^{20}-N^+(CH_3)_2-(R^{20})_s-(R^6)_q-R^{12}$, o) $-R^{20}-N^+(CH_3)_2-(R^6)_m-R^4$, p) $-(R^{20})_n-N^+(CH_3)_2-(R^6)_q-(R^{20})_n-(R^6)_m-R^{12}$, q) $-R^{20}-N^+(CH_3)_2-(R^6)_m-(R^{20})_n-N^+(CH_3)_2-(R^{20})_n-(R^6)_q-R^{12}$, r) $-R^5-N^+(CH_3)_2-(R^6)_m-R^5-N^+(CH_3)_2-(R^{20})_n-(R^6)_q-R^{12}$, and s) $-CR^b_2-(R^{20})_n-(R^6)_m-R^{12}$;

$R^{12}$ is independently selected from $-C_{11-20}$ alkyl-$R^d$, $-(CR_2)_x-O-(CR_2)_x-R^d$, $-C_{1-20}$ alkyl-C(O)NR$-(CR^d_2)_2$H, and $C_{2-16}$ alkenyl;

$R^{20}$ is independently selected from a) $-(CR^a_2)_tO(CR^a_2)_qO-(CR^a_2)_t-$, b) $-(CR^a_2)_tO(CR^a_2)_qO-(CR^a_2)_t-NRC(O)-$, c) $-(CR^a_2)_tO(CR^a_2)_q-NRC(O)-(CR^a_2)_nO(CR^a_2)_nO-$, d) $-(CR^a_2)_t-NRC(O)-(CR^a_2)_qO(CR^a_2)_qO-(CR^a_2)_t-$, e) $-(CR^a_2)_tO(CR^a_2)_qO-(CR^a_2)_t-$, and f) $-(CR^a_2)_t-O-(CR^a_2)_qO(CR^a_2)_qO-(CR^a_2)_t-$;

m is independently selected from 0, 1, 2, 3 or 4;

n is independently selected from 1, 2 or 3;

q is independently selected from 1, 2, 3 or 4;

r is independently selected from 0, 1, 2, 3 or 4;

s is independently selected from 0, 1, 2 or 3;

t is independently selected from 0, 1, 2 or 3;

u is 1 or 2;

x is independently selected from 1, 2, 3, 4, 5, 6, 7, or 8;

z is independently selected from 1, 2, 3, 4, 5 or 6;

or a pharmaceutically acceptable salt of any thereof.

In an embodiment of the compounds of Formula I, A is selected from $C_{2-6}$ alkyl, or $-(CR_2)_nR^x(CR_2)_n-$. In another embodiment of the compounds of Formula I, A is $C_{2-6}$ allyl. In a further embodiment, A is $-(CH_2)_{4-6}$. In another embodiment, A is $-(CR_2)_nR^x(CR_2)_n-$.

In an embodiment, $A^1$ is

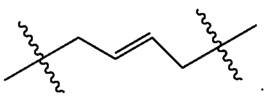 [SMILES: *C/C=C/C*]

.

In another embodiment, $A^1$ is

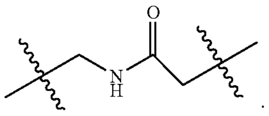 [SMILES: *CNC(=O)C*]

In an embodiment of the compounds of Formula I, $A^2$ is selected from

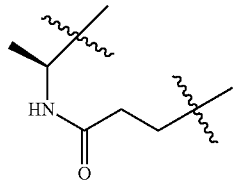 [SMILES: *CCC(=O)N[C@H](*)C]

or $-(CR_2)_nX(CR_2)_n-$, where X is O or $CH_2$. In another embodiment, $A^2$ is $-(CH_2)_2O(CH_2)_2$ or $(CH_2)_{4-6}$. In another embodiment, $A^2$ is

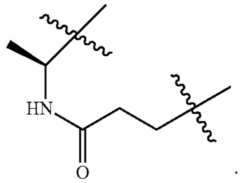 [SMILES: *CCC(=O)N[C@H](*)C]

In an embodiment of the compounds of Formula I, $R^1$ is selected from $-(CR_2)_z-R^x-(CR_2)_zNR_2$, $-(CR_2)_z-R^x-(CR_2)_z$ $NR-C(O)-(CR_2)_z[O(CR_2)_n]_r-N^+(CH_3)_3$, and $-(CR_2)_z-R^x-(CR_2)_z-NR^b-C(O)R^{10}$.

In an embodiment of the compounds of Formula I, $R^1$ is H; and $R^2$ is selected from $-(CR_2)_z-NR^b-C(O)R^{10}$ and $-(CR_2)_z-NR-C(O)-(CR_2)_z[O(CR_2)_n]_r-N^+(CH_3)_3$.

In an embodiment of the compounds of Formula I, $R^2$ is selected from $-(CR_2)_z-NR-C(O)-(CR_2)_z[O(CR_2)_n]_r-N^+(CH_3)_3$. In another embodiment, $R^2$ is $-(CR_2)_z-NR^b-C(O)R^{10}$. In a further embodiment, $R^2$ is $-(CH_2)_z-NH-C(O)R^{10}$.

In an embodiment of the compounds of Formula I, $R^s$ is $C_{1-8}$ alkyl.

In an embodiment of the compound of Formula I, $R^6$ is $-(CR^a{}_2)_xNRC(O)-$. In a further embodiment, $R^6$ is selected from:

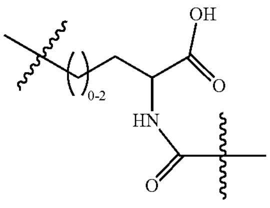

or

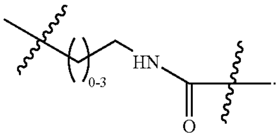

In an embodiment of the compounds of Formula I, $R^{10}$ is selected from a) $-(R^{20})_n-(R^6)_m-R^5-N^+(CH_3)_2-R^6-R^{12}$, b) $-R^{20}-N^+(CH_3)_2-(R^6)_m-(R^{20})_n-(R^6)_q-R^{12}$ c) $-(R^{20})_n-(R^6)_m-R^{12}$, d) $-(R^{20})_n-N^+(CH_3)_2-(R^{20})_n-(R^6)_q-R^{12}$, e) $-(R^{20})_n-N^+(CH_3)_2-(R^6)_q-R^{12}$, f) $-(R^{20})_n-(R^6)_m-R^{20}-N^+(CH_3)_2-(R^{20})_s-(R^6)_q-R^{12}$, and g) $-(R^{20})_n-N^+(CH_3)_2-(R^6)_q-(R^{20})_n-(R^6)_m-R^{12}$.

In another embodiment of the compounds of Formula I, $R^{10}$ is selected from a) $-R^{20}-N^+(CH_3)_2-(R^6)_m-(R^{20})_n-(R^6)_q-R^{12}$, b) $-(R^{20})_n-(R^6)_m-R^{12}$, c) $-(R^{20})_n-N^+(CH_3)_2-(R^{20})_n-(R^6)_q-R^{12}$, and d) $-(R^{20})_n-(R^6)_m-R^{20}-N^+(CH_3)_2-(R^{20})_s-(R^6)_q-R^{12}$.

In further embodiment, $R^{10}$ is $-(R^{20})_n-N^+(CH_3)_2-(R^{20})_n-(R^6)_q-R^{12}$.

Also provided herein are compounds of Formula I, selected from Ex-1, Ex-2, Ex-3, Ex-4, Ex-5, Ex-6, Ex-7, Ex-8, Ex-9, Ex-10, Ex-11, Ex-12, and Ex-13 or any pharmaceutically acceptable salt thereof.

An embodiment of the invention comprises compounds selected from Ex-7, Ex-9, Ex-11, and Ex-13, or a pharmaceutically acceptable salt thereof.

The compounds shown below in Table 1 are also referred to herein as "compounds of the invention". In Table 1, the * denotes that the compound includes "$A^-$", which represents any pharmaceutically acceptable counter ion, including those depicted in the experimental section.

TABLE 1
| Ex No | Structure |
|---|---|
| 1* | 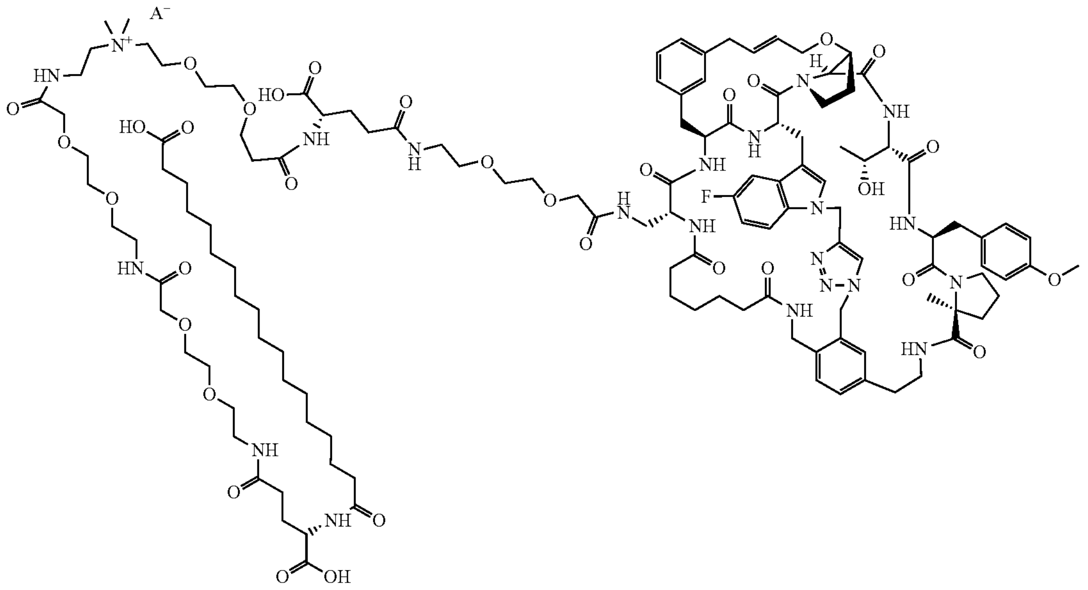 |
| 2* | 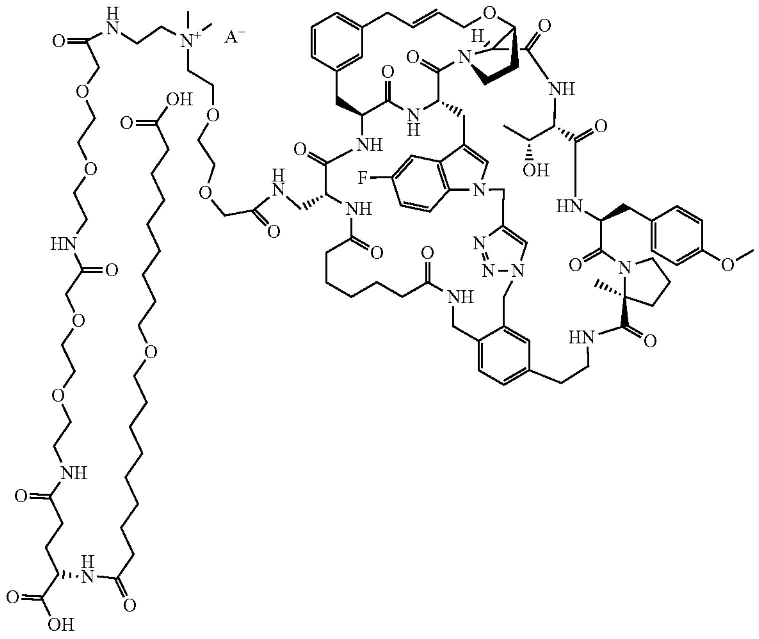 |

TABLE 1-continued
| Ex No | Structure |
|---|---|
| 3* | 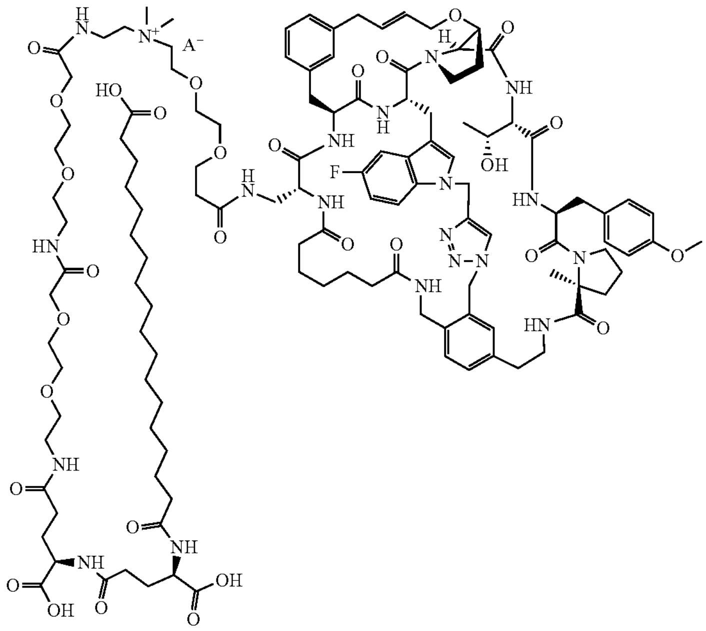 |
| 4* | 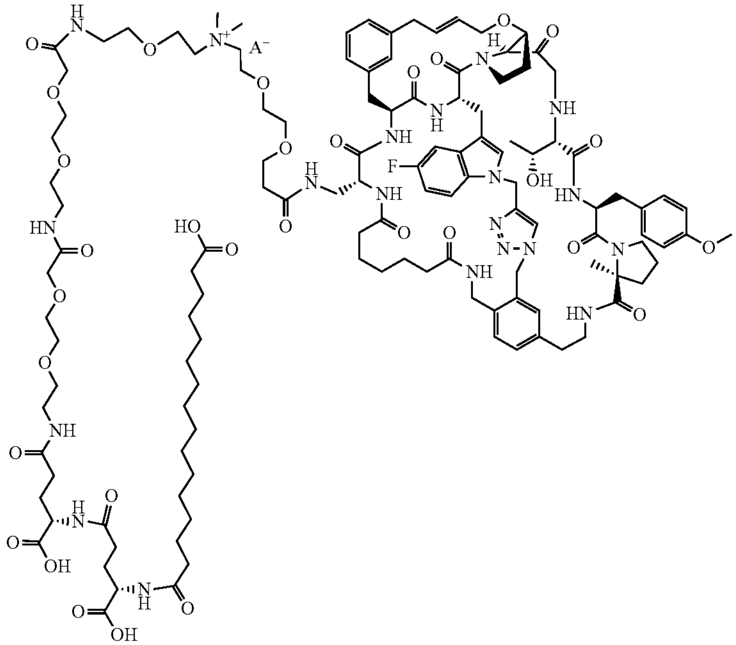 |

TABLE 1-continued
| Ex No | Structure |
|---|---|
| 5* | 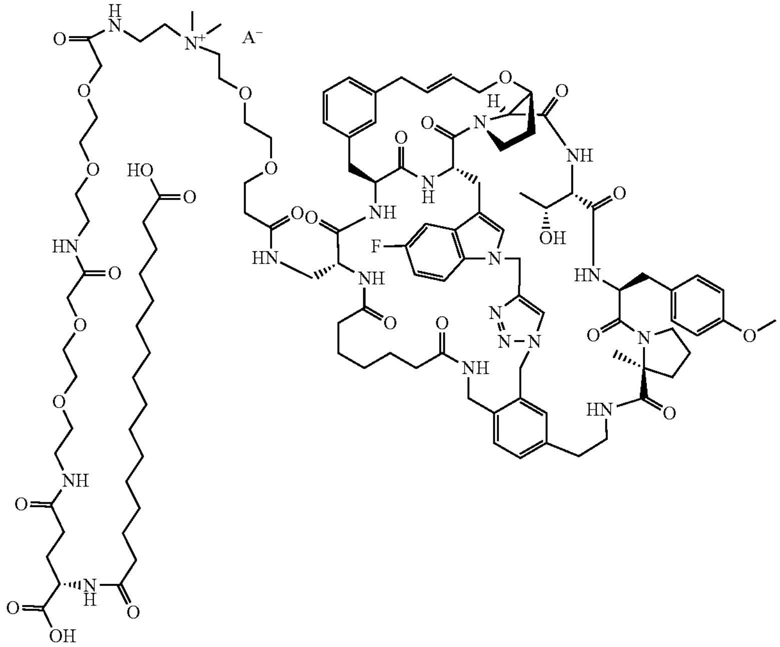 |
| 6* | 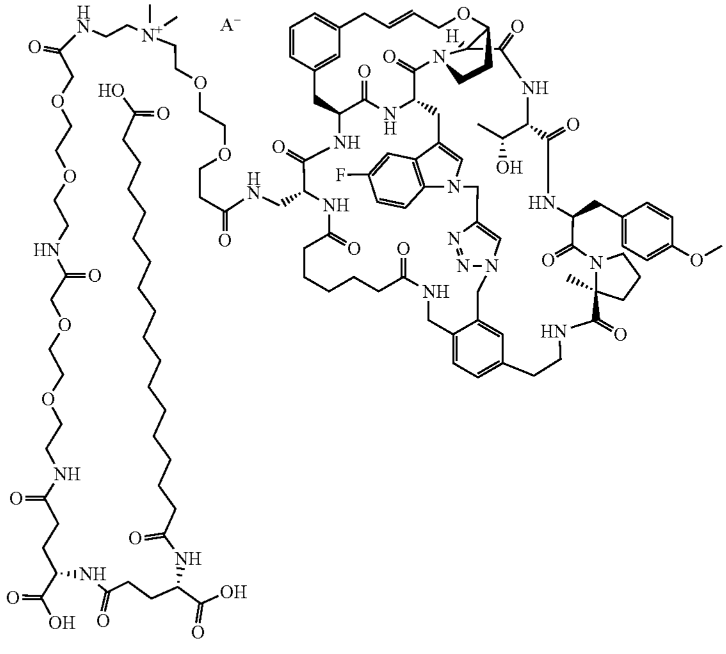 |

TABLE 1-continued
| Ex No | Structure |
|---|---|
| 7* | 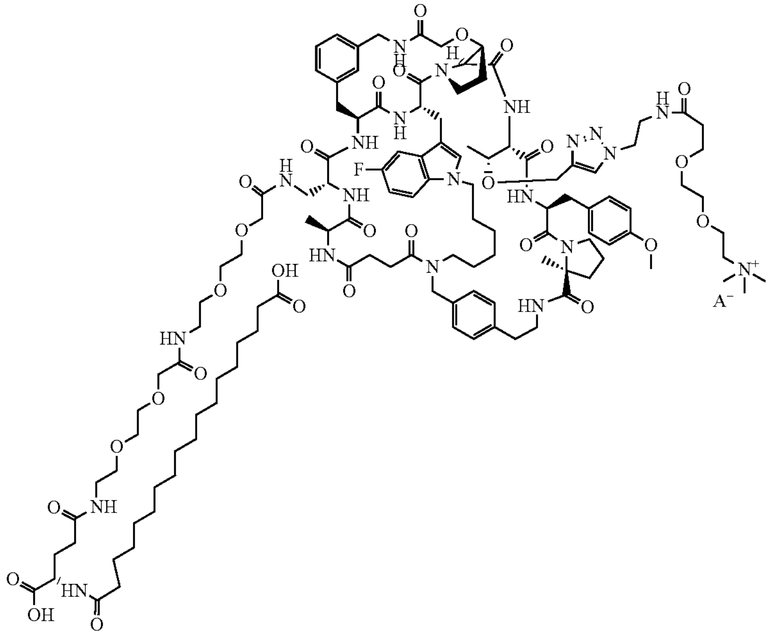 |
| 8* | 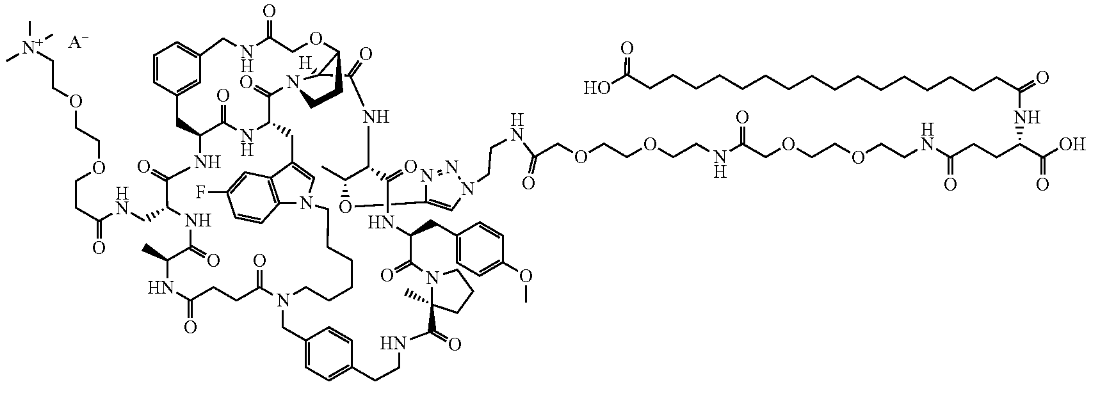 |
| 9* | 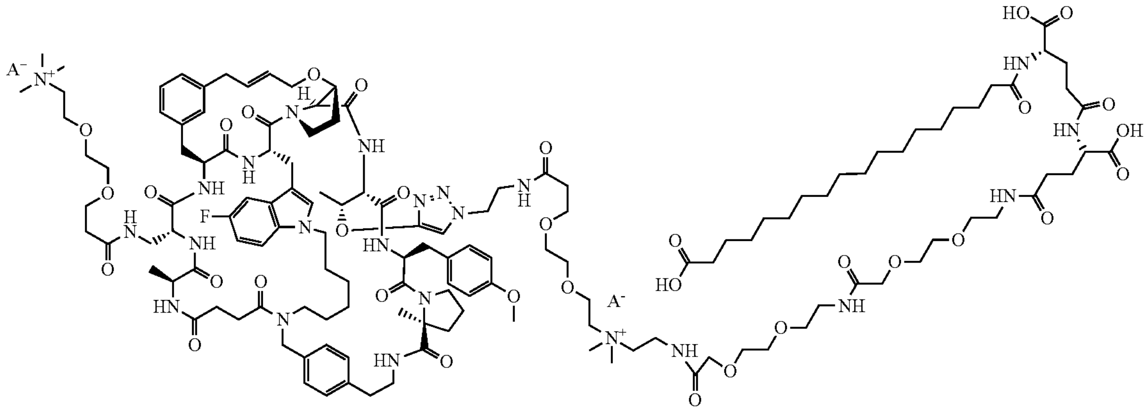 |

TABLE 1-continued
| Ex No | Structure |
|---|---|
| 10* | 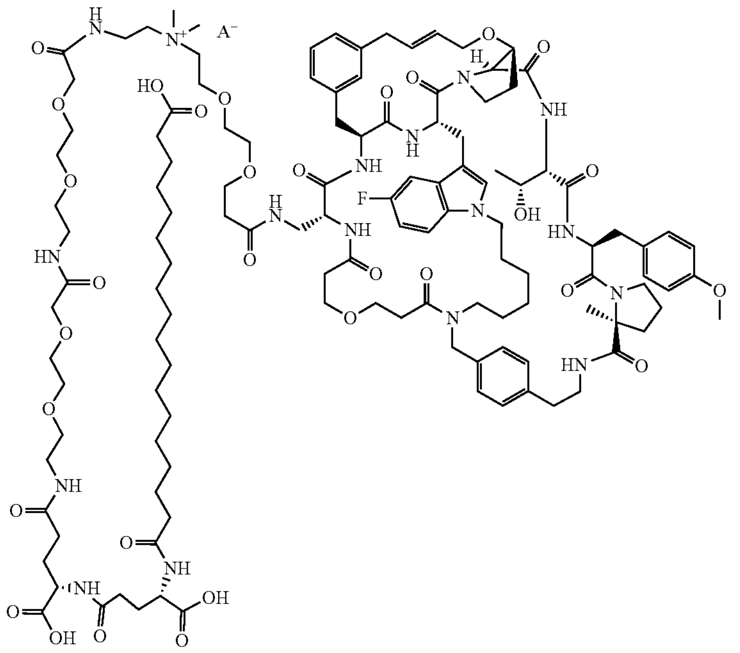 |
| 11* | 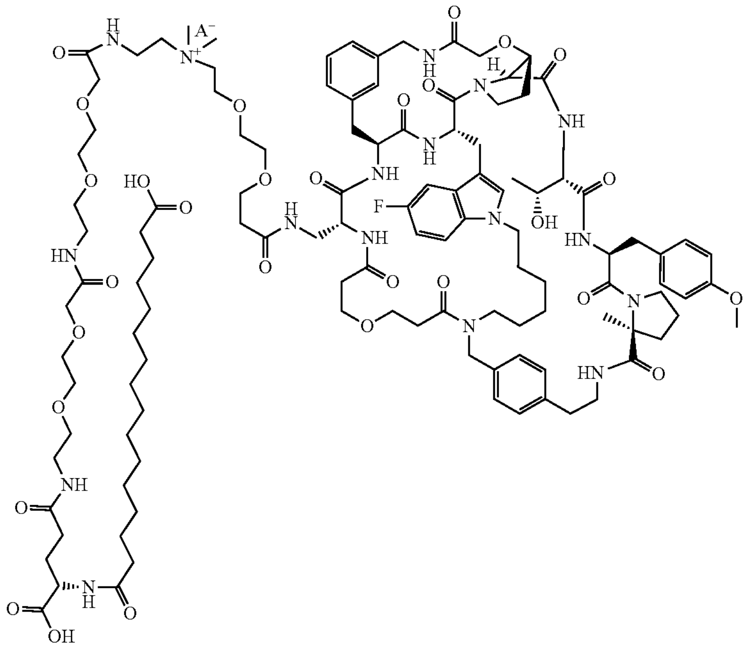 |

TABLE 1-continued

| Ex No | Structure |
|---|---|
| 12* | 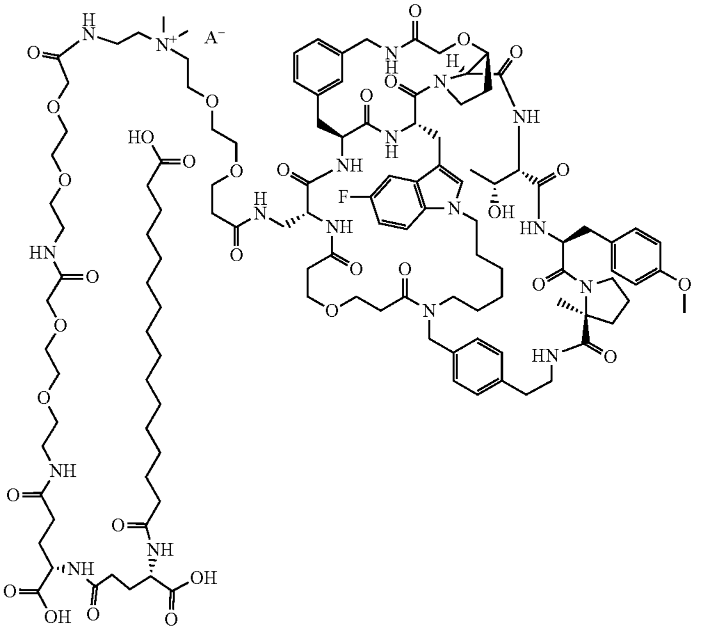 |
| 13* | 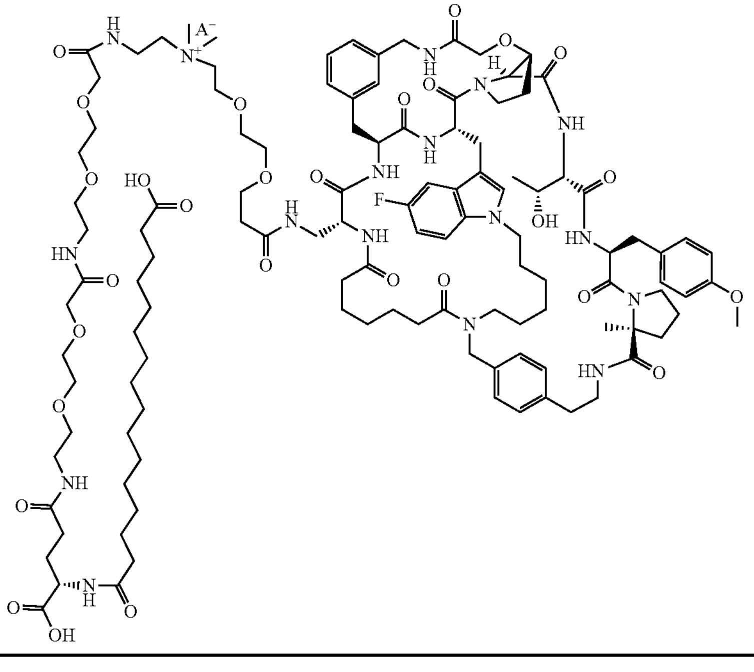 |

or a pharmaceutically acceptable salt thereof.

The term "salt(s)", and its use in the phrase "pharmaceutically acceptable salts" employed herein, includes any of the following: acidic salts formed with inorganic and/or organic acids, basic salts formed with inorganic and/or organic bases, zwitterionic and quaternary ammonium complexes. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization. As used herein, a pharmaceutically acceptable salt of the compounds of Table 1 may be different from the compound associated with a counter ion (A−).

Compounds of the invention contain tri-coordinate nitrogen atoms, for example, primary, secondary or tertiary amino moieties, wherein, as is known, the lone pair of electrons residing on the nitrogen atom may be protonated with an appropriate acid or alkylated with an appropriate reagent, for example, alkyl bromide, under the appropriate reaction conditions to provide tetracoordinate charged nitrogen stabilized by an anion generated in the process, for example, a halogen ion or conjugate base. Accordingly, compounds of the invention may be prepared in the form of a free-base or isolated in the form of a quaternary complex or a salt complex. In some instances where there is an appropriate acidic proton proximal to a basic nitrogen, formation of a zwitterionic complex is possible. As the term is employed herein, salts of the inventive compounds, are included in the scope of the invention, whether acidic salts formed with inorganic and/or organic acids, basic salts formed with inorganic and/or organic bases, salts formed which include zwitterionic character (for example, where a compound contains both a basic moiety, for example, but not limited to, a nitrogen atom, for example, an amine, pyridine or imidazole, and an acidic moiety, for example, but not limited to a carboxylic acid), and quaternary ammonium complexes.

Accordingly, structural representation of compounds of the invention, whether in a free-base form, a salt form, a zwitterionic form or a quaternary ammonium form, also include all other forms of such compounds discussed above. Thus, one aspect of the invention is the provision of compounds of the invention in the form of a pharmaceutically acceptable salt, zwitterionic complex or quaternary ammonium complex. Those skilled in the art will recognize those instances in which the compounds of the invention may form such complexes, including where a tetracoordinate nitrogen can be quaternized or protonated and the charged nitrogen form stabilized by an associated anion. The term "pharmaceutically acceptable salt" refers to a salt (including a quaternary ammonium complex and an inner salt such as a zwitterion complex) which possesses effectiveness similar to or greater than a free-base form of the compound and which is not biologically or otherwise undesirable (e.g., is neither toxic nor otherwise deleterious to the recipient thereof).

The formation of pharmaceutically useful salts from basic (or acidic) pharmaceutical compounds are discussed, for example, by S. Berge et al., Journal of Pharmaceutical Sciences (1977) 66 (1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates both freebase forms of the compounds of the invention and all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". As will be appreciated, freebase compounds may be prepared by controlling the conditions of isolation of the compound during synthesis or by neutralization and ion exchange from salt forms of compounds of the invention.

Examples of pharmaceutically acceptable acid salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quaternized with agents such as lower allyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Further examples of pharmaceutically acceptable salts that may be used with the instant invention include, but are not limited to, fluoride, chloride, bromide and iodide.

In general, salts of compounds are intended to be pharmaceutically acceptable salts within the scope of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan. Compounds of the invention include any form of the compound including in situ in a reaction mixture as well as in isolated and purified form obtained by routine techniques. Also included are polymorphic forms of the compounds of the invention and solvates and prodrugs thereof.

Certain compounds of the invention may exist in different tautomeric forms, for example, but are not limited to, ketone/enol tautomeric forms, imine-enamine tautomeric forms, and for example heteroaromatic forms such as the following moieties:

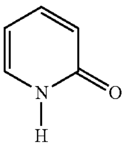
and
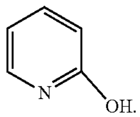

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention.

In another aspect, the present invention provides pharmaceutical compositions comprising one or more compounds of the invention. As used herein, the term "pharmaceutical composition" comprises at least one pharmaceutically active compound and at least one excipient, and is intended to encompass both the combination of the specified ingredients in the specified amounts, and any product which results, directly or indirectly, from combination of the specified ingredients in the specified amounts.

As will be appreciated by the ordinarily skilled artisan, excipients are any constituent which adapts the composition to a particular route of administration or aids the processing of a composition into a dosage form without itself exerting an active pharmaceutical effect. In general compositions comprise more than one excipient depending upon the route of administration and the characteristics of the active being administered. Examples of excipients which impart to the composition properties which make it easier to handle or process include, but are not limited to, lubricants or pressing aids in powdered medicaments intended to be tableted, and emulsion stabilizers in compositions in which the active is present in the form of an emulsion. Examples of excipients which adapt a composition to a desired route of administration are, for example, but not limited to, for oral administration, absorption enhancers promoting absorption from the gastrointestinal tract, for transdermal or transmucosal administration, penetration enhancers, for example, those employed in adhesive skin "patch" or compositions for buccal administration.

Notwithstanding the function excipients perform in a composition, excipients are collectively termed herein "a carrier". Typically, formulations may comprise up to about 95 percent active ingredient and the balance carrier, although formulations with different ratios may be prepared. In general, acceptable pharmaceutical compositions contain a suitable concentration of the active that an effective amount of the PCSK9 antagonist can be provided in an individual dosage form of acceptable volume based upon the route of administration such that it can provide a therapeutic serum level of the active for an acceptable period of time in a subject to whom the composition is administered and the composition will retain biological activity during storage within an acceptable temperature range for an acceptable period of time.

Pharmaceutical composition, as used herein, refers both to a bulk composition, that is, formulated material that has not yet been formed into individual dosage units for administration, and the composition contained within individual dosage units.

While compositions of the invention may be employed in bulk form, it will be appreciated that for most applications compositions will be incorporated into a dosage form providing individual units suitable for administration to a patient, each dosage form comprising an amount of the selected composition which contains an effective amount of said one or more compounds of Formula I. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for administration through tissues of the oral cavity, for example, a rapidly dissolving tablet, a lozenge, a solution, a gel, a sachet or a needle array suitable for providing intramucosal administration; (iii) a dosage form adapted for administration via the mucosa of the nasal or upper respiratory cavity, for example a solution, suspension or emulsion formulation for dispersion in the nose or airway; (iv) a dosage form adapted for transdermal administration, for example, a patch, cream or gel; (v) a dosage form adapted for intradermal administration, for example, a microneedle array; (vi) a dosage form adapted for intravenous (IV) infusion, for example, over a prolonged period using an I.V. infusion pump; (vii) a dosage form adapted for intramuscular administration (IM), for example, an injectable solution or suspension, and which may be adapted to form a depot having extended release properties; (viii) a dosage form adapted for drip intravenous administration (IV), for example, a solution or suspension, for example, as an IV solution or a concentrate to be injected into a saline IV bag; (ix) a dosage form adapted for subcutaneous administration, including administration over an extended time period by implanting a rod or other device which diffuses the compound into the surround tissue and thereby provides a continuous serum therapeutic level; or (x) a dosage form adapted for delivery via rectal or vaginal mucosa, for example, a suppository.

Pharmaceutical compositions can be solid, semi-solid or liquid. Solid, semi-solid and liquid form preparations can be adapted to a variety of modes of administration, examples of which include, but are not limited to, powders, dispersible granules, mini-tablets, beads, which can be used, for example, for tableting, encapsulation, or direct administration. In addition, liquid form preparations include, but are not limited to, solutions, suspensions and emulsions which for example, but not exclusively, can be employed in the preparation of formulations intended for ingestion, inhalation or intravenous administration (IV), for example, but not limited to, administration via drip IV or infusion pump, intramuscular injection (IM), for example, of a bolus which is released over an extended duration, direct IV injection, or adapted to subcutaneous routes of administration.

Other routes of administration which may be contemplated include intranasal administration, or for administration to some other mucosal membrane. Formulations prepared for administration to various mucosal membranes may also include additional components adapting them for such administration, for example, viscosity modifiers.

Although in some embodiments, compositions suitable for use in a solid oral dosage form, for example, a tablet or quick-melt mouth-dissolving formulation are preferable routes of administration for a compound of the invention or a salt thereof, a composition of the invention may be formulated for administration via other routes mentioned above. Examples include aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

For example, the compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20 Edition, (2000), Lippincott Williams & Wilkins, Baltimore, MD Additional examples of publications addressing formulation issues may be found in: Pharmaceutical compositions may be formulated by any number of strategies known in the art, see, e.g., McGoff and Scher, 2000 *Solution Formulation of Proteins/Peptides*: In—McNally, E. J., ed. Protein Formulation and Delivery. New York, NY: Marcel Dekker; pp. 139-158; Akers & Defilippis, 2000, *Peptides and Proteins as Parenteral Solutions*. In—Pharmaceutical Formulation Development of Peptides and Proteins. Philadelphia, PA: Taylor and Francis; pp. 145-177; Akers et al., 2002, *Pharm. Biotechnol.* 14:47-127.

In another aspect the present invention provides methods of employing PCSK9-specific antagonist compounds described herein for antagonizing PCSK9 function; said methods of which are further described below. Use of the term "antagonizing" throughout the present application refers to providing to the affected tissue(s) a substance which opposes the action of, inhibits, counteracts, neutralizes or curtails one or more functions of PCSK9 in the affected tissues. Inhibition or antagonism of one or more of PCSK9-associated functional properties can be readily determined according to methodologies known to the art (see, e.g., Barak & Webb, 1981 *J. Cell Biol.* 90:595-604; Stephan & Yurachek, 1993 *J. Lipid Res.* 34:325330; and McNamara et al., 2006 *Clinica Chimica Acta* 369:158-167) as well as those described herein. Inhibition or antagonism will effectuate a decrease in PCSK9 activity relative to that seen in the absence of the antagonist or, for example, that seen relative to the activity observed when a control antagonist of irrelevant specificity is present. Preferably, a PCSK9-specific antagonist in accordance with the present invention antagonizes PCSK9 functioning to the point that there is a decrease of at least 10%, of the measured parameter including but not limited to the activities disclosed herein, and more preferably, a decrease of at least 20%, 30%, 40%, 50%, 60%, 70%, 80%, 90% and 95% of the measured parameter. Such inhibition/antagonism of PCSK9 functioning is particularly effective in those instances where PCSK9 functioning is contributing at least in part to a particular phenotype, disease, disorder or condition which is negatively impacting the subject.

In one aspect, the present invention provides a method for antagonizing the activity of PCSK9, which comprises contacting a cell, population of cells or tissue sample capable of being affected by PCSK9 (i.e., which expresses and/or comprises LDL receptors) with a PCSK9-specific antagonist disclosed herein under conditions that allow said antagonist to bind to PCSK9 when present and inhibit PCSK9's inhibition of cellular LDL uptake. In some embodiments of the present invention include such methods wherein the cell is a human cell. Additional embodiments of the present invention include such methods wherein the cell is a murine cell.

In one aspect, the present invention provides a method for antagonizing the activity of PCSK9 in a subject, which comprises administering to the subject a therapeutically effective amount of a PCSK9-specific antagonist of the present invention. In some embodiments, the methods for antagonizing PCSK9 function are for the treatment, as defined herein, of a PCSK9-associated disease, disorder or condition or, alternatively, for providing therapy in a disease, disorder or condition that could benefit from the effects of a PCSK9 antagonist.

The present invention, thus, contemplates the use of PCSK9-specific antagonists described herein in various methods of treatment where antagonizing PCSK9 function is desirable. As used herein, the term "method of treatment" relates to a course of action resulting in a change in at least one symptom of a disease state which can be prophylactic or therapeutic in nature. In some embodiments, the present invention relates to a method of treatment for a condition associated with and/or attributed to PCSK9 activity, or a condition where the functioning of PCSK9 is contraindicated for a particular subject, the method comprising administering to the subject a therapeutically effective amount of a PCSK9—antagonist compound of Formula I, or pharmaceutically acceptable salt thereof. In some embodiments, the condition may be atherosclerosis, hypercholesterolemia, coronary heart disease, metabolic syndrome, acute coronary syndrome or related cardiovascular disease and cardiometabolic conditions, or may be a disease state or condition in which PCSK9 activity is contraindicated.

Methods of treatment in accordance with the present invention comprise administering to an individual a therapeutically (or prophylactically) effective amount of a PCSK9-specific antagonist of the present invention. Use of the terms "therapeutically effective" or "prophylactically effective" in reference to an amount refers to the amount necessary at the intended dosage to achieve the desired therapeutic and/or prophylactic effect for the period of time desired. The desired effect may be, for example, the alleviation, amelioration, reduction or cessation of at least one symptom associated with the treated condition. These amounts will vary, as the skilled artisan will appreciate, according to various factors, including but not limited to the disease state, age, sex, and weight of the individual, and the ability of the PCSK9-specific antagonist to elicit the desired effect in the individual. The response may be documented by in vitro assay, in vivo non-human animal studies, and/or further supported from clinical trials.

In some embodiments it is preferred to administer a PCSK9 antagonist compound of the invention in the form of a pharmaceutical composition as described herein.

Dosing of antagonist therapeutics is well within the realm of the skilled artisan, see, e.g., Lederman et al., 1991 *Int. J. Cancer* 47:659-664; Bagshawe et al., 1991 *Antibody, Immunoconjugates and Radiopharmaceuticals* 4:915-922, and will vary based on a number of factors, for example, but not limited to, those mentioned above, including the condition of the patient, the area being treated, the route of administration, and the treatment desired, for example, prophylaxis or acute treatment and the like. A physician or veterinarian of ordinary skill can readily determine and prescribe the effective therapeutic amount of the antagonist.

The subject may be in need of, or desire, treatment for an existing disease or medical condition. As used herein, the subject "in need" of treatment of an existing condition encompasses both a determination of need by a medical professional as well as the desire of the subject for such treatment. When a compound or a salt thereof is provided in combination with one or more other active agents, "administration" and its variants are each understood to include provision of the compound or its salt and the other agents contemporaneously or simultaneously or over a course of separate administrations over a period of time. When the agents of a combination are administered at the same time, they can be administered together in a single composition or they can be administered separately. It is understood that a "combination" of active agents can be a single composition containing all of the active agents or multiple compositions each containing one or more of the active agents. In the case of two active agents a combination can be either a single composition comprising both agents or two separate compositions each comprising one of the agents; in the case of three active agents a combination can be either a single composition comprising all three agents, three separate compositions each comprising one of the agents, or two compositions one of which comprises two of the agents and the other comprises the third agent; and so forth.

The compositions and combinations of the present invention are suitably administered in effective amounts. The term "effective amount" means the amount of active compound sufficient to antagonize PCSK9 and thereby elicit the response being sought (i.e., induce a therapeutic response in the treatment or management of conditions associated with or impacted by PCSK9 function, including, but not limited to atherosclerosis, hypercholesterolemia, coronary heart disease, metabolic syndrome, acute coronary syndrome, and related cardiovascular disease and cardiometabolic conditions in an animal or human).

The actual dosage employed may be varied depending upon the requirements of the patient and the severity of the condition being treated. Determination of the proper dosage regimen for a particular situation is within the skill in the art, for example, as described in the standard literature, for example, as described in the "Physicians' Desk Reference" (PDR), e.g., 1996 edition (Medical Economics Company, Montvale, NJ 07645-1742, USA), the Physician's Desk Reference, 56$^{th}$ Edition, 2002 (published by Medical Economics company, Inc. Montvale, NJ 07645-1742), or the Physician's Desk Reference, 57$^{th}$ Edition, 2003 (published by Thompson PDR, Montvale, NJ 07645-1742); the disclosures of which is incorporated herein by reference thereto. For convenience, the total daily dosage may be divided and administered in portions during the day as required or delivered continuously.

The PCSK9-specific antagonist may be administered to an individual by any route of administration appreciated in the art, including but not limited to oral administration, administration by injection (specific embodiments of which include intravenous, subcutaneous, intraperitoneal or intramuscular injection), or administration by inhalation, intranasal, or topical administration, either alone or in combination with other agents designed to assist in the treatment of the individual. The PCSK9-specific antagonist may also be administered by injection devices, injector pens, needleless devices; and subcutaneous patch delivery systems. The route of administration should be determined based on a number of considerations appreciated by the skilled artisan including, but not limited to, the desired physiochemical characteristics of the treatment.

One or more additional pharmacologically active agents may be administered in combination with a compound of Formula I. An additional active agent (or agents) is intended to mean a pharmaceutically active agent (or agents) that is active in the body, including pro-drugs that convert to pharmaceutically active form after administration, which are different from the compound of Formula I, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formula I in a single dosage formulation (a fixed dose drug combination), or may be administered to the subject in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives, peptidyl amino diols and peptidyl beta-aminoacyl aminodiol carbamates, and small molecule renin inhibitors (including diol sulfonamides and sulfinyls), N-morpholino derivatives, N-heterocyclic alcohols and pyrolimidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, verapamil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), crivastatin, and pitavastatin; a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, torcetrapib, and evacetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, ertugliflozin, remogloflozin, TS-071, tofogliflozin, ipragliflozin, and LX-4211); inhibitors of acyl coenzyme A:diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBAR1, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the treatment of the above-mentioned conditions or disorders including the free-acid, free-base, and pharmaceutically acceptable salt forms of the above active agents where chemically possible.

The compounds of the present invention can be readily prepared according to the following reaction schemes and examples, or modifications thereof, using readily available starting materials, reagents and conventional synthesis procedures. In these reactions, it is also possible to make use of known variants. For purification of the compounds using reverse phase chromatography (either HPLC or MPLC, as noted below), a C18 column was used. Other methods for preparing compounds of the invention will be readily apparent to the person of ordinary skill in the art in light of the following reaction schemes and examples. Abbreviations listed below may be used in the exemplary schemes and/or examples herein.

Abbreviations

ACN is acetonitrile; AcOH is acetic acid; Boc is t-butoxycarbonyl; $Boc_2O$ is di-tert-butyl dicarbonate; BnBr is benzyl bromide; BzCl is benzoyl chloride; $CBr_4$ is perbromomethane or tetrabromomethane; Cbz-Cl is benzyl chloroformate; Cbz-OSu is is N-(benzyloxycarbonyloxy)succinimide; $CD_3OD$ is deuterated methanol; $CDCl_3$ is deuterated chloroform; $Cs_2CO_3$ is cesium carbonate; DCC is N,N'-Dicyclohexylcarbodiimide; DCE is 1,2-dichloroethane; DCM is dichloromethane; D-Dap(Boc)-OMe is methyl (S)-2-amino-3-((tert-butoxycarbonyl)amino)propanoate; DIEA or DIPEA is N,N-diisopropylethylamine; DMF is N,N-dimethylformamide; DMAP is 4-dimethylaminopyridine; DMSO is dimethyl sulfoxide; DIAD is (E)-diisopropyl diazene-1,2-dicarboxylate; DMP is Dess-Martin periodinane; $Et_3N$ is triethylamine; EA or EtOAc is ethyl acetate; $Et_2O$ is diethyl ether; EtOH is ethanol; Fmoc is fluorenylmethyloxycarbonyl protecting group; Fmoc-Cl is (9H-fluoren-9-yl)methyl carbonochloridate; Fmoc-Osu is Fmoc N-hydroxysuccinimide ester; HATU is 1-[bis(dimethylamino)methylene]-1H-1,2,3-triazolo[4,5-b]pyridinium 3-oxid hexafluorophosphate; HPLC is high pressure liquid chromatography; IPA is isopropyl alcohol; IPAc is isopropyl acetate; LC/MS or LCMS is liquid chromatography mass spectrometry; LiOH is lithium hydroxide; Me is methyl; MeOH is methanol; MeI is methyl iodide; $MgSO_4$ is magnesium sulfate; MPLC is medium pressure liquid chromatography; MTBE is methyl tert-butyl ether; $Na_2SO_4$ is sodium sulfate; $NaHCO_3$ is sodium bicarbonate; $Na_2CO_3$ is sodium carbonate; $NaBH_3CN$ is sodium cyanoborohydride; $NaBH(OAc)_3$ is sodium triacetoxyborohydride; $NaN_3$ is sodium azide; $NH_4Cl$ is ammonium chloride; $NH_4HCO_3$ is ammonium bicarbonate; NMR is Nuclear Magnetic Resonance; NsCl is 4-nitrobenzene-1-sulfonyl chloride; Oxyma is ethyl 2-cyano-2-(hydroxyimino)acetate; Pd/C is palladium on carbon; PE is petroleum ether; $Pd_2(dba)_3(HCCl_3)$ is tris(dibenzylideneacetone)dipalladium(0)-chloroform adduct; $PPh_3$ or $Ph_3P$ is triphenylphosphine; Pd(dppf)$Cl_2.CH_2Cl_2$ is dichloro[1,1'-bis(diphenylphosphino)ferrocene]palladium(II) dichloromethane adduct; $Pd(PPh_3)_4$ is tetrakis(triphenylphosphine)palladium; RP Flash is Reverse Phase Flash Chromatography; RT or r.t. or rt is room temperature; S-Phos is 2-dicyclohexylphosphino-2',6'-dimethoxybiphenyl; TBAB is tetrabutylammonium bromide; TBAF is tetrabutylammonium fluoride; TBAHS is tetrabutylammonium hydrogenosulfate; TEA is triethylamine; TFA is trifluoroacetic acid; THF is tetrahydrofuran; $Tf_2O$ is trifluoromethanesulfonic anhydride; TMS-diazomethane is trimethylsilyl-diazomethane and Zhan 1B is Dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II).

The compounds of the present invention can be readily prepared according to the following reaction schemes and examples, or modifications thereof, in conjunction with readily available starting materials, reagents and conventional synthesis procedures. Alternate salt forms for products and intermediates may also be present in the invention. Alternate methods for preparing compounds of the invention will be readily apparent to the person of ordinary skill in the art in light of the following reaction schemes and examples. For example, in these reactions it is possible to make use of known variants. Immediately following is a section describing the preparation of intermediates useful in the preparation of example compounds of the invention. Unless otherwise noted, reagents used in the preparation of intermediates and examples are commercially available or can be prepared by known methods.

Preparation of intermediate A

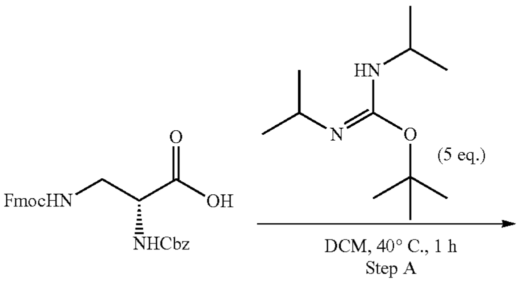

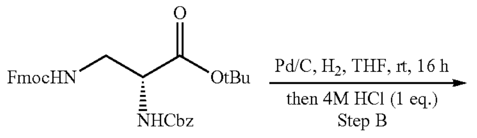

A-1

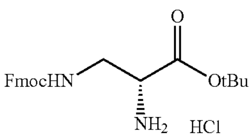

A-2

-continued

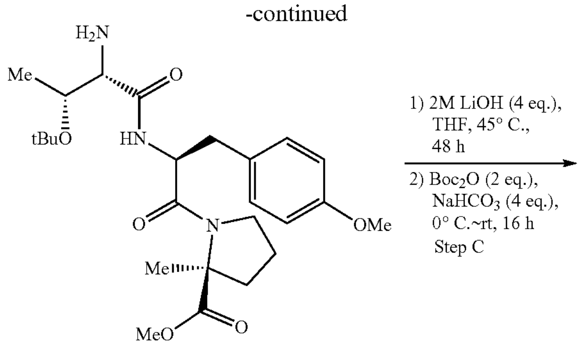

A-3

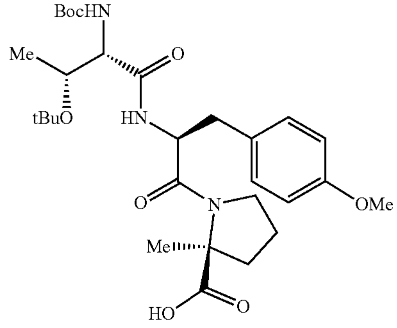

A

Step A: (R)-tert-butyl 3-((((9H-fluoren-9-yl)methoxy)carbonyl)amino)-2-(((benzyloxy)carbonyl)amino)propanoate A-1

To a stirred mixture of (R)-3-((((9H-fluoren-9-yl)methoxy)carbonyl)amino)-2-(((benzyloxy)carbonyl)amino)propanoic acid (5.00 g, 10.9 mmol) in DCM (100 mL) was added (E)-tert-butyl N,N'-diisopropylcarbamimidate (10.9 g, 54.3 mmol) at ambient temperature. The resulting mixture was stirred for 1 h at 40° C. The reaction mixture was filtered. The filtrate was concentrated under reduced pressure and the residue was purified by silica gel column chromatography, eluted with 30-60% EA in PE to obtain (R)-tert-butyl 3-((((9H-fluoren-9-yl)methoxy)carbonyl)amino)-2-(((benzyloxy)carbonyl)amino)propanoate A-1. LCMS (ESI) calc'd for $C_{30}H_{32}N_2O_6$ $[M+Na]^+$: 539.2, found 539.3.

Step B: (S)-tert-butyl 4-((((9H-fluoren-9-yl)methoxy)carbonyl)amino)-2-aminobutanoate hydrochloride A-2

To a stirred solution of (S)-tert-butyl 4-((((9H-fluoren-9-yl)methoxy)carbonyl)amino)-2-(((benzyloxy)carbonyl)amino)butanoate A-1 (4.0 g, 7.54 mmol) in THF (100 mL) was added Pd/C (10% wt, dry) (0.802 g, 0.754 mmol) under nitrogen atmosphere. The reaction mixture was degassed with hydrogen three times and stirred at room temperature for 16 h under hydrogen. The mixture was filtered. The filtrate was added 4 M HCl in dioxane (1.89 mL, 7.54 mmol). The mixture was concentrated under reduced pressure. The residue was added $Et_2O$ (100 mL) and stirred for 30 min and filtered. The filter cake was dried to afford (S)-tert-butyl 4-((((9H-fluoren-9-yl)methoxy)carbonyl)amino)-2-aminobutanoate hydrochloride A-2. LCMS (ESI) calc'd for $C_{22}H_{27}ClN_2O_4$ $[M-HCl+H]^+$: 383.2, found 383.3.

Step C: (S)-1-((S)-2-((2S,3R)-3-(tert-butoxy)-2-((tert-butoxycarbonyl)amino)butanamido)-3-(4-methoxyphenyl)propanoyl)-2-methylpyrrolidine-2-carboxylic acid A To a solution of (S)-methyl 1-((S)-2-((2S,3R)-2-amino-3-(tert-butoxy)butanamido)-3-(4-methoxyphenyl)propanoyl)-2-methylpyrrolidine-2-carboxylate A-2 (2.95 g, 6.18 mmol) in THF (30 mL) was added 2 M LiOH (12.4 mL, 24.7 mmol) at room temperature. The reaction mixture was stirred at 45° C. for 48 h. The reaction mixture was cooled to 0° C. and added 1 M HCl (24.7 mL). The above mixture were added $NaHCO_3$ (2.07 g, 24.9 mmol) and $Boc_2O$ (2.86 mL, 12.3 mmol) at 0° C. The mixture was stirred at room temperature for 16 h. The mixture was added 1 M HCl (25 mL) at 0° C., extracted with EA (100 mL). The organic layer was washed with brine (50×2 mL), dried over anhydrous $MgSO_4$ and filtered. The filtrate was concentrated under reduced pressure. The residue purified by silica gel column chromatography, eluted with gradient 0%-8% MeOH in DCM to afford (S)-1-((S)-2-((2S,3R)-3-(tert-butoxy)-2-((tert-butoxycarbonyl)amino)butanamido)-3-(4-methoxyphenyl)propanoyl)-2-methylpyrrolidine-2-carboxylic acid A. LCMS (ESI) calc'd for $C_{29}H_{45}N_3O_8$ $[M+H]^+$: 564.3, found 564.2.

Preparation of Intermediate B

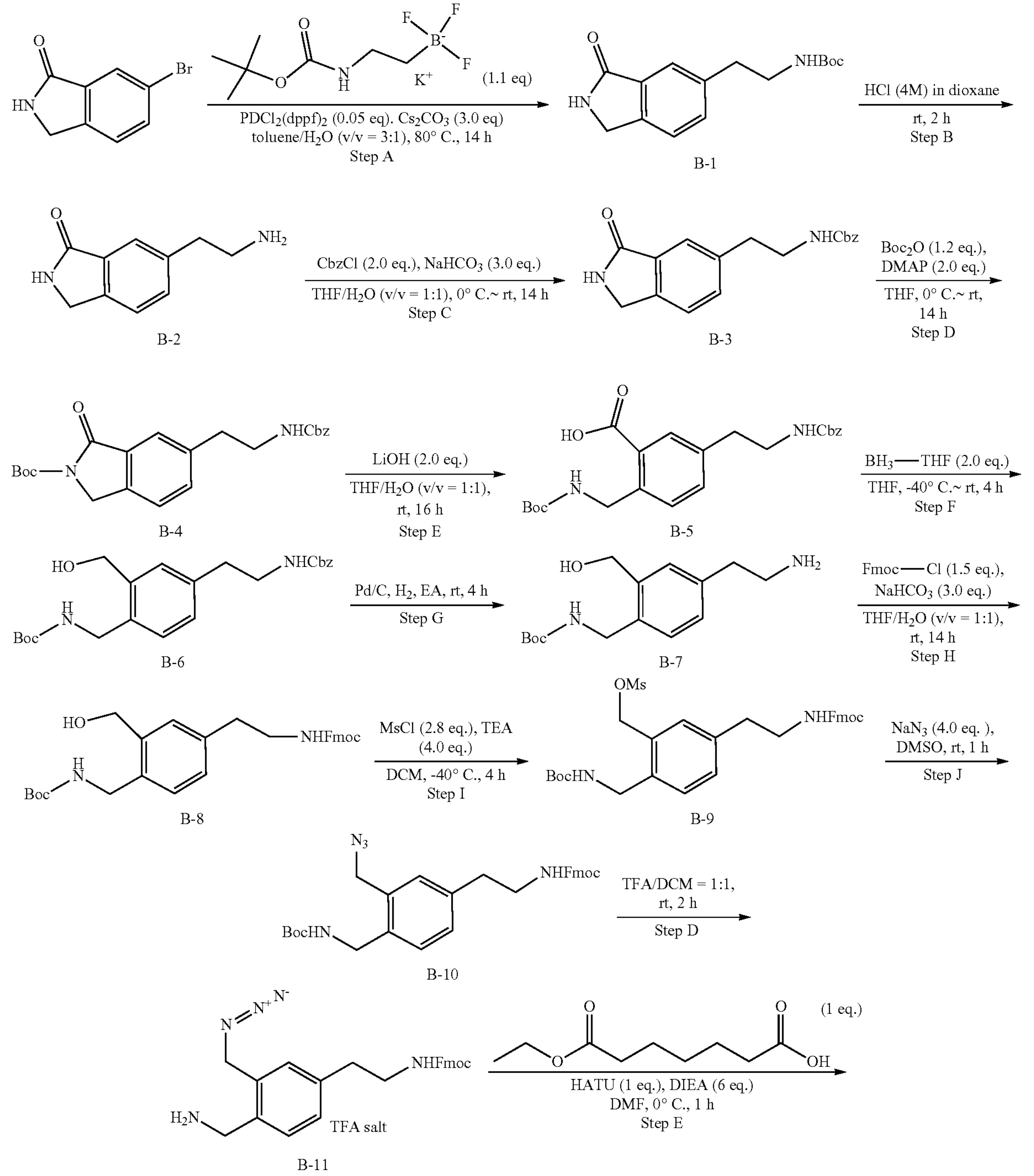

-continued

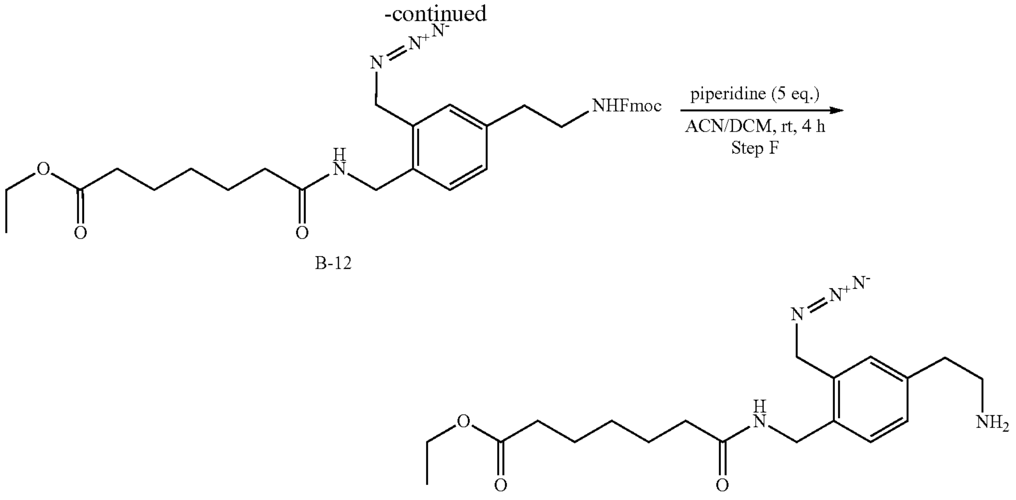

B-12

B

Step A: Tert-butyl (2-(3-oxoisoindolin-5-yl)ethyl)carbamate B-1

To a solution of 6-bromoisoindolin-1-one (4.00 g, 18.9 mmol) in toluene (210 mL) and water (70 mL) were added potassium (2-((tert-butoxycarbonyl)amino)ethyl)trifluoroborate (5.21 g, 20.8 mmol), $PdCl_2(dppf)_2$ (0.350 g, 0.470 mmol) and $Cs_2CO_3$ (18.4 g, 56.6 mmol) under N2. The reaction mixture was stirred for 14 h at 80° C. The solution was allowed to warm to 25° C. and saturated $NH_4Cl$ (200 mL) was added. The aqueous mixture was extracted with EA (3x250 mL), and the combined organic layer was washed with brine (3x100 mL). The organic layer was dried over anhydrous $Na_2SO_4$ and filtered. The filtrate was concentrated under reduced pressure. The residue was purified by a silica gel column chromatography, eluted with gradient 1%-100% EA in PE. The fractions containing desired product were combined and concentrated under reduced pressure to afford tert-butyl (2-(3-oxoisoindolin-5-yl)ethyl)carbamate B-1. LCMS (ESI) calc'd for $C_{15}H_{20}N_2O_3$ $[2M+H]^+$: 553.3, found 553.4; $^1H$ NMR (300 MHz, $CDCl_3$) δ 7.74 (s, 1H), 7.68 (s, 1H), 7.41 (s, 2H), 4.64 (br, 1H), 4.43 (s, 2H), 3.43-3.37 (m, J=6.1 Hz, 2H), 2.90 (t, J=7.0 Hz, 2H), 1.42 (s, 9H).

Step B: 6-(2-aminoethyl)isoindolin-1-one B-2

To a solution of HCl (4 M) in 1,4-Dioxane (150 mL) was added tert-butyl (2-(3-oxoisoindolin-5-yl)ethyl)carbamate (15.0 g, 54.3 mmol) at 0° C. The reaction mixture was stirred for 2 h at 25° C. The solution was concentrated under reduced pressure to afford 6-(2-aminoethyl)isoindolin-1-one B-2. LCMS (ESI) calc'd for $C_{10}H_{12}N_2O$ $[M+H]^+$: 177.1, found 177.2.

Step C: Benzyl (2-(3-oxoisoindolin-5-yl)ethyl)carbamate B-3

To a solution of 6-(2-aminoethyl)isoindolin-1-one B-2 (2.50 g, 14.2 mmol) in THF (10 mL) and water (10 mL) were added Cbz-Cl (4.84 g, 28.4 mmol) and $NaHCO_3$ (3.58 g, 42.6 mmol) at 0° C. The reaction mixture was stirred for 14 h at 25° C. The resulting solution was diluted with water (50 mL) and the aqueous layer was extracted with EA (3x100 mL). The combined organic layer was washed with brine (3x100 mL) and dried over anhydrous $Na_2SO_4$ and filtered. The filtrate was concentrated under reduced pressure. The residue was purified by a silica gel column chromatography, eluted with gradient 1%-100% EA in PE. The fractions containing desired product were combined and concentrated under reduced pressure to afford benzyl (2-(3-oxoisoindolin-5-yl)ethyl)carbamate B-3. LCMS (ESI) calc'd for $C_{18}H_{18}N_2O_3$ $[M+H]^+$: 311.1, found 311.2; $^1H$ NMR (300 MHz, $CDCl_3$) δ 7.67 (s, 1H), 7.37 (s, 3H), 7.31 (d, J=3.1 Hz, 4H), 5.06 (s, 2H), 4.91 (br, 1H), 4.37 (s, 2H), 3.45 (d, J=8.4 Hz, 2H), 2.90 (t, J=7.0 Hz, 2H).

Step D: Tert-butyl 6-(2-(((benzyloxy)carbonyl)amino)ethyl)-1-oxoisoindoline-2-carboxylate B-4

To a solution of benzyl (2-(3-oxoisoindolin-5-yl)ethyl)carbamate B-3 (500 mg, 1.61 mmol) in THF (5 mL) were added $Boc_2O$ (422 mg, 1.93 mmol) and DMAP (394 mg, 3.22 mmol) at 0° C. The reaction mixture was stirred for 14 h at 25° C. The resulting solution was concentrated under reduced pressure. The residue was purified by a silica gel column chromatography, eluted with gradient 10%-60% EA in PE. The fractions containing desired product were combined and concentrated under reduced pressure to afford tert-butyl 6-(2-(((benzyloxy)carbonyl)amino)ethyl)-1-oxoisoindoline-2-carboxylate B-4. LCMS (ESI) calc'd for $C_{23}H_{26}N_2O_5$ $[M+H]^+$: 411.2, found 411.3; $^1H$ NMR (300 MHz, $CDCl_3$) δ 7.72 (s, 1H), 7.50-7.23 (m, 7H), 5.08 (s, 2H), 4.78 (br, 1H), 4.72 (s, 2H), 3.48 (d, J=6.3 Hz, 2H), 2.92 (t, J=6.8 Hz, 2H), 1.25 (s, 9H).

Step E: 5-(2-(((benzyloxy)carbonyl)amino)ethyl)-2-(((tert-butoxycarbonyl)amino)methyl)benzoic acid B-5

To a solution of tert-butyl 6-(2-(((benzyloxy)carbonyl)amino)ethyl)-1-oxoisoindoline-2-carboxylate B-4 (12.5 g, 30.5 mmol) in THF (120 mL) and water (120 mL) was added LiOH (1.46 g, 60.9 mmol) at 0° C. The reaction mixture was stirred for 16 h at 25° C. The resulting solution was adjusted pH to 4~5 with HCl (1M). The solution was extracted with EA (3x300 mL) and the combined organic layer was washed with brine (3x100 mL), dried over anhydrous $Na_2SO_4$ and filtered. The filtrate was concentrated under reduced pressure. The residue was purified by a silica gel column chromatography, eluted with gradient 1%-10% MeOH in DCM. The fractions containing desired product were combined and concentrated under reduced pressure to afford 5-(2-(((benzyloxy)carbonyl)amino)ethyl)-2-(((tert-butoxycarbonyl)amino)methyl)benzoic acid B-5. LCMS (ESI) calc'd for $C_{23}H_{28}N_2O_6$ $[M+H]^+$: 429.2, found 429.3; $^1H$ NMR (300 MHz, $CDCl_3$) δ 7.99 (s, 2H), 7.33 (t, J=5.1 Hz, 8H), 5.09 (s, 2H), 4.53 (d, J=6.2 Hz, 2H), 3.46 (d, J=6.5 Hz, 2H), 2.88-2.81 (m, 2H), 1.46 (s, 9H).

Step F: Benzyl (4-(((tert-butoxycarbonyl)amino) methyl)-3-(hydroxymethyl)phenethyl) carbamate B-6

To a solution of 5-(2-(((benzyloxy)carbonyl)amino) ethyl)-2-(((tert-butoxycarbonyl)amino)methyl)benzoic acid (10.3 g, 24.1 mmol) in THF (100 mL) was added borane (0.670 g, 48.1 mmol) at −40° C. The reaction mixture was stirred for 4 h at room temperature. The resulting solution was concentrated under reduced pressure. The residue was purified by a silica gel column chromatography, eluted with gradient 1%-60% EA in PE. The fractions containing desired product were combined and concentrated under reduced pressure to afford benzyl (4-(((tert-butoxycarbonyl)amino) methyl)-3-(hydroxymethyl)phenethyl)carbamate B-6. LCMS (ESI) calc'd for $C_{23}H_{30}N_2O_5$ $[M+Na]^+$: 437.2, found 437.1; $^1H$ NMR (300 MHz, $CDCl_3$) δ 7.34 (s, 5H), 7.28-7.22 (m, 1H), 7.15-7.08 (m, 2H), 5.19 (br, 1H), 5.07 (s, 2H), 4.87 (br, 1H), 4.66 (s, 2H), 4.33 (d, J=5.2 Hz, 2H), 3.46-3.39 (m, J=6.8 Hz, 2H), 2.78 (t, J=7.0 Hz, 2H), 1.42 (s, 9H).

Step G: Tert-butyl 4-(2-aminoethyl)-2-(hydroxymethyl)benzylcarbamate B-7

To a solution of benzyl (4-(((tert-butoxycarbonyl)amino) methyl)-3-(hydroxymethyl)phenethyl)carbamate B-6 (8.10 g, 19.5 mmol) in EA (500 mL) was added palladium (1.60 g, 14.9 mmol, dry) at 25° C. under nitrogen atmosphere. The mixture was degassed with hydrogen for 3 times and stirred for 4 h at room temperature. The reaction mixture was filtered and the filtrate was concentrated under reduced pressure to afford tert-butyl 4-(2-aminoethyl)-2-(hydroxymethyl)benzylcarbamate B-7. LCMS (ESI) calc'd for $C_{15}H_{24}N_2O_3$ $[M+H]^+$: 281.2, found 281.2.

Step H: (9H-fluoren-9-yl)methyl (4-(((tert-butoxycarbonyl)amino)methyl)-3-(hydroxyl methyl)phenethyl)carbamate B-8

To a solution of tert-butyl 4-(2-aminoethyl)-2-(hydroxymethyl)benzylcarbamate B-7 (3.80 g, 13.6 mmol) in THF (30 mL) and water (30 mL) were added Fmoc-Cl (5.26 g, 20.3 mmol) and $NaHCO_3$ (3.40 g, 40.7 mmol) at 0° C. The reaction mixture was stirred for 14 h at 25° C. The resulting solution was diluted with water (50 mL) and the aqueous layer was extracted with EA (3×200 mL). The combined organic layer was washed with brine (3×150 mL) and dried over anhydrous $Na_2SO_4$ and filtered. The filtrate was concentrated under reduced pressure. The residue was purified by a silica gel column chromatography, eluted with gradient 1%-60% EA in PE. The fractions containing desired product were combined and concentrated under reduced pressure to afford (9H-fluoren-9-yl)methyl(4-(((tert-butoxycarbonyl) amino)methyl)-3-(hydroxymethyl) phenethyl)carbamate B-8. LCMS (ESI) calc'd for $C_{30}H_{34}N_2O_5$ $[M+Na]^+$: 525.3, found 525.4; $^1H$ NMR (300 MHz, $CDCl_3$) δ 7.76 (d, J=7.5 Hz, 2H), 7.57 (d, J=7.4 Hz, 2H), 7.46-7.20 (m, 5H), 7.20-7.05 (m, 2H), 4.87 (br, 1H), 4.68 (s, 2H), 4.44-4.31 (m, 4H), 4.19 (t, J=7.0 Hz, 1H), 3.43 (d, J=6.8 Hz, 2H), 2.79 (t, J=6.9 Hz, 2H), 1.43 (s, 9H).

Step I: 5-(2-((((9H-fluoren-9-yl)methoxy)carbonyl) amino)ethyl)-2-(((tert-butoxycarbonyl) amino)methyl)benzyl methanesulfonate B-9

To a solution of (9H-fluoren-9-yl)methyl (4-(((tert-butoxycarbonyl)amino)methyl)-3-(hydroxyl methyl)phenethyl)carbamate B-8 (4.00 g, 7.96 mmol) in DCM (200 mL) were added MsCl (2.56 g, 22.3 mmol) and TEA (3.20 g, 31.8 mmol). The reaction mixture was stirred for 4 h at −40° C. The resulting solution was washed with 1% HCl (3×50 mL) and saturated $NaHCO_3$ (3×50 mL). The organic layer was washed with brine (3×50 mL) and dried over anhydrous $Na_2SO_4$ and filtered. The filtrate was concentrated under reduced pressure to afford 5-(2-((((9H-fluoren-9-yl) methoxy)carbonyl)amino)ethyl)-2-(((tert-butoxycarbonyl) amino)methyl) benzyl methanesulfonate B-9. LCMS (ESI) calc'd for $C_{31}H_{36}N_2O_7S$ $[M+Na]^+$: 603.2, found 603.3.

Step J: (9H-fluoren-9-yl)methyl (3-(azidomethyl)-4-(((tert-butoxycarbonyl)amino)methyl) phenethyl) carbamate B-10

To a solution of 5-(2-((((9H-fluoren-9-yl)methoxy)carbonyl)amino)ethyl)-2-(((tert-butoxycarbonyl)amino)methyl) benzyl methanesulfonate B-9 (8.80 g, 15.2 mmol) in DMSO (35 mL) was added $NaN_3$ (3.94 g, 60.6 mmol). The reaction mixture was stirred for 1 h at 25° C. The resulting solution was diluted with water (100 mL) and the aqueous layer was extracted with EA (3×200 mL). The combined organic layer was washed with brine (3×150 mL) and dried over anhydrous $Na_2SO_4$ and filtered. The filtrate was concentrated under reduced pressure. The residue was purified by a silica gel column chromatography, eluted with gradient 1%-60% EA in PE. The fractions containing desired product were combined and concentrated under reduced pressure to afford (9H-fluoren-9-yl)methyl (3-(azidomethyl)-4-(((tert-butoxycarbonyl)amino) methyl)phenethyl)carbamate B-10. LCMS (ESI) calc'd for $C_{30}H_{33}N_5O_4$ $[M+Na]^+$: 550.3, found 550.3; $^1H$ NMR (300 MHz, DMSO-$d_6$) δ 7.87 (d, J=7.5 Hz, 2H), 7.66 (d, J=7.4 Hz, 2H), 7.46-7.26 (m, 5H), 7.21-7.12 (m, 3H), 4.48 (s, 2H), 4.33-4.06 (m, 5H), 3.18 (d, J=7.2 Hz, 2H), 2.69 (t, J=7.5 Hz, 2H), 1.37 (s, 9H).

Step K: (9H-fluoren-9-yl)methyl 4-(aminomethyl)-3-(azidomethyl)phenethylcarbamate 2,2,2-trifluoroacetate B-11

To a solution of (9H-fluoren-9-yl)methyl (3-(azidomethyl)-4-(((tert-butoxycarbonyl)amino)methyl)phenethyl) carbamate B-10 (5.0 g, 9.48 mmol) in DCM (50 mL) was added TFA (50 mL) at −10° C. The mixture was stirred at RT for 2 h. The resulting mixture was concentrated under reduced pressure to afford (9H-fluoren-9-yl)methyl 4-(aminomethyl)-3-(azidomethyl)phenethylcarbamate 2,2,2-trifluoroacetate B-11. LCMS (ESI) calc'd for $C_{27}H_{26}F_3N_5O_4$ $[M-TFA+H]^+$: 428.2, found 428.3.

Step L: Ethyl 7-((4-(2-((((9H-fluoren-9-yl)methoxy) carbonyl)amino)ethyl)-2-(azidomethyl)benzyl) amino)-7-oxoheptanoate B-12

To a solution of 7-ethoxy-7-oxoheptanoic acid (1.77 g, 9.42 mmol) in DMF (50 mL) were added (9H-fluoren-9-yl)

methyl 4-(aminomethyl)-3-(azidomethyl)phenethylcarbamate 2,2,2-trifluoroacetate B-11 (5.10 g, 9.42 mmol), HATU (3.58 g, 9.42 mmol) and DIEA (7.30 g, 56.5 mmol) at 0° C. The mixture was stirred at 0° C. for 1 h. The mixture was diluted with brine (200 mL), extracted with EA (2×200 mL), washed brine (2×100 mL), dried over anhydrous $MgSO_4$ and filtered, the filtrate was concentrated under reduced pressure. The residue purified by silica gel column chromatography, eluted with gradient 10%-6% MeOH in DCM. The fractions containing desired product were combined and concentrated to afford ethyl 7-((4-(2-((((9H-fluoren-9-yl)methoxy)carbonyl)amino)ethyl)-2-(azidomethyl)benzyl)amino)-7-oxoheptanoate B-12. LCMS (ESI) calc'd for $C_{34}H_{39}N_5O_5$ $[M+H]^+$: 598.3, found 598.2.

Step M: Ethyl 7-((4-(2-aminoethyl)-2-(azidomethyl)benzyl)amino)-7-oxoheptanoate B To a solution of ethyl 7-((4-(2-((((9H-fluoren-9-yl)methoxy)carbonyl)amino)ethyl)-2-(azidomethyl)benzyl)amino)-7-oxoheptanoate B-12 (5.00 g, 8.37 mmol) in DCM (20 mL) were added ACN (20 mL), piperidine (3.56 g, 41.8 mmol) at 0° C. The mixture was stirred at rt for 4 h. The mixture was concentrated under reduced pressure. The residue purified by silica gel column chromatography, eluted with gradient 1%-20% MeOH in DCM to afford ethyl 7-((4-(2-aminoethyl)-2-(azidomethyl)benzyl)amino)-7-oxoheptanoate B, LCMS (ESI) calc'd for $C_{19}H_{29}N_5O_3$ $[M+H]^+$: 376.2, found 376.2.

Preparation of Intermediate C

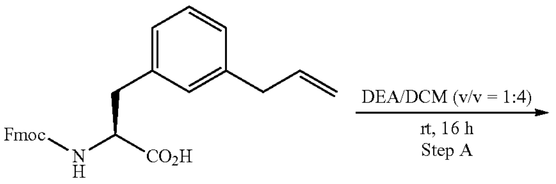

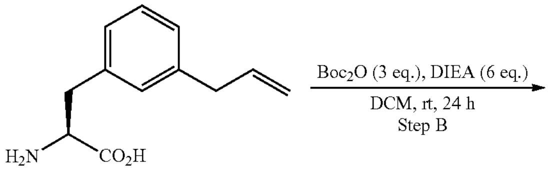

C-1

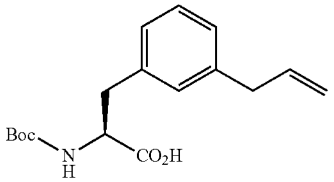

C-2

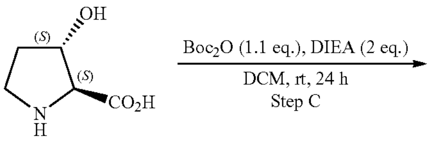

-continued

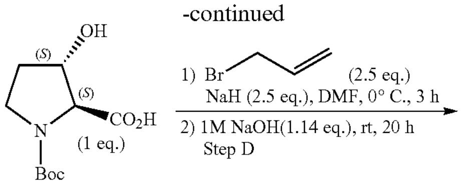

C-3

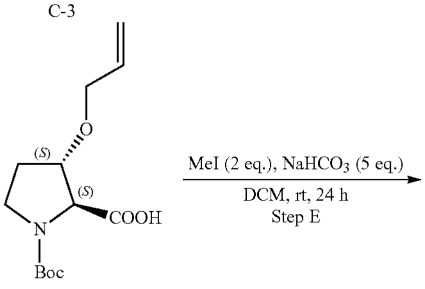

C-4

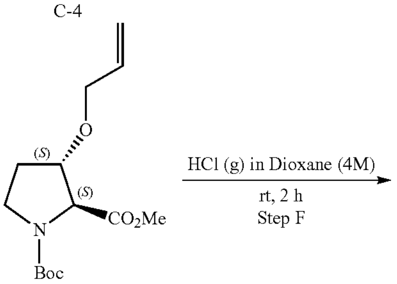

C-5

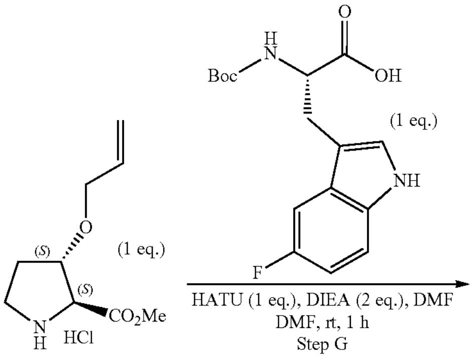

C-6

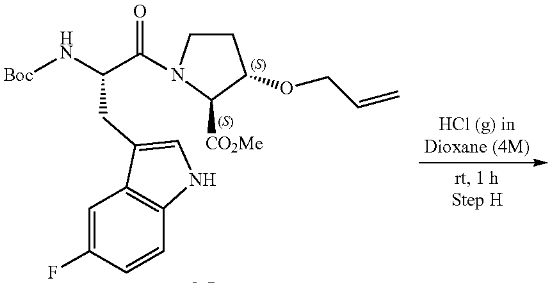

C-7

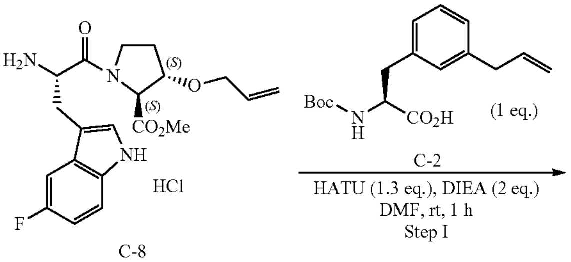

C-8

-continued

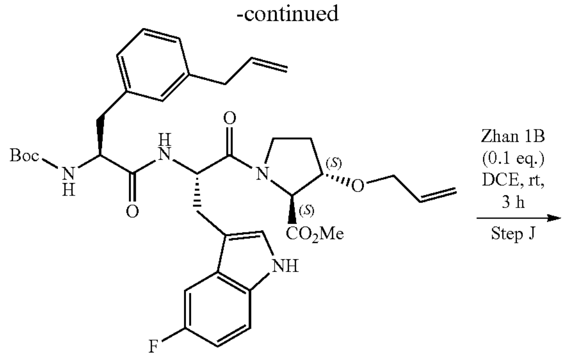

C-9

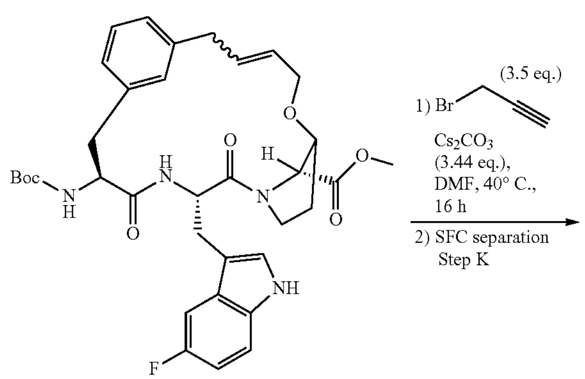

C-10
Trans/Cis olefin ratio based on SFC: 9/1 (220 nm)

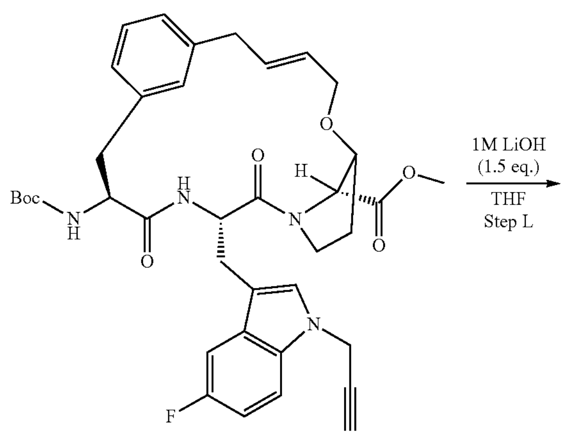

C-11

-continued

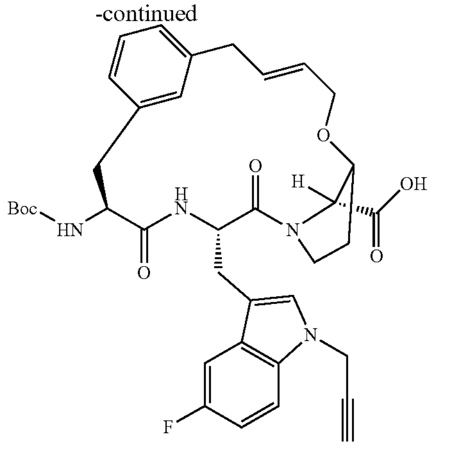

C

Step A: (S)-3-(3-allylphenyl)-2-aminopropanoic acid C-1

To a stirred solution of (S)-2-((((9H-fluoren-9-yl) methoxy)carbonyl)amino)-3-(3-allylphenyl)propanoic acid (500 mg, 1.17 mmol) in DCM (40 mL) was added DEA (10 mL, 1.17 mmol) at room temperature. The mixture was stirred at room temperature for 16 h and concentrated under reduced pressure. The residue was added water (30 mL) and washed with MTBE (2×50 mL), the aqueous phase was concentrated under reduced pressure to afford (S)-3-(3-allylphenyl)-2-aminopropanoic acid C-1. LCMS (ESI) calc'd for $C_{12}H_{15}NO_2$ $[M+H]^+$: 206.1, found 206.0.

Step B: (S)-3-(3-allylphenyl)-2-((tert-butoxycarbonyl)amino)propanoic acid C-2

To a solution of (S)-3-(3-allylphenyl)-2-aminopropanoic acid C-1 (300 mg, 1.02 mmol) in DCM (20 mL) were added DIPEA (1.07 mL, 6.14 mmol) and $Boc_2O$ (0.71 mL, 3.07 mmol) at room temperature. The mixture was stirred at room temperature for 24 h under argon atmosphere. The reaction solution was concentrated under reduced pressure. The residue was diluted with water (20 mL) and the pH value of the solution was adjusted to 3 with aqueous HCl (1 M). The aqueous phase was extracted with EA (2×20 mL). The combined organic layer was washed with brine (30 mL), dried over anhydrous $MgSO_4$ and filtered. The filtrate was concentrated under reduced pressure. The residue was purified by Flash (Column: Flash $C^{18}$ 120 g; Mobile Phase A: water, Mobile Phase B: ACN; Flow rate: 45 mL/min; Gradient: 10% B to 20% B in 10 min, 20% B to 80% B in 25 min; Detector: UV 220 nm; Rt=30 min) to afford (S)-3-(3-allylphenyl)-2-((tert-butoxycarbonyl)amino)propanoic acid C-2. LCMS (ESI) calc'd for $C_{17}H_{23}NO_4$ $[M+H-56]^+$: 250.1, found 250.1; $^1H$ NMR (300 MHz, $CD_3OD$): δ 7.13 (t, J=7.6 Hz, 1H), 7.08-6.93 (m, 3H), 5.92 (m, 1H), 5.08-4.93 (m, 2H), 4.17 (dd, J=8.3, 4.8 Hz, 1H), 3.31 (d, J=6.6 Hz, 2H), 3.13 (dd, J=13.7, 4.7 Hz, 1H), 2.84 (dd, J=13.7, 8.2 Hz, 1H), 1.40-1.20 (m, 9H).

Step C: (2S,3S)-1-(tert-butoxycarbonyl)-3-hydroxypyrrolidine-2-carboxylic acid C-3

To a solution of (2S,3S)-3-hydroxypyrrolidine-2-carboxylic acid (9.00 g, 68.6 mmol) in DCM (180 mL) were added DIEA (24.0 mL, 137 mmol) and $Boc_2O$ (17.5 mL, 75 mmol) at room temperature. The mixture was stirred at room temperature for 24 h under argon atmosphere. The reaction solution was extracted with aq. NaOH (100 mL, 1M). The aqueous phase was cooled to 0° C. The pH value of the aqueous phase was adjusted to 2 with aqueous HCl (1 M). The aqueous phase was extracted with 2-Me-THF (100 mL). The aqueous phase was re-acidified and extracted with 2-Me-THF (100 mL). The combined organic layer was dried over anhydrous $MgSO_4$ and filtered. The filtrate was concentrated under reduced pressure. The residue was dissolved in MTBE (200 mL) and stirred at room temperature for 2 h. The solid was filtered and washed with MTBE to give (2S,3S)-1-(tert-butoxycarbonyl)-3-hydroxypyrrolidine-2-carboxylic acid C-3. LCMS (ESI) calc'd for $C_{10}H_7NO_5$ $[M+H\text{-}Boc]^+$: 131.1, found 131.3; $^1H$ NMR (300 MHz, $CD_3OD$): δ 4.40-4.30 (m, 1H), 4.20-4.10 (m, 1H), 3.60-3.43 (m, 2H), 2.10-1.75 (m, 2H), 1.50-1.30 (m, 9H).

Step D: (S)-2-amino-3-(3-(2-(tert-butoxy)-2-oxoethyl)phenyl)propanoic acid C-4

To a solution of (2S,3S)-1-(tert-butoxycarbonyl)-3-hydroxypyrrolidine-2-carboxylic acid C-3 (1.50 g, 6.49 mmol) in DMF (20 mL) was added NaH (0.65 g, 16.2 mmol, 60% in mineral oil) at 0° C. under argon atmosphere. After the reaction mixture was stirred for 15 minutes, 3-bromoprop-1-ene (1.96 g, 16.2 mmol) was added to the mixture at 0° C. The reaction mixture was stirred for 3 h at 0° C. The reaction mixture was quenched by ice water (1.7 mL). Carefully added 1M NaOH (7.4 mL) to hydrolyze ester, removed ice bath, stirred at room temperature for 20 hours. The reaction was poured into water (120 mL), extracted with EA (2×30 mL). The pH value of the aqueous phase was adjusted to 3 with aqueous HCl (1 M). The aqueous phase was extracted with DCM (3×20 mL). The combined organic layer was washed with brine (30 mL), dried with anhydrous $MgSO_4$ and filtered. The filtrate was concentrated under reduced pressure to give (2S,3S)-3-(allyloxy)-1-(tert-butoxycarbonyl)pyrrolidine-2-carboxylic acid C-4. LCMS (ESI) calc'd for $C_{13}H_{21}NO_5$ $[M+H\text{-}Boc]^+$: 172.1, found 171.9; $^1H$ NMR (400 MHz, $CDCl_3$) δ 5.95-5.80 (m, 1H), 5.42-5.08 (m, 2H), 4.40-4.25 (m, 1H), 4.22-3.93 (m, 3H), 3.75-3.42 (m, 2H), 2.17-1.89 (m, 2H), 1.50-1.35 (m, 9H).

Step E: (2S,3S)-1-tert-butyl 2-methyl 3-(allyloxy)pyrrolidine-1,2-dicarboxylate C-5

To a solution of (2S,3S)-3-(allyloxy)-1-(tert-butoxycarbonyl)pyrrolidine-2-carboxylic acid C-4 (6.00 g, 5.53 mmol) (purity: 25%) in DMF (10 mL) were added $NaHCO_3$ (930 mg, 11.1 mmol) and MeI (1.73 mL, 27.6 mmol) at room temperature. The mixture was stirred at room temperature for 24 h. The reaction solution was diluted with water (120 mL), extracted with MTBE (2×200 mL). The combined organic layer was washed with water (100 mL), brine (2×100 mL), dried over anhydrous $MgSO_4$ and filtered. The filtrate was concentrated under reduced pressure to give (2S,3S)-1-tert-butyl 2-methyl 3-(allyloxy)pyrrolidine-1,2-dicarboxylate C-5. LCMS (ESI) calc'd for $C_{14}H_{23}NO_5$ $[M+NH_4]^+$: 186.1, found 186.0; $^1H$ NMR (400 MHz, $CDCl_3$) δ 5.98-5.80 (m, 1H), 5.33 (d, J=17.2 Hz, 1H), 5.24 (d, J=10.4 Hz, 1H), 4.46-4.25 (m, 1H), 4.13-3.99 (m, 3H), 3.77 (d, J=2.5 Hz, 3H), 3.71-3.47 (m, 2H), 2.20-2.0 (m, 2H), 1.49 (s, 4H), 1.44 (s, 5H).

Step F: (2S,3S)-methyl 3-(allyloxy)pyrrolidine-2-carboxylate hydrochloride C-6

To a solution of HCl (15 mL, 4 M in dioxane) was added (2S,3S)-1-tert-butyl 2-methyl 3-(allyloxy)pyrrolidine-1,2-dicarboxylate C-5 (1.6 g, 5.61 mmol) at room temperature. The mixture was stirred at room temperature for 2 h. The reaction solution was concentrated under reduced pressure. The residue was crystallized from heptane to afford (2S,3S)-methyl 3-(allyloxy)pyrrolidine-2-carboxylate hydrochloride C-6. LCMS (ESI) calc'd for $C_9H_{16}ClNO_3$ $[M+H—HCl]^+$: 186.1, found 185.9; $^1H$ NMR (300 MHz, $CDCl_3$) δ 11.06 (br, 1H), 9.51 (br, 1H), 5.96-5.76 (m, 1H), 5.40-5.20 (m, 2H), 4.44 (s, 1H), 4.33 (q, J=4.1, 3.2 Hz, 1H), 4.20-4.00 (m, 1H), 3.98-3.85 (m, 1H), 3.84 (s, 3H), 3.71-3.50 (m, 2H), 2.20-2.06 (m, 2H).

Step G: (2S,3S)-methyl 3-(allyloxy)-1-((S)-2-((tert-butoxycarbonyl)amino)-3-(5-fluoro-JH-indol-3-yl)propanoyl)pyrrolidine-2-carboxylate C-7

To a solution of (2S,3S)-methyl 3-(allyloxy)pyrrolidine-2-carboxylate hydrochloride C-6 (400 mg, 1.80 mmol) in DMF (5 mL) were added (S)-2-((tert-butoxycarbonyl)amino)-3-(5-fluoro-1H-indol-3-yl)propanoic acid (582 mg, 1.80 mmol), HATU (686 mg, 1.80 mmol), and DIEA (0.630 mL, 3.61 mmol) at 0° C. The mixture was stirred at rt. for 1 h. The reaction solution was diluted with water (20 mL) and extracted with EA (20 mL). The combined organic layer was washed with brine (2×10 mL), dried over anhydrous $MgSO_4$ and filtered. The filtrate was concentrated under reduced pressure and the residue was purified by a silica gel column chromatography, eluted with gradient 10%-60% EA in PE. The fractions containing desired product were combined and concentrated under reduced pressure to afford (2S,3S)-methyl 3-(allyloxy)-1-((S)-2-((tert-butoxycarbonyl)amino)-3-(5-fluoro-1H-indol-3-yl)propanoyl)pyrrolidine-2-carboxylate C-7. LCMS (ESI) calc'd for $C_{25}H_{32}FN_3O_6$$[M+H]^+$: 490.2, found 490.2. $^1H$ NMR (400 MHz, $CDCl_3$) δ 8.07 (br, 1H), 7.36 (d, J=9.9 Hz, 1H), 7.28-7.21 (m, 2H), 6.95 (t, J=8.9 Hz, 1H), 5.96-5.80 (m, 1H), 5.39-5.14 (m, 3H), 4.79 (br, 1H), 4.63 (s, 1H), 4.16-3.91 (m, 2H), 3.78 (s, 3H), 3.76-3.67 (m, 2H), 3.34-3.06 (m, 2H), 2.08-1.94 (m, 2H), 1.47-1.41 (m, 9H).

Step H: (2S,3S)-methyl 3-(allyloxy)-1-((S)-2-amino-3-(5-fluoro-1H-indol-3-yl)propanoyl)pyrrolidine-2-carboxylate hydrochloride C-8

To a solution of HCl (5 mL, 4 M in 1,4-dioxane) was added (2S,3S)-methyl 3-(allyloxy)-1-((S)-2-((tert-butoxycarbonyl)amino)-3-(5-fluoro-1H-indol-3-yl)propanoyl)pyrrolidine-2-carboxylate C-7 (500 mg, 1.02 mmol) at room temperature. The mixture was stirred at room temperature for 1 h. The reaction solution was concentrated under reduced pressure to afford (2S,3S)-methyl 3-(allyloxy)-1-((S)-2-amino-3-(5-fluoro-1H-indol-3-yl)propanoyl)pyrrolidine-2-carboxylate hydrochloride C-8. LCMS (ESI) calc'd for $C_{20}H_{25}ClFN_3O_4$$[M+H—HCl]^+$: 390.2, found: 390.2.

Step I: (2S,3S)-methyl 3-(allyloxy)-1-((S)-2-((S)-3-(3-allylphenyl)-2-((tert-butoxycarbonyl)amino)propanamido)-3-(5-fluoro-1H-indol-3-yl)propanoyl)pyrrolidine-2-carboxylate C-9

To a solution of (S)-3-(3-allylphenyl)-2-((tert-butoxycarbonyl)amino)propanoic acid C-2 (143 mg, 0.470 mmol) in DMF (5 mL) were added (2S,3S)-methyl 3-(allyloxy)-1-((S)-2-amino-3-(5-fluoro-1H-indol-3-yl)propanoyl)pyrrolidine-2-carboxylate hydrochloride C-8 (200 mg, 0.47 mmol), HATU (232 mg, 0.61 mmol), and DIEA (0.16 mL, 0.94 mmol) at 0° C. The mixture was stirred at rt. for 1 h. The reaction solution was diluted with water (20 mL), extracted with EA (20 mL). The organic layer was washed with brine (2×10 mL), dried over anhydrous $MgSO_4$ and filtered. The filtrate was concentrated under reduced pressure. The residue was purified by silica gel column chromatography, eluted with gradient 10%-60% EA in PE. The fractions containing desired product were combined and concentrated to afford (2S,3S)-methyl 3-(allyloxy)-1-((S)-2-((S)-3-(3-allylphenyl)-2-((tert-butoxycarbonyl)amino)propanamido)-3-(5-fluoro-1H-indol-3-yl)propanoyl)pyrrolidine-2-carboxylate C-9. LCMS (ESI) calc'd for $C_{37}H_{45}FN_4O_7[M+H]^+$: 677.3, found 677.4; $^1H$ NMR (300 MHz, $CDCl_3$): δ 8.04 (br, 1H), 7.45-7.35 (m, 1H), 7.28-7.12 (m, 2H), 7.07-6.88 (m, 4H), 6.66 (d, J=8.4 Hz, 1H), 6.02-5.76 (m, 2H), 5.34-5.15 (m, 2H), 5.12-5.00 (m, 2H), 4.95 (br, 1H), 4.80 (br, 1H), 4.52 (s, 1H), 4.32 (br, 1H), 4.08-3.90 (m, 2H), 3.80-3.70 (m, 3H), 3.55 (br, 1H), 3.35 (t, J=7.7 Hz, 2H), 3.19-2.99 (m, 3H), 2.00-1.75 (m, 2H), 1.44-1.32 (m, 9H).

Step J: Methyl (12S,13S,9S,12S,E)-9-((tert-butoxycarbonyl)amino)-12-((5-fluoro-1H-indol-3-yl)methyl)-10,13-dioxo-2-oxa-11-aza-1 (3,1)-pyrrolidina-7 (1,3)-benzenacyclotridecaphan-4-ene-12-carboxylate C-10

To a stirred solution of (2S,3S)-methyl 3-(allyloxy)-1-((S)-2-((S)-3-(3-allylphenyl)-2-((tert-butoxycarbonyl)amino)propanamido)-3-(5-fluoro-1H-indol-3-yl)propanoyl)pyrrolidine-2-carboxylate C-9 (2.00 g, 2.96 mmol) in DCE (200 mL) was added Zhan 1B (0.22 g, 0.30 mmol) in 10 min. The mixture was stirred at room temperature for 3 h under nitrogen atmosphere and concentrated under reduced pressure. The residue was purified by silica gel column chromatography, eluted with gradient 1%-60% EA in PE. The fractions containing desired product were combined and concentrated to afford methyl (12S,13S,9S,12S)-9-((tert-butoxycarbonyl)amino)-12-((5-fluoro-1H-indol-3-yl)methyl)-10,13-dioxo-2-oxa-11-aza-1 (3,1)-pyrrolidina-7 (1,3)-benzenacyclotridecaphan-4-ene-12-carboxylate C-10. LCMS (ESI) calc'd for $C_{35}H_{41}FN_4O_7[M+H]^+$: 649.3, found 649.4; $^1H$ NMR (400 MHz, $CD_3OD$) δ 7.35-7.25 (m, 2H), 7.26-7.16 (m, 2H), 7.07 (d, J=7.7 Hz, 1H), 6.98 (d, J=7.6 Hz, 1H), 6.95-6.82 (m, 2H), 5.77-5.68 (m, 1H), 5.45 (d, J=15.6 Hz, 1H), 4.97-4.87 (m, 3H), 4.71 (s, 1H), 4.41 (t, J=6.5 Hz, 1H), 4.24 (d, J=14.8 Hz, 1H), 4.09 (d, J=3.8 Hz, 1H), 3.95-3.86 (m, 1H), 3.78-3.68 (m, 4H), 3.31-2.95 (m, 5H), 2.00-1.78 (m, 2H), 1.49 (s, 9H).

Step K: Methyl (12S,13S,9S,12S,E)-9-((tert-butoxycarbonyl)amino)-12-((5-fluoro-1-(prop-2-yn-1-yl)-1H-indol-3-yl)methyl)-10,13-dioxo-2-oxa-11-aza-1 (3,1)-pyrrolidina-7 (1,3)-benzenacyclotridecaphan-4-ene-12-carboxylate C-11

To a solution of $Cs_2CO_3$ (171 mg, 0.52 mmol) in DMF (1.5 mL) was added methyl (12S,13S,9S,12S,E)-9-((tert-butoxycarbonyl)amino)-12-((5-fluoro-1H-indol-3-yl)methyl)-10,13-dioxo-2-oxa-11-aza-1 (3,1)-pyrrolidina-7 (1,3)-benzenacyclotridecaphan-4-ene-12-carboxylate C-10 (100.0 mg, 0.154 mmol) (including 10% Cis olefin) and 3-bromoprop-1-yne (64.2 mg, 0.540 mmol) at room temperature under nitrogen atmosphere. The mixture was stirred at 40° C. for 16 h. The reaction was cooled to rt. and poured into 10 mL of 50% sat brine/10% citric acid solution, extracted with EA (2×10 mL). The organic layer was washed with brine (2×10 mL), dried over anhydrous $MgSO_4$ and filtered. The filtrate was concentrated under reduced pressure. The residue was purified by silica gel column chromatography, eluted with gradient 1%-60% EA in PE. The fractions containing desired product were combined and concentrated to afford a mixture of trans/cis product, which was dissolved in EtOH (5 mL) and separated by Prep-SFC (Column: Reg IA Column, 5×25 cm, 5 um; Mobile Phase A: $CO_2$, 60%, Mobile Phase B: MeOH, 40%; Flow rate: 160 mL/min; Detector: UV 220 nm). The collected fractions were combined and concentrated under reduced pressure to give methyl (12S,13S,9S,12S,E)-9-((tert-butoxycarbonyl)amino)-12-((5-fluoro-1-(prop-2-yn-1-yl)-1H-indol-3-yl)methyl)-10,13-dioxo-2-oxa-11-aza-1 (3,1)-pyrrolidina-7 (1,3)-benzenacyclotridecaphan-4-ene-12-carboxylate ($RT_1$=3.8 min) C-11. LCMS (ESI) calc'd for $C_{38}H_{43}FN_4O_7$ $[M+H]^+$: 687.3, found 687.4; $^1H$ NMR (400 MHz, $CD_3OD$) δ 7.43 (dd, J=8.9, 4.3 Hz, 1H), 7.34 (dd, J=9.6, 2.5 Hz, 1H), 7.21 (t, J=7.5 Hz, 1H), 7.07 (d, J=7.7 Hz, 1H), 7.01-6.90 (m, 3H), 5.78-5.68 (m, 1H), 5.44 (d, J=15.3 Hz, 1H), 4.96 (d, J=2.5 Hz, 2H), 4.90-4.83 (m, 1H), 4.72 (s, 1H), 4.42 (t, J=6.3 Hz, 1H), 4.24 (d, J=15.1 Hz, 1H), 4.09 (d, J=3.9 Hz, 1H), 3.90 (dd, J=14.7, 4.9 Hz, 1H), 3.73 (s, 3H), 3.71-3.64 (m, 1H), 3.32-3.25 (m, 2H), 3.18 (dd, J=14.3, 8.4 Hz, 1H), 3.12-2.98 (m, 4H), 2.81 (t, J=2.5 Hz, 1H), 1.96-1.78 (m, 2H), 1.50 (s, 9H).

Step L: (12S,13S,9S,12S,E)-9-((tert-butoxycarbonyl)amino)-12-((5-fluoro-1-(prop-2-yn-1-yl)-JH-indol-3-yl)methyl)-10,13-dioxo-2-oxa-11-aza-1 (3,1)-pyrrolidina-7 (1,3)-benzenacyclotridecaphan-4-ene-12-carboxylic acid C To a solution of methyl (12S,13S,9S,12S,E)-9-((tert-butoxycarbonyl)amino)-12-((5-fluoro-1-(prop-2-yn-1-yl)-1H-indol-3-yl)methyl)-10,13-dioxo-2-oxa-11-aza-1 (3,1)-pyrrolidina-7 (1,3)-benzenacyclotridecaphan-4-ene-12-carboxylate C-11 (850 mg, 1.24 mmol) in THF (20 mL) was added 1 M LiOH (2.5 mL) at room temperature. The reaction mixture was stirred at room temperature for 3 h. The reaction was partitioned with pH 4 Phosphate buffer (1M $KH_2PO_4$, 30 mL), extracted with EA (50 mL). The organic layer was washed with brine (2×50 mL), dried over anhydrous $MgSO_4$ and filtered. The filtrate was concentrated under reduced pressure. The crude was further purified by Flash (Column: Flash $C^{18}$ 120 g; Mobile Phase A: water, Mobile Phase B: ACN; Flow rate: 45 mL/min; Gradient: 10% B to 20% B in 10 min, 20% B to 60% B in 25 min; Detector: UV 254 nm; RT=20 min) to afford (12S,13S,9S,12S,E)-9-((tert-butoxycarbonyl)amino)-12-((5-fluoro-1-(prop-2-yn-1-yl)-1H-indol-3-yl)methyl)-10,13-dioxo-2-oxa-11-aza-1 (3,1)-pyrrolidina-7 (1,3)-benzenacyclotridecaphan-4-ene-12-carboxylic acid C. LCMS (ESI) calc'd for $C_{37}H_{41}FN_4O_7$ $[M+H]^+$: 673.3, found 673.4; $^1H$ NMR (400 MHz, $CD_3OD$) δ 8.14 (d, J=7.7 Hz, 1H), 7.42 (dd, J=8.9, 4.3 Hz, 1H), 7.34 (dd, J=9.6, 2.5 Hz, 1H), 7.27 (s, 1H), 7.21 (t, J=7.5 Hz, 1H), 7.07 (d, J=7.8 Hz, 1H), 7.01-6.90 (m, 3H), 5.78-5.68 (m, 1H), 5.46 (d, J=15.2 Hz, 1H), 4.98-4.84 (m, 3H), 4.71 (s, 1H), 4.41 (t, J=6.3 Hz, 1H), 4.24 (d, J=14.4 Hz, 1H), 4.15 (d, J=3.5 Hz, 1H), 3.99-3.90 (m, 1H), 3.73-3.63 (m, 1H), 3.31-3.00 (m, 7H), 2.79 (t, J=2.5 Hz, 1H), 1.95-1.86 (m, 2H), 1.50 (s, 9H).

Preparation of Intermediate D
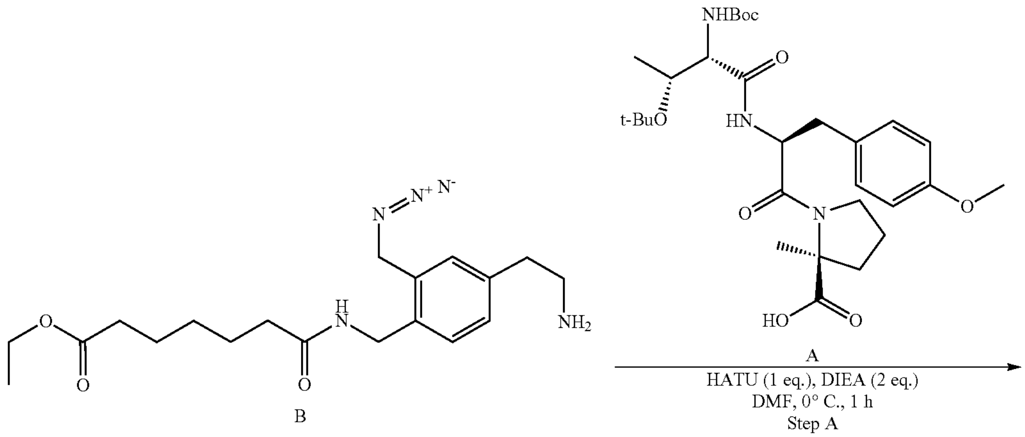
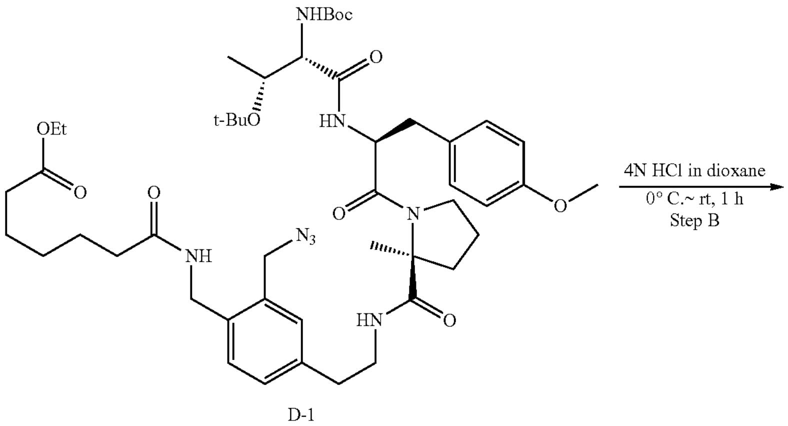
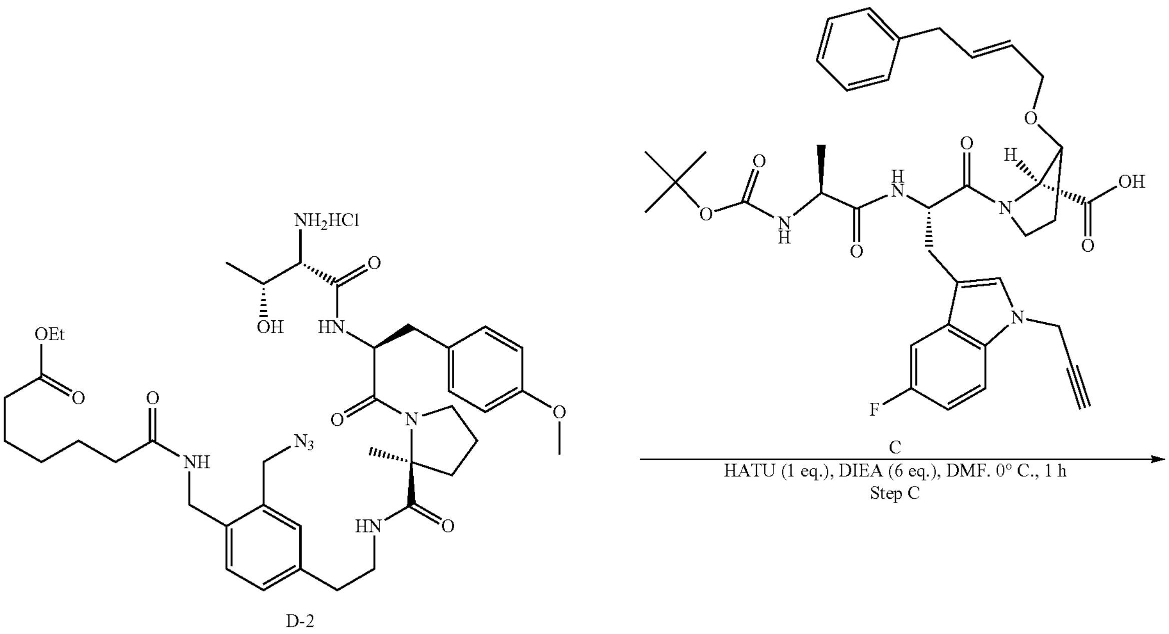

-continued
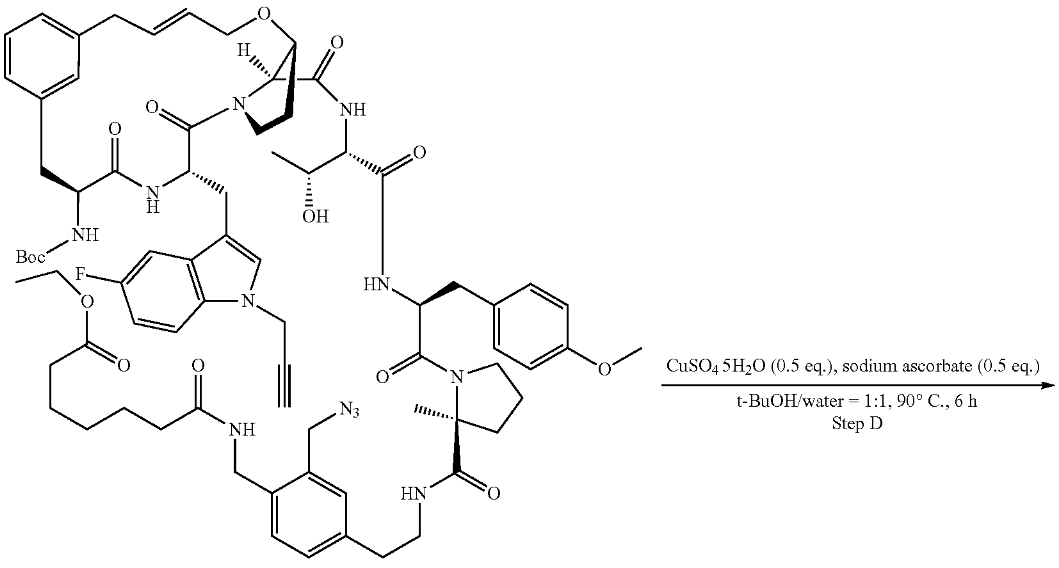
D-3
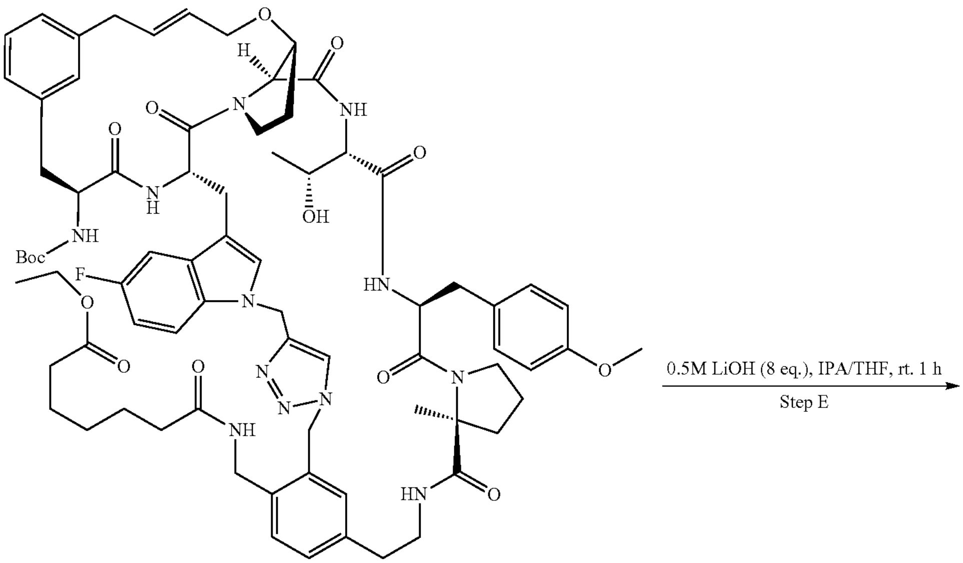
D-4

-continued
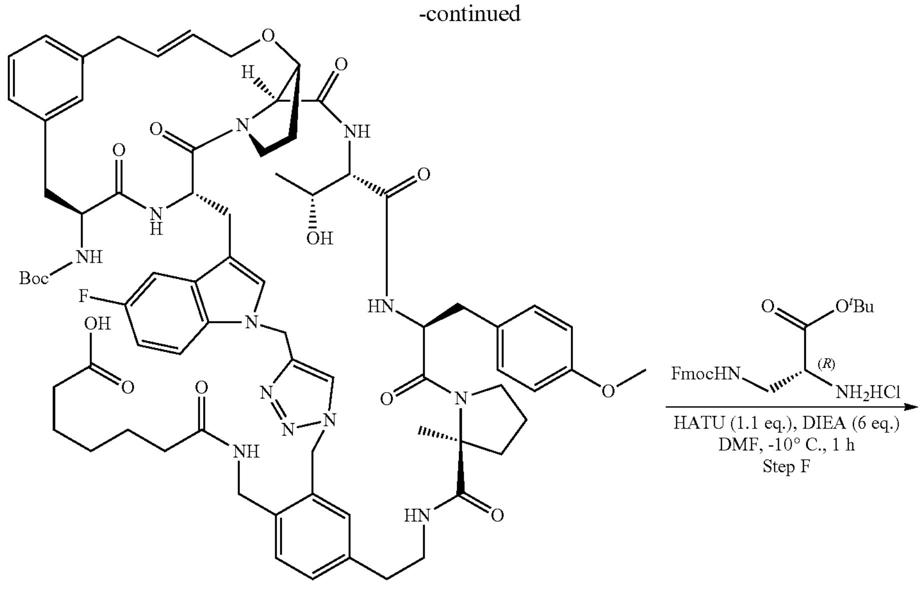
D-5
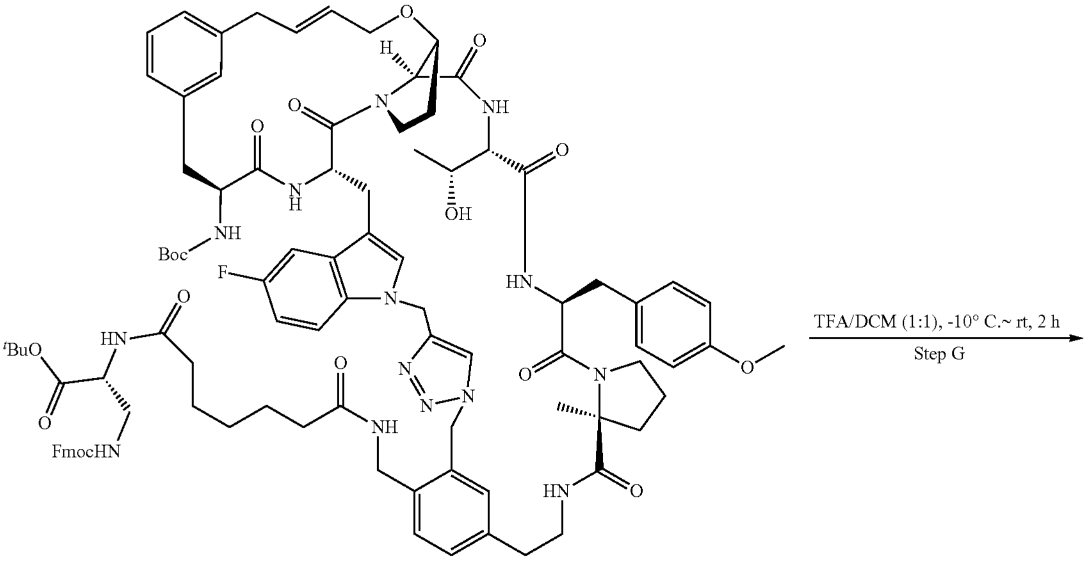
D-6

-continued
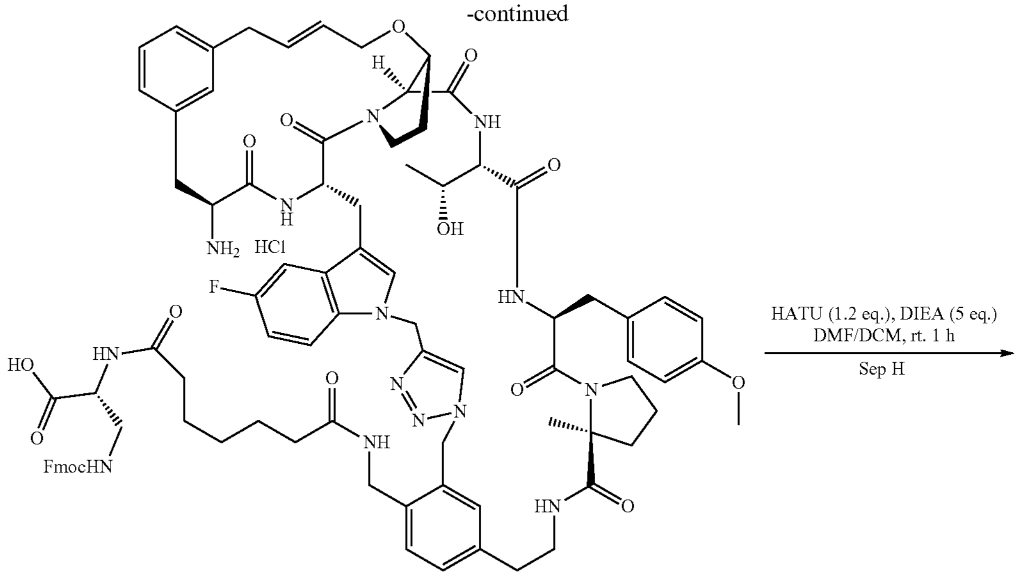
D-7
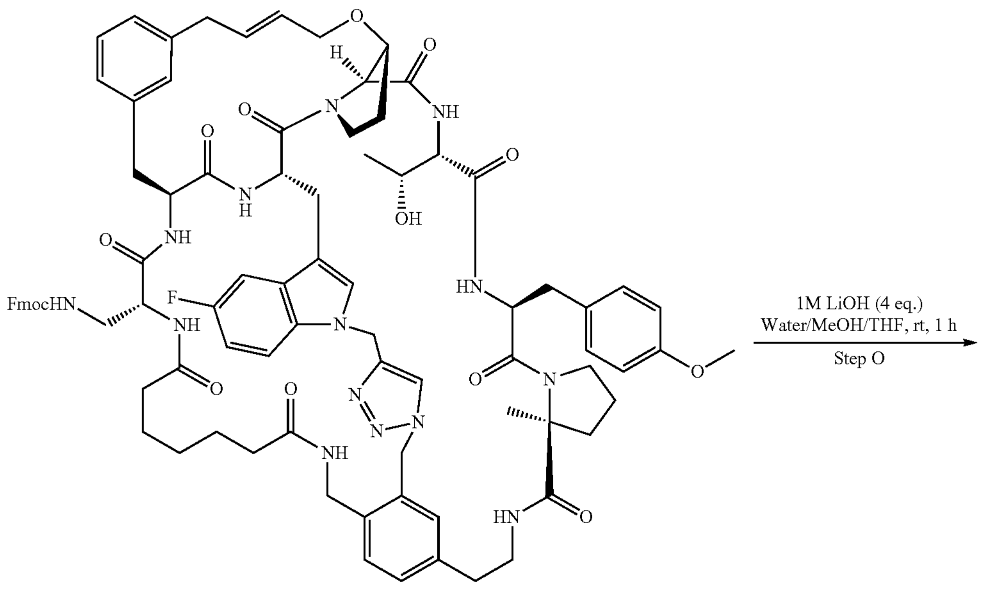
D-8

-continued

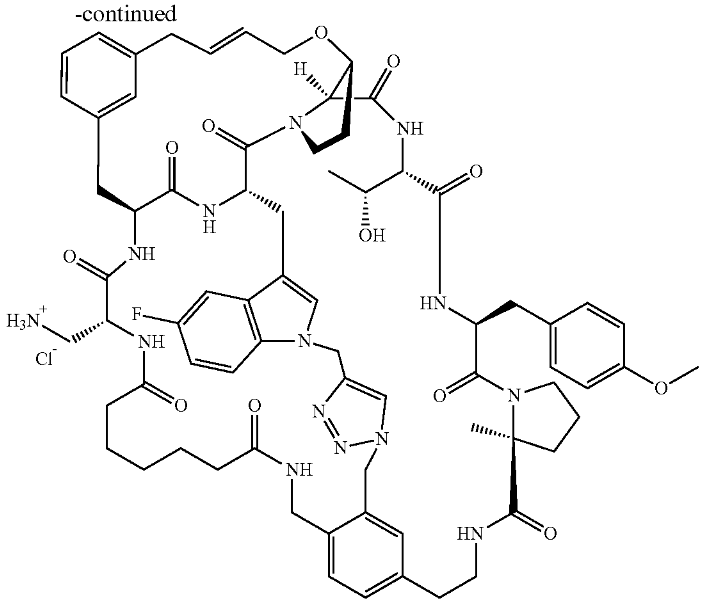

D

Step A: Preparation of Intermediate D-1

To a solution of (S)-1-((S)-2-((2S,3R)-3-(tert-butoxy)-2-((tert-butoxycarbonyl)amino)butanamido)-3-(4-methoxyphenyl)propanoyl)-2-methylpyrrolidine-2-carboxylic acid A (2.70 g, 4.79 mmol) in DMF (30 mL) were added HATU (1.82 g, 4.79 mmol), ethyl 7-((4-(2-aminoethyl)-2-(azidomethyl)benzyl)amino)-7-oxoheptanoate B (1.80 g, 4.79 mmol) and DIEA (1.86 g, 14.4 mmol) at 0° C. The mixture was stirred at 0° C. for 1 h. The mixture was diluted with brine (120 mL), extracted with EA (2×120 mL), washed brine (2×100 mL), dried over anhydrous $MgSO_4$ and filtered, the filtrate was concentrated under reduced pressure. The residue purified by silica gel column chromatography, eluted with gradient 1%-10% MeOH in DCM. The fractions containing desired product were combined and concentrated to afford intermediate D-1. LCMS (ESI) calc'd for $C_{48}H_{72}N_8O_{10}$ $[M+H]^+$: 921.5, found 921.7.

Step B: Preparation of Intermediate D-2

To a solution of intermediate D-1 (3.0 g, 3.26 mmol) in 4 N HCl dioxane solution (30 mL) at 0° C. The mixture was stirred at RT for 1 h. The resulting mixture was concentrated under reduced pressure to afford intermediate D-2. LCMS (ESI) calc'd for $C_{39}H_{57}ClN_8O_8$$[M-HCl+H]^+$: 765.4, found 765.5.

Step C: Preparation of Intermediate D-3

To a solution of intermediate C (2.00 g, 2.97 mmol) in DMF (20 mL) were added HATU (1.13 g, 2.97 mmol), D-2 (2.38 g, 2.97 mmol) and DIEA (3.12 mL, 17.8 mmol) at 0° C. The mixture was stirred at 0° C. for 1 h. The mixture was diluted with brine (80 mL), extracted with EA (2×80 mL), washed brine (2×50 mL), dried over anhydrous $MgSO_4$ and filtered, the filtrate was concentrated under reduced pressure. The residue purified by silica gel column chromatography, eluted with gradient 10%-10% MeOH in DCM. The fractions containing desired product were combined and concentrated to afford D-3. LCMS (ESI) calc'd for $C_{76}H_{95}FN_{12}O_{14}$ $[M+H]^+$:1419.7, found 1419.5.

Step D: Preparation of Intermediate D-4

To a solution of D-3 (1.00 g, 0.704 mmol) in t-BuOH (250 mL) were added water (250 mL), $CuSO_4$ $5H_2O$ (0.088 g, 0.352 mmol) and sodium ascorbate (0.070 g, 0.352 mmol) at RT. The mixture was stirred at 90° C. for 6 h and concentrated under reduced pressure. The residue was diluted with brine (50 mL), extracted with EA (2×100 mL), washed brine (50 mL), dried over anhydrous $MgSO_4$ and filtered, the filtrate was concentrated under reduced pressure. The residue purified by silica gel column chromatography, eluted with gradient 1%-12% MeOH in DCM. The fractions containing desired product were combined and concentrated to afford D-4. LCMS (ESI) calc'd for $C_{76}H_{95}FN_{12}O_{14}$ $[M+H]^+$:1419.7, found 1419.5.

Step E: Preparation of Intermediate D-5

To a solution of D-4 (730 mg, 0.514 mmol) in THF (15 mL) were added IPA (15 mL) and 0.5 M LiOH (8.23 mL, 4.11 mmol) at RT. The mixture was stirred at RT for 2 h. The mixture was added 1 M HCl (4.1 mL) at 0° C. The mixture was concentrated under reduced pressure to afford D-5. LCMS (ESI) calc'd for $C_{74}H_{91}FN_{12}O_{14}$ $[M+H]^+$:1391.7, found 1391.6.

Step F: Preparation of Intermediate D-6

To a solution of above crude of D-5 in DMF (8 mL) were added HATU (215 mg, 0.566 mmol), (R)-tert-butyl 3-((((9H-fluoren-9-yl)methoxy)carbonyl)amino)-2-aminopropanoate hydrochloride (216 mg, 0.515 mmol) and DIEA (0.539 mL, 3.09 mmol) at 0° C. The mixture was stirred at 0° C. for 1 h. The mixture was diluted with brine (30 mL), extracted with EA (2×30 mL), washed brine (2×30 mL), dried over anhydrous $MgSO_4$ and filtered, the filtrate was concentrated under reduced pressure. The residue purified by silica gel column chromatography, eluted with gradient 10%-12% MeOH in DCM. The fractions containing desired product were combined and concentrated to afford D-6. LCMS (ESI) calc'd for $C_{96}H_{115}FN_{14}O_{17}$ [(M−HCl)/2+H]$^+$: 878.4, found 879.0.

Step G: Preparation of Intermediate D-7

To a solution of D-6 (800 mg, 0.456 mmol) in DCM (16 mL) was added TFA (16 mL) at −10° C. The mixture was stirred at RT for 2 h. The resulting mixture was concentrated under reduced pressure. The residue was purified by Flash (Column: Flash $C^{18}$ 330 g; Mobile Phase A: water (0.1% TFA), Mobile Phase B: ACN; Flow rate: 100 mL/min; Gradient: 2% B to 2% B in 5 min, 20% B to 50% B in 20 min; Detector: UV 220 nm; Rt=19 min) and concentrated under reduced pressure. The residue was re-dissolved in DCM (50 mL) and toluene (50 mL). The mixture was then concentrated under reduced pressure and the residue was re-dissolve in DCM (3 mL) and HCl (4 M in dioxane, 0.2 mL). The resulting mixture was concentrated under reduced pressure and the residue was re-dissolve in ACN (60 mL) and water (60 mL), and then added 1 M HCl (0.5 mL) at 0° C. and lyophilized to afford D-7. LCMS (ESI) calc'd for $C_{87}H_{100}ClFN_{14}O_{15}$ [(M−HCl)/2+H]$^+$: 800.4, found 800.8.

Step H: Preparation of Intermediate D-8

To a solution of D-7 (600 mg, 0.367 mmol) in DMF (60 mL) were added DIEA (237 mg, 1.83 mmol), DCM (750 mL) and HATU (167 mg, 0.440 mmol) at RT. The mixture was stirred at RT for 1 h. The mixture was concentrated under reduced pressure to remove DCM, and then diluted with brine (240 mL), extracted with EA (2×240 mL), washed brine (2×200 mL), dried over anhydrous $MgSO_4$ and filtered, the filtrate was concentrated under reduced pressure. The residue purified by silica gel column chromatography, eluted with gradient 1%-12% MeOH in DCM. The fractions containing desired product were combined and concentrated to afford D-8. LCMS (ESI) calc'd for $C_{87}H_{97}FN_{14}O_{14}$ [M+H]$^+$: 1581.7, found 1582.7.

Step I: Preparation of Intermediate D

To a solution of D-8 (450 mg, 0.284 mmol) in THF (10 mL) were added MeOH (3 mL), Water (3 mL) and 1 M LiOH (1.14 mL, 1.14 mmol) at 0° C. The mixture was stirred at RT for 1 h. The resulting mixture was concentrated under reduced pressure. The residue was directly purified by Flash (Column: Flash $C^{18}$ 330 g; Mobile Phase A: water, Mobile Phase B: ACN; Flow rate: 100 mL/min; Gradient: 2% B to 2% B in 5 min, 20% B to 60% B in 20 min; Detector: UV220 nm; Rt=15 min) and concentrated under reduced pressure. The residue was re-dissolved in ACN (30 mL) and water (30 mL), and then added 1 M HCl (0.4 mL) at 0° C. and lyophilized to afford D. LCMS (ESI) calc'd for $C_{72}H_{88}ClFN_{14}O_{12}$ [M−HCl+H]$^+$: 1359.7, found 1359.6.

Preparation of Intermediate E

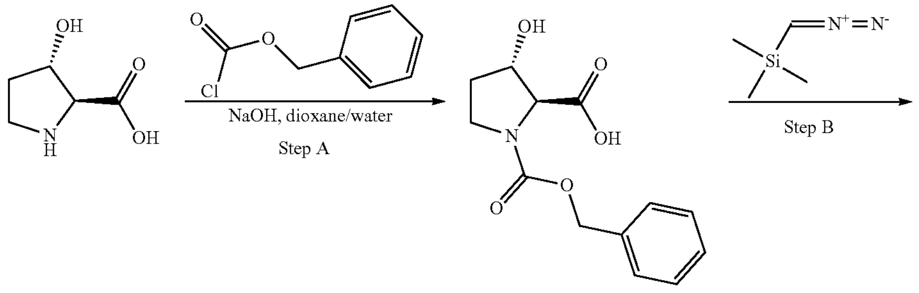

E-1

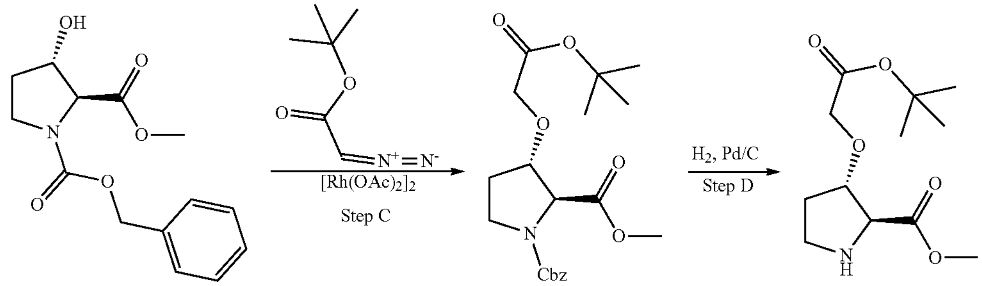

E-2 E-3 E-4

-continued
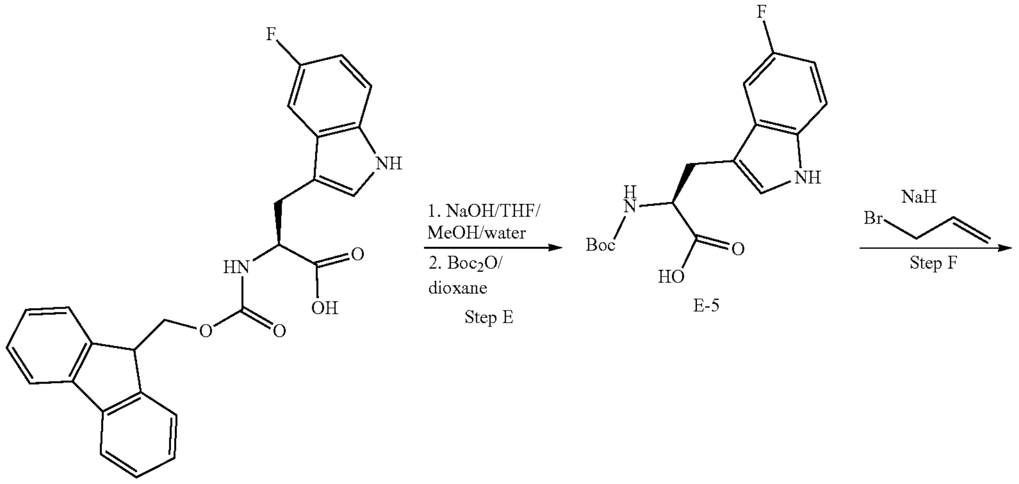
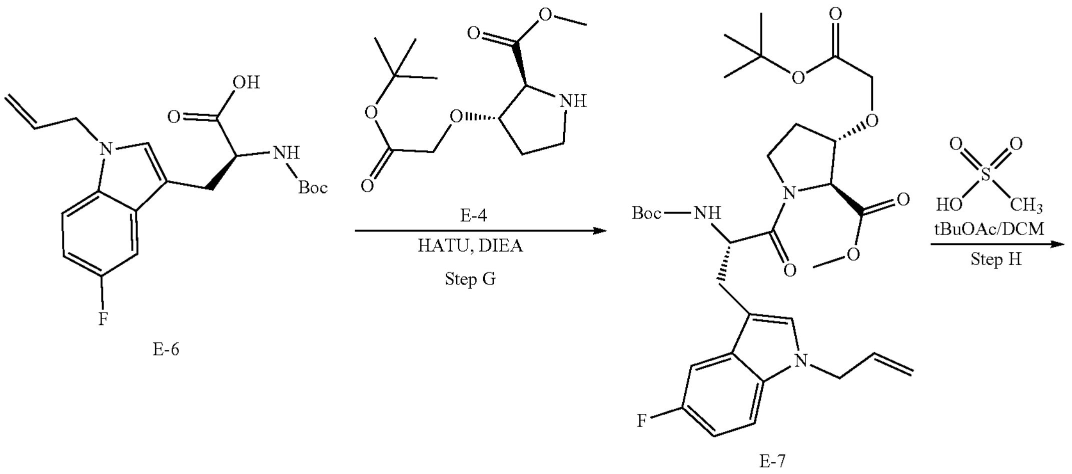
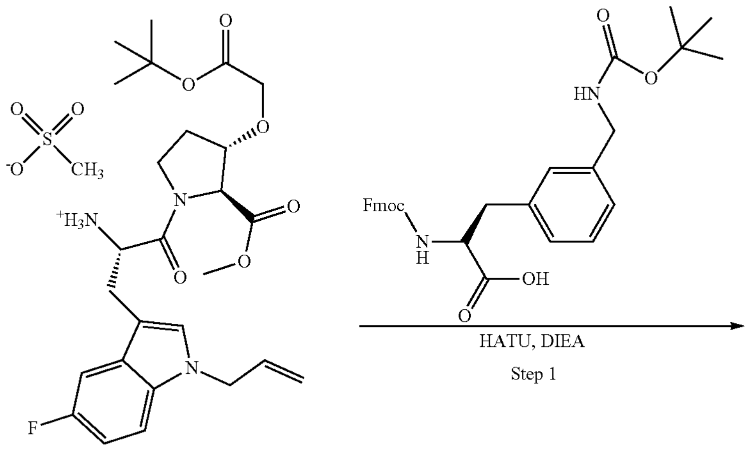
E-8

-continued

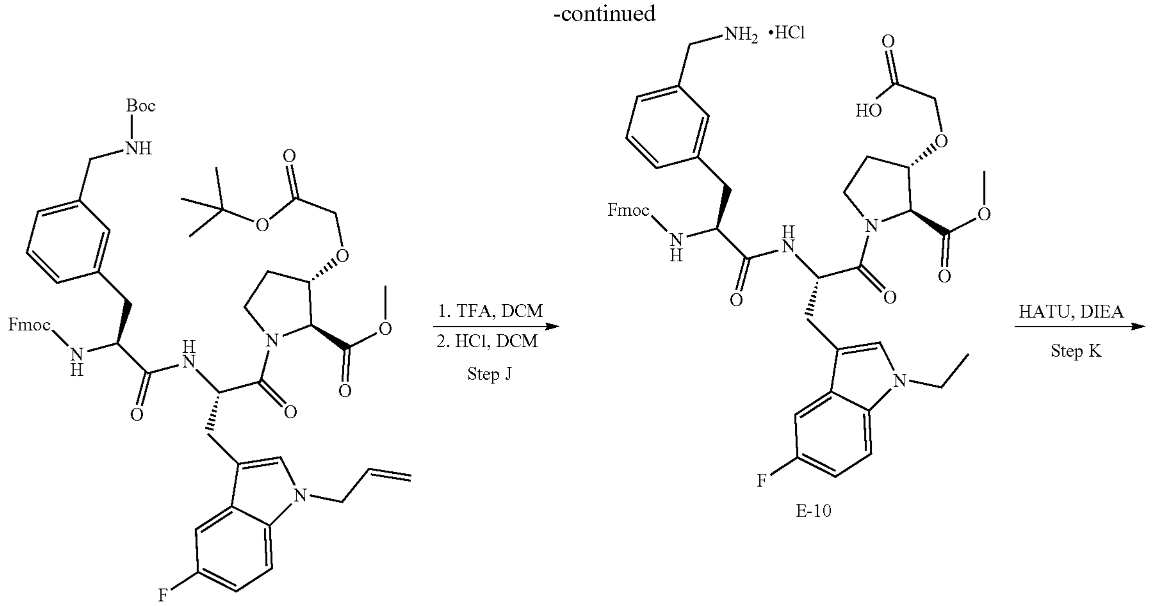

E-9 E-10

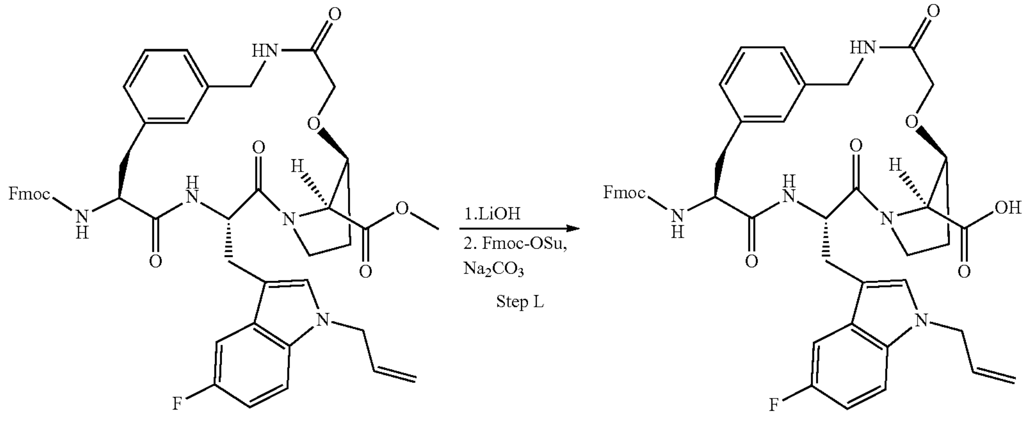

E-11 E

Step A—Synthesis of Intermediate E-1

To a suspension of (2S,3S)-3-hydroxypyrrolidine-2-carboxylic acid (5.32 g, 40.6 mmol) in dioxane (100 ml) at 0° C. was added 1N NaOH (122 ml, 122 mmol), followed by addition of benzyl chloroformate (6.50 ml, 44.6 mmol) dropwise then the resulting suspension was stirred at 0° C. for 5 h. The solution was concentrated, the aqueous layer was acidified to pH 3, partitioned between 30% IPA in DCM (200 mL) and brine (50 mL), and the aqueous phase was further extracted with 30% IPA in DCM (2×100 mL). The combined organic layers were dried over $Na_2SO_4$, filtered and the filtrate was concentrated to give E-1. LC/MS: $[M+H]^+$=266.1.

Step B—Synthesis of Intermediate E-2

To a solution of E-1 (7.48 g, 28.2 mmol) in MeOH (80 ml) was added TMS-diazomethane (70.5 ml, 141 mmol) dropwise, and the resulting solution was stirred at RT for 10 min, then quenched by addition of acetic acid (ca. 400 uL) dropwise. The solution was concentrated, and the residue was purified by MPLC over silica gel (eluting with a gradient of EtOAc in hexanes) to give E-2. LC/MS: $[M+H]^+$= 280.1.

Step C—Synthesis of Intermediate E-3

A solution of E-2 (4.81 g, 17.22 mmol) in DCM (200 mL) was bubbled with nitrogen for 30 min, followed by addition of rhodium(ii) acetate dimer (0.761 g, 1.722 mmol). The mixture was cooled in an ice-water bath, and tert-butyl diazoacetate (3.58 mL, 25.8 mmol) was added at 0° C. dropwise. The resulting mixture was stirred at 0° C. for 1.5 h. The final reaction was quenched by addition of water (100 mL), the mixture was extracted with DCM (3×100 mL), and the combined organic layers was dried over $Na_2SO_4$ and filtered. The filtrate was concentrated and the residue was purified by reverse phase MPLC over C18 (eluting with a gradient of acetonitrile (+0.05% TFA) in water (+0.05% TFA)). The fraction containing the product was concentrated and the resulting aqueous phase was extracted with DCM (2×100 mL). The combined organic phase was dried over $Na_2SO_4$, filtered and concentrated to give E-3. LC/MS: $[M+H]^+$=394.2.

Step D—Synthesis of Intermediate E-4

To a solution of E-3 (3.72 g, 9.46 mmol) in MeOH (80 ml) was added 10% Pd/C (0.805 g, 0.756 mmol) and the resulting mixture was hydrogenated using a balloon filled with hydrogen at RT for 2 h. The final mixture was filtered over Celite and the filtrate was concentrated to give E-4. LC/MS: $[M+H]^+$=259.9.

Step E—Synthesis of Intermediate E-5

To a solution of (S)-2-((((9H-fluoren-9-yl)methoxy)carbonyl)amino)-3-(5-fluoro-1H-indol-3-yl)propanoic acid (3 g, 6.75 mmol) in THF (20 ml), MeOH (10 mL), and water (20.00 ml) at 0° C. was added 1N NaOH (20.25 ml, 20.25 mmol), and the resulting solution was stirred at RT for 4 h then concentrated. To the aqueous mixture was added dioxane (50 ml) and water (20 mL), the resulting solution was cooled to 0° C. and $Boc_2O$ (1.881 ml, 8.10 mmol) was added. The resulting solution was stirred at 0° C. for 3 h, then concentrated and the aqueous phase was extracted with $Et_2O$ (3×40 mL), acidified to pH 3, then extracted with DCM (3×100 mL), followed by extraction with 30% IPA in DCM (2×80 mL). The combined organic layers were dried over $Na_2SO_4$, filtered and concentrated to give E-5. LC/MS: $[M+H]^+$=322.9.

Step F—Synthesis of Intermediate E-6

To a solution of E-5 (2.079 g, 6.45 mmol) in DMF (40 ml) at 0° C. was added 60% NaH in hexane (0.568 g, 14.19 mmol), and the resulting solution was stirred at 0° C. for 50 min followed by addition of allyl bromide (1.172 mL, 13.54 mmol) dropwise. The resulting solution was stirred at 0° C. for 1.5 h, then quenched by addition of 1N HCl (ca. 3.68 mL). The solution was then partitioned between EtOAc (200 mL) and water (100 mL), the organic phase was washed with brine (2×100 mL), dried over $Na_2SO_4$, filtered and concentrated and the residue was purified by MPLC over silica gel (eluting with a gradient of MeOH in DCM) to give E-6. LC/MS: $[M+H]^+$=363.0.

Step G—Synthesis of Intermediate E-7

To a solution of E-6 (2.239 g, 6.18 mmol) and E-4 (1.842 g, 7.11 mmol) in DMF (30 ml) were added HATU (2.82 g, 7.41 mmol) and DIEA (2.59 ml, 14.83 mmol) and the resulting solution was stirred at RT for 1 h. The mixture was partitioned between EtOAc (200 mL) and brine (100 mL), the organic phase was washed with brine (3×100 mL), dried over $Na_2SO_4$, filtered and concentrated and the residue was purified by MPLC over silica gel (eluting with a gradient of EtOAc in hexanes) to give E-7. LC/MS: $[M+H]^+$=604.2.

Step H—Synthesis of Intermediate E-8

To a solution of E-7 (2.83 g, 4.69 mmol) in DCM (20 ml) and tBuOAc (30 ml) at 0° C. was added methanesulfonic acid (1.218 ml, 18.75 mmol) and the resulting solution was stirred at 0° C. for 16.5 h, then at RT for 2.5 h. The solution containing the product E-8 was used in the next step without further purification. LC/MS: $[M+H]^+$=504.2.

Step I—Synthesis of Intermediate E-9

To a solution of (S)-2-((((9H-fluoren-9-yl)methoxy)carbonyl)amino)-3-(3-(((tert-butoxycarbonyl)amino)methyl)phenyl)propanoic acid (2.66 g, 5.16 mmol) in DMF (10 ml) was added HATU (1.961 g, 5.16 mmol) and DIEA (5.32 ml, 30.5 mmol), and the resulting solution was stirred at RT for 30 min, then added to an ice-cold bath of the above prepared solution containing E-8. The resulting solution was stirred at RT for 1 h then concentrated under reduced pressure. The residue was purified by reverse phase MPLC over C18 (eluting with a gradient of acetonitrile (+0.05% TFA) in water (+0.05% TFA)) to provide E-9. LC/MS: $[M+H]^+$=1002.1.

Step J—Synthesis of Intermediate E-10

To a solution of E-9 (3.235 g, 3.23 mmol) in DCM (4 ml) was added TFA (7.46 ml, 97 mmol), and the resulting solution was stirred at RT for 1 h, then concentrated. The residue was dissolved in DCM (10 mL), treated with 4 N HCl in dioxane (3.23 ml, 12.91 mmol), and concentrated. The residue was dissolved in acetonitrile (100 mL) and water (50 mL) and lyophilized to provide E-10. LC/MS: $[M+H]^+$=846.1.

Step K—Synthesis of Intermediate E-11

To a solution of E-10 (2.85 g, 3.23 mmol) in DMF (45 ml) was added HATU (1.474 g, 3.88 mmol), and the resulting solution was stirred at RT for 30 min, then diluted with DCM (600 ml) followed by addition of DIEA (1.692 ml, 9.69 mmol) dropwise. The resulting solution was stirred at ambient temperature for 1 h. The final solution was concentrated, and the residue was purified by reverse phase MPLC over C18 (eluting with a gradient of acetonitrile (+0.05% TFA) in water (+0.05% TFA). The fractions containing the product were concentrated and the aqueous layer was partitioned between DCM (200 mL) and saturated $NaHCO_3$ (200 mL). The aqueous phase was further extracted with DCM (2×100 mL) and the combined organic layers were dried over $Na_2SO_4$, filtered and concentrated to give E-11. LC/MS: $[M+H]^+$=828.1.

Step L—Synthesis of Intermediate E

To a solution of E-11 (1.93 g, 2.331 mmol) in THF (60 ml), MeOH (30 ml), and water (20 ml) at 0° C. was added 1N aqueous LiOH (9.9 ml, 9.90 mmol) dropwise, and the resulting solution was stirred at 0° C. for 16 h then quenched by addition of 1N HCl (9.9 mL). The mixture was concentrated under reduced pressure and to the resulting solution at 0° C. were added acetone (60 ml), sodium carbonate (0.371 g, 3.50 mmol), and Fmoc-Osu (0.802 g, 2.378 mmol). The resulting solution was stirred at 0° C. for 6 h, concentrated under reduced pressure, then the aqueous phase was acidified to pH 4 and extracted with 30% IPA in DCM (3×100 mL). The combined organic layers were dried over $Na_2SO_4$, filtered and concentrated and the residue was purified by MPLC over silica gel (eluting with a gradient of MeOH in DCM) to give intermediate E. LC/MS: $[M+H]^+$=814.2.

Preparation of Intermediate F

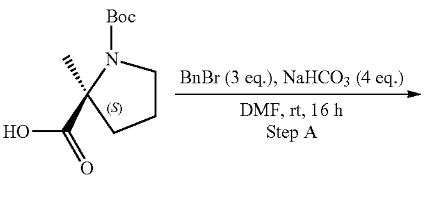

-continued

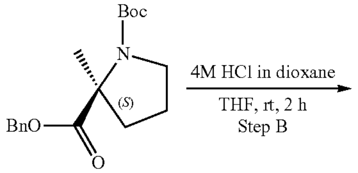

F-1

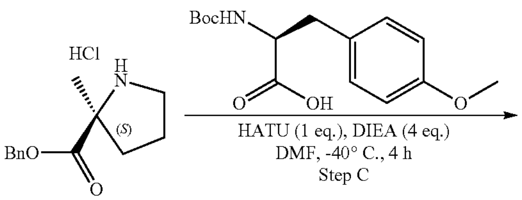

F-2

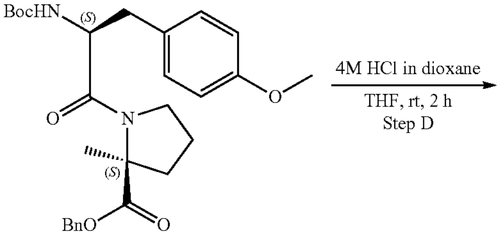

F-3

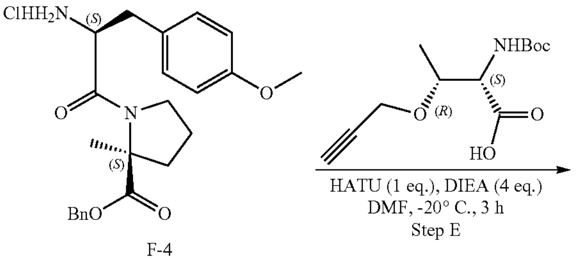

F-4

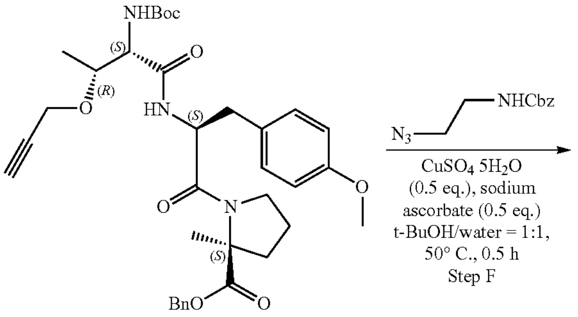

F-5

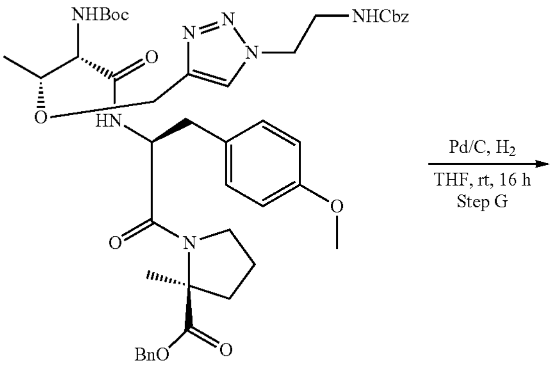

F-6

-continued

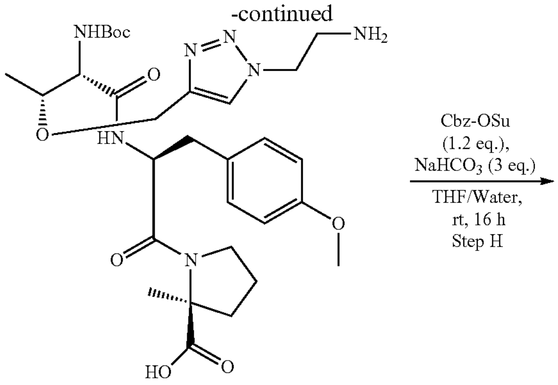

F-9

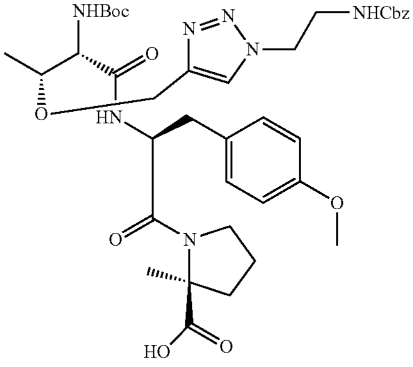

F

Step A: (S)-2-benzyl 1-tert-butyl 2-methylpyrrolidine-1,2-dicarboxylate F-1

To a solution of (S)-1-(tert-butoxycarbonyl)-2-methylpyrrolidine-2-carboxylic acid (5.00 g, 21.8 mmol) in DMF (50 mL) were added $NaHCO_3$ (7.33 g, 87 mmol) and BnBr (7.77 mL, 65.4 mmol) at 0° C. The mixture was stirred at room temperature for 16 h. The reaction solution was quenched with water (80 mL), extracted with EA (3×100 mL) and the combined organic layer was washed with brine (3×300 mL), dried over anhydrous $Na_2SO_4$ and filtered. The filtrate was concentrated under reduced pressure and the residue was purified by silica gel column chromatography, eluted with 0-45% EA in PE to afford (S)-2-benzyl 1-tert-butyl 2-methylpyrrolidine-1,2-dicarboxylate F-1. LCMS (ESI) calc'd for $C_{18}H_{25}NO_4$ $[M+H]^+$: 320.2, found 320.2. $^1H$ NMR (300 MHz, $CDCl_3$) δ 7.36-7.31 (m, 5H), 5.25-5.01 (m, 2H), 3.67-3.41 (m, 2H), 2.23-2.10 (m, 1H), 1.97-1.79 (m, 3H), 1.57 (d, J=17.9 Hz, 3H), 1.44-1.33 (m, 9H).

Step B: (S)-benzyl 2-methylpyrrolidine-2-carboxylate hydrochloride F-2

To a solution of (S)-2-benzyl 1-tert-butyl 2-methylpyrrolidine-1,2-dicarboxylate F-1 (6.10 g, 19.1 mmol) in THF (10 mL) was added 4 M HCl in dioxane (50 mL) at room temperature. The reaction solution was stirred at room temperature for 2 h. The resulting solution was concentrated under reduced pressure to afford (S)-benzyl 2-methylpyrrolidine-2-carboxylate hydrochloride F-2. LCMS (ESI) calc'd for $C_{13}H_{18}ClNO_2$ $[M-HCl+H]^+$: 220.1, found 220.1.

Step C: Preparation of Intermediate F-3

To a stirred solution of (S)-2-((tert-butoxycarbonyl)amino)-3-(4-methoxyphenyl)propanoic acid F-2 (5.77 g, 19.6 mmol) in DMF (50 mL) were added HATU (7.43 g, 19.6 mmol), (S)-benzyl 2-methylpyrrolidine-2-carboxylate hydrochloride (5.00 g, 19.6 mmol) and DIEA (12.9 mL, 78 mmol) at −40° C. The resulting mixture was stirred at −40° C. for 4 h. The reaction mixture was quenched by the addition of water (200 mL). The reaction solution was extracted with EA (2×200 mL) and the combined organic layer was washed with brine (3×400 mL), dried over anhydrous $Na_2SO_4$ and filtered. The residue was purified by silica gel column chromatography eluted with gradient 0%-60% EA in PE to afford F-3. LCMS (ESI) calc'd for $C_{28}H_{36}N_2O_6$ $[M+H]^+$: 497.3, found 497.2; $^1H$ NMR (400 MHz, $CDCl_3$) δ 7.39-7.28 (m, 5H), 7.08 (d, J=8.3 Hz, 2H), 6.74 (d, J=8.5 Hz, 2H), 5.26-5.10 (m, 2H), 4.53-4.47 (m, 1H), 3.75 (s, 3H), 3.71-3.63 (m, 1H), 3.22-3.16 (m, 1H), 2.89-2.84 (m, 1H), 2.65-2.60 (m, 1H), 2.14-2.05 (m, 1H), 1.58 (s, 6H), 1.36 (s, 9H).

Step D: Preparation of Intermediate F-4

To a solution of F-3 (6.70 g, 13.49 mmol) in THF (10 mL) was added 4 M HCl in 1,4-dioxane (60 mL). The reaction solution was stirred at room temperature for 2 h. The resulting solution was concentrated under reduced pressure to afford F-4. LCMS (ESI) calc'd for $C_{23}H_{29}ClN_2O_4$[M−HCl+H]$^+$: 397.2, found 397.1.

Step E: Preparation of Intermediate F-5

To a solution of (2S,3R)-2-((tert-butoxycarbonyl)amino)-3-(prop-2-yn-1-yloxy)butanoic acid (prepared by the process described in Henseler; *Advanced Synthesis & Catalysis,* 2014, 356(8), 1795-1802) (1.19 g, 4.62 mmol) in DMF (20 mL) were added HATU (1.76 g, 4.62 mmol), F-4 (2.00 g, 4.62 mmol) and DIEA (3.23 mL, 18.5 mmol) at 0° C. The mixture was stirred at 0° C. for 1 h. The mixture was diluted with brine (80 mL), extracted with EA (2×80 mL), washed brine (2×30 mL), dried over anhydrous $MgSO_4$ and filtered, the filtrate was concentrated under reduced pressure. The residue purified by silica gel column chromatography, eluted with gradient 1%-50% EA in PE. The fractions containing desired product were combined and concentrated to afford F-5. LCMS (ESI) calc'd for $C_{35}H_{45}N_3O_8$ $[(M+H)]^+$: 636.3, found 636.4; $^1H$ NMR (300 MHz, $CDCl_3$) δ 7.43-7.32 (m, 5H), 7.11 (d, J=8.2 Hz, 2H), 6.74 (d, J=8.3 Hz, 2H), 5.32-5.07 (m, 2H), 4.88-4.76 (m, 1H), 4.19-4.06 (m, 4H), 3.75 (s, 3H), 3.67 (br, 1H), 3.15 (br, 1H), 3.02-2.89 (m, 2H), 2.87-2.72 (m, 1H), 2.43 (t, J=2.5 Hz, 1H), 2.10 (br, 1H), 1.97-1.82 (m, 4H), 1.58 (d, J=9.0 Hz, 3H), 1.45 (s, 9H), 1.16 (d, J=6.3 Hz, 3H).

Step F: Preparation of Intermediate F-6

To a solution of F-5 (2.00 g, 3.15 mmol) and benzyl (2-azidoethyl)carbamate (830 mg, 3.78 mmol) in t-BuOH (250 mL) were added water (250 mL), $CuSO_45H_2O$ (390 mg, 1.57 mmol) and sodium ascorbate (0.312 g, 1.573 mmol) at room temperature. The mixture was stirred at 50° C. for 30 min and concentrated under reduced pressure. The residue was diluted with brine (50 mL), extracted with EA (2×100 mL), washed brine (50 mL), dried over anhydrous $MgSO_4$ and filtered, the filtrate was concentrated under reduced pressure. The residue purified by silica gel column chromatography, eluted with gradient 10%-10% MeOH in DCM. The fractions containing desired product were combined and concentrated to afford F-6. LCMS (ESI) calc'd for $C_{45}H_{57}N_7O_{10}$ $[M+H]^+$: 856.4, found 856.5.

Step G: Preparation of Intermediate F-7

To a solution of F-6 (2.00 g, 2.34 mmol) in THF (100 mL) was added Pd/C (200 mg, 0.188 mmol, dry, 10% wt) at room temperature under nitrogen atmosphere. The mixture was degassed with hydrogen three times and stirred at room temperature for 16 h. The resulting mixture was filtered and the filtrate was concentrated under reduced pressure to afford F-7. LCMS (ESI) calc'd for $C_{30}H_{45}N_7O_8$ $[M+H]^+$: 632.3, found 632.4.

Step H: Preparation of Intermediate F

To a solution of F-7 (1.00 g, 1.58 mmol) in THF (10 mL) and water (10 mL) were added $NaHCO_3$ (0.399 g, 4.75 mmol) and Cbz-OSu (0.473 g, 1.90 mmol) at 0° C. The reaction mixture was stirred for 16 h at room temperature. The pH value of the resulting solution was adjusted to 2 with 1 M HCl at 0° C. The mixture was extracted with EA (2×50 mL), dried over anhydrous $Na_2SO_4$ and filtered. The filtrate was concentrated under reduced pressure. The residue was purified by silica gel column chromatography, eluted with gradient 1%-10% MeOH in DCM. The fractions containing the desired product were combined and concentrated under reduced pressure to afford F. LCMS (ESI) calc'd for $C_{38}H_{51}N_7O_{10}$ $[M+H]^+$: 766.4, found 766.4; $^1H$ NMR (300 MHz, $CD_3OD$) δ 7.91-7.85 (m, 1H), 7.36-7.31 (m, 5H), 7.23-7.14 (m, 2H), 6.83-6.74 (m, 2H), 5.10-5.04 (m, 2H), 4.85-4.75 (m, 1H), 4.67-4.56 (m, 1H), 4.56-4.44 (m, 3H), 4.13-3.94 (m, 2H), 3.71 (s, 3H), 3.66-3.57 (m, 2H), 3.40-2.96 (m, 2H), 2.82-2.64 (m, 2H), 2.25-1.75 (m, 4H), 1.51-1.36 (m, 12H), 1.13 (d, J=6.2 Hz, 3H).

Preparation of Intermediate G

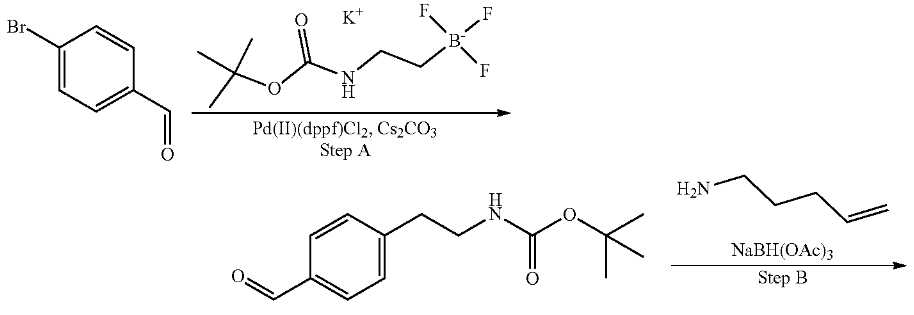

G-1

-continued

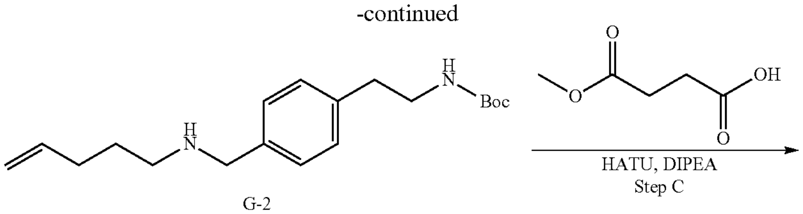

G-2

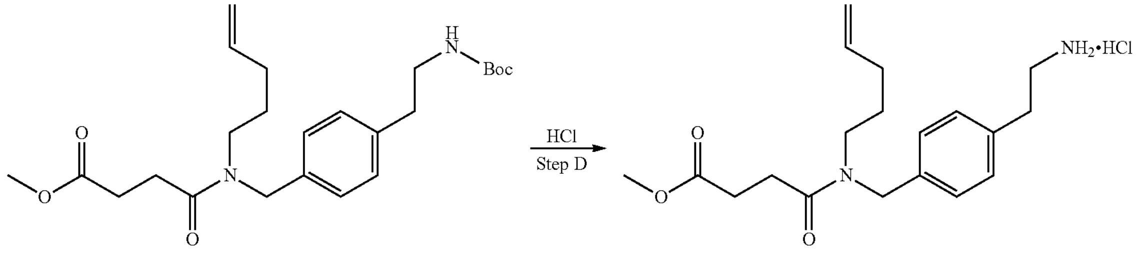

G-3 G

Step A—Synthesis of Intermediate G-1

A solution of 4-bromobenzaldehyde (15.00 g, 81 mmol), potassium tert-butyl N-[2-(trifluoroboranuidyl)ethyl]carbamate (20.97 g, 84 mmol), cesium carbonate (52.8 g, 162 mmol) and 1,1'-bis(diphenylphosphino)ferrocene-palladium (II)dichloride dichloromethane complex (1.99 g, 2.43 mmol) in degassed toluene (250 ml) and water (85 ml) was warmed to 76° C. and stirred overnight. The mixture was quenched at RT with half-saturated aqueous $NH_4Cl$ and extracted with EtOAc. The combined organic fractions were washed with brine, dried over $Na_2SO_4$, filtered and the filtrate was concentrated in vacuo. The residue was purified by MPLC over silica gel (eluting with a gradient of EtOAc in DCM) to give G-1. LC/MS: $[M-56]^+$=193.0.

Step B—Synthesis of Intermediate G-2

To a solution of G-1 (12.9 g, 51.7 mmol) and pent-4-en-1-amine (6.61 g, 78 mmol) in DCM (120 ml) and AcOH (3 ml) at RT in a water bath was added sodium triacetoxy borohydride (32.9 g, 155 mmol) portion wise and the mixture was stirred for 30 min. The reaction was slowly quenched at 0° C. with water (3 ml), poured into 1 N NaOH (500 ml), stirred for 15 min then extracted with DCM, dried over $Na_2SO_4$, and concentrated. The residue was purified by MPLC over silica gel (eluting with a gradient of MeOH in DCM) to give G-2. LC/MS: $[M+H]^+$-319.2.

Step C—Synthesis of Intermediate G-3

To a solution of G-2 (8.48 g, 20.77 mmol) and 4-methoxy-4-oxobutanoic acid (3.02 g, 22.85 mmol) in DMF (40 ml) were added HATU (9.48 g, 24.92 mmol) and DIPEA (8.71 ml, 49.8 mmol). The resulting solution was stirred at RT for 1 h, then quenched with aqueous saturated $NaHCO_3$ (10 mL). The mixture was partitioned between EtOAc (500 mL) and aqueous saturated $NaHCO_3$ (200 mL), the organic phase was washed with brine (3×200 mL), dried over $Na_2SO_4$, concentrated and the residue was purified by MPLC over silica gel (eluting with a gradient of EtOAc in hexanes) to give G-3. LC/MS: $[M+H]^+$ 433.4.

Step D—Synthesis of Intermediate G

To a solution of G-3 (2.9 g, 6.70 mmol) in DCM (15 mL) at RT was added 4 M HCl in dioxane (10 mL) and the reaction mixture was stirred at RT for 1 h. The mixture was concentrated under reduced pressure to give intermediate G. LC/MS: $[M+H]^+$=333.3.

Preparation of Intermediate H

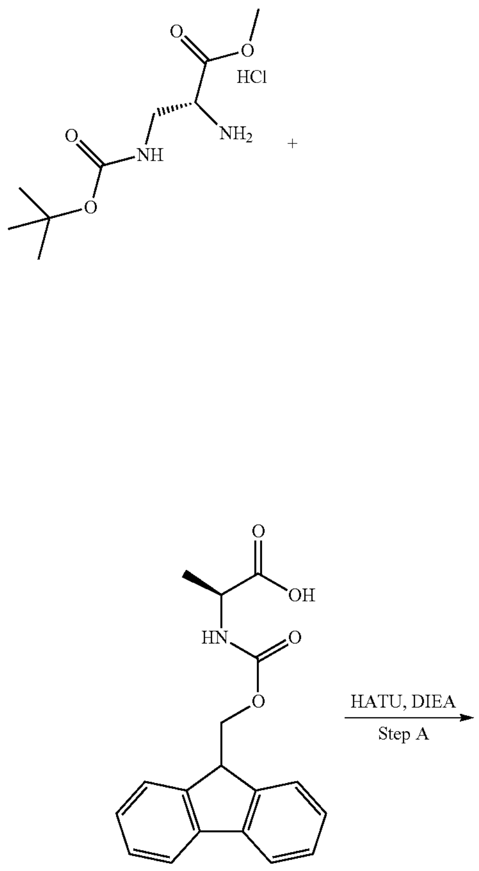

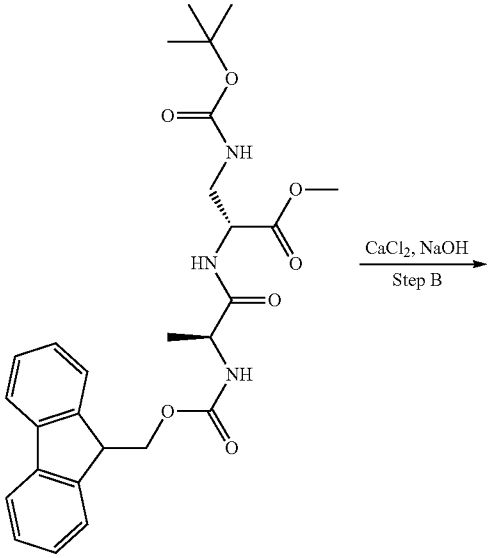

H-1

-continued

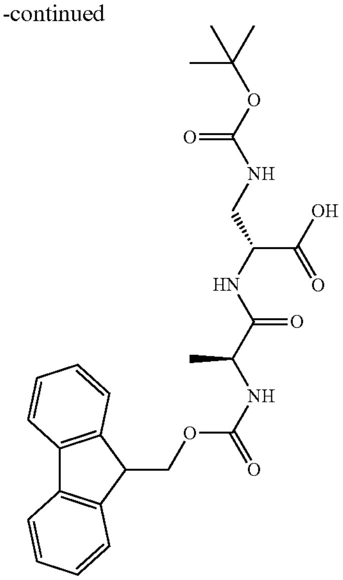

H

Step A—Synthesis of Intermediate H-1

To a solution of D-Dap(Boc)-OMe HCl salt (4.10 g, 16.10 mmol), Fmoc-Ala-OH (5.01 g, 16.10 mmol) and HATU (6.43 g, 16.90 mmol) in DMF (40 ml) at 0° C. was added DIPEA (7.03 ml, 40.2 mmol) and the mixture was stirred at 0° C. for 2 h then kept in the refrigerator overnight. The mixture was quenched at RT with water and extracted with EtOAc. The combined organic fractions were washed with half brine, dried over $Na_2SO_4$, filtered and the filtrate was concentrated in vacuo. The residue was purified by MPLC over silica gel (eluting with a gradient of EtOAc in hexanes) to give H-1. LC/MS: $[M+H]^+$=512.3.

Step B—Synthesis of Intermediate H

To a solution of H-1 (8.03 g, 15.70 mmol) and 0.8 N calcium chloride (19.62 ml, 15.70 mmol) in water (40 ml) and 2-propanol (120 ml) at RT was added solid sodium hydroxide (0.691 g, 17.27 mmol). The mixture was stirred at room temperature overnight. The final mixture was concentrated, acidified with 0.5 N to pH ~2 (~40 mL), extracted three times with EtOAc, washed with brine, dried over $Na_2SO_4$ and concentrated. The residue was purified by reverse phase MPLC over C18 (eluting with a gradient of acetonitrile in water (+0.1% TFA)) to give intermediate H. LC/MS: $[M+H]^+$=498.2.

Preparation of Intermediate I
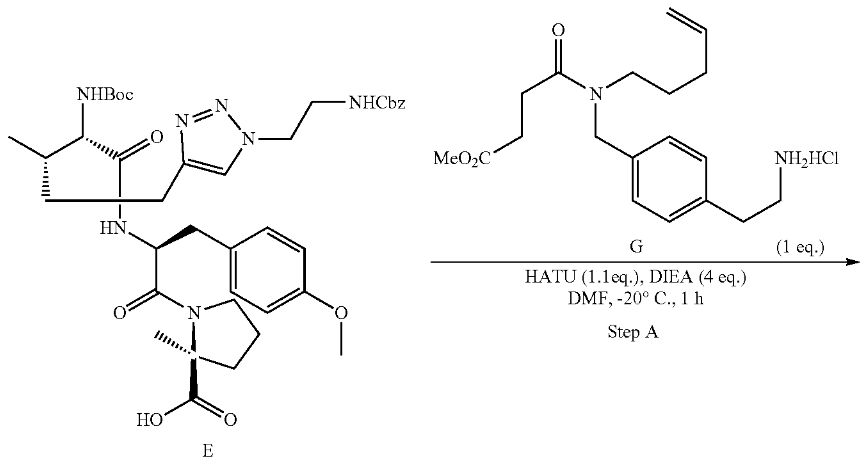
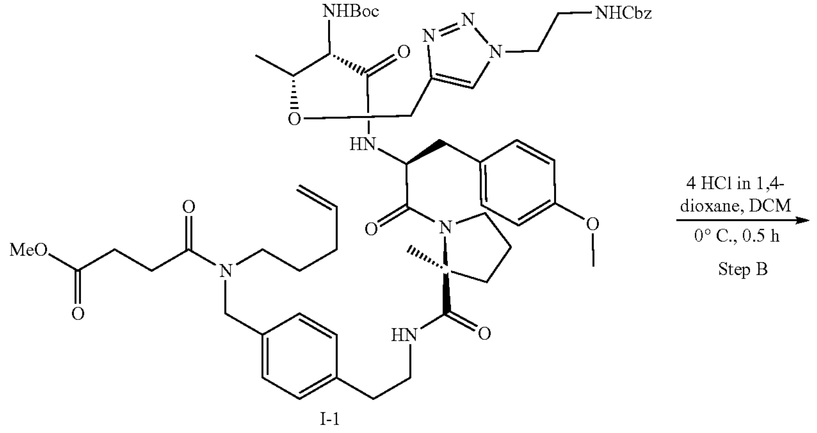
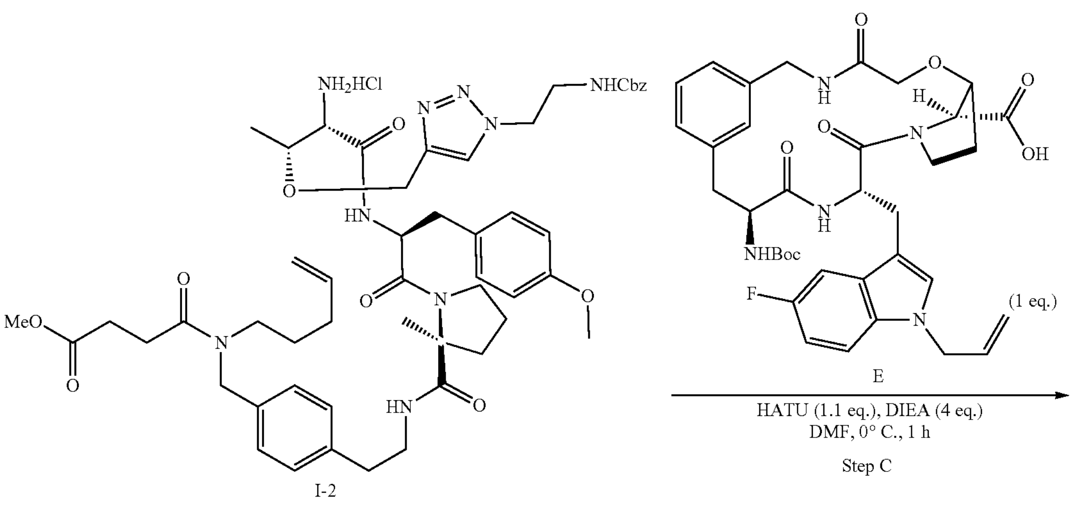

-continued
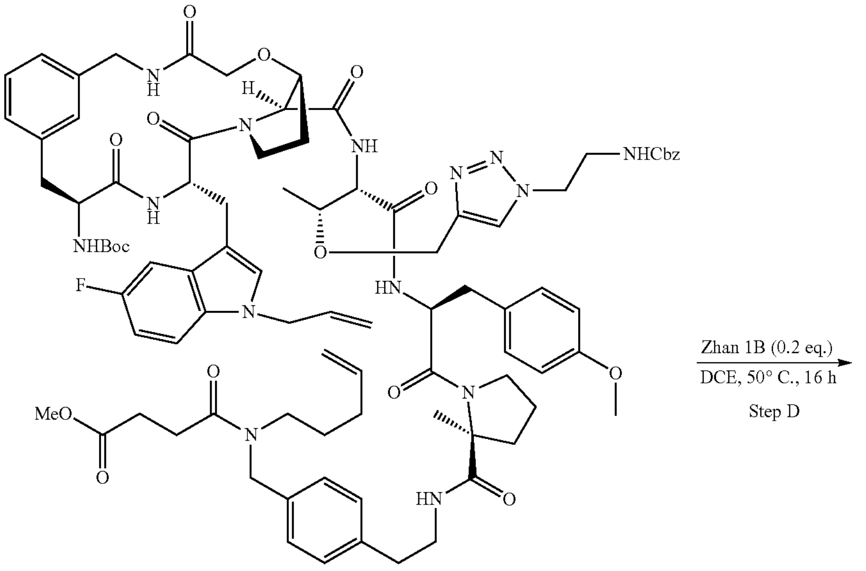
I-3
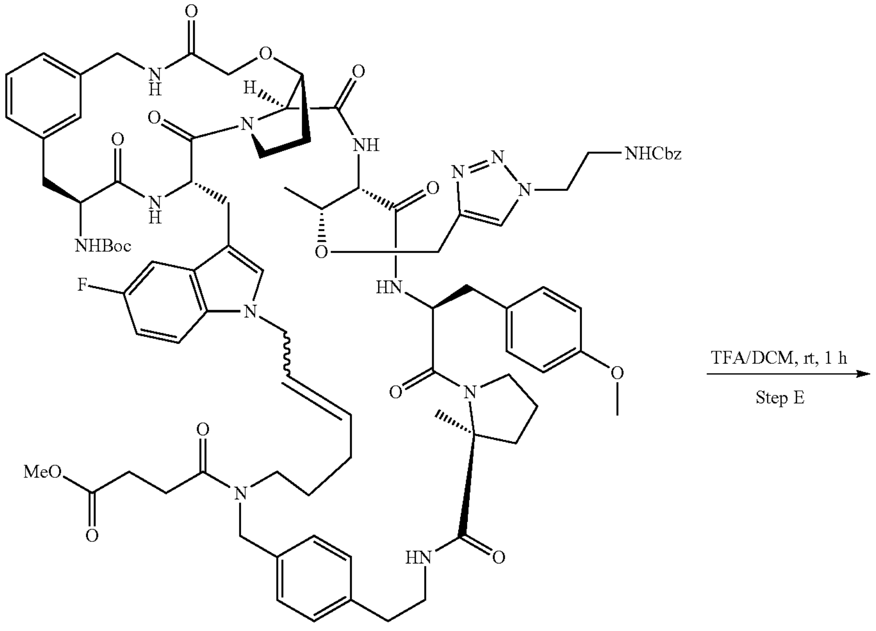
I-4

-continued
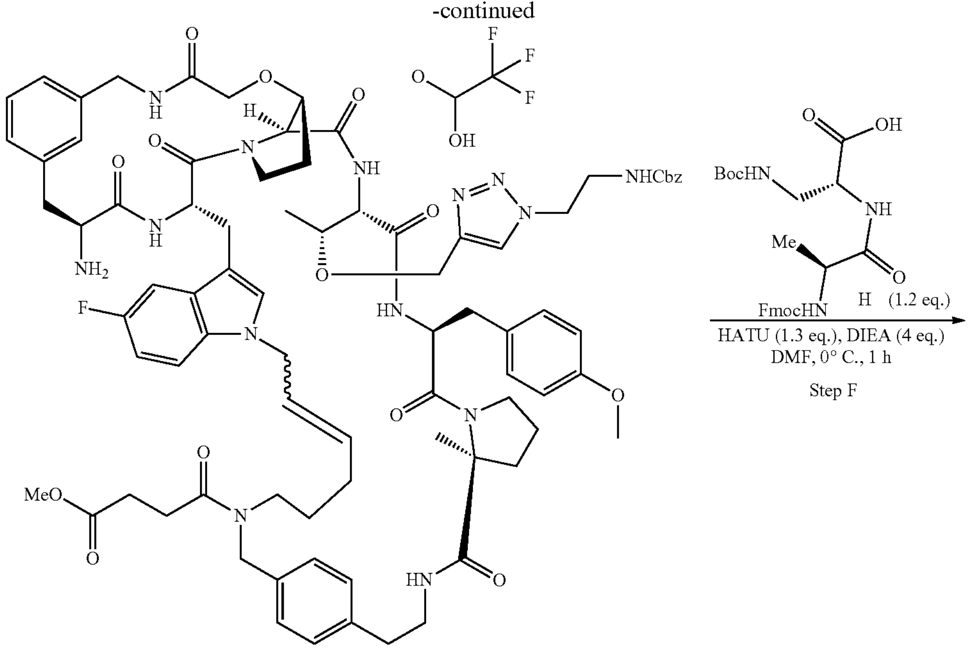
I-5
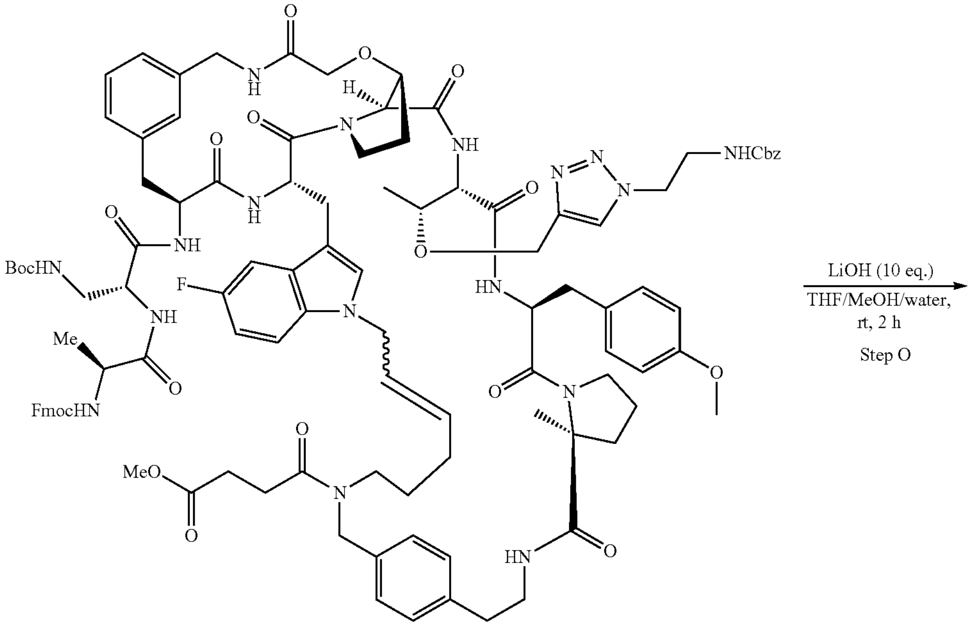
I-6

-continued
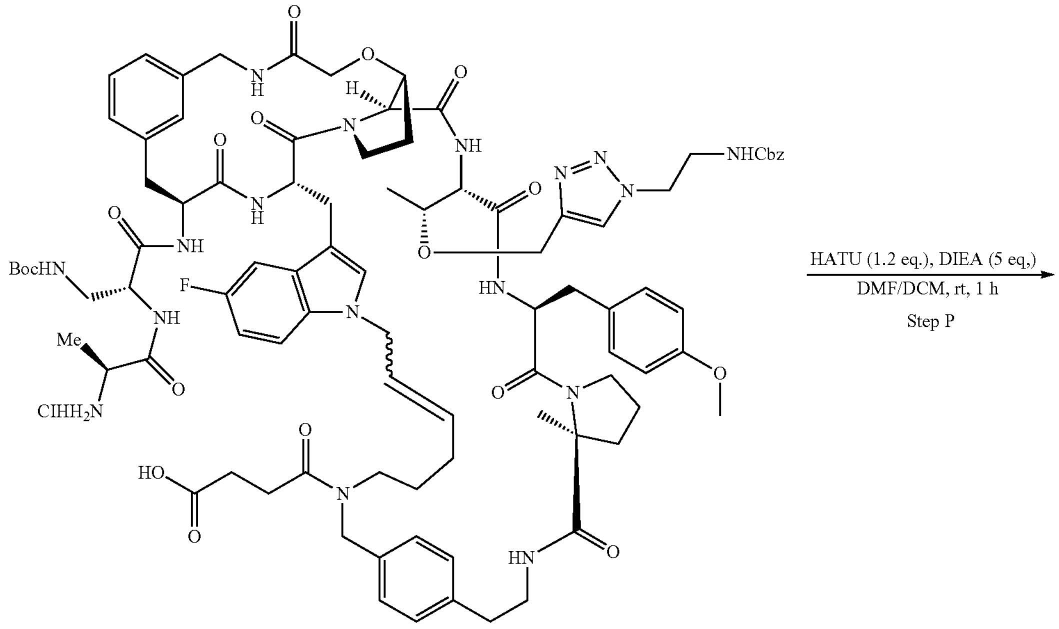
I-7
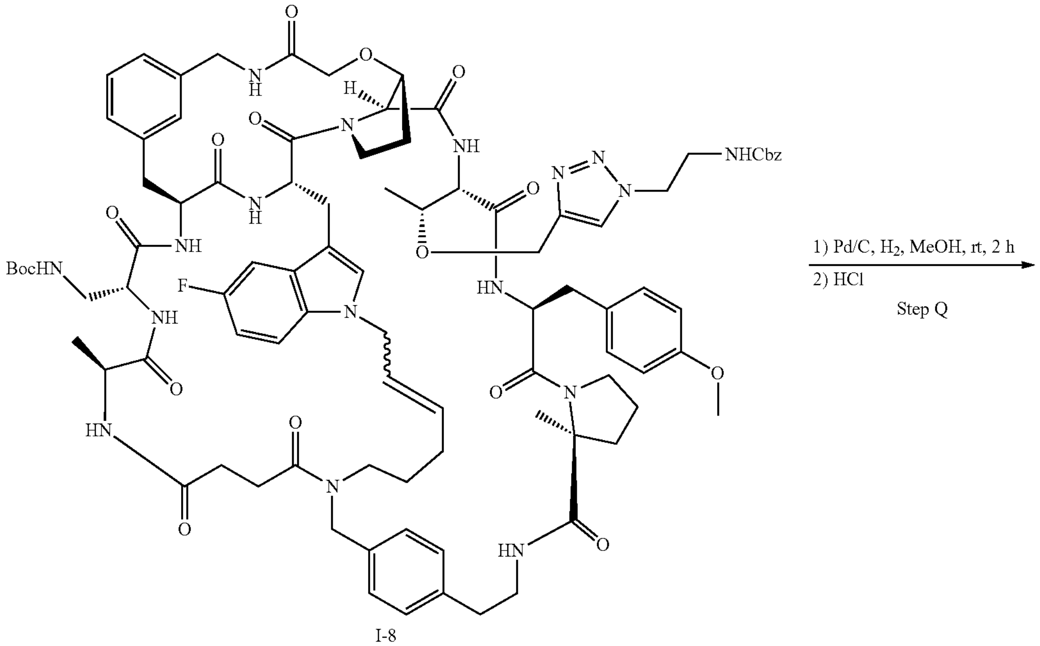
I-8

-continued
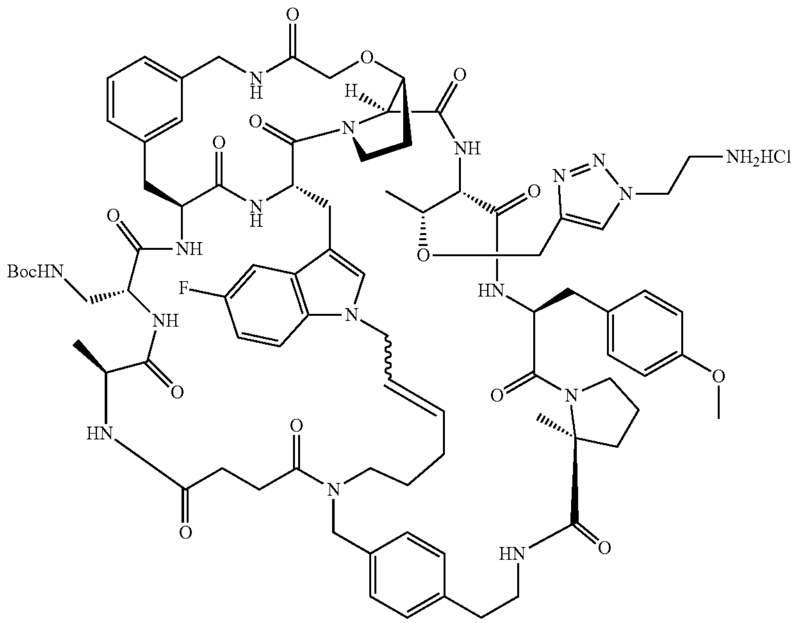
I-9
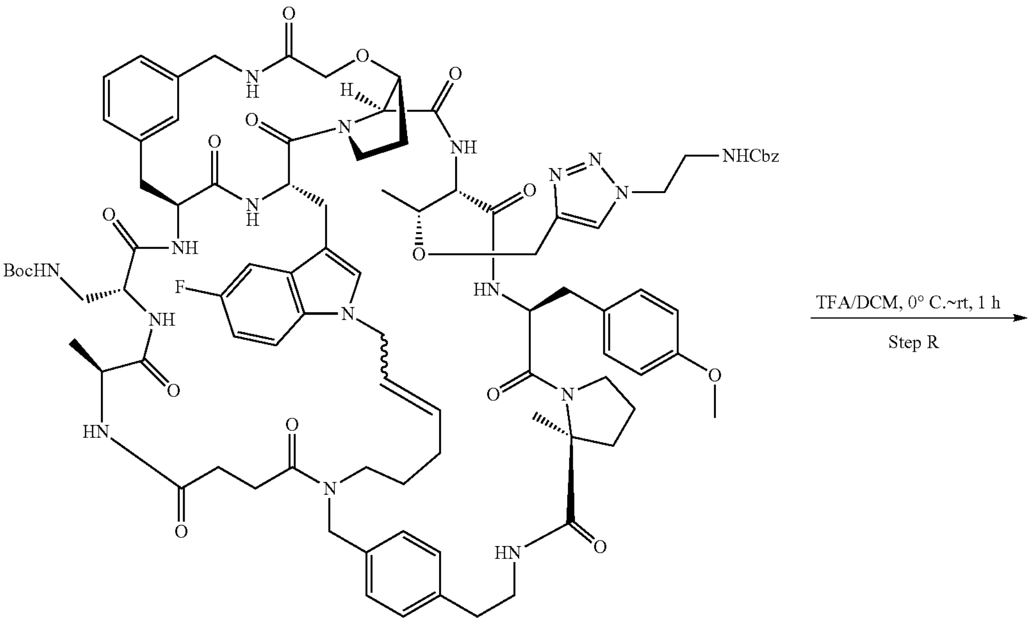
I-10

-continued
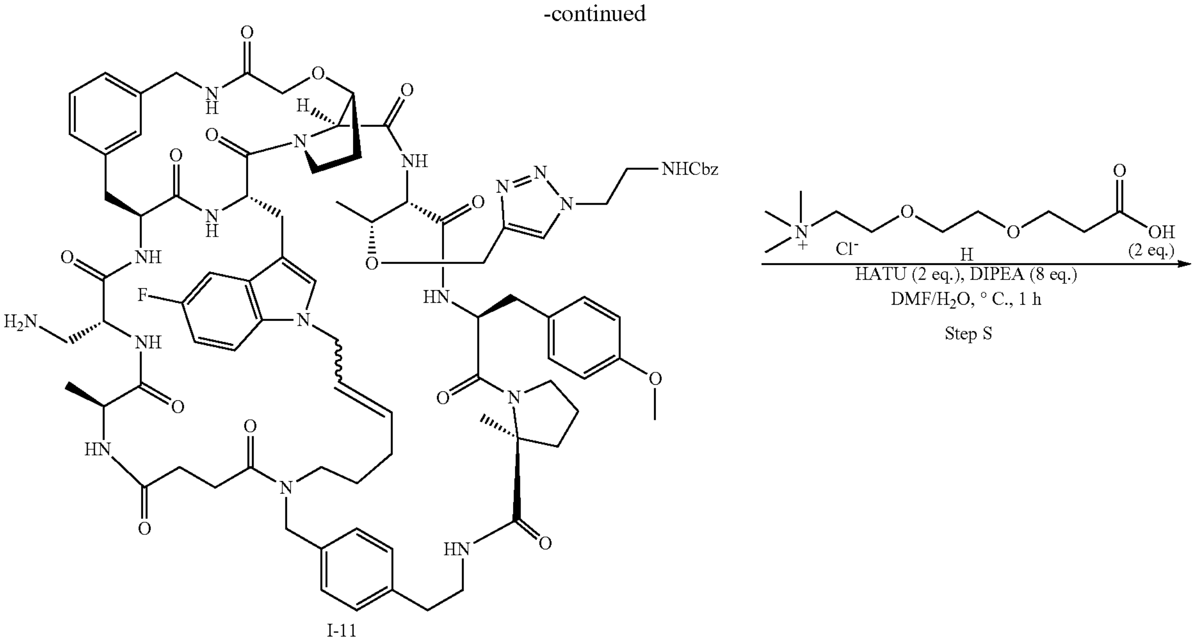
I-11
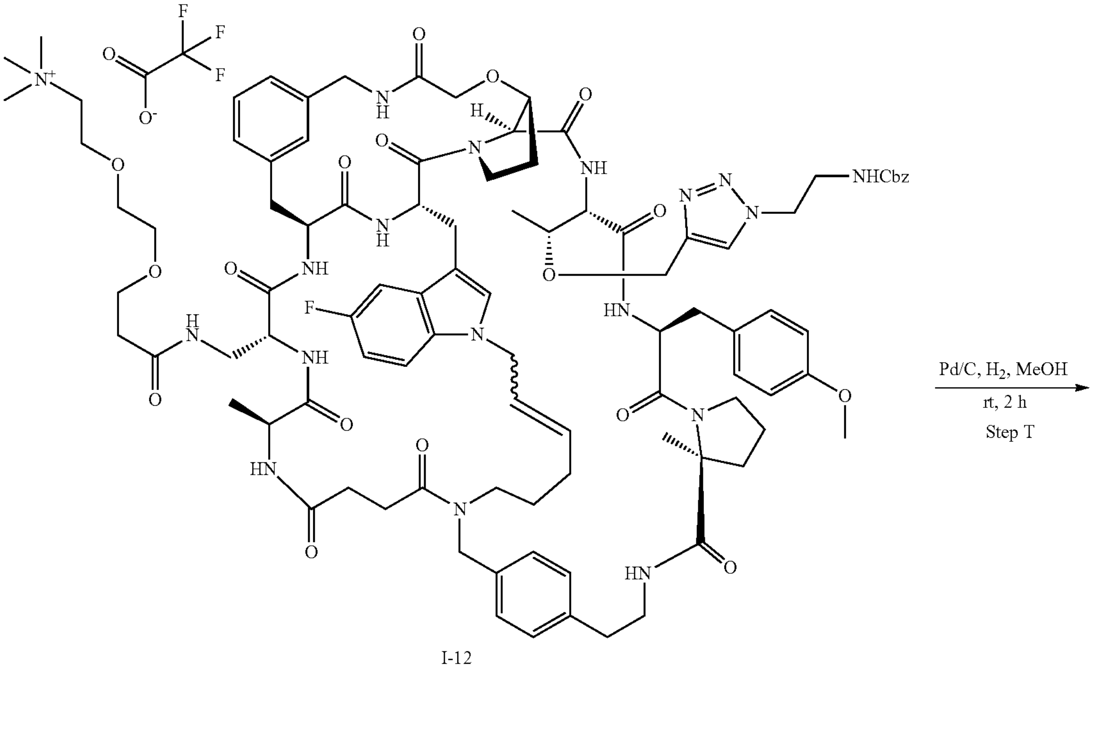
I-12

-continued

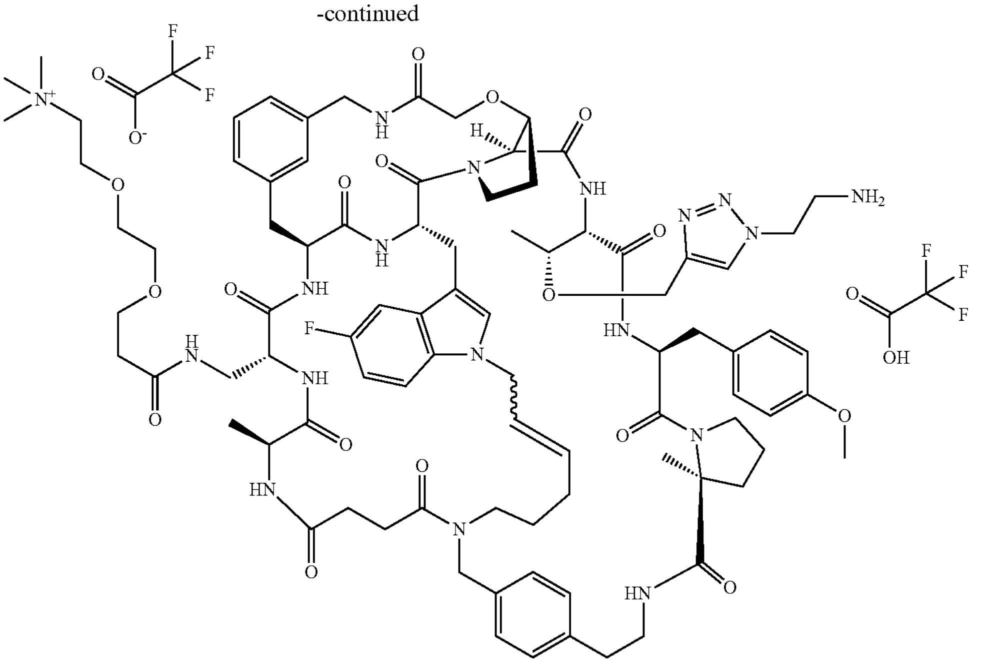

I

Step A: Preparation of Intermediate I-1

To the solution F (860 mg, 1.12 mmol) in DMF (10 mL) were added HATU (470 mg, 1.23 mmol), G (414 mg, 1.12 mmol) and DIEA (0.784 mL, 4.49 mmol) under nitrogen atmosphere at −20° C. The mixture was stirred at −20° C. for 1 h. The reaction solution was quenched with water (50 mL), extracted with EA (2×50 mL). The organic layer was washed with brine (3×100 mL), dried over anhydrous $Na_2SO_4$ and filtered. The filtrate was concentrated under reduced pressure. The residue was purified by silica gel column chromatography, eluted with gradient 1%-10% MeOH in DCM. The fractions containing desired product were combined and concentrated to afford I-1. LCMS (ESI) calc'd for $C_{57}H_{77}N_9O_{12}$ $[M+H]^+$: 1080.6, found 1080.6; $^1H$ NMR (400 MHz, $CD_3OD$) δ 7.86-7.82 (m, 1H), 7.38-7.12 (m, 11H), 6.84-6.78 (m, 2H), 5.83-5.71 (m, 1H), 5.08-5.04 (m, 2H), 5.03-4.78 (m, 4H), 4.63-4.55 (m, 3H), 4.52-4.42 (m, 3H), 3.99-3.94 (m, 1H), 3.72-3.63 (m, 6H), 3.64-3.56 (m, 2H), 3.52-3.25 (m, 8H), 2.84-2.56 (m, 8H), 2.10-1.96 (m, 3H), 1.91-1.55 (m, 6H), 1.44 (s, 9H), 1.12 (d, J=6.2 Hz, 3H).

Step B: Preparation of Intermediate I-2

To a stirred solution of I-1 (900 mg, 0.833 mmol) in DCM (2.7 mL) was added 4 N HCl in 1,4-dioxane (4.9 mL, 19.6 mmol) at −20° C. The reaction mixture was stirred at 0° C. for 0.5 h and concentrated under reduced pressure. The residue was re-dissolved in DCM and concentrated under reduced pressure to afford I-3. LCMS (ESI) calc'd for $C_{52}H_{70}ClN_9O_{10}$ $[M-HCl+H]^+$: 980.5, found 980.6.

Step C: Preparation of Intermediate 1-3

To a solution of E (572 mg, 0.826 mmol) in DMF (9 mL) were added HATU (346 mg, 0.909 mmol), I-2 (840 mg, 0.826 mmol) and DIEA (0.577 mL, 3.31 mmol) at 0° C. The mixture was stirred at 0° C. for 1 h. The reaction solution was quenched with water (50 mL) and extracted with EA (3×50 mL). The organic layer was washed with brine (3×100 mL), dried over anhydrous $MgSO_4$ and filtered. The filtrate was concentrated under reduced pressure. The residue was purified by silica gel column chromatography, eluted with gradient 1%-10% MeOH in DCM. The fractions containing desired product were combined and concentrated under reduced pressure to afford I-3. LCMS (ESI) calc'd for $C_{88}H_{109}FN_{14}O_{17}$ $[M+H]^+$: 1653.8, found 1653.8.

Step D: Preparation of Intermediate 1-4

To a stirred solution of I-3 (960 mg, 0.580 mmol) in DCE (580 mL) was added Zhan-1B (85.0 mg, 0.116 mmol) at room temperature. The reaction solution was stirred at 50° C. for 16 h. The mixture was cooled to rt, concentrated under reduced pressure and the residue was purified by silica gel column chromatography, eluted with gradient 1%-10% MeOH in DCM. The fractions containing desired product were combined and concentrated under reduced pressure to afford I-4. LCMS (ESI) calc'd for $C_{86}H_{105}FN_{14}O_{17}$ $[M+Na]^+$: 1647.8, found 1647.6.

Step E: Preparation of Intermediate I-5

To the solution of I-4 (900 mg, 0.554 mmol) in DCM (10 mL) was added TFA (2 mL, 26.0 mmol) at room temperature. The mixture was stirred at room temperature for 1 h. The resulting mixture was concentrated under reduced pressure and the residue was re-dissolved in DCM (5 mL) and toluene (5 mL). The mixture was concentrated under reduced pressure and the residue was re-dissolve in ACN (10 mL) and water (10 mL) and lyophilized to afford I-5. LCMS (ESI) calc'd for $C_{83}H_{98}F_4N_{14}O_{17}$ [M-TFA+H]$^+$: 1525.7, found 1527.0.

Step F: Preparation of Intermediate I-6

To a solution of G (313 mg, 0.629 mmol) in DMF (8 mL) were added HATU (259 mg, 0.682 mmol), I-5 (800 mg, 0.524 mmol) and DIEA (0.366 mL, 2.10 mmol) at 0° C. The mixture was stirred at 0° C. for 1 h. The reaction solution was quenched with water (50 mL) and extracted with EA (2×50 mL). The organic layer was washed with brine (3×100 mL), dried over anhydrous $MgSO_4$ and filtered. The filtrate was concentrated under reduced pressure. The residue was purified by silica gel column chromatography, eluted with gradient 10%-10% MeOH in DCM. The fractions containing desired product were combined and concentrated to afford I-6 LCMS (ESI) calc'd for $C_{107}H_{126}FN_{17}O_{21}$ $[(M+2H)/2]^+$: 1003.0, found 1003.5.

Step G: Preparation of Intermediate I-7

To a solution of I-6 (790 mg, 0.394 mmol) in THF (7.8 mL) were added MeOH (2.3 mL), water (2.3 mL) and 1 M LiOH (3.94 mL, 3.94 mmol) at 0° C. The mixture was stirred at 0° C. for 1 h. The resulting mixture was concentrated under reduced pressure. The residue was purified by Flash (Column: Flash $C^{18}$ 330 g; Mobile Phase A: water (0.1% TFA), Mobile Phase B: ACN; Flow rate: 100 mL/min; Gradient: 2% B to 2% B in 5 min, 20% B to 60% B in 20 min; Detector: UV 254/210 nm; Rt=23 min). The fractions containing desired product were concentrated under reduced pressure. The residue was re-dissolved in ACN (10 mL) and water (10 mL), added 1 M HCl (0.5 mL) at 0° C., and lyophilized to afford I-7. LCMS (ESI) calc'd for $C_{91}H_{115}ClFN_{17}O_{19}$ $[(M-HCl+2H)/2]^+$: 884.9, found 885.5.

Step H: Preparation of Intermediate I-8

To the solution of I-7 (480 mg, 0.266 mmol) in DMF (48 mL) were added DIEA (0.232 mL, 1.33 mmol), DCM (600 mL) and HATU (121 mg, 0.319 mmol) at room temperature. The mixture was stirred at room temperature for 1 h. The reaction solution was concentrated under reduced pressure to remove DCM and diluted with brine (200 mL), extracted with EA (2×200 mL). The organic layer was washed with brine (3×400 mL), dried over anhydrous $MgSO_4$ and filtered. The filtrate was concentrated under reduced pressure. The residue was purified by silica gel column chromatography, eluted with gradient 1%-10% MeOH in DCM. The fractions containing desired product were combined and concentrated under reduced pressure to afford I-8. LCMS (ESI) calc'd for $C_{91}H_{112}FN_{17}O_{18}$ $[(M+2H)/2]^+$:875.9, found 876.3.

Step I: Preparation of Intermediate I-9

To a stirred solution of I-8 (25.0 mg, 0.014 mmol) in MeOH (3 mL) was added Pd/C (5 mg, 4.70 µmol, dry, 10% wt) at room temperature. The mixture was degassed with hydrogen for 3 times and stirred at room temperature under hydrogen atmosphere for 2 h. The reaction solution was filtered and the filtrate was concentrated under reduced pressure. The residue was re-dissolved in ACN (5 mL) and water (5 mL), added 1 M HCl (28 µL) and lyophilized to afford I-9. LCMS (ESI) calc'd for $C_{83}H_{109}ClFN_{17}O_{16}$ $[M-HCl+H]^+$: 1618.8, found 1619.8.

Step J: Preparation of Intermediate I-10

To a solution of I-9 (140 mg, 0.080 mmol) in DCM (5 mL) was added TFA (1 mL, 13.0 mmol) at 0° C. The reaction mixture was stirred at room temperature for 1 h. The resulting solution was concentrated under reduced pressure and the residue was re-dissolved in DCM (5 mL) and toluene (5 mL). The mixture was concentrated under reduced pressure, re-dissolved in ACN (5 mL) and water (5 mL), and lyophilized to afford I-10. LCMS (ESI) calc'd for $C_{88}H_{105}F_4N_{17}O_{18}$ $[(M-TFA+2H)/2]^+$: 825.9, found 826.5.

Step K: Preparation of Intermediate I-11

To a solution of I-10 (140 mg, 0.083 mmol) in DMF (2 mL) and water (200 µL) were added 2-(2-(2-carboxyethoxy) ethoxy)-N,N,N-trimethylethanaminium chloride (42.4 mg, 0.166 mmol), HATU (63.1 mg, 0.166 mmol) and DIEA (0.116 mL, 0.664 mmol) at −20° C. The mixture was stirred at 0° C. for 1 h. The reaction solution was quenched with water (100 µL) and purified Flash (Column: Flash $C^{18}$ 80 g; Mobile Phase A: water (0.1% TFA), Mobile Phase B: ACN; Flow rate: 65 mL/min; Gradient: 2% B to 2% B in 5 min, 40% B to 80% B in 20 min; Detector: UV 254/210 nm; Rt=20 min). The fractions containing desired product were combined and concentrated under reduced pressure. The residue was re-dissolved in ACN (10 mL) and water (10 mL), lyophilized to afford I-11. LCMS (ESI) calc'd for $C_{98}H_{126}F_4N_{18}O_{21}$ $[(M-TFA^-+H)/2]^+$:927.5, found 927.1.

Step L: Preparation of Intermediate I

To a stirred solution of I-10 (70.0 mg, 0.036 mmol) in MeOH (5 mL) was added Pd/C (10 mg, 9.40 µmol, dry, 10% wt) at room temperature. The reaction mixture was degassed with hydrogen for three times and stirred at room temperature under hydrogen atmosphere for 2 h. The resulting mixture was filtered and the filtrate was concentrated under reduced pressure. The residue was purified by Flash (Column: Flash $C^{18}$ 80 g; Mobile Phase A: water (0.1% TFA), Mobile Phase B: ACN; Flow rate: 65 mL/min; Gradient: 2% B to 2% B in 5 min, 20% B to 50% B in 15 min; Detector: UV 254/210 nm; Rt=13 min). The fractions containing desired product were combined and concentrated under reduced pressure. The residue was re-dissolved in ACN (10 mL) and water (10 mL), and lyophilized to afford Intermediate I. LCMS (ESI) calc'd for $C_{92}H_{121}F_7N_{18}O_{21}$ $[M-2TFA^-+H]^+$: 1719.9, found 1720.9.

Preparation of Intermediate J
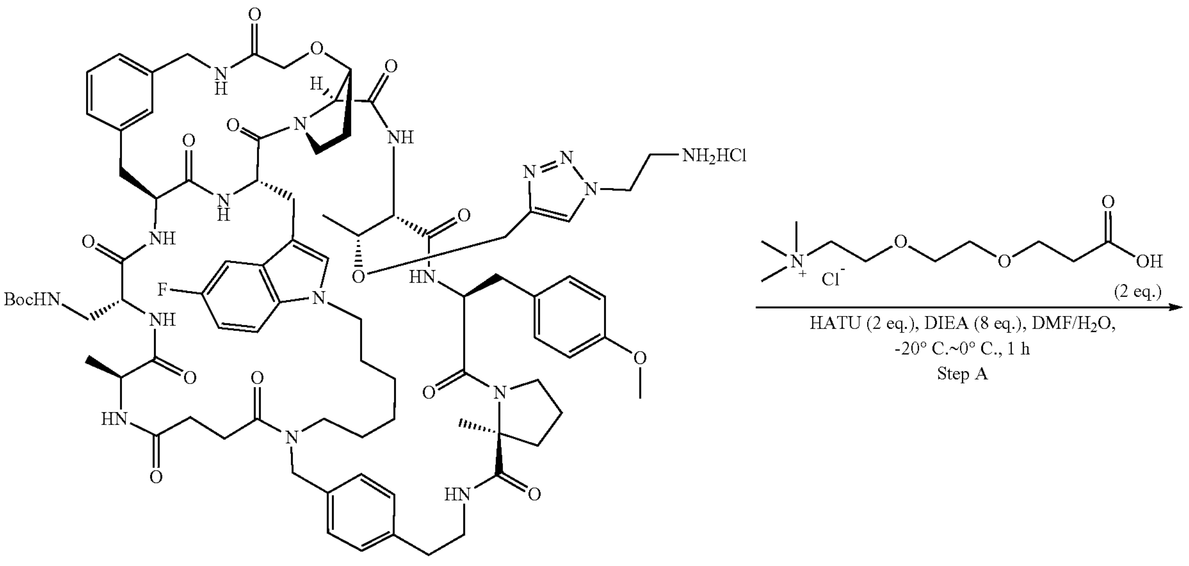
I-9
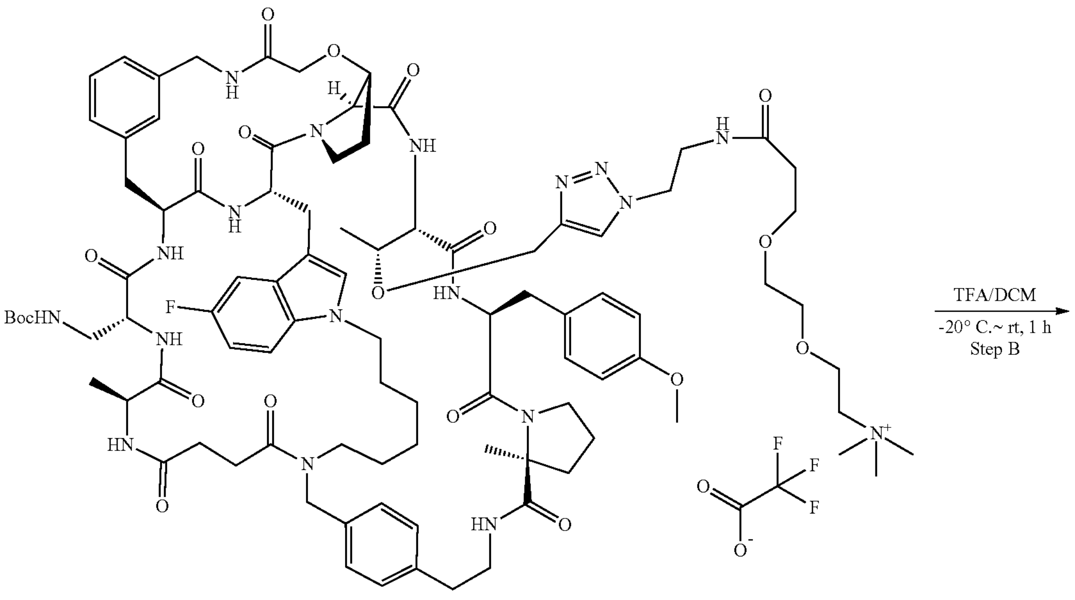
J-1

-continued

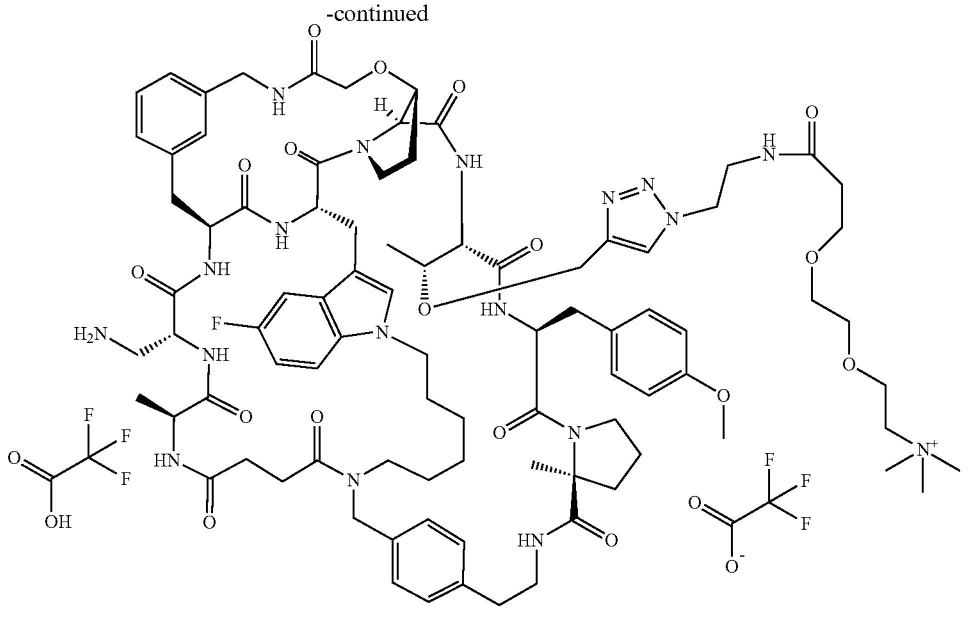

J

Step A: Preparation of Intermediate J-1

To a solution of I-9 (30.0 mg, 0.018 mmol) in DMF (300 μL) and water (30 μL) were added 2-(2-(2-carboxyethoxy) ethoxy)-N,N,N-trimethylethanaminium chloride (9.27 mg, 0.036 mmol), HATU (13.8 mg, 0.036 mmol) and DIEA (25.3 μL, 0.145 mmol) at −20° C. The mixture was stirred at 0° C. for 1 h. The reaction solution was quenched with water (100 μL) and purified Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 20% B to 60% B in 20 min; Detector: UV 254/210 nm; Rt=18 min). The fractions containing desired product were combined and concentrated under reduced pressure. The residue was re-dissolved in ACN (5 mL) and water (5 mL), lyophilized to afford J-1. LCMS (ESI) calc'd for $C_{95}H_{128}F_4N_{18}O_{21}$ $[(M-TFA^{-}+H)/2]^{+}$: 910.5, found 910.8.

Step B: Preparation of Intermediate J

To a solution of J-1 (23.0 mg, 0.012 mmol) in DCM (5 mL) was added TFA (1 mL, 13.0 mmol) at −20° C. The reaction mixture was stirred at room temperature for 2 h. The resulting solution was concentrated under reduced pressure and the residue was purified by Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 20% B to 60% B in 20 min; Detector: UV 210 nm; Rt=15 min). The fractions containing desired product were combined and concentrated under reduced pressure. The residue was re-dissolved in ACN (5 mL) and water (5 mL), and lyophilized to afford Intermediate J. LCMS (ESI) calc'd for $C_{92}H_{121}F_7N_{18}O_{21}$ $[M-TFA^{-}-TFA]^{+}$: 1719.9, found 1720.8.

Preparation of Intermediate K

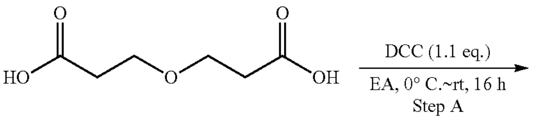

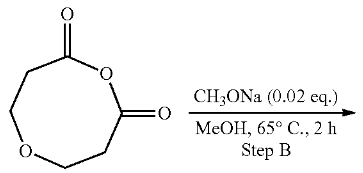

K-1

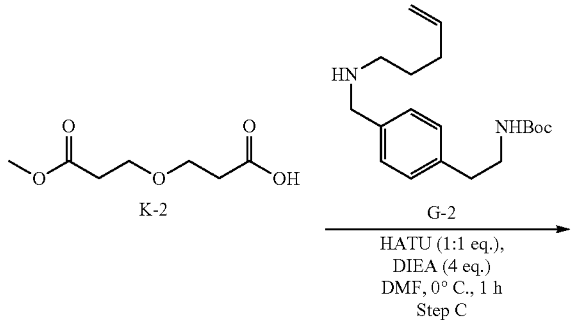

-continued

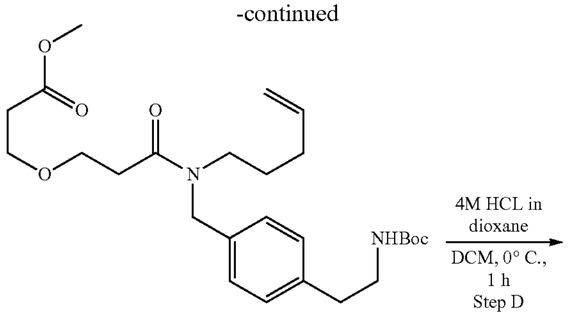

K-3

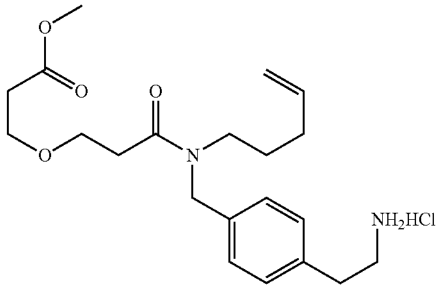

K

Step A: 1,5-dioxocane-2,8-dione K-1

To a stirred solution of 3,3'-oxydipropanoic acid (5 g, 30.8 mmol) in EA (50 mL) was added DCC (7.00 g, 33.9 mmol) at 0° C. under nitrogen atmosphere. The reaction solution was stirred at room temperature for 16 h. The reaction mixture was filtered and the filtrate was concentrated under reduced pressure to afford 1,5-dioxocane-2,8-dione K-1.

Step B: 3-(3-methoxy-3-oxopropoxy)propanoic acid K-2

To a solution of 1,5-dioxocane-2,8-dione K-1 (5.0 g, 34.7 mmol) in MeOH (50 mL) was added $CH_{30}Na$ (0.037 g, 0.694 mmol) at room temperature. The mixture was stirred at 65° C. for 2 h. The resulting mixture was concentrated under reduced pressure and the residue was purified by silica gel column chromatography, eluted with 0-7% MeOH in DCM to afford 3-(3-methoxy-3-oxopropoxy)propanoic acid K-2. LCMS (ESI) calc'd for $C_7H_{12}O_5[M+H]^+$: 177.1, found 177.0; $^1H$ NMR (300 MHz, $CD_3OD$) δ 3.78-3.65 (m, 7H), 2.66-2.48 (m, 4H).

Step C: Methyl 3-(3-((4-(2-((tert-butoxycarbonyl) amino)ethyl)benzyl)(pent-4-en-1-yl) amino)-3-oxo-propoxy)propanoate K-3

To a solution of 3-(3-methoxy-3-oxopropoxy)propanoic acid K-2 (1.25 g, 7.07 mmol) in DMF (20 mL) were added HATU (2.96 g, 7.77 mmol), tert-butyl 4-((pent-4-en-1-ylamino)methyl)phenethylcarbamate G-2 (2.25 g, 7.07 mmol) and DIEA (4.94 mL, 28.3 mmol) at 0° C. The mixture was stirred at 0° C. for 1 h. The resulting mixture was diluted with brine (80 mL), extracted with EA (2×80 mL), washed brine (2×30 mL), dried over anhydrous $MgSO_4$ and filtered, the filtrate was concentrated under reduced pressure. The residue was purified by silica gel column chromatography, eluted with gradient 10%-50% EA in PE. The fractions containing desired product were combined and concentrated to afford methyl 3-(3-((4-(2-((tert-butoxycarbonyl)amino) ethyl)benzyl)(pent-4-en-1-yl)amino)-3-oxopropoxy)propanoate K-3. LCMS (ESI) calc'd for $C_{26}H_{40}N_2O_6$ $[M+Na]^+$: 499.6, found 499.30. $^1H$ NMR (300 MHz, $CDCl_3$) δ 7.23-7.04 (m, 4H), 5.87-5.63 (m, 1H), 5.09-4.88 (m, 2H), 4.55 (d, J=15.9 Hz, 3H), 3.88-3.65 (m, 6H), 3.36 (td, J=9.5, 8.3, 4.6 Hz, 3H), 3.27-3.17 (m, 1H), 2.78 (q, J=6.6 Hz, 2H), 2.72-2.49 (m, 4H), 2.03 (h, J=6.4 Hz, 2H), 1.64 (td, J=7.6, 3.2 Hz, 2H), 1.44 (s, 9H).

Step D: Methyl 3-(3-((4-(2-aminoethyl)benzyl) (pent-4-en-1-yl)amino)-3-oxopropoxy)propanoate hydrochloride Intermediate K To a solution of methyl 3-(3-((4-(2-((tert-butoxycarbonyl) amino)ethyl)benzyl)(pent-4-en-1-yl)amino)-3-oxopropoxy) propanoate K-3 (2.2 g, 4.62 mmol) in DCM (9 mL) was added 4 N HCl in dioxane (16.5 mL) and stirred at 0° C. for 1 h. The resulting mixture was concentrated under reduced pressure to afford methyl 3-(3-((4-(2-aminoethyl)benzyl) (pent-4-en-1-yl)amino)-3-oxopropoxy)propanoate hydrochloride Intermediate K. LCMS (ESI) calc'd for $C_{21}H_{33}ClN_2O_4[M-HCl+H]^+$: 377.2, found 377.2.

Preparation of Intermediate L

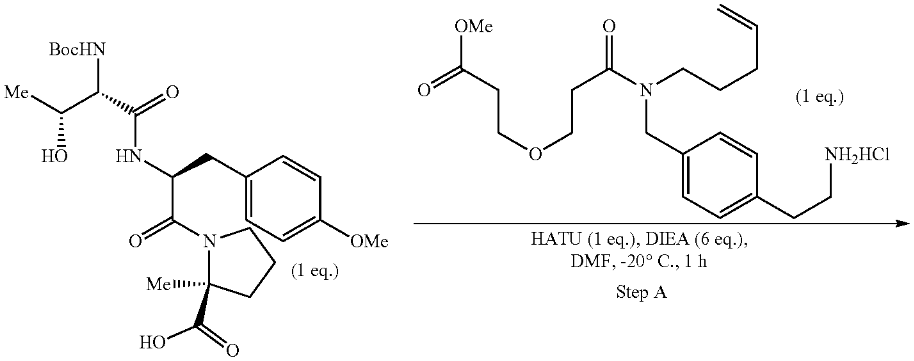

A

-continued
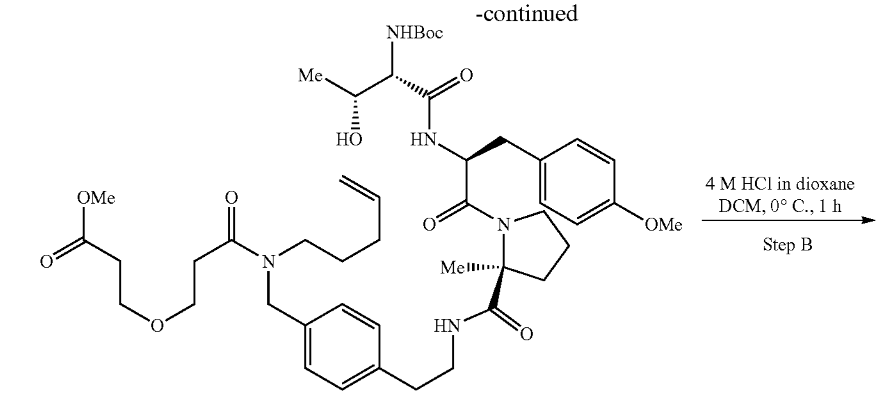
L-1
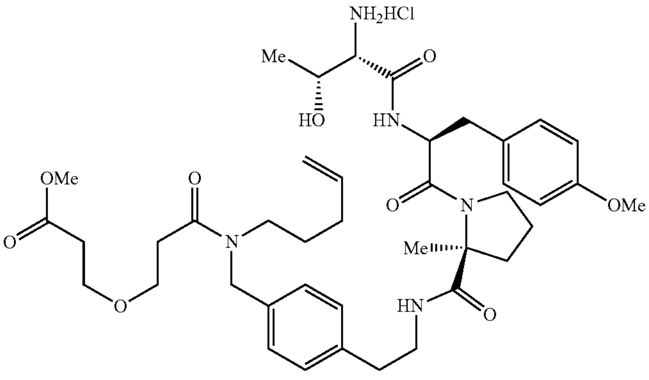
L-2
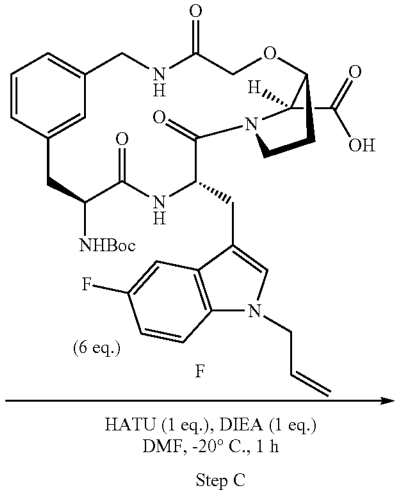
(6 eq.)
F
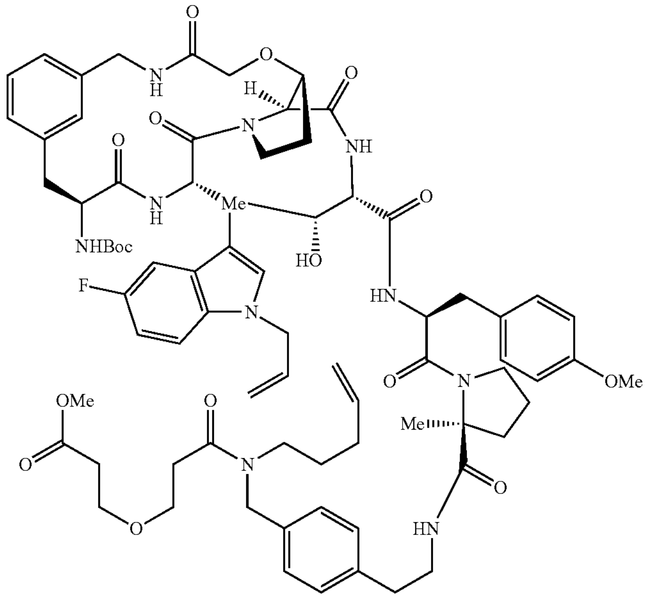
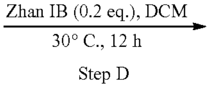
L-3

-continued
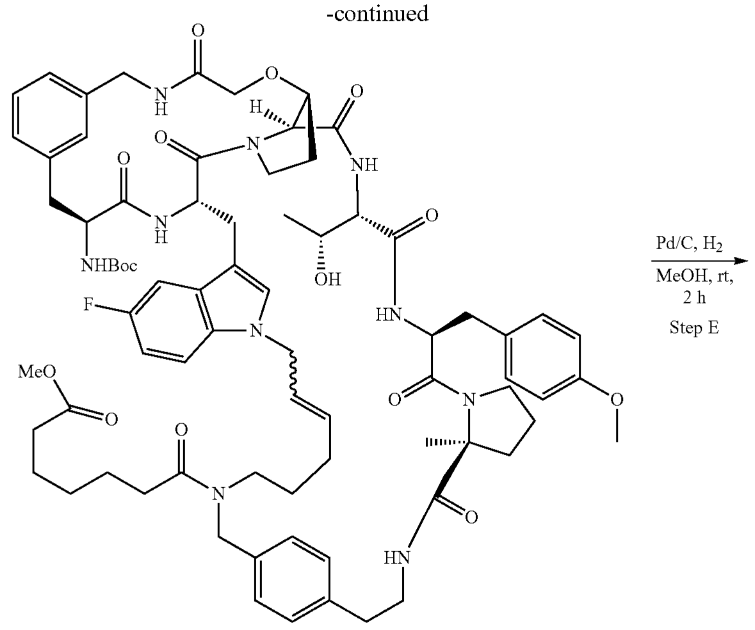
L-4
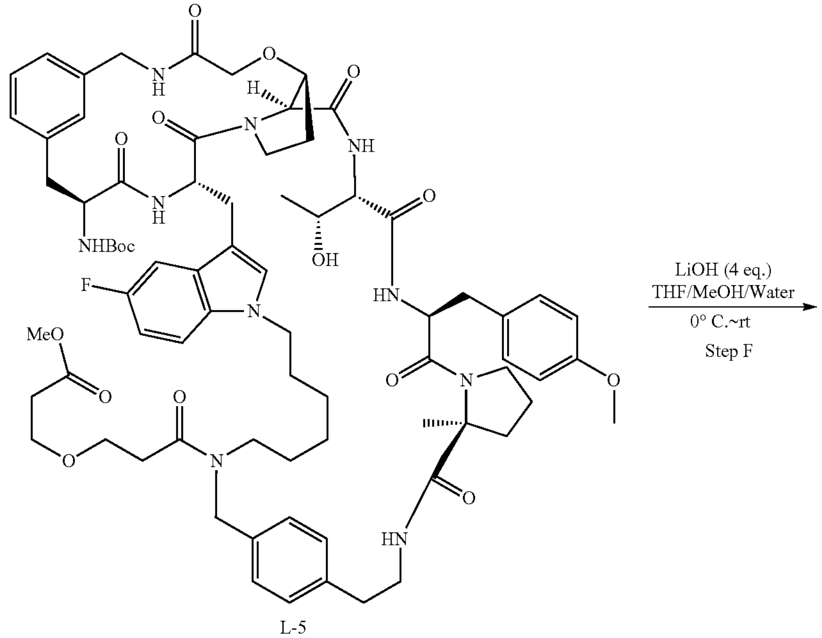
L-5

-continued
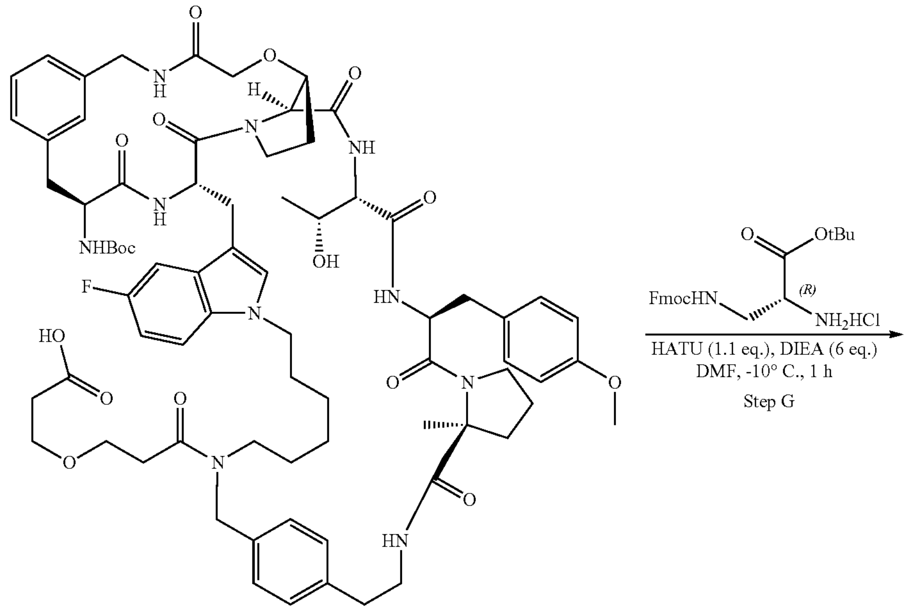
L-7
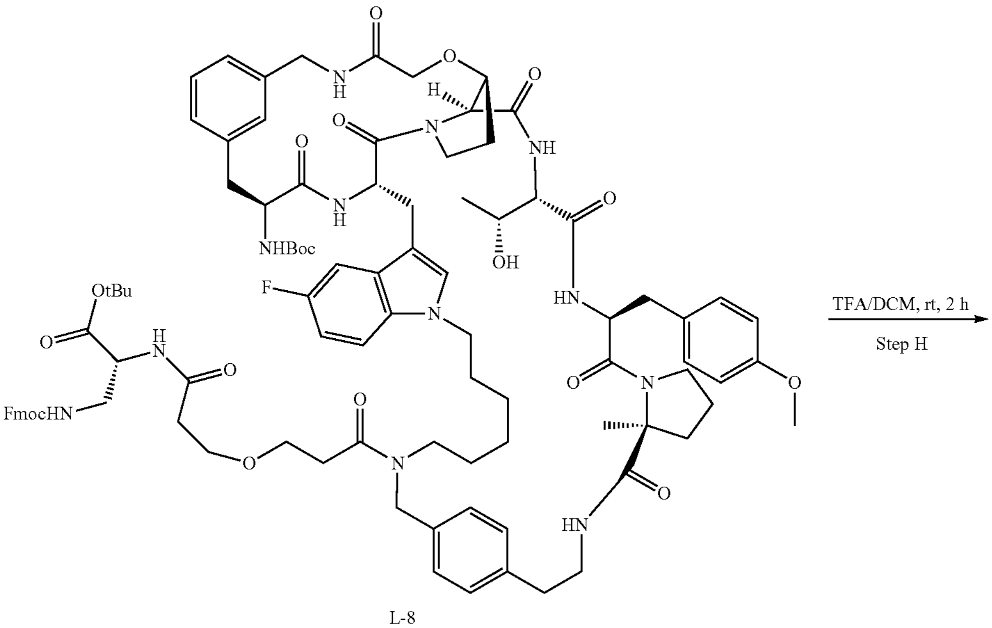
L-8

-continued
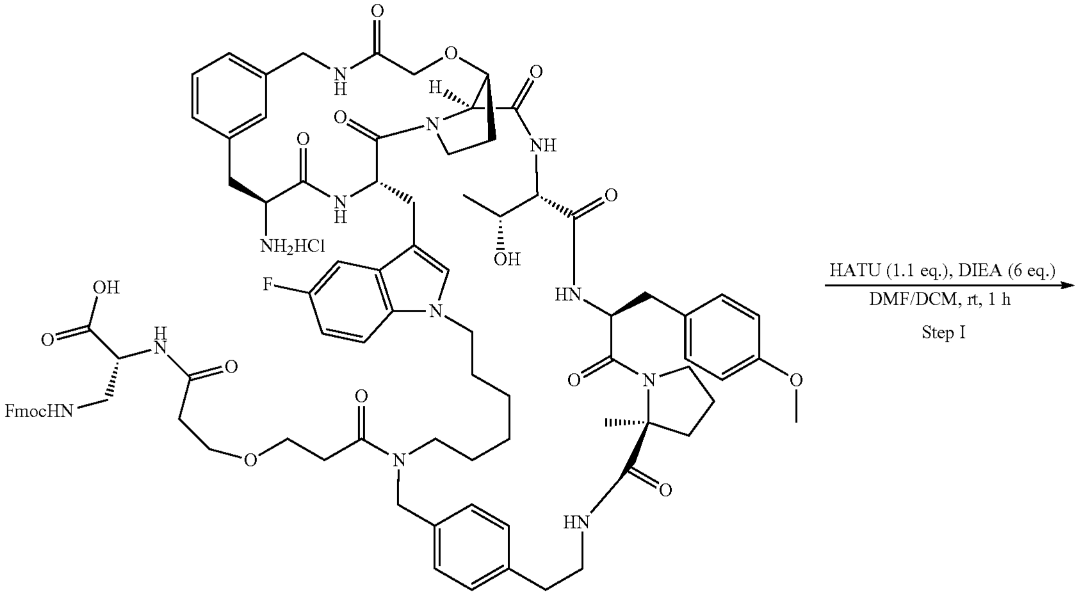
L-9
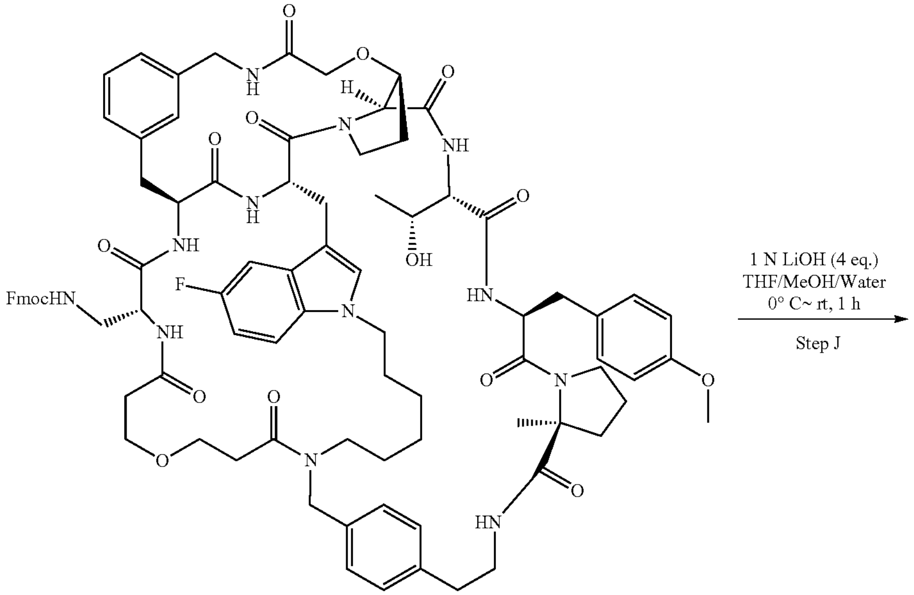
L-10

-continued

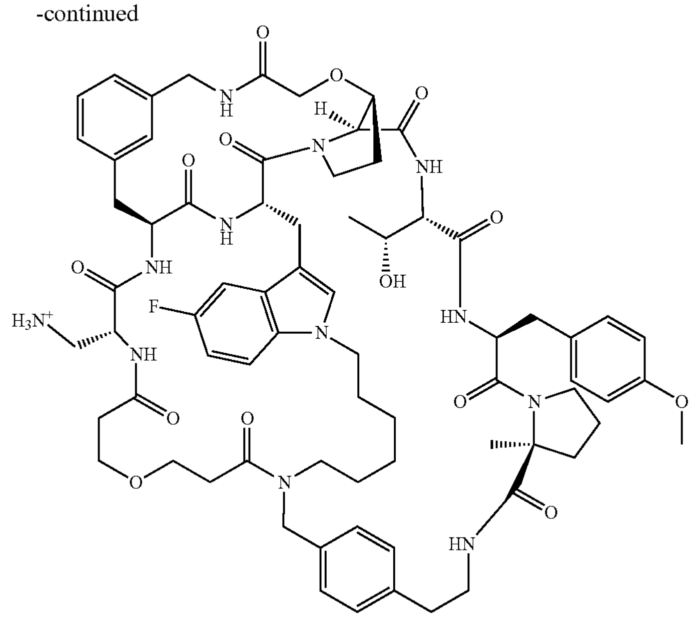

L

Step A: Preparation of Intermediate L-1

To a solution of (S)-1-((S)-2-((2S,3R)-2-((tert-butoxycarbonyl)amino)-3-hydroxybutanamido)-3-(4-methoxyphenyl)propanoyl)-2-methylpyrrolidine-2-carboxylic acid Intermediate A (2.2 g, 4.33 mmol) in DMF (40 mL) were added HATU (1.69 g, 4.33 mmol), methyl 3-(3-((4-(2-aminoethyl)benzyl)(pent-4-en-1-yl)amino)-3-oxopropoxy)propanoate hydrochloride Intermediate K (1.79 g, 4.33 mmol) and DIEA (4.54 mL, 26.0 mmol) at 0° C. The mixture solution was stirred at 0° C. for 1 h. The resulting mixture was diluted with brine (160 mL), extracted with EA (2×160 mL), washed brine (2×50 mL), dried over anhydrous $MgSO_4$ and filtered, the filtrate was concentrated under reduced pressure. The residue purified by silica gel column chromatography, eluted with gradient 1%-5% MeOH in DCM. The fractions containing desired product were combined and concentrated to afford L-1. LCMS (ESI) calc'd for $C_{46}H_{67}N_5O_{11}$ $[M+H]^+$: 866.5, found 866.6.

Step B: Preparation of Intermediate L-2

To a solution of L-1 (1.45 g, 1.674 mmol) in DCM (6 mL) was added 4 N HCl in dioxane (11 mL) and stirred at 0° C. for 1 h. The resulting mixture was concentrated under reduced pressure to afford L-2 LCMS (ESI) calc'd for $C_{41}H_{60}ClN_5O_9$$[M-HCl+H]^+$: 766.5, found. 766.5.

Step C: Preparation of Intermediate L-3

To a solution of F (1.16 g, 1.670 mmol) in DMF (20 mL) were added HATU (0.64 g, 1.67 mmol), L-2 (1.34 g, 1.67 mmol) and DIEA (1.75 mL, 10.0 mmol) at 0° C. The mixture was stirred at −20° C. for 1 h. The resulting mixture was diluted with brine (80 mL), extracted with EA (2×80 mL), washed brine (2×30 mL), dried over anhydrous $MgSO_4$ and filtered, the filtrate was concentrated under reduced pressure. The residue was purified by silica gel column chromatography, eluted with gradient 10%-10% MeOH in DCM. The fractions containing desired product were combined and concentrated to afford L-3. LCMS (ESI) calc'd for $C_{77}H_{99}FN_{10}O_{16}$ $[M+H]^+$: 1439.8, found 1440.0.

Step D: Preparation of Intermediate L-4

To a stirred solution of Zhan 1B (0.168 g, 0.229 mmol) in DCM (1100 mL) was stirred at room temperature under nitrogen atmosphere. The mixture was stirred at 30° C. for 0.5 h and was added a solution of L-3 (1.65 g, 1.146 mmol) in DCM (10 mL) in 30 min. The reaction mixture was stirred at 30° C. for 12 h under nitrogen atmosphere and concentrated under reduced pressure. The residue was purified by silica gel column chromatography, eluted with gradient 0-10% MeOH in DCM. The fractions containing desired product were combined and concentrated to afford L-4. LCMS (ESI) calc'd for $C_{75}H_{95}FN_{10}O_{16}$ $[M+H]^+$: 1411.7, found 1411.6.

Step E: Preparation of Intermediate L-5

To a stirred solution of L-4 (1.39 g, 0.985 mmol) in MeOH (30 mL) was added Pd/C (0.14 g, 0.132 mmol) (dry, 10% wt). The reaction mixture was degassed with hydrogen for three times and stirred at room temperature for 4 h under hydrogen 1.5 atm. The resulting mixture was filtered and the filtrate was concentrated under reduced pressure to afford L-5. LCMS (ESI) calc'd for $C_{75}H_{97}FN_{10}O_{16}$ $[M+H]^+$: 1413.7, found 1414.0.

Step F: Preparation of Intermediate L-6

To a solution of L-5 (1.18 g, 0.835 mmol) in THF (10 mL) were added MeOH (3 mL), Water (3 mL) and 1 M LiOH (3.34 mL, 3.34 mmol) at 0° C. The reaction mixture was stirred at room temperature for 1 h. The resulting mixture was added 1 M HCl (3.34 mL) at 0° C. The mixture was concentrated under reduced pressure to afford L-6. The crude was directly used for next step without further purification. LCMS (ESI) calc'd for $C_{74}H_{95}FN_{10}O_{16}$ $[(M+Na]^+$: 1421.70, found 1421.9.

Step G: Preparation of Intermediate L-7

To a solution of L-6 (1.17 g, 0.835 mmol) in DMF (20 mL) were added HATU (0.35 g, 0.92 mmol), (R)-tert-butyl 3-((((9H-fluoren-9-yl)methoxy)carbonyl)amino)-2-aminopropanoate hydrochloride (0.350 g, 0.835 mmol) and DIEA (0.875 mL, 5.01 mmol) at 0° C. The reaction mixture was stirred at −10° C. for 1 h. The resulting mixture was diluted with brine (80 mL), extracted with EA (2×80 mL), washed brine (2×100 mL), dried over anhydrous $MgSO_4$ and filtered, the filtrate was concentrated under reduced pressure. The residue was purified by silica gel column chromatography, eluted with gradient 1%-12% MeOH in DCM. The fractions containing desired product were combined and concentrated to afford L-7. LCMS (ESI) calc'd for $C_{96}H_{119}FN_{12}O_{19}$ $[M+Na]^+$: 1785.9, found 1786.7.

Step H: Preparation of Intermediate L-8

To a solution of L-7 (500 mg, 0.283 mmol) in DCM (10 mL) was added TFA (10 mL) at −10° C. The reaction mixture was stirred at room temperature for 2 h. The resulting mixture was concentrated under reduced pressure. The residue was purified by Flash (Column: Flash $C^{18}$ 330 g; Mobile Phase A: water (0.1% TFA), Mobile Phase B: ACN; Flow rate: 100 mL/min; Gradient: 2% B to 2% B in 5 min, 20% B to 50% B in 20 min; Detector: UV 220 nm; Rt=18 min). The product containing fractions were combined, concentrated under reduced pressure and the residue was re-dissolved in DCM (50 mL) and toluene (50 mL). The mixture was then concentrated under reduced pressure and the residue was re-dissolve in DCM (20 mL) and HCl (4 M in dioxane, 0.2 mL). The resulting mixture was concentrated under reduced pressure and the residue was re-dissolve in ACN (30 mL) and water (30 mL), and added 1 M HCl (0.3 mL) at 0° C. and lyophilized to afford L-8. LCMS (ESI) calc'd for $C_{87}H_{104}ClFN_{12}O_{17}$ $[M-HCl+H]^+$: 1607.8, found 1608.6.

Step I: Preparation of Intermediate L-9

To a solution of I-8 (400 mg, 0.243 mmol) in DMF (40 mL) were added DIEA (189 mg, 1.460 mmol), DCM (500 mL) and HATU (102 mg, 0.268 mmol) at room temperature. The reaction mixture was stirred at room temperature for 1 h. The resulting mixture was concentrated under reduced pressure to remove DCM, and then diluted with brine (160 mL), extracted with EA (2×160 mL), washed brine (2×160 mL), dried over anhydrous $MgSO_4$ and filtered, the filtrate was concentrated under reduced pressure. The residue was purified by silica gel column chromatography, eluted with gradient 1%-12% MeOH in DCM. The fractions containing desired product were combined and concentrated to afford I-9. LCMS (ESI) calc'd for $C_{87}H_{101}FN_{12}O_{16}$ $[M+H]^+$: 1589.8, found 1590.6.

Step J: Preparation of Intermediate L-10

To a solution of I-9 (270 mg, 0.170 mmol) in THF (5 mL) were added MeOH (1.5 mL), Water (1.5 mL) and 1 M LiOH (0.68 mL, 0.68 mmol) at 0° C. The mixture was stirred at room temperature for 1 h. The resulting mixture was concentrated under reduced pressure. The residue was directly purified by Flash (Column: Flash $C^{18}$ 330 g; Mobile Phase A: water, Mobile Phase B: ACN; Flow rate: 100 mL/min; Gradient: 2% B to 2% B in 5 min, 20% B to 50% B in 20 min; Detector: UV 220 nm; Rt=20 min) and concentrated under reduced pressure. The residue was re-dissolved in ACN (30 mL) and water (30 mL), then added 1 M HCl (0.2 mL) at 0° C. and lyophilized to afford I-10. LCMS (ESI) calc'd for $C_{72}H_{92}ClFN_{12}O_{14}$ $[M-Cl-]^+$: 1367.7, found 1367.8. 6 g of AG MP-1 Resin (cat #141-1841 BIO-RAD) was packed in column. The column was washed with water (2×10 mL), followed by 20% ACN in water (2×10 mL). A solution of above 17 mg TFA salt in 65% ACN in water (2 mL×2) was loaded onto the resin column, the column was eluted with 65% ACN in water (80 mL). The eluents were combined and lyophilized to give I HCl salt, LCMS (ESI) calc'd for $C_{72}H_{92}ClFN_{12}O_{14}$ $[M-Cl^-]^+$: 1367.7, found 1367.8.

Preparation of Intermediate M

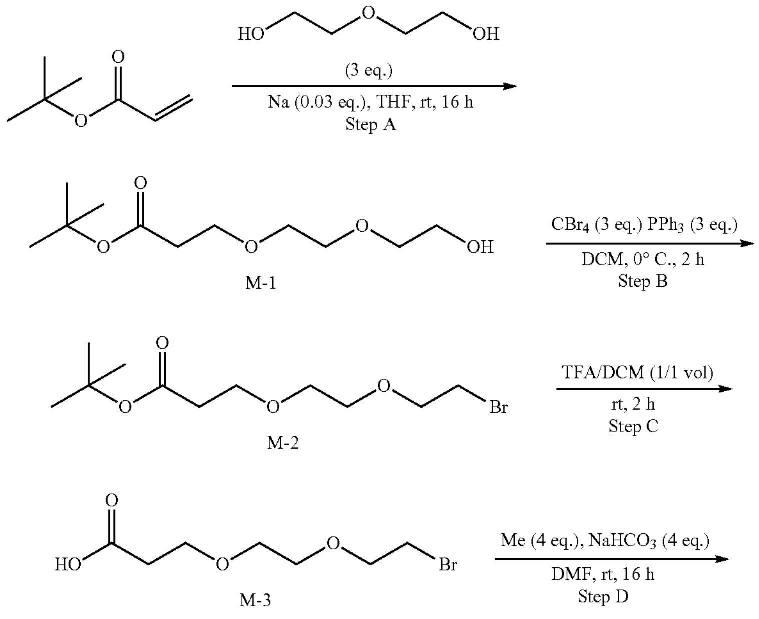

-continued

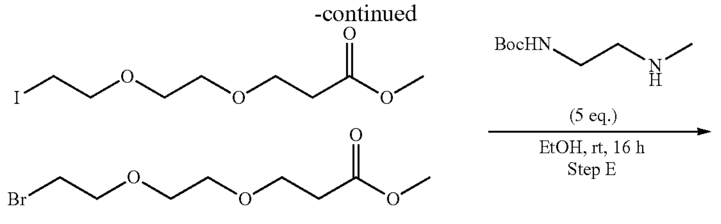

1:1 (1 eq.)
M-4

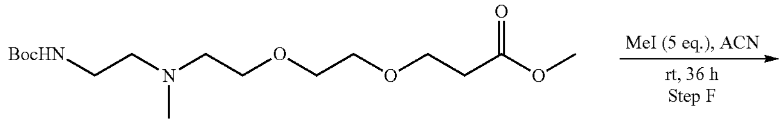

M-5

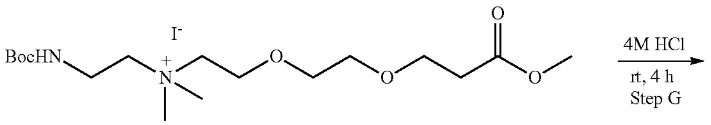

M-6

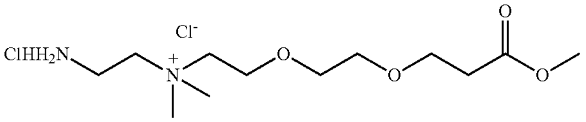

M

Step A: Tert-butyl 3-(2-(2-hydroxyethoxy)ethoxy)propanoate M-1

To a stirred mixture of 2, 2'-oxydiethanol (24.8 g, 234 mmol) in THF (150 mL) was added sodium (0.054 g, 2.34 mmol) at ambient temperature and added tert-butyl acrylate (10 g, 78 mmol) at ambient temperature until the sodium was dissolved. The resulting mixture was stirred for 16 h at ambient temperature. The reaction mixture was quenched by the addition of sat $NH_4Cl$ (100 mL). The mixture was extracted with EA (3×100 mL). The organic extracts were combined, washed with brine (100 mL), dried over anhydrous $Na_2SO_4$ and filtered. The filtrate was concentrated under vacuum. The residue was purified by silica gel column chromatography, eluted with gradient 40%-60% EA in PE. The fractions containing desired product were combined and concentrated under reduced pressure to afford tert-butyl 3-(2-(2-hydroxyethoxy)ethoxy)propanoate M-1. $^1H$ NMR (300 MHz, $CDCl_3$) δ 3.79-3.70 (m, 4H), 3.68-3.56 (m, 6H), 2.51 (t, J=6.3 Hz, 2H), 2.37 (s, 1H), 1.45 (s, 9H).

Step B: Tert-butyl 3-(2-(2-bromoethoxy)ethoxy)propanoate M-2

To a stirred mixture of tert-butyl 3-(2-(2-hydroxyethoxy)ethoxy)propanoate M-1 (5.00 g, 21.3 mmol) and $CBr_4$ (21.2 g, 64.0 mmol) in DCM (50 mL) was added $PPh_3$ (16.8 g, 64.0 mmol) at 0° C. The resulting mixture was stirred at 0° C. for 2 h. The reaction mixture was quenched by the addition of water (100 mL). The solid was collected by filtration. The filtrate was extracted with EA (3×100 mL). The organic extracts were combined, washed with saturated aqueous sodium chloride (100 mL), dried over anhydrous $Na_2SO_4$ and filtered. The filtrate was concentrated under vacuum. The residue was purified by silica gel column chromatography, eluted with gradient 20%-50% EA in PE. The fractions containing desired product were combined and concentrated under reduced pressure to afford tert-butyl 3-(2-(2-bromoethoxy)ethoxy)propanoate M-2. $^1H$ NMR (400 MHz, $CD_3OD$) δ 3.81 (t, J=6.0 Hz, 2H), 3.73 (t, J=6.4 Hz, 2H), 3.68-3.60 (m, 4H), 3.52 (t, J=6.0 Hz, 2H), 2.50 (t, J=6.2 Hz, 2H), 1.48 (s, 9H).

Step C: 3-(2-(2-Bromoethoxy)ethoxy)propanoic acid M-3

To a stirred mixture of tert-butyl 3-(2-(2-bromoethoxy)ethoxy)propanoate (4.90 g, 16.49 mmol) in DCM (25 mL) was added TFA (25 mL) at 0° C. The resulting mixture was stirred for 2 h at ambient temperature. The solution was evaporated under vacuum to afford 3-(2-(2-bromoethoxy)ethoxy)propanoic acid M-3. $^1H$ NMR (300 MHz, DMSO-$d_6$) δ 3.78-3.70 (m, 2H), 3.67-3.48 (m, 8H), 2.46 (t, J=6.3 Hz, 2H).

Step D: Methyl 3-(2-(2-bromoethoxy)ethoxy)propanoate and methyl 3-(2-(2-iodoethoxy)ethoxy)propanoate (1:1) M-4

To a stirred mixture of 3-(2-(2-bromoethoxy)ethoxy)propanoic acid M-3 (3.50 g, 14.5 mmol) and $NaHCO_3$ (4.88 g, 58.1 mmol) in DMF (20 mL) was added MeI (8.24 g, 58.1 mmol) at 0° C. The resulting mixture was stirred at ambient temperature for 16 h. The reaction mixture was quenched by the addition of water (200 mL). The mixture was extracted with EA (3×100 mL). The organic extracts were combined, washed with brine (100 mL), dried over anhydrous $Na_2SO_4$ and filtered. The filtrate was concentrated under vacuum. The residue was purified by silica gel column chromatography, eluted with gradient 20%-45% EA in PE. The fractions containing desired product were combined and concentrated under reduced pressure to afford the mixture of methyl-3-(2-(2-bromoethoxy)ethoxy)propanoate and methyl-3-(2-(2-iodoethoxy)ethoxy)propanoate (1:1) M-4. LCMS (ESI) calc'd for $C_8H_{15}BrO_4$ $[M+H]^+$: 255.0, 257.0, found 255.1 and 257.1; LCMS (ESI) calc'd for $C_8H_{15}IO_4$ $[M+H]^+$: 303.0, found 303.0. $^1H$ NMR (400 MHz, $CDCl_3$) δ 3.86-3.75 (m, 4H), 3.72 (s, 3H), 3.69-3.63 (m, 4H), 3.50 (t, J=6.4 Hz, 1H), 3.28 (t, J=6.8 Hz, 1H), 2.64 (t, J=6.4 Hz, 2H).

Step E: Methyl 2,2,8-trimethyl-4-oxo-3,11,14-trioxa-5,8-diazaheptadecan-17-oate M-5

To a solution of methyl 3-(2-(2-bromoethoxy)ethoxy) propanoate compound with methyl 3-(2-(2-iodoethoxy) ethoxy)propanoate M-4 (1:1) (400.0 mg, 1.436 mmol) in EtOH (4 mL) was added tert-butyl (2-(methylamino)ethyl) carbamate (1251 mg, 7.18 mmol) at RT. The mixture was stirred at RT for 16 h. The resulting mixture was concentrated under reduced pressure and the residue was purified by silica gel column chromatography, eluted with gradient 0-5% MeOH in DCM. The fractions containing desired product were combined and concentrated to afford methyl 2,2,8-trimethyl-4-oxo-3,11,14-trioxa-5,8-diazaheptadecan-17-oate M-5. LCMS (ESI) calc'd for $C_{16}H_{32}N_2O_6$ $[M+H]^+$: 349.2, found 349.3. $^1H$ NMR (400 MHz, $CDCl_3$): δ 3.76 (t, J=6.5 Hz, 2H), 3.69 (s, 3H), 3.67-3.51 (m, 6H), 3.21 (q, J=6.1, 5.6 Hz, 2H), 2.68-2.48 (m, 6H), 2.30 (s, 3H), 1.44 (s, 9H).

Step F: 2-((Tert-butoxycarbonyl)amino)-N-(2-(2-(3-methoxy-3-oxopropoxy)ethoxy)ethyl)-N,N-dimethylethanaminium iodide M-6

To a stirred solution of methyl 2,2,8-trimethyl-4-oxo-3,11,14-trioxa-5,8-diazaheptadecan-17-oate M-5 (440.0 mg, 1.263 mmol) in ACN (10 mL) was added MeI (0.395 mL, 6.31 mmol). The reaction mixture was stirred at RT for 36 h. The resulting mixture was concentrated under reduced pressure to afford 2-((tert-butoxycarbonyl)amino)-N-(2-(2-(3-methoxy-3-oxopropoxy)ethoxy)ethyl)-N,N-dimethylethanaminium iodide M-6. LCMS (ESI) calc'd for $C_{17}H_{35}IN_2O_6[M-I^-]^+$: 363.3, found 363.3.

Step G: 2-amino-N-(2-(2-(3-methoxy-3-oxopropoxy)ethoxy)ethyl)-N,N-dimethylethanaminium chloride hydrochloride M To a stirred solution of 2-((tert-butoxycarbonyl)amino)-N-(2-(2-(3-methoxy-3-oxopropoxy)ethoxy)ethyl)-N,N-dimethylethanaminium iodide M-6 (600 mg, 1.224 mmol) in 4 M HCl in dioxane (12 mL) was stirred at RT for 4 h. The resulting mixture was concentrated under reduced pressure. The residue was dissolved in $Et_{20}$, stirred at RT for 2 h. Filtered solids, washed with $Et_2O$ (100 mL) to afford 2-amino-N-(2-(2-(3-methoxy-3-oxopropoxy)ethoxy)ethyl)-N,N-dimethylethanaminium chloride hydrochloride M. LCMS (ESI) calc'd for $C_{12}H_{28}C_{12}N204$ $[M-HCl—Cl^-]^+$: 263.2, found 263.3.

Preparation of Intermediate N

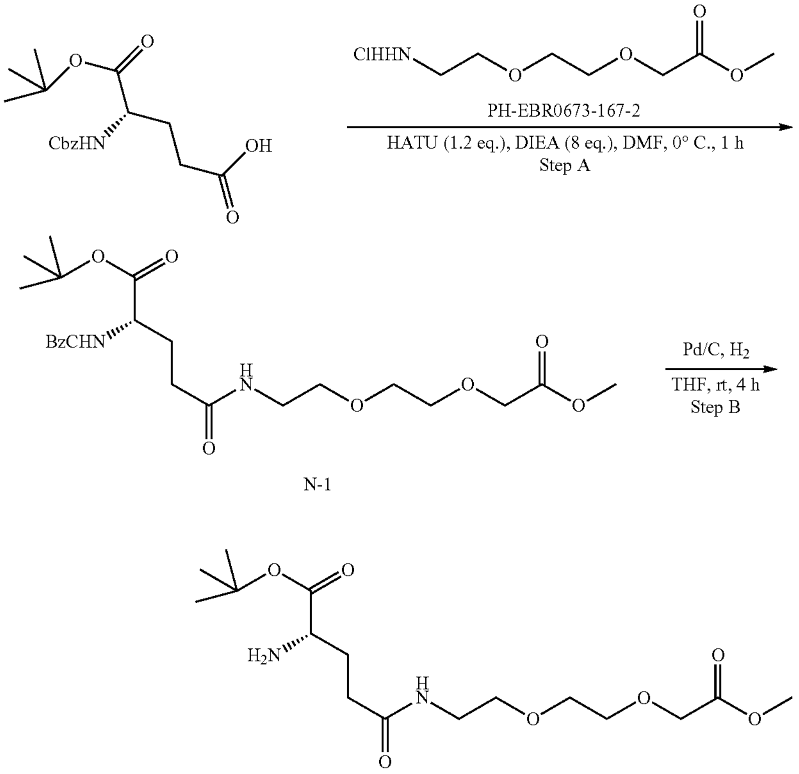

N-1

N

Step A: (S)-methyl 5-(tert-butoxycarbonyl)-3,8-dioxo-1-phenyl-2,12,15-trioxa-4,9-diazaheptadecan-17-oate N-1

To a stirred solution of (S)-4-(((benzyloxy)carbonyl) amino)-5-(tert-butoxy)-5-oxopentanoic acid (8.68 g, 25.7 mmol) in DMF (50 mL) were added HATU (10.7 g, 28.1 mmol), methyl 2-(2-(2-aminoethoxy)ethoxy)acetate hydrochloride (5.00 g, 23.40 mmol) and DIEA (32.7 mL, 187 mmol) at 0° C. under nitrogen atmosphere. The reaction solution was stirred at 0° C. for 1 h. The reaction was quenched with water (200 mL), extracted with EA (2×100 mL). The combined organic layer was washed with brine (3×200 mL), dried over anhydrous $Na_2SO_4$ and filtered. The filtrate was concentrated under reduced pressure and the residue was purified by silica gel column chromatography, eluted with 0-30% EA in PE to afford (S)-methyl 5-(tert-butoxycarbonyl)-3,8-dioxo-1-phenyl-2,12,15-trioxa-4,9-diazaheptadecan-17-oate N-1. LCMS (ESI) calc'd for $C_{24}H_{36}N_2O_9$[M+H]$^+$: 497.2, found 497.2; $^1$H NMR (400 MHz, $CDCl_3$): δ 7.37-7.28 (m, 5H), 5.10 (s, 2H), 4.30-4.16 (m, 1H), 4.14 (s, 2H), 3.74 (s, 3H), 3.72-3.67 (m, 2H), 3.67-3.62 (m, 2H), 3.69-3.63 (m, 2H), 3.50-3.36 (m, 2H), 2.37-1.84 (m, 4H), 1.45 (s, 9H).

Step B: (S)-tert-butyl 2-amino-5-((2-(2-(2-methoxy-2-oxoethoxy)ethoxy)ethyl)amino)-5-oxopentanoate N To a solution of (S)-methyl 5-(tert-butoxycarbonyl)-3,8-dioxo-1-phenyl-2,12,15-trioxa-4,9-diazaheptadecan-17-oate N-1 (9 g, 18.13 mmol) in THF (150 mL) was added Pd/C (900 mg, 0.846 mmol, dry, 10% wt) at room temperature under nitrogen atmosphere. The mixture was degassed with hydrogen for 3 times and stirred for 16 h at room temperature. The reaction mixture was filtered and the filtrate was concentrated under reduced pressure to afford (S)-tert-butyl 2-amino-5-((2-(2-(2-methoxy-2-oxoethoxy)ethoxy)ethyl)amino)-5-oxopentanoate Intermediate N. LCMS (ESI) calc'd for $C_{16}H_{30}N_2O_7$ [M+H]$^+$: 363.2, found 363.2.

Preparation of Intermediate O

Synthesis of Example 1

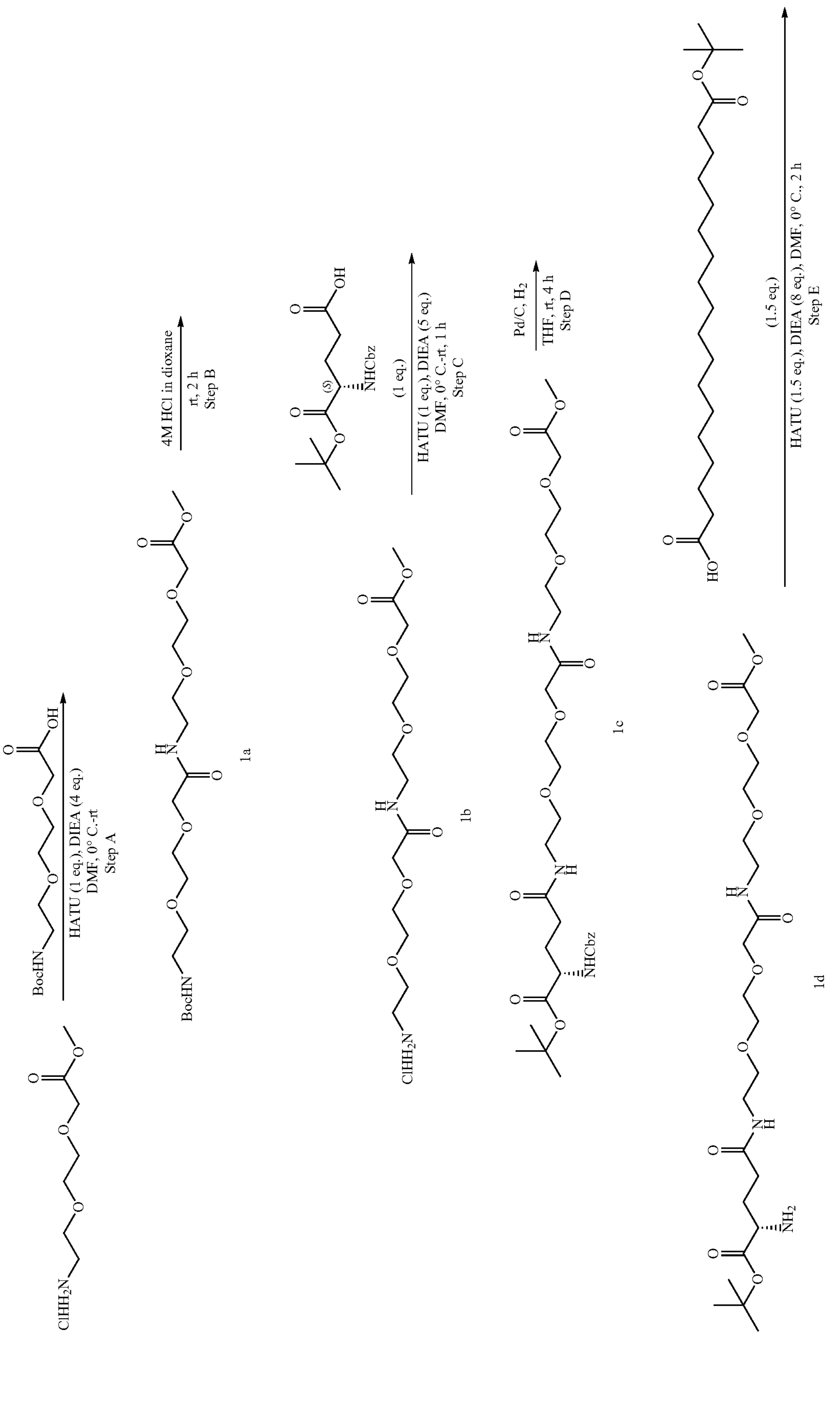
HATU (1 eq.), DIEA (4 eq.)
DMF, 0° C.-rt
Step A
1a
4M HCl in dioxane
rt, 2 h
Step B
1b
(1 eq.)
HATU (1 eq.), DIEA (5 eq.)
DMF, 0° C.-rt, 1 h
Step C
1c
Pd/C, $H_2$
THF, rt, 4 h
Step D
1d
(1.5 eq.)
HATU (1.5 eq.), DIEA (8 eq.), DMF, 0° C., 2 h
Step E -continued
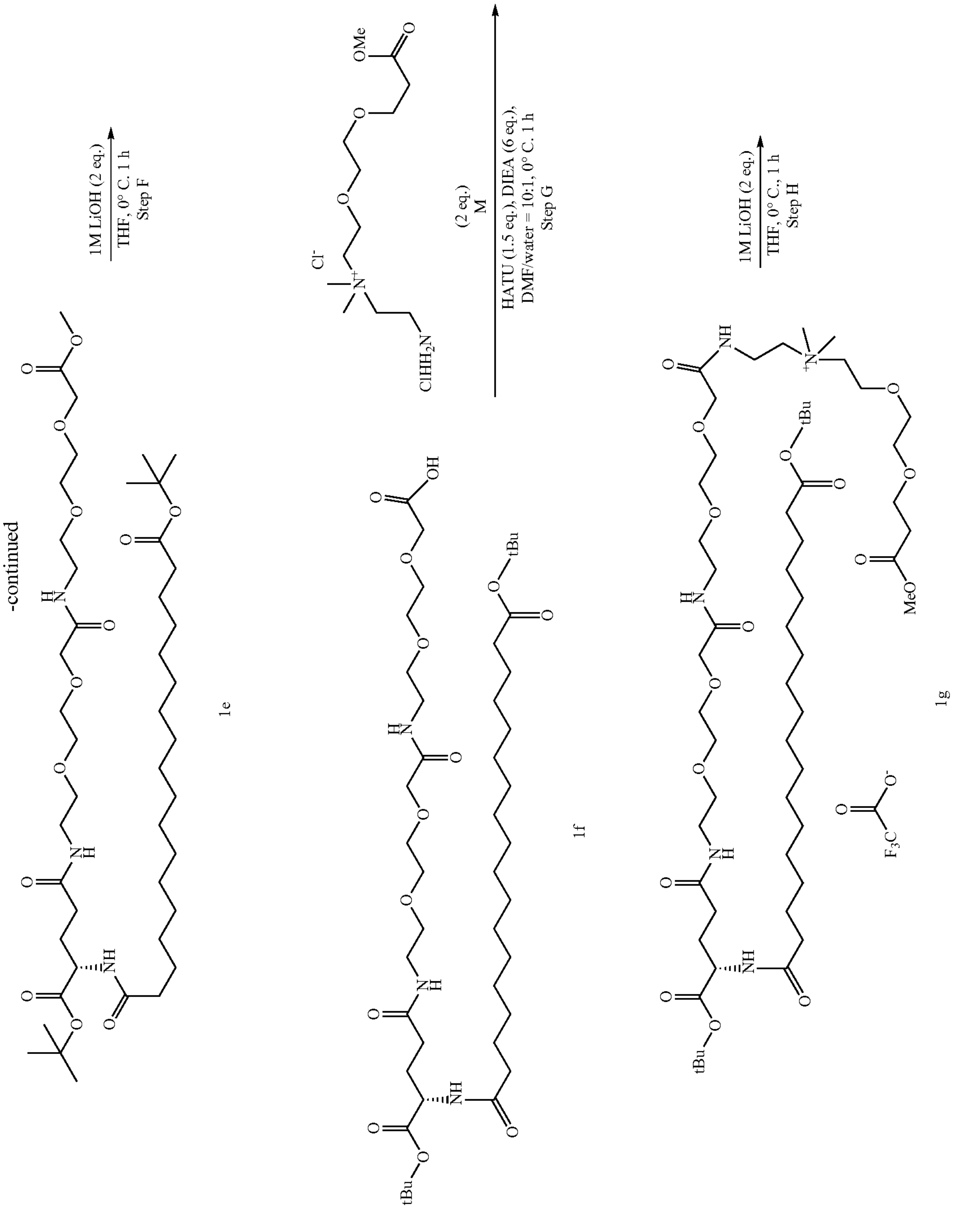
1e
1f
1g -continued
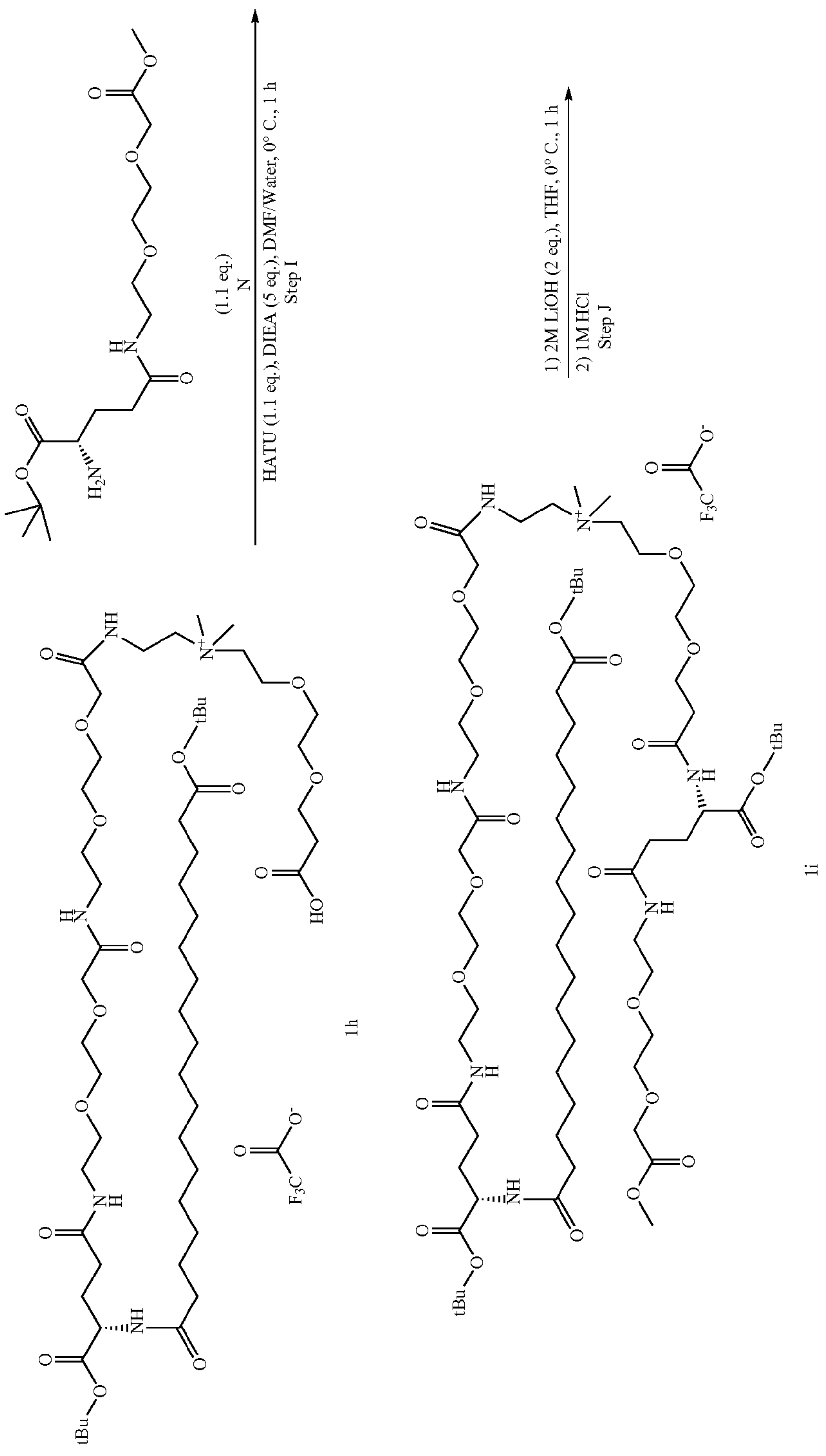
1h
1i -continued
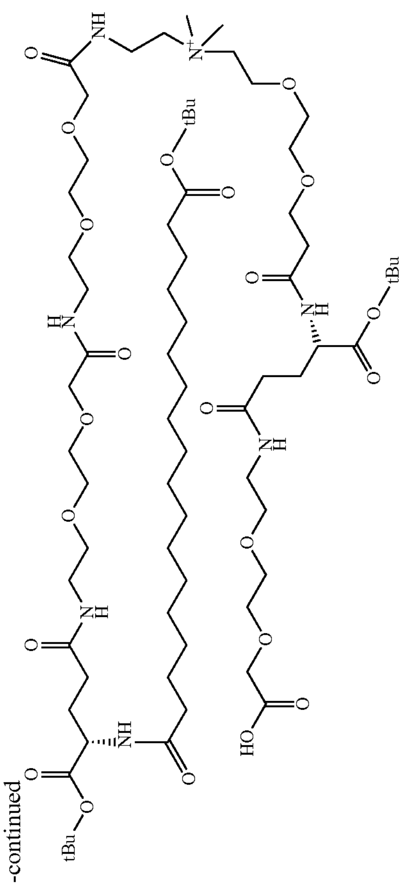
1j
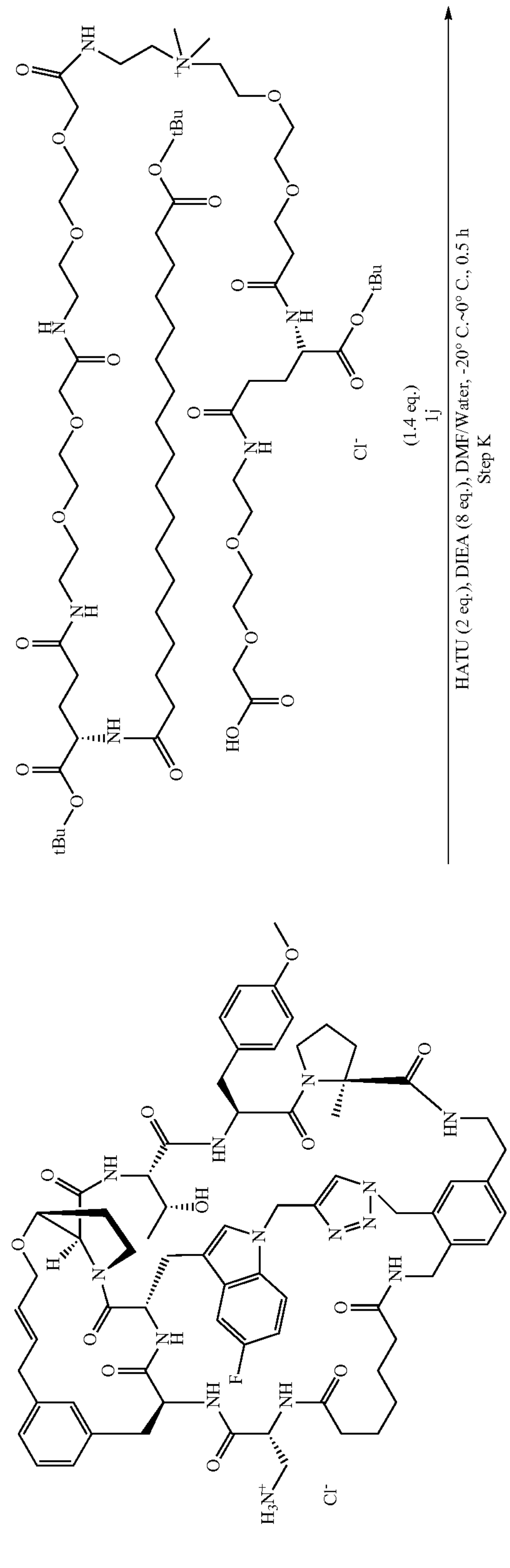
D -continued
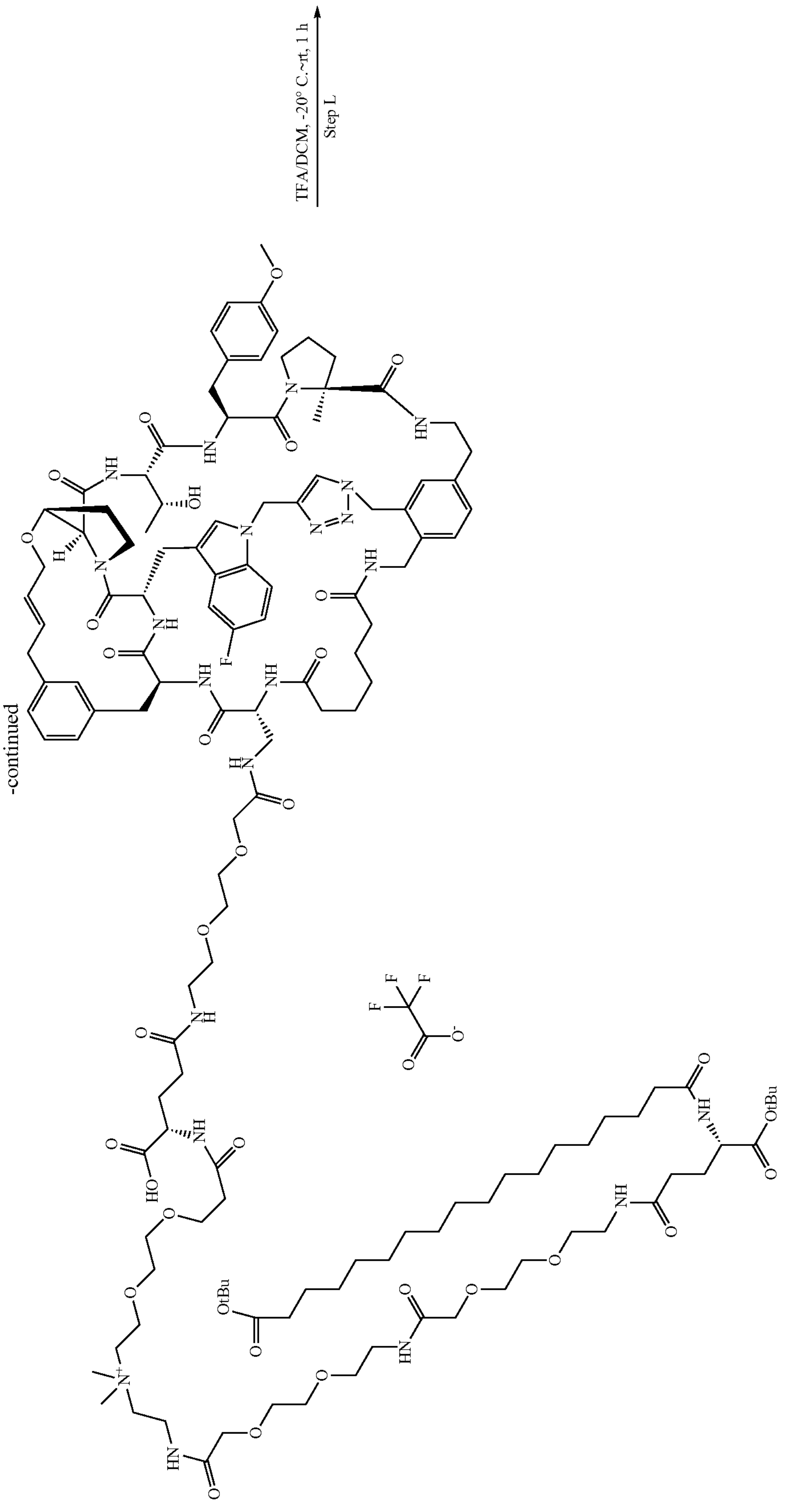
1k -continued
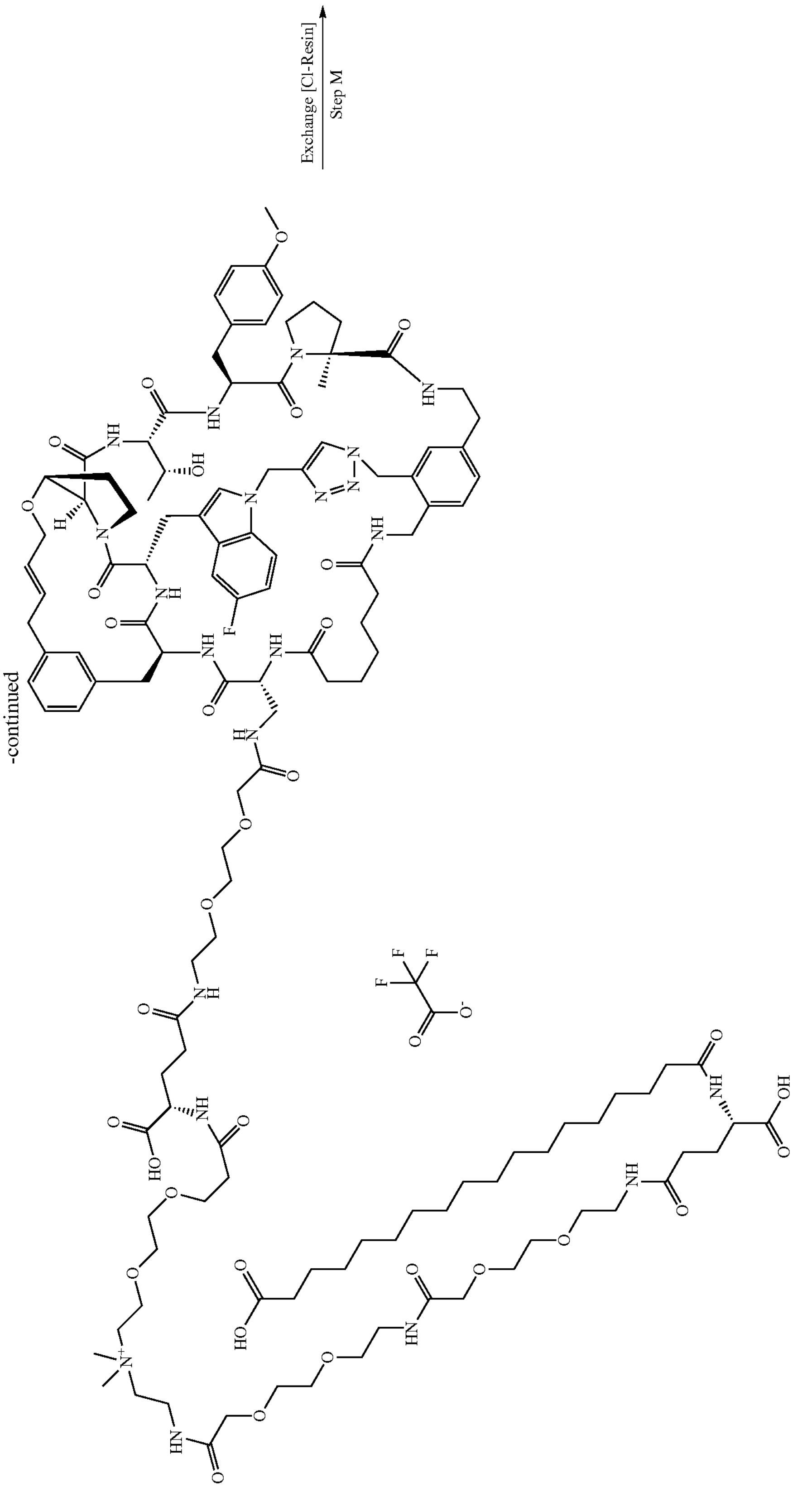
11

-continued
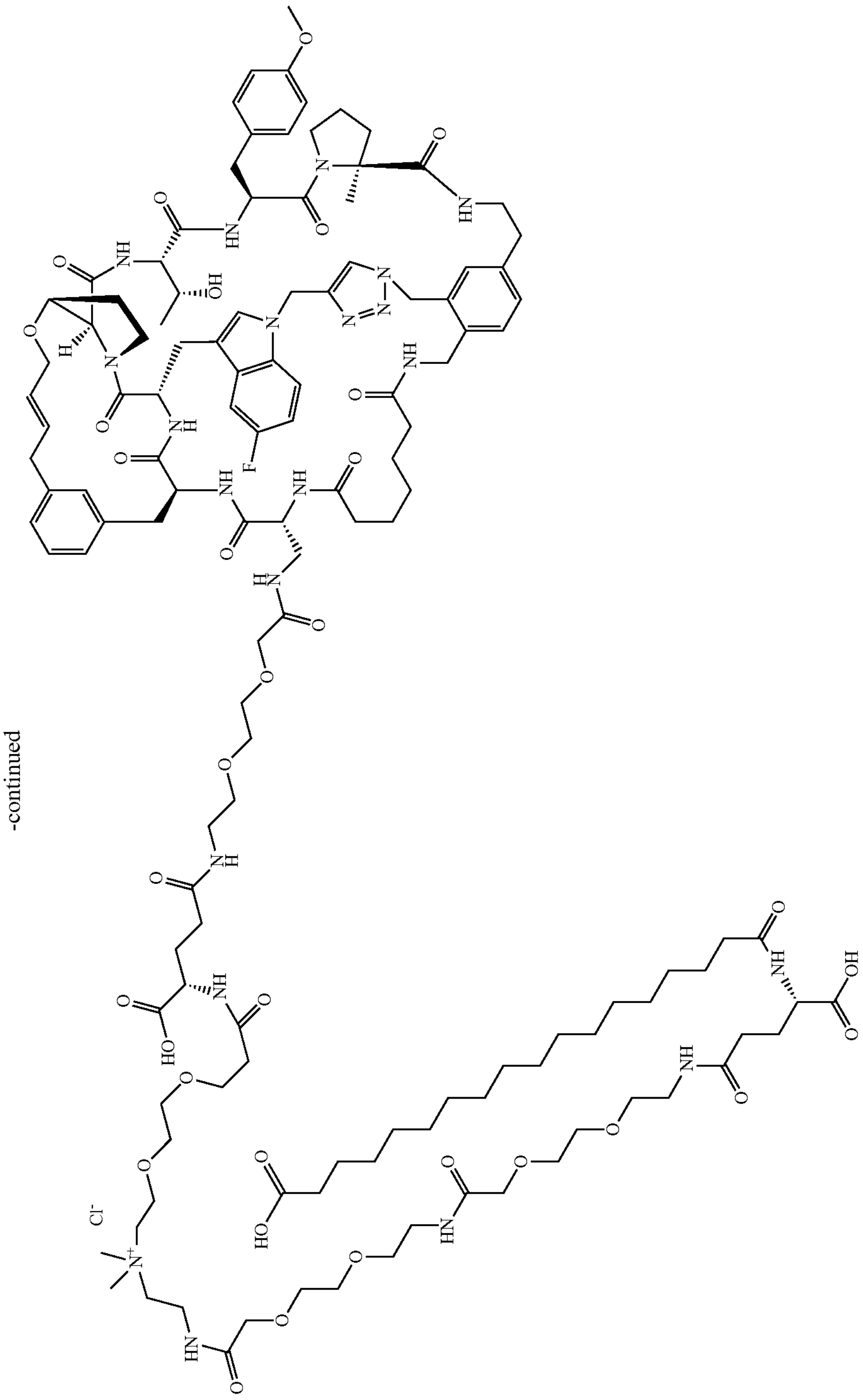
Example 1

Step A: Methyl 2,2-dimethyl-4,13-dioxo-3,8,11,17,20 pentaoxa-5,14-diazadocosan-22-oate 1a To a solution of 2,2-dimethyl-4-oxo-3,8,11-trioxa-5-azatridecan-13-oic acid (3.33 g, 12.6 mmol) in DMF (30 mL) were added methyl 2-(2-(2-aminoethoxy)ethoxy)acetate hydrochloride (2.70 g, 12.6 mmol), HATU (4.80 g, 12.6 mmol) and DIEA (6.53 g, 50.5 mmol) at 0° C. The mixture was stirred at RT for 1 h. The mixture was diluted with brine (120 mL), extracted with EA (2×120 mL), washed brine (2×50 mL), dried over anhydrous $MgSO_4$ and filtered, the filtrate was concentrated under reduced pressure. The residue was purified by silica gel column chromatography, eluted with gradient 10%-8% MeOH in DCM. The fractions containing desired product were combined and concentrated to give methyl 2,2-dimethyl-4,13-dioxo-3,8,11,17,20-pentaoxa-5,14-diazadocosan-22-oate 1a. LCMS (ESI) calc'd for $C_{18}H_{34}N_2O_9$ $[M+H]^+$: 445.2, found 445.3. $^1H$ NMR (400 MHz, $CDCl_3$): δ 4.16 (s, 2H), 4.02 (s, 2H), 3.77 (s, 3H), 3.76-3.71 (m, 2H), 3.69 (dq, J=5.3, 2.2 Hz, 4H), 3.66-3.59 (m, 4H), 3.54 (dq, J=10.5, 5.2 Hz, 4H), 3.34 (d, J=5.6 Hz, 2H), 1.45 (s, 91H).

Step B: Methyl 17-amino-10-oxo-3,6,12,15-tetraoxa-9-azaheptadecan-1-oate hydrochloride 1b To a stirred solution of methyl 2,2-dimethyl-4,13-dioxo-3,8,11,17,20-pentaoxa-5,14-diazadocosan-22-oate 1a (3.00 g, 7.10 mmol) in 4 M HCl in dioxane (30 mL) was stirred at room temperature for 2 h and concentrated under reduced pressure. The residue was re-dissolved in DCM (30 mL) and concentrated under reduced pressure to afford methyl 17-amino-10-oxo-3,6,12,15-tetraoxa-9-azaheptadecan-1-oate hydrochloride 1b. LCMS (ESI) calc'd for $C_{13}H_{27}ClN_2O_7$$[M-HCl+H]^+$: 323.2, found 323.2.

Step C: (S)-23-tert-butyl 1-methyl 22-(((benzyloxy)carbonyl)amino)-10,19-dioxo-3,6,12,15-tetraoxa-9,18-diazatricosane-1,23-dioate 1c To a solution of (S)-4-(((benzyloxy)carbonyl)amino)-5-(tert-butoxy)-5-oxopentanoic acid 1b (0.940 g, 2.79 mmol) in DMF (10 mL) were added methyl 17-amino-10-oxo-3,6,12,15-tetraoxa-9-azaheptadecan-1-oate hydrochloride (1.00 g, 2.79 mmol), HATU (1.06 g, 2.79 mmol) and DIEA (1.80 g, 13.9 mmol) at 0° C. The mixture was stirred at RT for 1 h. The mixture was diluted with brine (40 mL), extracted with EA (2×40 mL), washed brine (2×30 mL), dried over anhydrous $MgSO_4$ and filtered, the filtrate was concentrated under reduced pressure. The residue was purified by silica gel column chromatography, eluted with gradient 1%-8% MeOH in DCM. The fractions containing desired product were combined and concentrated to give (S)-23-tert-butyl 1-methyl 22-(((benzyloxy)carbonyl)amino)-10,19-dioxo-3,6,12,15-tetraoxa-9,18-diazatricosane-1,23-dioate 1c. LCMS (ESI) calc'd for $C_{30}H_{47}N_3O_{12}$ $[M+H]^+$: 642.3, found 642.3. $^1H$ NMR (400 MHz, $CDCl_3$): δ 7.42-7.30 (m, 5H), 5.11 (s, 2H), 4.22 (br, 1H), 4.15 (s, 2H), 4.04 (s, 2H), 3.75 (s, 3H), 3.74-3.61 (m, 8H), 3.58 (dt, J=10.4, 4.9 Hz, 4H), 3.49 (dt, J=17.2, 6.2 Hz, 4H), 2.33 (t, J=7.3 Hz, 2H), 2.26-2.13 (m, 1H), 2.01-1.91 (m, 1H), 1.47 (s, 9H).

Step D: (S)-23-tert-butyl 1-methyl 22-amino-10,19-dioxo-3,6,12,15-tetraoxa-9,18-diazatricosane-1,23-dioate 1d To a stirred solution of (S)-23-tert-butyl 1-methyl 22-(((benzyloxy)carbonyl)amino)-10,19-dioxo-3,6,12,15-tetraoxa-9,18-diazatricosane-1,23-dioate 1c (700 mg, 1.091 mmol) in THF (20 mL) was added Pd—C (70 mg, 0.066 mmol) (dry, 10% wt). The reaction mixture was degassed with hydrogen for three times and stirred at room temperature for 4 h under hydrogen 1.5 atm. The resulting mixture was filtered and the filtrate was concentrated under reduced pressure to afford (S)-23-tert-butyl 1-methyl 22-amino-10,19-dioxo-3,6,12,15-tetraoxa-9,18-diazatricosane-1,23-dioate 1d. LCMS (ESI) calc'd for $C_{22}H_{41}N_3O_{10}$ $[M+H]^+$: 508.3, found 508.3; $^1H$ NMR (400 MHz, $CDCl_3$) δ 4.15 (s, 2H), 4.02 (s, 2H), 3.75 (s, 3H), 3.74-3.65 (m, 6H), 3.66-3.59 (m, 4H), 3.59-3.41 (m, 6H), 3.36 (dd, J=8.7, 4.7 Hz, 1H), 2.36 (t, J=7.5 Hz, 2H), 2.17-2.04 (m, 1H), 1.87-1.72 (m, 1H), 1.47 (s, 9H).

Step E: Synthesis of Intermediate 1e

To a stirred solution of 18-(tert-butoxy)-18-oxooctadecanoic acid (1.64 g, 4.43 mmol) in DMF (15 mL) were added HATU (1.68 g, 4.43 mmol), (S)-23-tert-butyl 1-methyl 22-amino-10,19-dioxo-3,6,12,15-tetraoxa-9,18-diazatricosane-1,23-dioate 1d (1.5 g, 2.96 mmol) and DIEA (3.91 mL, 23.64 mmol) at 0° C. The reaction solution was stirred at 0° C. for 1 h. The resulting solution was quenched with water (1 mL) and purified by Flash (Column: Flash $C^{18}$ 330 g; Mobile Phase A: water, Mobile Phase B: ACN; Flow rate: 85 mL/min; Gradient: 5% B to 60% B in 10 min, 60% B to 90% B in 25 min; Detector: UV 220 nm; Rt=30 min) to afford 1e. LCMS (ESI) calc'd for $C_{44}H_{81}N_3O_{13}$ $[M+H]^+$: 860.6, found 860.6. $^1H$ NMR (300 MHz, $CD_3OD$) δ 4.26 (dd, J=9.1, 5.1 Hz, 1H), 4.19 (s, 2H), 4.02 (s, 2H), 3.75 (s, 3H), 3.74-3.63 (m, 8H), 3.63-3.55 (m, 4H), 3.50-3.37 (m, 4H), 2.37-2.04 (m, 7H), 2.00-1.81 (m, 1H), 1.68-1.53 (m, 4H), 1.49 (s, 9H), 1.46 (s, 9H), 1.36-1.28 (m, 24H).

Step F: Synthesis of Intermediate if

To a stirred solution of 1e (1.4 g, 1.63 mmol) in THF (14 mL) was added 1 M LiOH (3.26 mL, 3.26 mmol) at 0° C. The reaction solution was stirred at 0° C. for 1 h. The resulting solution was quenched with 1 M HCl (3.26 mL) and purified by Flash (Column: Flash $C^{18}$ 80 g; Mobile Phase A: water, Mobile Phase B: ACN; Flow rate: 60 mL/min; Gradient: 1% B to 1% B in 5 min, 60% B to 90% B in 20 min; Detector: UV 220 nm; Rt=20 min). The fractions containing desired product were combined and concentrated to afford 1f. LCMS (ESI) calc'd for $C_{43}H_{79}N_3O_{13}$ $[M+H]^+$: 846.6, found 846.6. $^1H$ NMR (400 MHz, $CD_3OD$) δ 4.27 (dd, J=9.2, 5.0 Hz, 1H), 4.15 (s, 2H), 4.03 (s, 2H), 3.76-3.64 (m, 8H), 3.64-3.55 (m, 4H), 3.49-3.44 (m, 2H), 3.40 (t, J=5.6 Hz, 2H), 2.37-2.20 (m, 6H), 2.18-2.05 (m, 1H), 1.99-1.84 (m, 1H), 1.71-1.53 (m, 4H), 1.49 (s, 9H), 1.46 (s, 9H), 1.36-1.28 (m, 24H).

Step G: Synthesis of Intermediate 1g

To a stirred solution of if (300 mg, 0.36 mmol) in DMF (3 mL) and water (0.3 mL) were added M (238 mg, 0.71 mmol), HATU (202 mg, 0.53 mmol) and DIEA (0.37 mL, 2.13 mmol) at 0° C. The reaction mixture was stirred at 0° C. for 1 h. The resulting solution was quenched with water (1 mL) and purified by Flash (Column: Flash $C^{18}$ 80 g; Mobile Phase A: water (0.05% TFA), Mobile Phase B: ACN; Flow rate: 65 mL/min; Gradient: 10% B to 30% B in 10 min, 30% B to 70% B in 20 min; Detector: UV 220 nm; Rt=25 min) to afford 1g. LCMS (ESI) calc'd for $C_{57}H_{104}F_3N_5O_{18}$ $[M-TFA-]^+$: 1090.7, found 1090.7. $^1H$ NMR (400 MHz, $CD_3OD$): δ 4.27 (dd, J=9.2, 5.2 Hz, 1H), 4.06 (s, 2H), 4.03 (s, 2H), 4.00-3.94 (m, 2H) 3.76 (t, J=6.0 Hz, 3H), 3.73-3.55 (m, 24H), 3.48 (t, J=5.6 Hz, 2H), 3.44-3.36 (m, 2H), 3.25 (s, 6H), 2.61 (t, J=6.0 Hz, 2H), 2.35-2.19 (m, 6H), 2.18-2.05 (m, 1H), 1.98-1.84 (m, 1H), 1.68-1.53 (m, 4H), 1.48 (s, 9H), 1.46 (s, 9H), 1.36-1.28 (m, 24H).

Step H: Synthesis of Intermediate 1h

To a stirred solution of 1g (370 mg, 0.31 mmol) in THF (4 mL) was added 1 M LiOH (0.62 mL, 0.62 mmol) at 0° C. The reaction mixture was stirred at 0° C. for 1 h. The resulting solution was quenched with 1 M HCl (0.62 mL) and purified by Flash (Column: Flash $C^{18}$ 80 g; Mobile Phase A: water (0.05% TFA), Mobile Phase B: ACN; Flow rate: 60 mL/min; Gradient: 1% B to 30% B in 10 min, 30% B to 60% B in 15 min; Detector: UV 220 nm; Rt=22 min) to 1h. LCMS (ESI) calc'd for $C_{56}H_{102}F_3N_5O_{18}$ $[M-TFA^-]^+$: 1076.7, found 1076.7. $^1H$ NMR (400 MHz, $CD_3OD$): δ 4.26 (dd, J=9.0, 5.1 Hz, 1H), 4.05 (s, 2H), 4.02 (s, 2H), 3.99-3.92 (m, 2H), 3.79-3.53 (m, 24H), 3.47 (t, J=5.6 Hz, 2H), 3.42-3.35 (m, 2H), 3.23 (s, 6H), 2.56 (t, J=5.9 Hz, 2H), 2.35-2.02 (m, 7H), 1.98-1.82 (m, 1H), 1.70-1.51 (m, 4H), 1.48 (s, 9H), 1.45 (s, 9H), 1.39-1.24 (m, 24H).

Step I: Synthesis of Intermediate 1i

To a stirred solution of 1h (300 mg, 0.25 mmol) in DMF (3 mL) and water (0.3 mL) were added (S)-tert-butyl 2-amino-5-((2-(2-(2-methoxy-2-oxoethoxy)ethoxy)ethyl) amino)-5-oxopentanoate (100 mg, 0.28 mmol), HATU (105 mg, 0.28 mmol) and DIEA (0.22 mL, 1.26 mmol) at 0° C. The reaction mixture was stirred at 0° C. for 1 h. The resulting solution was quenched with water (2 mL) and purified by Flash (Column: Flash $C^{18}$ 80 g; Mobile Phase A: water (0.05% TFA), Mobile Phase B: ACN; Flow rate: 65 mL/min; Gradient: 10% B to 30% B in 10 min, 30% B to 70% B in 20 min; Detector: UV 220 nm; Rt=24 min) to afford 1i. LCMS (ESI) calc'd for $C_{72}H_{130}F_3N_7O_{24}$ $[M-TFA-]^+$: 1420.9, found 1420.8. $^1H$ NMR (400 MHz, $CD_3OD$): δ 4.35-4.22 (m, 2H), 4.18 (s, 2H), 4.05 (s, 2H), 4.02 (s, 2H), 3.99-3.93 (m, 2H), 3.81-3.52 (m, 33H), 3.51-3.34 (m, 6H), 3.24 (s, 6H), 2.57-2.45 (m, 2H), 2.40-2.00 (m, 10H), 1.98-1.84 (m, 2H), 1.68-1.53 (m, 4H), 1.52-1.42 (m, 27H), 1.38-1.27 (m, 24H).

Step J: Synthesis of Intermediate 1j

To a solution of 1i (250 mg, 0.16 mmol) in THF (2.5 mL) was added 1 M LiOH (0.32 mL, 0.32 mmol) at 0° C. The reaction mixture was stirred at 0° C. for 1 h. The resulting solution was quenched with 1 M HCl (0.32 mL) and purified by Flash (Column: Flash $C^{18}$ 80 g; Mobile Phase A: water, Mobile Phase B: ACN; Flow rate: 60 mL/min; Gradient: 1% B to 30% B in 10 min, 30% B to 60% B in 15 min; Detector: UV 220 nm; Rt=18 min). The fractions containing desired product were combined and concentrated. The residue was re-dissolved in ACN (3 mL) and water (5 mL), and added 1 N HCl (0.12 mL) at 0° C. The solution was lyophilized to afford 1j. LCMS (ESI) calc'd for $C_{69}H_{128}ClN_7O_{22}$ $[M-Cl^-]^+$: 1406.9, found 1406.9. $^1H$ NMR (400 MHz, $CD_3OD$): δ 4.33-4.27 (m, 2H), 4.15 (s, 2H), 4.06 (s, 2H), 4.03 (s, 2H), 3.98 (s, 2H), 3.82-3.65 (m, 24H), 3.64-3.54 (m, 6H), 3.48 (t, J=5.6 Hz, 2H), 3.43-3.36 (m, 4H), 3.26 (s, 6H), 2.60-2.48 (m, 2H), 2.37-2.18 (m, 10H), 2.18-2.05 (m, 1H), 2.02-1.85 (m, 1H), 1.67-1.54 (m, 4H), 1.52-1.44 (m, 27H), 1.38-1.27 (m, 24H).

Step K: Synthesis of 1k

To a solution of D (15.0 mg, 10.7 μmol) in DMF (300 μL) and water (30 μL) was added 1j (21.7 mg, 0.015 mmol) at room temperature. After cooling to −20° C., HATU (8.17 mg, 0.021 mmol) and DIEA (15 μL, 0.086 mmol) were added to the mixture. The solution was stirred at 0° C. for 0.5 h. The reaction solution was quenched with water (100 μL) and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 20% B to 60% B in 20 min; Detector: UV 254/210 nm; Rt=22 min). The fractions containing desired product were combined and concentrated under reduced pressure. The residue was re-dissolved in ACN (5 mL) and water (5 mL), lyophilized to afford 1k. LCMS (ESI) calc'd for $C_{139}H_{205}F_4N_{21}O_{35}$ $[(M-TFA^-+H)/2]^+$: 1346.1, found 1346.6.

Step L: Synthesis of 1l

To a solution of 1k (24.0 mg, 8.55 μmol) in DCM (4.8 mL) was added TFA (6 mL, 78 mmol) at −20° C. The reaction mixture was stirred at room temperature for 1 h. The reaction solution was concentrated under reduced pressure and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 20% B to 60% B in 20 min; Detector: UV 220 nm; Rt=20 min). The fractions containing desired product were combined and concentrated under reduced pressure. The residue was re-dissolved in ACN (5 mL) and water (5 mL), lyophilized to afford 1l. LCMS (ESI) calc'd for $C_{131}H_{189}F_4N_{21}O_{35}$ $[(M-TFA^-+H)/2]^+$: 1290.2, found 1291.2.

Step M: Synthesis of Example 1

5 g of AG MP-1 Resin (cat #141-1841 BIO-RAD) was packed in column. The column was washed with water (2×10 mL), followed by 20% ACN in water (2×10 mL). A solution of 1l (14 mg, 5.20 μmol) in 60% ACN in water (20 mL) was loaded onto the resin column, and the column was eluted with 60% ACN in water (4×20 mL). The eluents were combined, water (5×4 mL) added, lyophilized to afford Example 1. LCMS (ESI) calc'd for $C_{129}H_{189}ClFN_{21}O_{33}$ $[M-Cl^-]^+$: 2579.4, found 2579.4; $[(M-Cl^-+H)/2]^+$: 1290.2, found 1290.8.

Preparatory Example 2

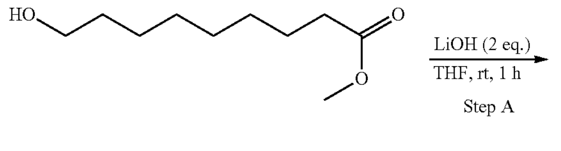

-continued
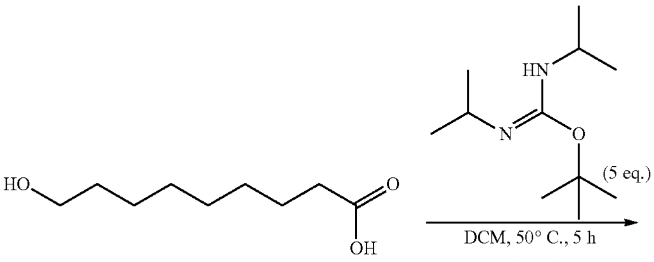
2a
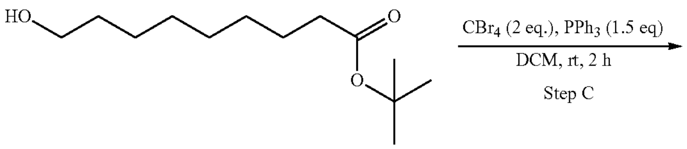
2b
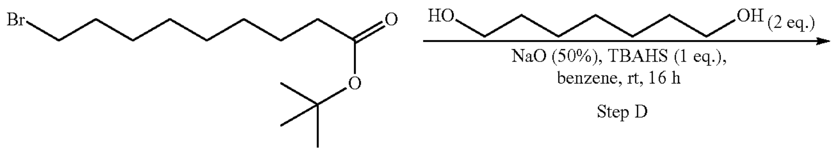
2c
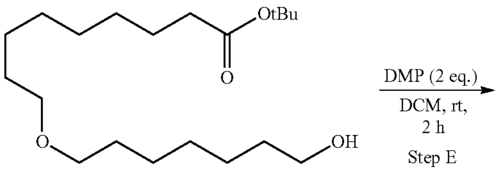
2d
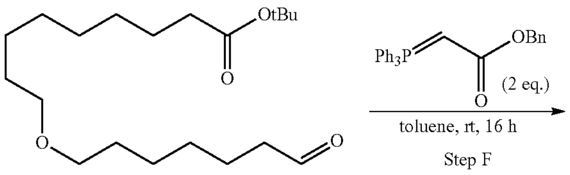
2e
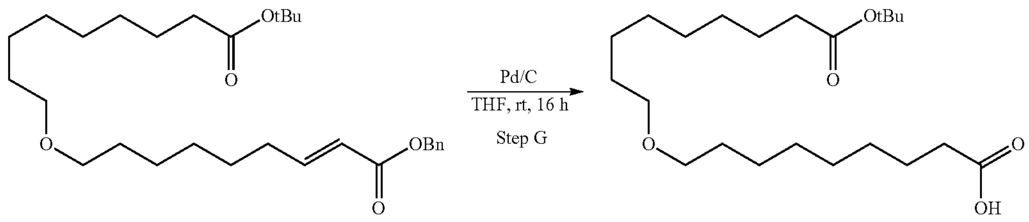
2f 2g
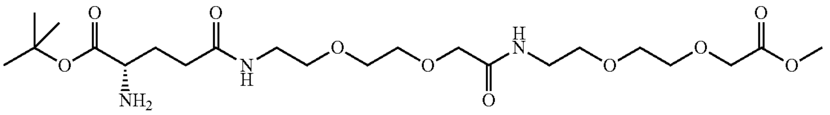
1d
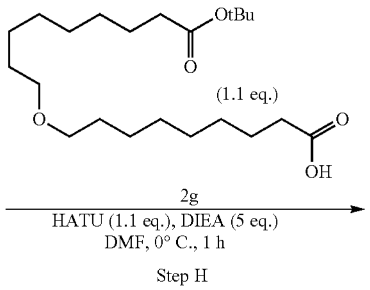

-continued

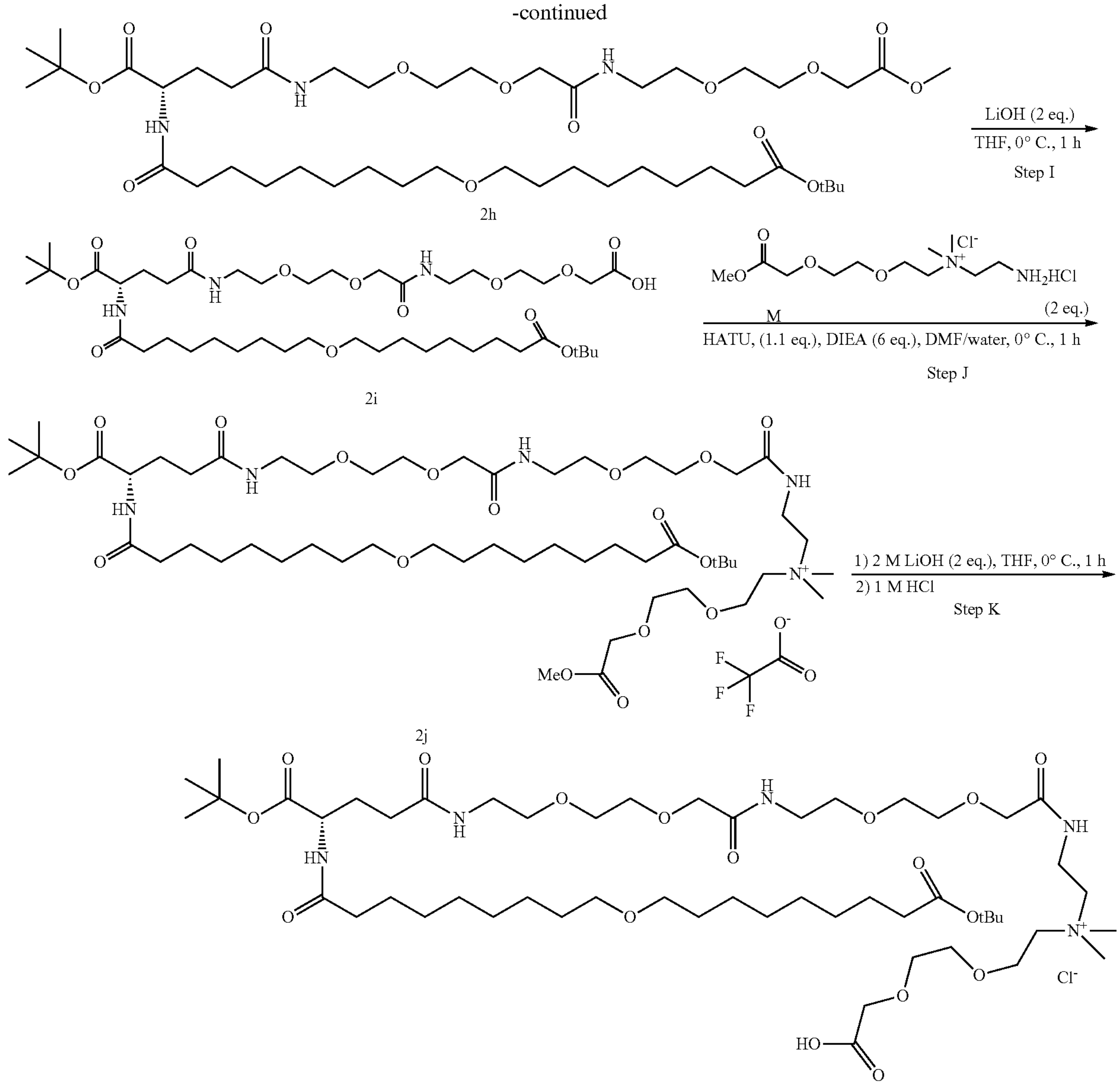

2h

2i

2j

2k

Step A: 9-Hydroxynonanoic acid 2a

To a stirred solution of methyl 9-hydroxynonanoate (5.00 g, 26.6 mmol) in THF (50 mL) was added 1 M LiOH (53.1 mL, 53.1 mmol) at room temperature. The reaction solution was stirred at room temperature for 1 h. The pH value of the solution was adjusted to 2 with 1 N HCl. The solution was extracted with EA (2×100 mL). The combined organic layer was washed with brine (3×200 mL), dried over anhydrous $Na_2SO_4$ and filtered. The filtrate was concentrated under reduced pressure to afford 9-hydroxynonanoic acid 2a. $^1H$ NMR (400 MHz, $CDCl_3$) $\delta$ 3.64 (t, J=6.6 Hz, 2H), 2.34 (t, J=7.5 Hz, 2H), 1.66-1.52 (m, 4H), 1.38-1.29 (in, 8H).

Step B: Tert-butyl 9-hydroxynonanoate 2b

To a solution of 9-hydroxynonanoic acid 2a (4.60 g, 26.4 mmol) in DCM (50 mL) was added tert-butyl N,N'-diisopropylcarbamimidate (26.4 g, 132 mmol) at room temperature. The reaction solution was stirred at 50° C. for 5 h. The resulting solution was concentratred under reduced pressure. The residue was purified by silica gel column chromatography, eluted with gradient 1%-30% EA in PE. The fractions containing desired product were combined and concentrated under reduced pressure to afford tert-butyl 9-hydroxynonanoate 2b. pH NMR (400 MHz, $CDCl_3$) 3.64 (t, J 6.6 Hz, 2H), 2.20 (t, J=7.5 Hz, 2H), 1.61-1.52 (m, 4H), 1.44 (s, 9H), 1.36-1.27 (in, 8H).

Step C: Tert-butyl 9-bromononanoate 2c

To a stirred solution of tert-butyl 9-hydroxynonanoate (3.00 g, 13.0 mmol) in DCM (10 mL) were added $CBr_4$ (8.64 g, 26.0 mmol) and $Ph_3P$ (5.12 g, 19.5 mmol) at 0° C. under nitrogen atmosphere. The reaction solution was stirred at room temperature for 2 h. The resulting solution was concentrated under reduced pressure and the residue was purified by silica gel column chromatography, eluted with 0-10% EA in PE to afford tert-butyl 9-bromononanoate 2c. $^1$H NMR (400 MHz, $CDCl_3$): δ 3.41 (t, J=6.8 Hz, 2H), 2.20 (t, J=7.5 Hz, 2H), 1.90-1.80 (m, 2H), 1.61-1.39 (m, 13H), 1.36-1.26 (m, 6H).

Step D: Tert-butyl 9-((6-hydroxyhexyl)oxy)nonanoate 2d

To a stirred solution of tert-butyl 9-bromononanoate 2c (3.30 g, 11.2 mmol) and heptane-1,7-diol (2.98 g, 22.5 mmol) in benzene (40 mL) were added 50% aqueous NaOH (16 mL) and TBAHS (3.82 g, 11.25 mmol) at 0° C. The reaction mixture was stirred at room temperature for 16 h. The resulting solution was diluted with water (50 mL). The solution was extracted with EA (3×100 mL). The organic layer was washed with brine (3×300 mL), dried over anhydrous $Na_2SO_4$ and filtered. The residue was purified by silica gel column chromatography, eluted with gradient 0%-30% EA in PE. The fractions containing desired product were combined and concentrated under reduced pressure to afford tert-butyl 9-((6-hydroxyhexyl)oxy)nonanoate 2d. $^1$H NMR (400 MHz, $CDCl_3$) δ 3.64 (t, J=6.6 Hz, 2H), 3.45-3.33 (m, 4H), 2.20 (t, J=7.5 Hz, 2H), 1.59-1.55 (m, 8H), 1.44 (s, 9H), 1.39-1.25 (m, 14H).

Step E: Tert-butyl 9-((7-oxoheptyl)oxy)nonanoate 2e

To a stirred solution of tert-butyl 9-((7-hydroxyheptyl)oxy)nonanoate 2d (1.90 g, 5.50 mmol) in DCM (20 mL) was added DMP (4.68 g, 11.0 mmol) at 0° C. The reaction mixture was stirred at room temperature for 2 h. The resulting solution was quenched by sat'd $Na_2S_2O_3/NaHCO_3$ solution (100 mL) and diluted with EA (2×50 mL). The organic layer was washed by brine (3×100 mL), dried with anhydrous $Na_2SO_4$ and filtered. The filtrate was concentrated under reduced pressure and purified by a silica gel column chromatography, eluted with gradient 0%-10% EA in PE. The fractions containing desired product were combined and concentrated under reduced pressure to afford tert-butyl 9-((7-oxoheptyl)oxy)nonanoate 2e. $^1$H NMR (400 MHz, $CDCl_3$) δ 9.76 (t, J=1.8 Hz, 1H), 3.45-3.29 (m, 4H), 2.47-2.38 (m, 2H), 2.20 (t, J=7.5 Hz, 2H), 1.68-1.53 (m, 8H), 1.44 (s, 9H), 1.40-1.26 (m, 12H).

Step F: (E)-benzyl 9-((9-(tert-butoxy)-9-oxononyl)oxy)non-2-enoate 2f

To a stirred solution of tert-butyl 9-((7-oxoheptyl)oxy)nonanoate 2e (1.20 g, 3.50 mmol) in toluene (20 mL) was added benzyl (triphenyl phosphaneylidene) acetate (2.88 g, 7.01 mmol) at room temperature. The reaction solution was stirred at room temperature for 16 h. The solution was concentrated under reduced pressure and the residue was purified by silica gel column chromatography, eluted with gradient 0%-5% EA in PE. The fractions containing the desired product were combined and concentrated under reduced pressure to afford (E)-benzyl 9-((9-(tert-butoxy)-9-oxononyl)oxy)non-2-enoate 2f. $^1$H NMR (400 MHz, $CDCl_3$) δ 7.42-7.28 (m, 5H), 7.01 (dt, J=15.7, 7.0 Hz, 1H), 5.86 (dt, J=15.7, 1.6 Hz, 1H), 5.17 (s, 2H), 3.38 (td, J=6.7, 1.0 Hz, 4H), 2.26-2.14 (m, 4H), 1.61-1.53 (m, 6H), 1.50-1.41 (s, 11H), 1.38-1.24 (m, 12H).

Step G: 9-((9-(Tert-butoxy)-9-oxononyl)oxy)nonanoic acid 2g

To a solution of (E)-benzyl 9-((9-(tert-butoxy)-9-oxononyl)oxy)non-2-enoate 2f (900 mg, 1.90 mmol) in THF (20 mL) was added Pd/C (100 mg, 0.094 mmol, dry, 10% wt) at room temperature under nitrogen atmosphere. The mixture was degassed with hydrogen for three times and stirred at room temperature for 16 h under hydrogen (1.5 atm). The reaction mixture was filtered and the filtrate was concentrated under reduced pressure to afford 9-((9-(tert-butoxy)-9-oxononyl)oxy)nonanoic acid 2g. $^1$H NMR (400 MHz, $CDCl_3$) δ 3.39 (t, J=6.7 Hz, 4H), 2.35 (t, J=7.5 Hz, 2H), 2.20 (t, J=7.5 Hz, 2H), 1.67-1.49 (m, 8H), 1.44 (s, 9H), 1.38-1.26 (m, 16H).

Step H: (S)-21,40-di-tert-butyl 1-methyl 9,18,23-trioxo-2,5,11,14,32-pentaoxa-8,17,22-triazatetracontane-1,21,40-tricarboxylate 2h To a solution of 9-((9-(tert-butoxy)-9-oxononyl)oxy)nonanoic acid 2g (293 mg, 0.759 mmol) in DMF (4 mL) were added HATU (288 mg, 0.759 mmol), (S)-23-tert-butyl 1-methyl 22-amino-10,19-dioxo-3,6,12,15-tetraoxa-9,18-diazatricosane-1,23-dioate 1d (350 mg, 0.690 mmol) and DIEA (0.602 mL, 3.45 mmol) at 0° C. The reaction mixture was stirred at 0° C. for 1 h. The resulting solution was quenched with water (200 μL) and purified by reversed phrase Flash (Column: Flash $C^{18}$ 80 g; Mobile Phase A: water (0.05% TFA), Mobile Phase B: ACN; Flow rate: 65 mL/min; Gradient: 2% B to 2% B in 5 min, 30% B to 60% B in 15 min, 60% B to 98% B in 20 min; Detector: UV 210 nm; Rt=25 min). The fractions containing desired product were combined and concentrated under reduced pressure to afford 2h. LCMS (ESI) calc'd for $C_{44}H_{81}N_3O_{14}$ $[M+H]^+$: 876.6, found 876.6; $^1$H NMR (400 MHz, $CD_3OD$) δ 4.27-4.21 (m, 1H), 4.17 (s, 2H), 4.00 (s, 2H), 3.78-3.61 (m, 11H), 3.61-3.52 (m, 4H), 3.46-3.36 (m, 8H), 2.32-2.17 (m, 6H), 2.15-1.84 (m, 2H), 1.64-1.51 (m, 8H), 1.48-1.42 (m, 18H), 1.38-1.30 (m, 16H).

Step I: Synthesis of Intermediate 2i

To a solution of 2h (500 mg, 0.57 mmol) in THF (5 mL) was added 1 M LiOH (1.14 mL, 1.14 mmol) at 0° C. The reaction mixture was stirred at 0° C. for 1 h. The resulting solution was quenched with 1 M HCl (1 mL) and purified by reversed phrase Flash (Column: Flash $C^{18}$ 80 g; Mobile Phase A: water (0.05% TFA), Mobile Phase B: ACN; Flow rate: 65 mL/min; Gradient: 2% B to 2% B in 5 min, 30% B to 60% B in 15 min; Detector: UV 210 nm; Rt=20 min). The fractions containing desired product were combined and concentrated under reduced pressure to afford 2i. LCMS (ESI) calc'd for $C_{43}H_{79}N_3O_{14}$ $[M+H]^+$: 862.6, found 862.5. $^1$H NMR (300 MHz, $CD_3OD$) δ 4.29-4.19 (m, 1H), 4.13 (s, 2H), 4.00 (s, 2H), 3.73-3.62 (m, 8H), 3.61-3.52 (m, 4H), 3.48-3.34 (m, 8H), 2.34-2.16 (m, 6H), 2.16-1.82 (m, 2H), 1.66-1.48 (m, 8H), 1.48-1.42 (m, 18H), 1.40-1.26 (m, 16H).

Step J: Synthesis of Intermediate 2j

To a solution of 2i (200 mg, 0.232 mmol) in DMF (2 mL) and water (200 μL) were added HATU (97.0 mg, 0.255 mmol), M (148 mg, 0.464 mmol) and DIEA (0.243 mL, 1.392 mmol) at 0° C. The reaction mixture was stirred at 0° C. for 1 h. The esulting solution was purified by reversed phrase Flash (Column: Flash $C^{18}$ 80 g; Mobile Phase A: water (0.05% TFA), Mobile Phase B: ACN; Flow rate: 65 mL/min; Gradient: 2% B to 2% B in 5 min, 30% B to 60% B in 15 min, 60% B to 98% B in 20 min; Detector: UV 210 nm; Rt=23 min). The fractions containing desired product were combined and concentrated under reduced pressure to afford 2j. LCMS (ESI) calc'd for $C_{56}H_{102}F_3N_5O_{19}$ $[M-TFA^-]^+$: 1092.7, found 1092.7; $^1H$ NMR (400 MHz, $CD_3OD$) δ 4.28-4.20 (m, 1H), 4.18-4.10 (m, 2H), 4.06-3.96 (m, 6H), 3.78-3.63 (m, 18H), 3.62-3.53 (m, 6H), 3.52-3.33 (m, 9H), 3.27-3.21 (m, 6H), 2.32-2.16 (m, 6H), 2.10-1.82 (m, 2H), 1.68-1.50 (m, 8H), 1.50-1.40 (m, 18H), 1.40-1.28 (m, 16H).

Step K: Synthesis of 2k

To a solution of 2j (240 mg, 0.199 mmol) in THF (2.5 mL) was added 1M LiOH (0.398 mL, 0.398 mmol) at 0° C. The reaction mixture was stirred at 0° C. for 1 h. The resulting solution was quenched with 1 M HCl (0.4 mL) and purified by Flash (Column: Flash $C^{18}$ 80 g; Mobile Phase A: water, Mobile Phase B: ACN; Flow rate: 65 mL/min; Gradient: 2% B to 2% B in 5 min, 30% B to 60% B in 15 min; Detector: UV 210 nm; Rt=20 min). The fractions containing desired product were combined and concentrated under reduced pressure. The residue was re-dissolved in ACN (3 mL) and water (5 mL), and added 1 N HCl (0.2 mL) at 0° C. The solution was lyophilized to afford 2k. LCMS (ESI) calc'd for $C_{53}H_{100}ClN_5O_{17}$ $[M-Cl^-]^+$: 1078.7, found 1078.7. $^1H$ NMR (400 MHz, $CD_3OD$) δ 4.27-4.21 (m, 1H), 4.13 (s, 2H), 4.06-4.96 (m, 6H), 3.79-3.63 (m, 16H), 3.63-3.52 (m, 6H), 3.49-3.35 (m, 8H), 3.28-3.20 (m, 6H), 2.34-2.17 (m, 6H), 2.10-1.83 (m, 2H), 1.65-1.51 (m, 8H), 1.49-1.41 (m, 18H), 1.40-1.29 (m, 16H).

Step L: Synthesis of 2l

To a solution of D (20.0 mg, 0.014 mmol) in DMF (300 μL) and water (30 μL) was added 2k (22.4 mg, 0.020 mmol) at room temperature. After cooling to −20° C., HATU (10.9 mg, 0.029 mmol) and DIEA (20 μL, 0.115 mmol) were added to the mixture. The mixture was stirred at 0° C. for 0.5 h. The reaction solution was quenched with water (100 μL) and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 25% B to 80% B in 25 min; Detector: UV 254/210 nm; Rt=23 min). The fractions containing desired product were combined and concentrated under reduced pressure. The residue was re-dissolved in ACN (5 mL) and water (5 mL), lyophilized to afford 21. LCMS (ESI) calc'd for $C_{127}H_{185}F_4N_{19}O_{30}$ $[(M-TFA^-+H)/2]^+$: 1210.2, found 1211.1.

Step M: Synthesis of 2m

To a solution of 21 (30.0 mg, 0.012 mmol) in DCM (6 mL) was added TFA (7.5 mL, 97 mmol) at −20° C. The reaction mixture was stirred at room temperature for 1 h. The reaction solution was concentrated under reduced pressure and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 20% B to 60% B in 20 min; Detector: UV 254/210 nm; Rt=20 min). The fractions containing desired product were combined and concentrated under reduced pressure. The residue was re-dissolved in ACN (5 mL) and water (5 mL), lyophilized to afford 2m. LCMS (ESI) calc'd for $C_{119}H_{169}F_4N_{19}O_{30}$ $[(M-TFA^-+H)/2]^+$: 1154.1, found 1154.9.

Step N: Synthesis of Example 2

5 g of AG MP-1 Resin (cat #141-1841 BIO-RAD) was packed in column. The column was washed with water (2×10 mL), followed by 20% ACN in water (2×10 mL). A solution of 2m (18.0 mg, 7.43 μmol) in 60% ACN in water (20 mL) was loaded onto the resin column, and the column was eluted with 60% ACN in water (4×20 mL). The eluents were combined, water (5×4 mL) added, lyophilized to afford Example 2. LCMS (ESI) calc'd for $C_{117}H_{169}ClFN_{19}O_{28}$ $[M-Cl^-]^+$: 2307.2, found 2307.2; $[(M-Cl^-+H)/2]^+$: 1154.1, found 1154.8.

Preparation of Example 3

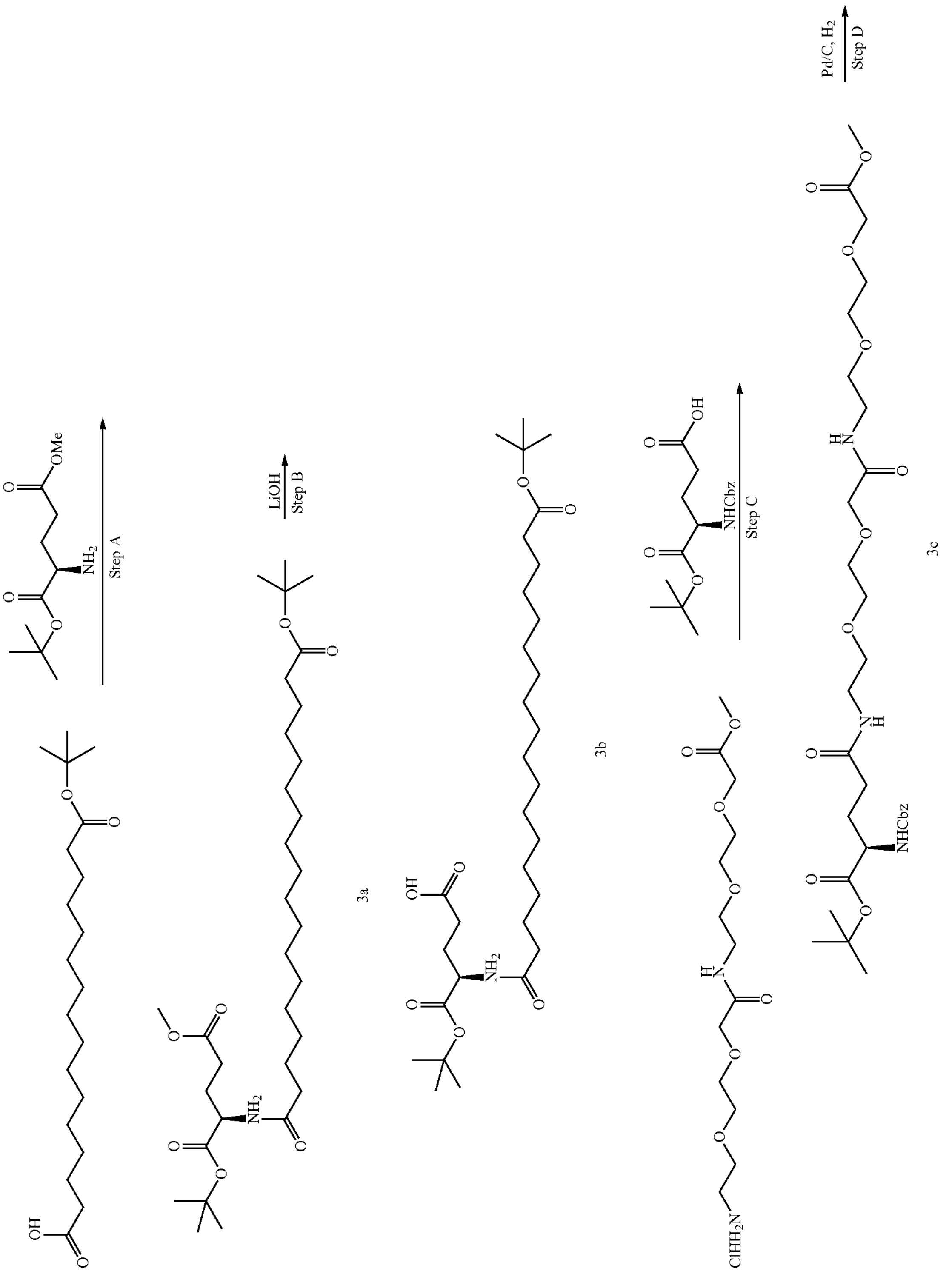
3a
3b
3c

-continued
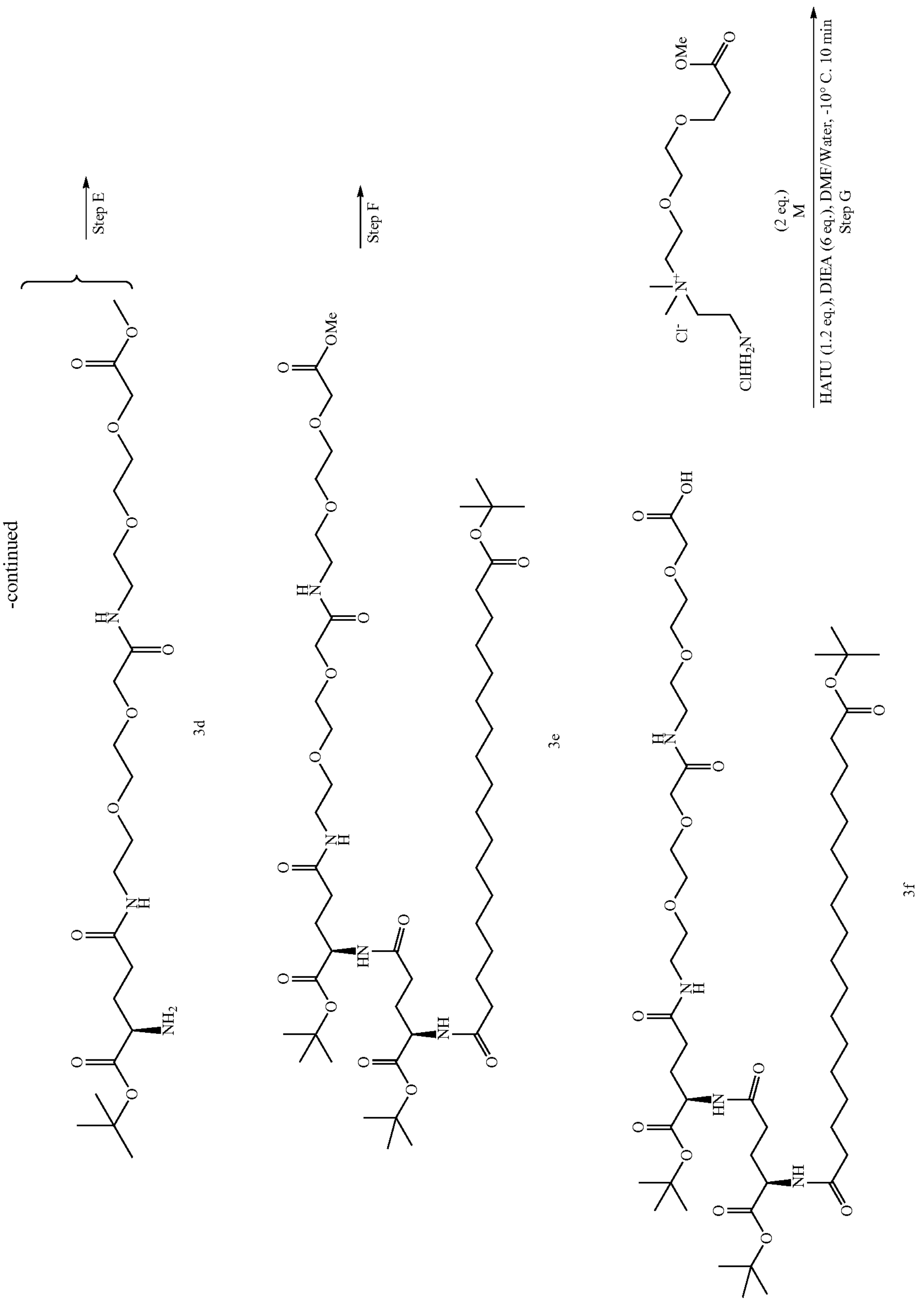
3d
3e
3f

-continued
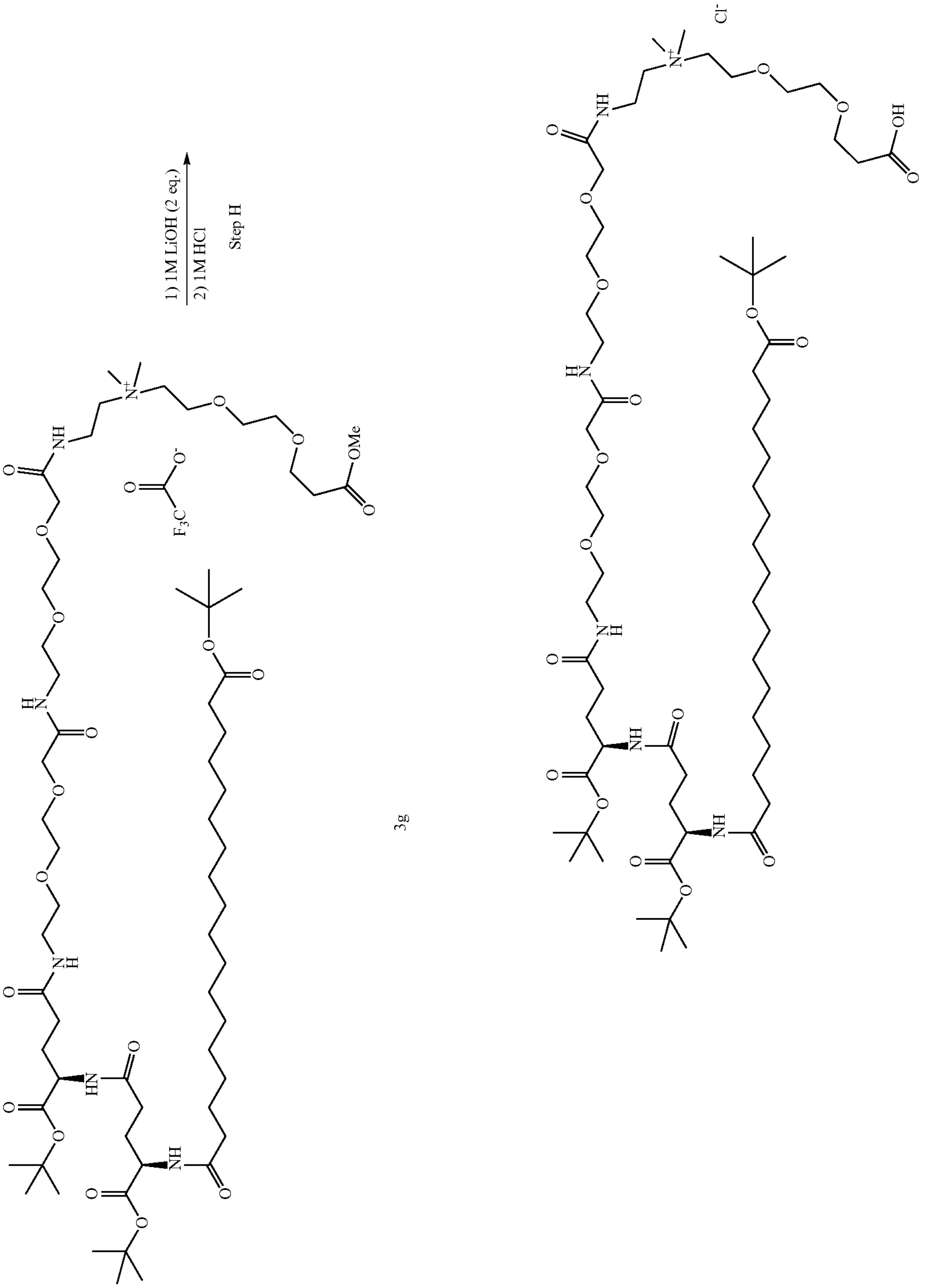
3g
3h

-continued
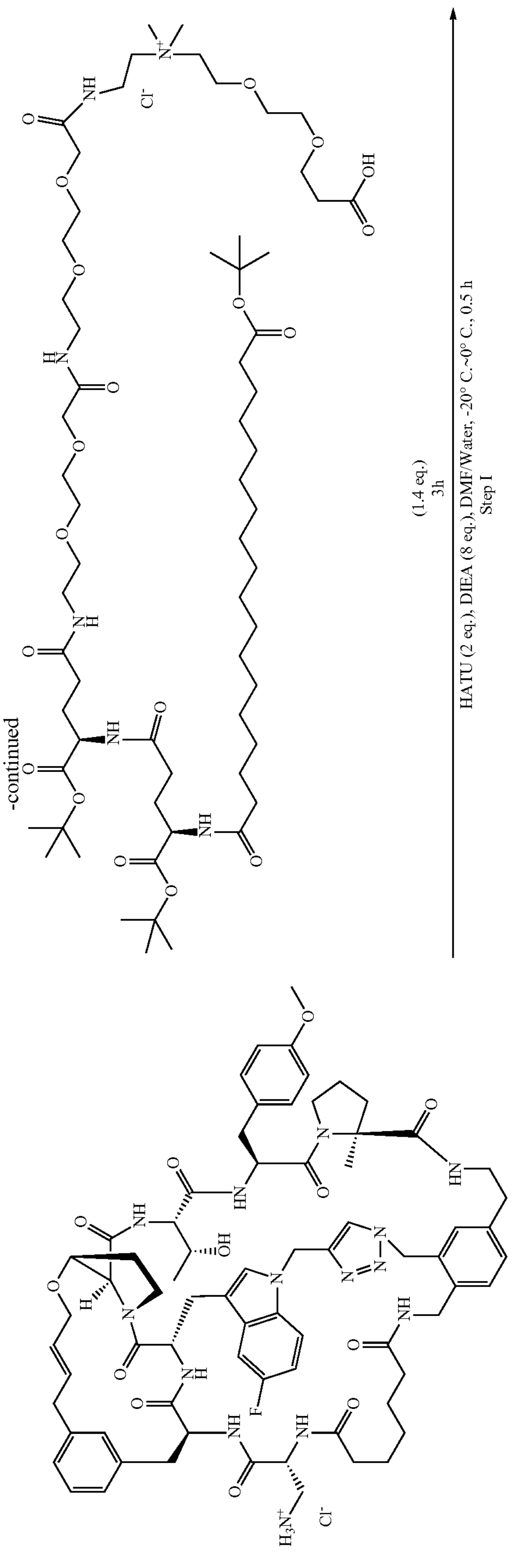
D

-continued
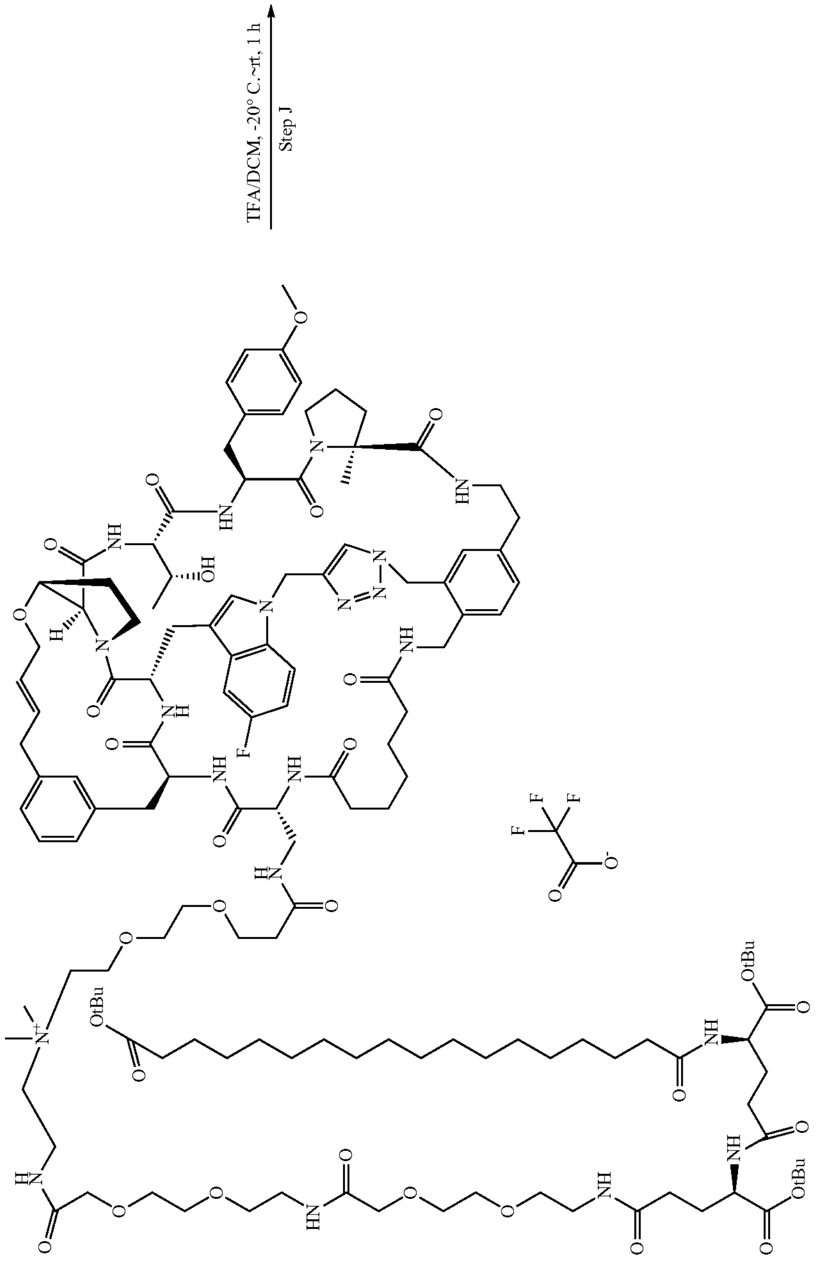
3i

-continued
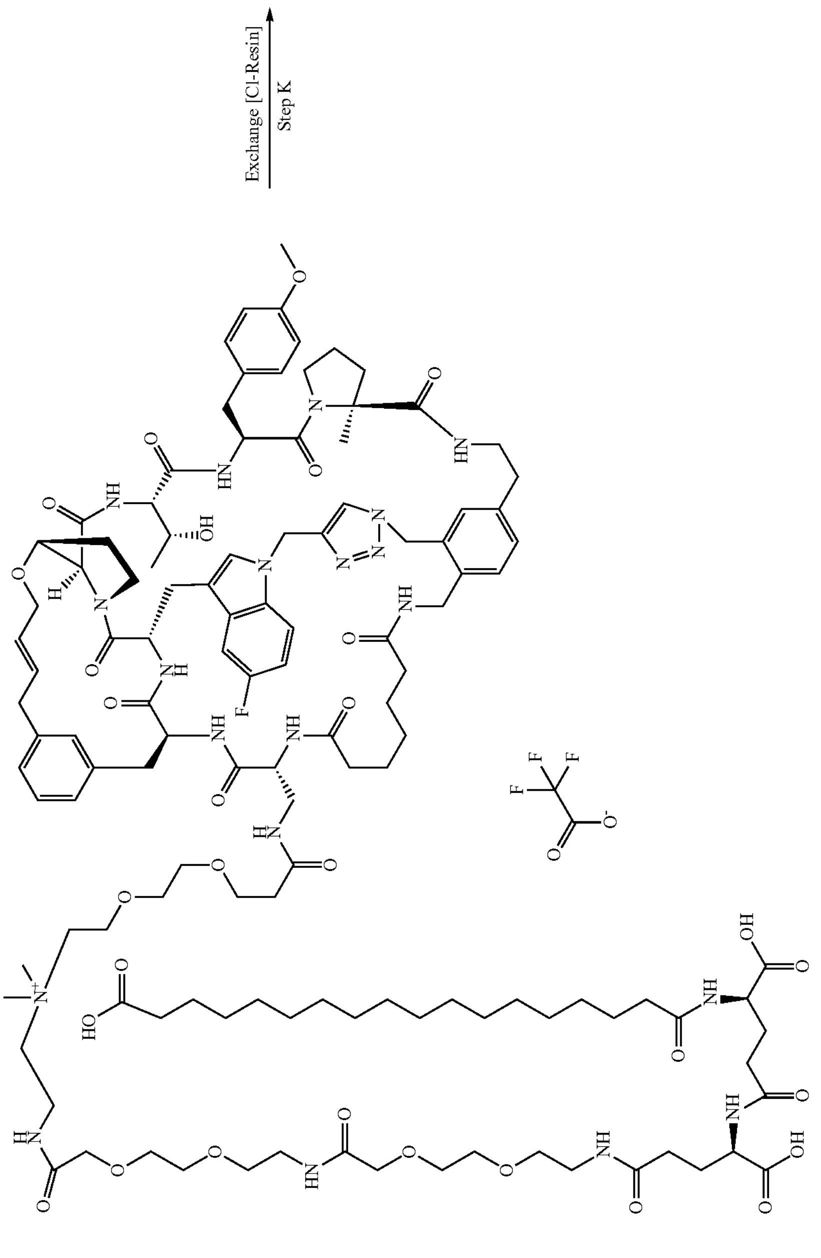
3j

-continued
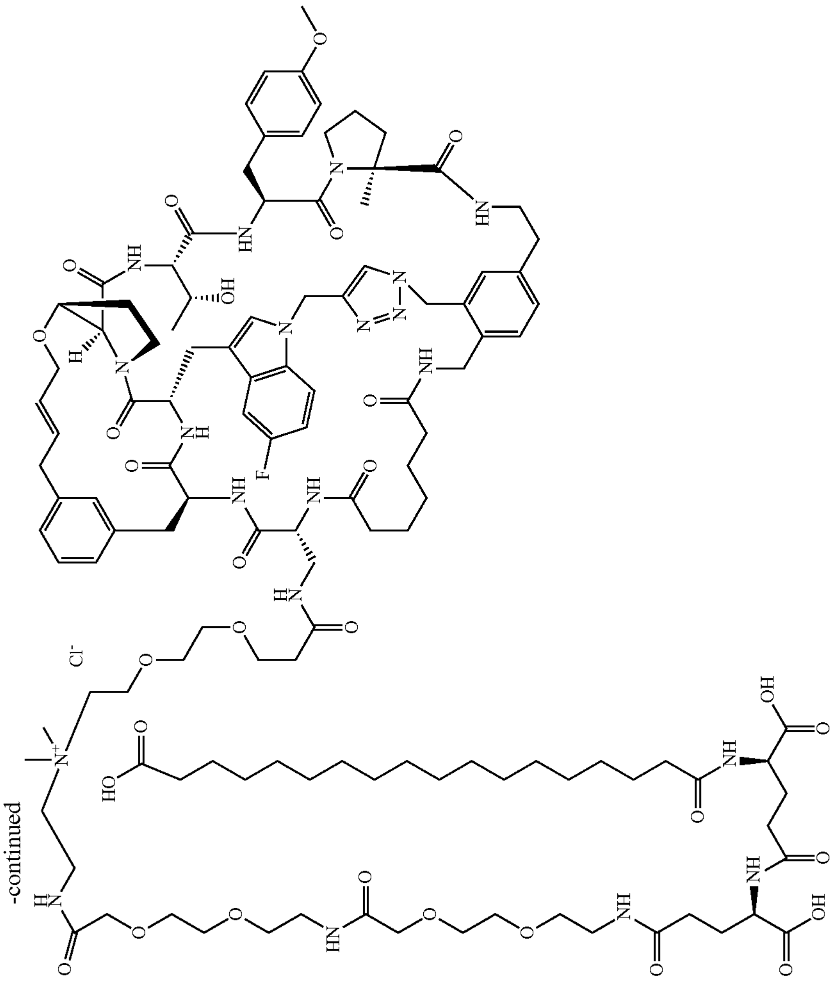
Example 3

Step A: Synthesis of Intermediate 3a

To a stirred mixture of (R)-4-(((benzyloxy)carbonyl) amino)-5-(tert-butoxy)-5-oxopentanoic acid (1.5 g, 4.45 mmol) in DMF (15 ml) were added methyl 17-amino-10-oxo-3,6,12,15-tetraoxa-9-azaheptadecan-1-oate hydrochloride (2.393 g, 6.67 mmol) and N-ethyl-N-isopropylpropan-2-amine (0.575 g, 4.45 mmol) at 0° C. The resulting mixture was stirred for 1 h at 0° C. The reaction was quenched by water (10 ml). The mixture was purified by reverse phase with the following conditions: Column, Xbridge C18, 19×150 mm; mobile phase: acetonitrile in Water (0.1% TFA), 34%-95% in 8 min; Detector, UV 254 nm. RT: 6.82 min. The collected fractions were combined and concentrated under reduced pressure to give (R)-23-tert-butyl 1-methyl 22-(((benzyloxy)carbonyl)amino)-10,19-dioxo-3,6,12,15-tetraoxa-9,18-diazatricosane-1,23-dioate 3a. LCMS (ESI) calc'd for $C_{30}H_{47}N_3O_{12}$ $[M+H]^+$: 642.3, found 642.3. $^1H$ NMR (400 MHz, Methanol-d4) δ 7.42-7.27 (m, 5H), 5.11 (s, 2H), 4.18 (s, 2H), 4.13-4.04 (m, 1H), 4.02 (s, 2H), 3.75 (s, 3H), 3.73-3.68 (m, 4H), 3.68-3.63 (m, 4H), 3.61-3.54 (m, 4H), 3.49-3.43 (m, 2H), 3.41-3.36 (m, 2H), 2.38-2.30 (m, 2H), 2.22-2.08 (m, 1H), 1.98-1.79 (m, 1H), 1.47 (s, 9H).

Step B: Synthesis of Intermediate 3b

To a stirred solution of (R)-23-tert-butyl 1-methyl 22-(((benzyloxy)carbonyl)amino)-10,19-dioxo-3,6,12,15-tetraoxa-9,18-diazatricosane-1,23-dioate 3a (2.1 g, 3.27 mmol) in THF (20 ml) was added Pd/C (10% wt, dry) (0.348 g, 0.327 mmol) under nitrogen atmosphere. The reaction mixture was degassed with hydrogen three times and stirred at room temperature for 16 h under hydrogen. The mixture was filtered and the filtrate was concentrated under vacuum to afford (R)-23-tert-butyl 1-methyl 22-amino-10,19-dioxo-3,6,12,15-tetraoxa-9,18-diazatricosane-1,23-dioate 3b. LCMS (ESI) calc'd for $C_{22}H_{41}N_3O_{10}$ $[M+H]^+$: 508.2, found 508.2.

Step C: Synthesis of Intermediate 3c

To a stirred mixture of 18-(tert-butoxy)-18-oxooctadecanoic acid (1 g, 2.70 mmol) in DMF (10 ml) were added HATU (1.129 g, 2.97 mmol), (R)-1-tert-butyl 5-methyl 2-(18-(tert-butoxy)-18-oxooctadecanamido)pentanedioate 3b (1.2 g, 2.106 mmol, 78% yield) and N-ethyl-N-isopropylpropan-2-amine (1.744 g, 13.49 mmol) at 0° C. The resulting mixture was stirred for 1 h at 0° C. The reaction was quenched by water (50 ml) and extracted with EA (30 ml×3). The combined organic layers was washed with brine (20 ml×3), dried over $Na_2SO_4$ and filtered. The filtrate was concertrated under reduced pressure and the residue was purified by flash chromatography on silica gel, eluted with 0-30% EA in PE to afford (R)-1-tert-butyl 5-methyl 2-(18-(tert-butoxy)-18-oxooctadecanamido)pentanedioate 3c. LCMS (ESI) calc'd for $C_{32}H_{59}NO_7$ $[M+H]^+$: 570.2, found 570.3. $^1H$ NMR (400 MHz, Chloroform-d) δ 6.11 (d, J=7.8 Hz, 1H), 4.59-4.49 (m, 1H), 3.70 (s, 3H), 2.52-2.30 (m, 2H), 2.28-2.14 (m, 5H), 2.03-1.90 (m, 1H), 1.73-1.43 (m, 22H), 1.38-1.20 (m, 24H).

Step D: Synthesis of Intermediate 3d

To a stirred mixture of (R)-1-tert-butyl 5-methyl 2-(18-(tert-butoxy)-18-oxooctadecanamido) pentanedioate (1.2 g, 2.106 mmol) in THF (12 ml) was added a solution of lithium hydroxide (0.403 g, 16.85 mmol) in water (8 ml) four times on average every other hour at 0° C. The resulting mixture was stirred for 1 h at 0° C. The PH of the reaction was adjusted to 6 with HCl (1 N). The mixture was purified by reverse phase with the following conditions: Column, Xbridge C18, 330 g, 19×150 mm; mobile phase: acetonitrile in Water (0.1% TFA), 34%-98% in 25 min; Detector, UV 254 nm. RT: 20 min. The collected fractions were combined and concentrated under reduced pressure to give (R)-5-(tert-butoxy)-4-(18-(tert-butoxy)-18-oxooctadecanamido)-5-oxopentanoic acid 3d. LCMS (ESI) calc'd for $C_{31}H_{57}NO_7$ $[M+H]^+$: 556.4, found 556.4. $^1H$ NMR (400 MHz, Chloroform-d) δ 6.29 (d, J=7.7 Hz, 1H), 4.66-4.45 (m, 1H), 2.51-2.40 (m, 2H), 2.31-2.18 (m, 5H), 1.97-1.86 (m, 1H), 1.71-1.42 (m, 22H), 1.38-1.22 (m, 24H).

Step E: Synthesis of Intermediate 3e

To a stirred mixture of (R)-5-(tert-butoxy)-4-(18-(tert-butoxy)-18-oxooctadecanamido)-5-oxopentanoic acid 3b (770 mg, 1.385 mmol) in DMF (7 ml) were added HATU (579 mg, 1.524 mmol), (R)-23-tert-butyl 1-methyl 22-amino-10,19-dioxo-3,6,12,15-tetraoxa-9,18-diazatricosane-1,23-dioate 3d (844 mg, 1.663 mmol) and N-ethyl-N-isopropylpropan-2-amine (1432 mg, 11.08 mmol) at 0° C. The resulting mixture was stirred for 1 h at 0° C. The reaction was quenched by water (5 ml). The mixture was purified by reverse phase with the following conditions: Column, Xbridge C18, 19×150 mm; mobile phase: acetonitrile in Water (0.1% TFA), 34%-95% in 8 min; Detector, UV 254 nm. RT: 6.82 min. The collected fractions were combined and concentrated under reduced pressure to give 3e. LCMS (ESI) calc'd for $C_{53}H_{96}N_4O_{16}$ $[M+H]^+$: 1045.6, found 1045.6. $^1H$ NMR (400 MHz, Chloroform-d) δ 7.26 (s, 1H), 7.10 (t, J=5.5 Hz, 1H), 7.02 (d, J=7.6 Hz, 1H), 6.53 (d, J=7.9 Hz, 1H), 4.52-4.39 (m, 2H), 4.18 (s, 2H), 4.05 (s, 2H), 3.76-3.43 (m, 16H), 2.96 (s, 3H), 2.34-2.29 (m, 4H), 2.28-2.17 (m, 6H), 2.01-1.81 (m, 2H), 1.70-1.55 (m, 4H), 1.54-1.40 (m, 27H), 1.37-1.23 (m, 24H).

Step F: Synthesis of Intermediate 3f

To a solution of 3e (0.3 g, 0.287 mmol) in THF (3 mL) was added 1 M lithium hydroxide (0.574 mL, 0.574 mmol) at 0° C. The mixture was stirred at 0° C. for 1 h. The reaction solution was quenched with 1 M HCl (0.58 mL) and purified by Flash (Column: Flash C18 120 g; Mobile Phase A: water, Mobile Phase B: ACN; Flow rate: 60 mL/min; Gradient: 1% B to 75% B in 10 min, 75% B to 90% B in 20 min; Detector: UV 220 nm; Rt=28 min) to afford 3f. LCMS (ESI) calc'd for $C_{52}H_{94}N_4O_{16}$ $[M+H]^+$: 1031.7, found 1031.6.

Step G: Synthesis of Intermediate 3g

To a solution of 3f (200 mg, 0.19 mmol) in DMF (2 mL) were added HATU (88 mg, 0.233 mmol), DIEA (0.203 mL, 1.16 mmol), and a solution of M (130 mg, 0.388 mmol) in DMF (0.5 mL) and water (0.2 mL) at −10° C. The mixture was stirred at −10° C. for 10 min. The reaction solution was quenched with water (200 µL) and purified by Flash (Column: Flash $C^{18}$ 80 g; Mobile Phase A: water (0.05% TFA), Mobile Phase B: ACN; Flow rate: 70 mL/min; Gradient: 2% B to 2% B in 5 min, 30% B to 60% B in 15 min, 60% B to 80% B in 10 min; Detector: UV 220 nm; Rt=22 min). The fractions containing desired product were combined and concentrated. The residue was re-dissolved in ACN (10 mL)

and water (10 mL), and lyophilized to afford 3g. LCMS (ESI) calc'd for $C_{66}H_{119}F_3N_6O_{21}$ [M-TFA$^-$]$^+$: 1275.9, found 1275.8.

Step H: Synthesis of Intermediate 3h

To a solution of 3g (220 mg, 0.158 mmol) in THF (2.2 mL) was added 1M LiOH (0.317 mL, 0.317 mmol) at 0° C. The mixture was stirred at 0° C. for 1 h. The reaction solution was quenched with 1 M HCl (0.32 mL) and purified by Flash (Column: Flash $C^{18}$ 80 g; Mobile Phase A: water, Mobile Phase B: ACN; Flow rate: 70 mL/min; Gradient: 1% B to 1% B in 5 min, 35% B to 70% B in 20 min; Detector: UV 220 nm; Rt=22 min). The fractions containing desired product were combined and concentrated. The residue was re-dissolved in ACN (5 mL) and water (5 mL), and added 1 N HCl (0.1 mL) at 0° C. and lyophilized to afford 3h. LCMS (ESI) calc'd for $C_{63}H_{117}ClN_6O_{19}$ [M-Cl-]$^+$: 1261.8, found 1261.8 $^1$H NMR (300 MHz, $CD_3OD$) δ 4.28 (dd, J=9.3, 4.7 Hz, 2H), 4.05 (s, 2H), 4.02 (s, 2H), 3.96 (s, 2H), 3.81-3.26 (m, 28H), 3.23 (s, 6H), 2.56 (t, J=6.0 Hz, 2H), 2.40-2.17 (m, 10H), 1.88 (s, 2H), 1.58 (s, 4H), 1.48 (d, J=0.9 Hz, 18H), 1.45 (s, 9H), 1.30 (s, 24H).

Step I: Synthesis of 3i

To a solution of D (15.0 mg, 10.7 μmol) in DMF (300 μL) and water (30 μL) was added 3h (19.5 mg, 0.015 mmol) at room temperature. After cooling to −20° C., HATU (8.17 mg, 0.021 mmol) and DIEA (15.0 μL, 0.086 mmol) were added to the mixture at −20° C. The mixture was stirred at 0° C. for 0.5 h. The mixture was purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 20% B to 70% B in 25 min; Detector: UV 254/210 nm; Rt=25 min). The fractions containing desired product were combined and concentrated under reduced pressure. The residue was re-dissolved in ACN (5 mL) and water (5 mL), lyophilized to afford 3i. LCMS (ESI) calc'd for $C_{137}H_{202}F_4N_{20}O_{32}$ [(M-TFA$^-$+H)/2]$^+$: 1301.8, found 1302.4.

Step J: Synthesis of 3j

To a solution of 3i (22.0 mg, 8.10 μmol) in DCM (4.4 mL) was added TFA (5.5 mL, 71.4 mmol) at −20° C. The reaction mixture was stirred at room temperature for 1 h. The reaction solution was concentrated under reduced pressure and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 20% B to 60% B in 20 min; Detector: UV 254/210 nm; Rt=15 min). The fractions containing desired product were combined and concentrated under reduced pressure. The residue was re-dissolved in ACN (5 mL) and water (5 mL), lyophilized to afford 3j. LCMS (ESI) calc'd for $C_{125}H_{178}F_4N_{20}O_{32}$ [(M-TFA$^-$+H)/2]$^+$: 1217.6, found 1218.5.

Step K: Synthesis of Example 3

5 g of AG MP-1 Resin (cat #141-1841 BIO-RAD) was packed in column. The column was washed with water (2×10 mL), followed by 20% ACN in water (2×10 mL). A solution of 3j (14 mg, 5.49 μmol) in 60% ACN in water (20 mL) was loaded onto the resin column, and the column was eluted with 60% ACN in water (3×20 mL). The eluents were combined, water (4×4 mL) added, lyophilized to afford Example 3. LCMS (ESI) calc'd for $C_{123}H_{178}ClFN_{20}O_{30}$ [M-Cl$^-$]$^+$: 2434.3, found 2434.3; [(M-Cl$^-$+H)/2]$^+$: 1217.6, found 1218.2.

Preparation of Example 4

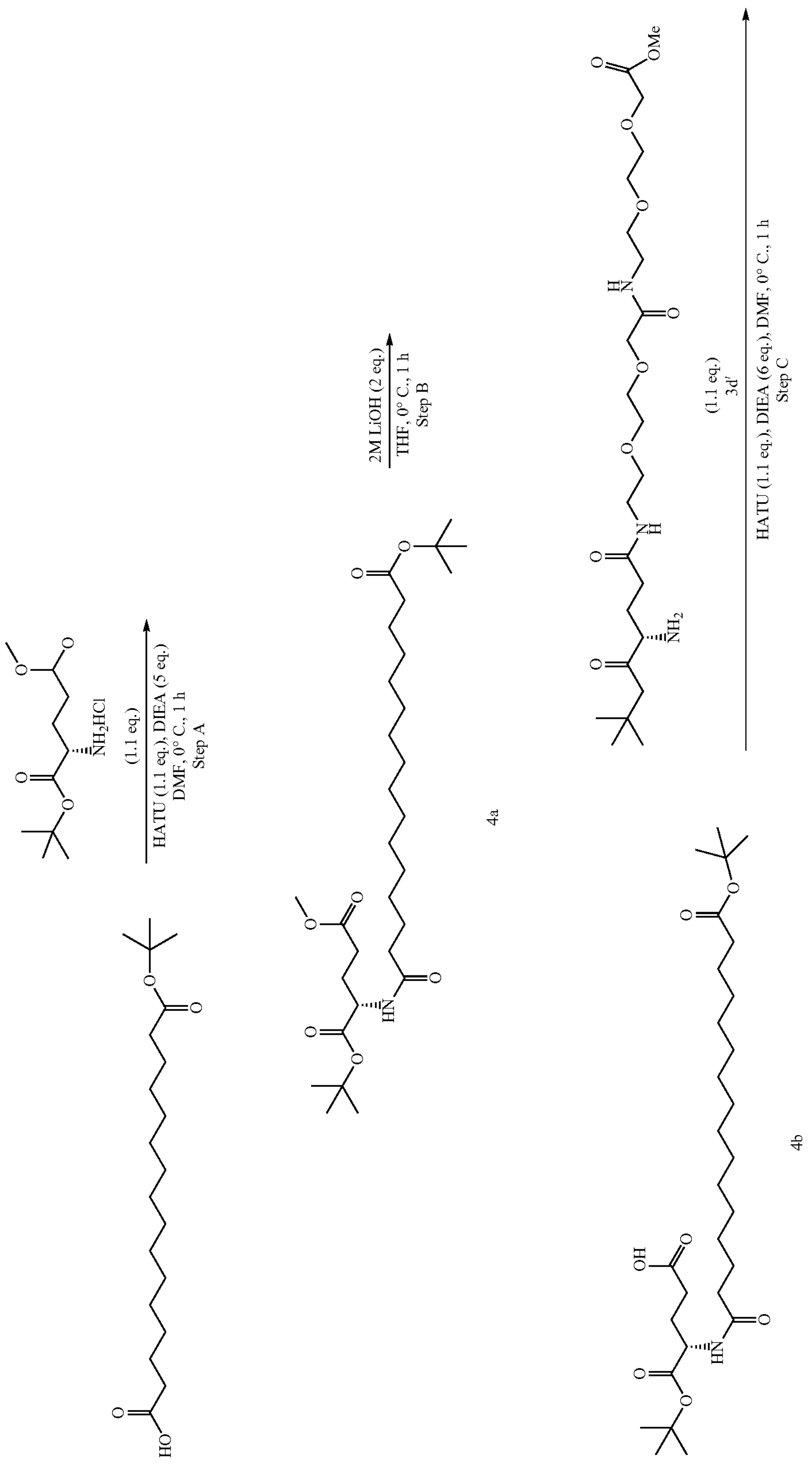
4a
4b

-continued
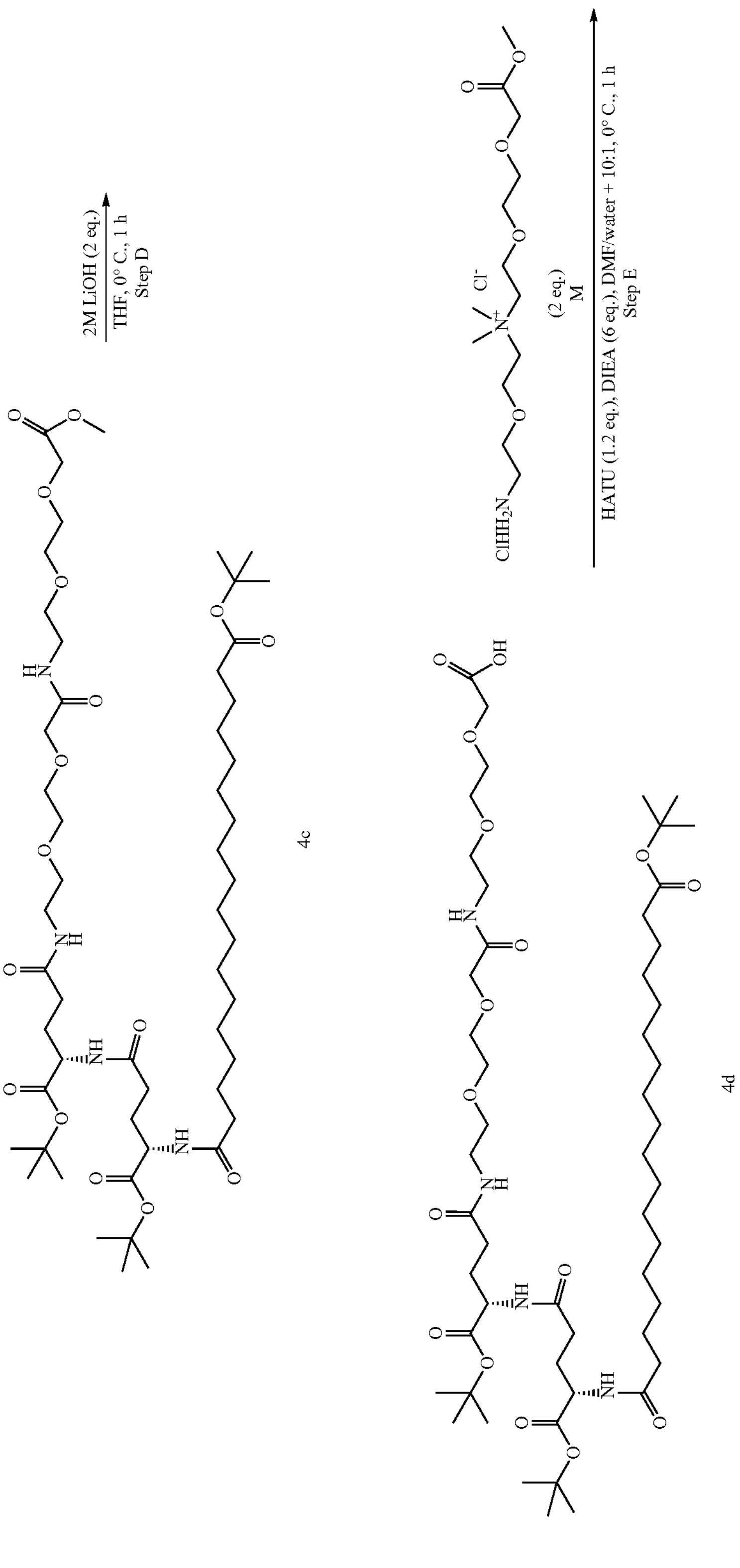
4c
4d

-continued
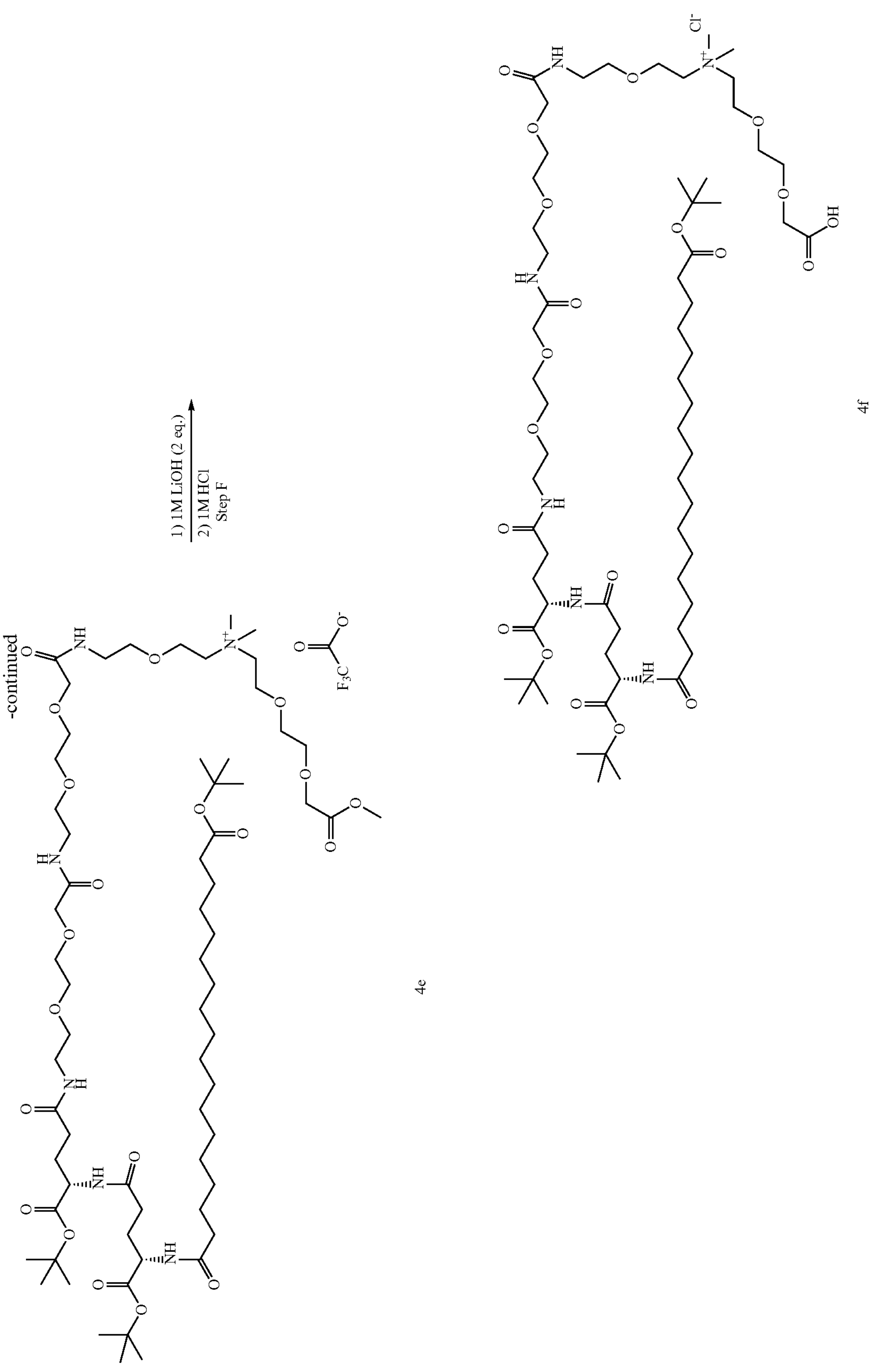
4e
4f

-continued
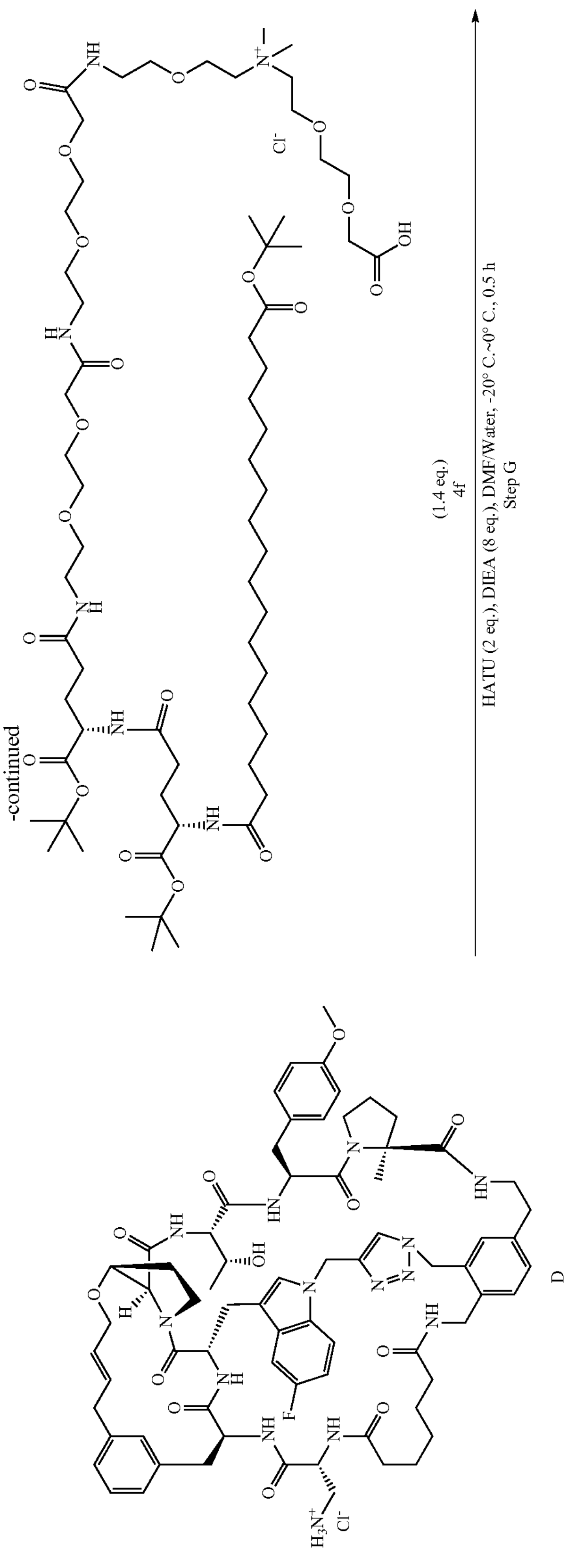
D

-continued
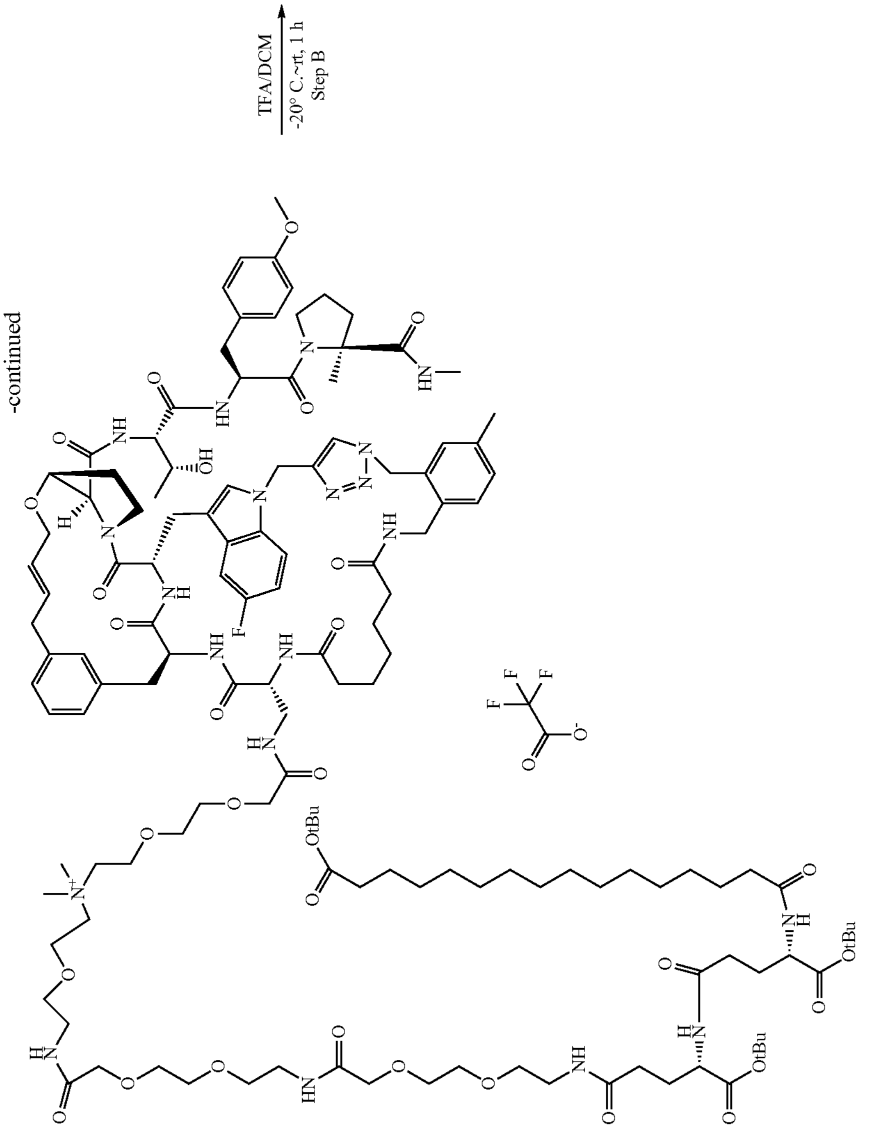
4g

-continued
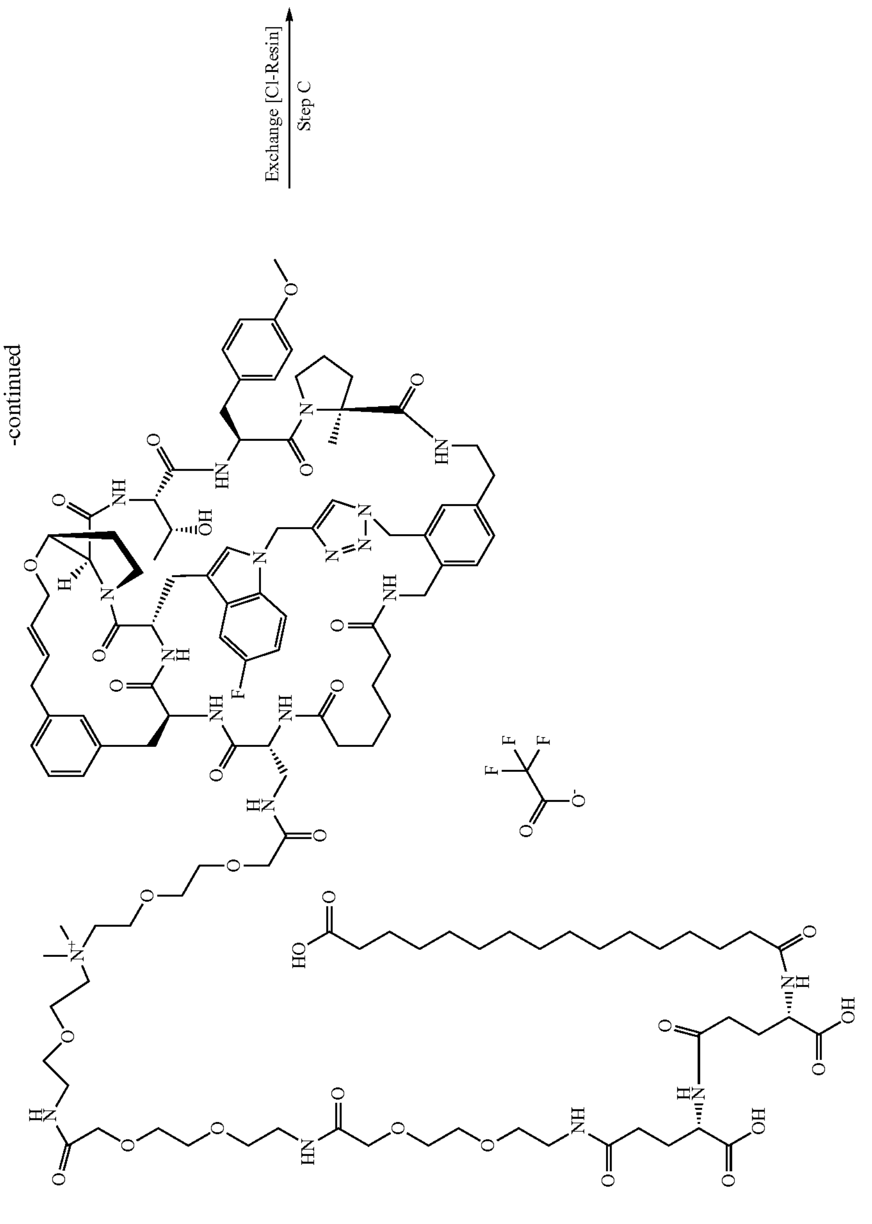
4h

-continued
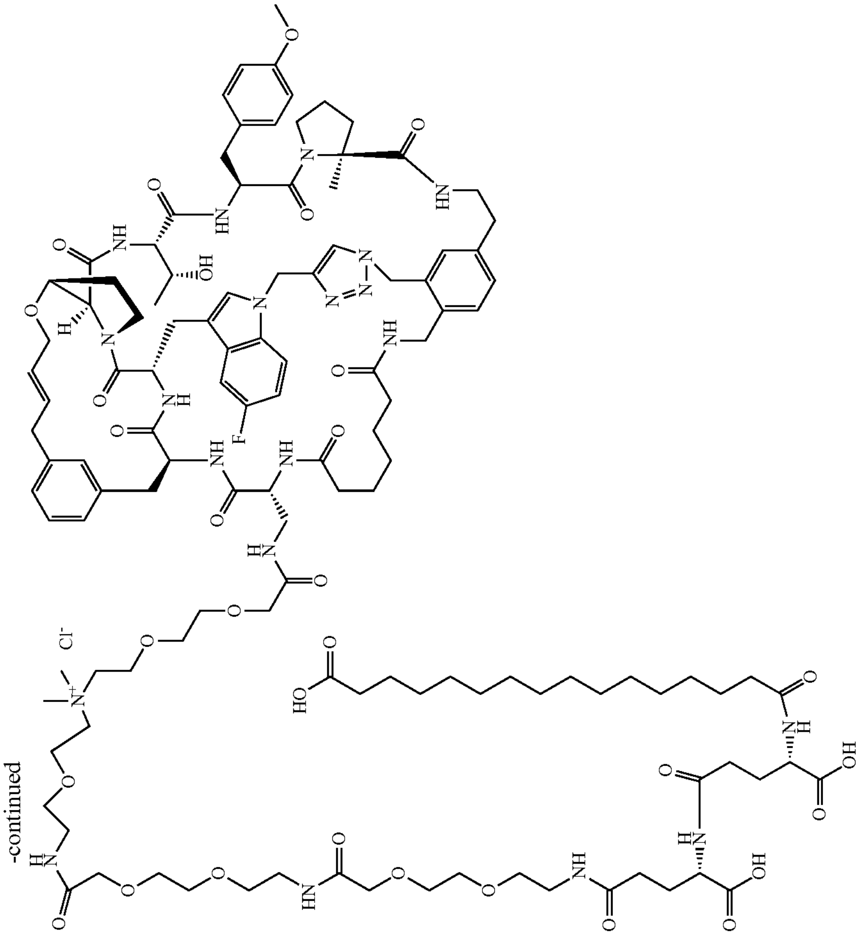
Example 4

Step A: (S)-1-tert-butyl 5-methyl 2-(16-(tert-butoxy)-16-oxohexadecanamido)pentanedioate 4a To a stirred solution of 16-(tert-butoxy)-16-oxohexadecanoic acid (1 g, 2.92 mmol) in DMF (12 mL) were added (S)-1-tert-butyl 5-methyl 2-aminopentanedioate hydrochloride (0.82 g, 3.21 mmol), HATU (1.22 g, 3.21 mmol) and DIEA (2.55 mL, 14.60 mmol) at 0° C. The reaction mixture was stirred at 0° C. for 1 h. The resulting solution was quenched with water (2 mL) and purified by Flash (Column: Flash $C^{18}$ 120 g; Mobile Phase A: water (0.05% TFA), Mobile Phase B: ACN; Flow rate: 80 mL/min; Gradient: 10% B to 70% B in 10 min, 70% B to 98% B in 20 min; Detector: UV 220 nm; Rt=28 min) to afford (S)-1-tert-butyl 5-methyl 2-(16-(tert-butoxy)-16-oxohexadecanamido)pentanedioate 4a. LCMS (ESI) calc'd for $C_{30}H_{55}NO_7$ $[M+H]^+$: 542.4, found 542.4. $^1H$ NMR (300 MHz, $CD_3OD$): δ 4.31 (dd, J=9.1, 5.3 Hz, 1H), 3.68 (s, 3H), 2.42 (t, J=7.5 Hz, 2H), 2.22 (q, J=7.1 Hz, 4H), 2.18-2.05 (m, 1H), 2.01-1.82 (m, 1H), 1.69-1.52 (m, 4H), 1.47 (s, 9H), 1.45 (s, 9H), 1.38-1.28 (m, 20H).

Step B: (S)-5-(tert-butoxy)-4-(16-(tert-butoxy)-16-oxohexadecanamido)-5-oxopentanoic acid 4b To a stirred solution of (S)-1-tert-butyl 5-methyl 2-(16-(tert-butoxy)-16-oxohexadecanamido)pentanedioate 4a (1.3 g, 2.40 mmol) in THF (13 mL) was added 1 M LiOH (4.80 mL, 4.80 mmol) at 0° C. The reaction mixture was stirred at 0° C. for 1 h. The resulting solution was quenched with 1 M HCl (4.80 mL) and purified by Flash (Column: Flash $C^{18}$ 120 g; Mobile Phase A: water, Mobile Phase B: ACN; Flow rate: 80 mL/min; Gradient: 1% B to 80% B in 15 min, 80% B to 98% B in 15 min; Detector: UV 220 nm; Rt=28 min) to afford (S)-5-(tert-butoxy)-4-(16-(tert-butoxy)-16-oxohexadecanamido)-5-oxopentanoic acid 4b. LCMS (ESI) calc'd for $C_{29}H_{53}NO_7$ $[M+H]^+$: 528.4, found 528.4. $^1H$ NMR (400 MHz, $CD_3OD$): δ 4.32 (dd, J=9.0, 5.4 Hz, 1H), 2.40 (t, J=7.5 Hz, 2H), 2.24 (dt, J=10.0, 7.4 Hz, 4H), 2.18-2.04 (m, 1H), 1.99-1.84 (m, 1H), 1.71-1.52 (m, 4H), 1.49 (s, 9H), 1.46 (s, 9H), 1.37-1.29 (m, 20H).

Step C: (21S,26S)-21,26,42-tri-tert-butyl 1-methyl 9,18,23,28-tetraoxo-2,5,11,14-tetraoxa-8,17,22,27-tetraazadotetracontane-1,21,26,42-tetracarboxylate 4c To a stirred solution of (S)-5-(tert-butoxy)-4-(16-(tert-butoxy)-16-oxohexadecanamido)-5-oxopentanoic acid 4b (600 mg, 1.14 mmol) in DMF (6 mL) were added (S)-23-tert-butyl 1-methyl 22-amino-10,19-dioxo-3,6,12,15-tetraoxa-9,18-diazatricosane-1,23-dioate 3d' (635 mg, 1.25 mmol, 3d' prepared in the same way as 3d using (S)-4-(((benzyloxy)carbonyl)amino)-5-(tert-butoxy)-5-oxopentanoic acid (1.5 g, 4.45 mmol) in Step A of Example 3), HATU (476 mg, 1.25 mmol) and DIEA (1.19 mL, 6.82 mmol) at 0° C. The reaction mixture was stirred at 0° C. for 1 h. The resulting solution was quenched with water (2 mL) and purified by Flash (Column: Flash $C^{18}$ 120 g; Mobile Phase A: water (0.05% TFA), Mobile Phase B: ACN; Flow rate: 80 mL/min; Gradient: 10% B to 70% B in 10 min, 70% B to 90% B in 20 min; Detector: UV 220 nm; Rt=28 min) to afford (21S,26S)-21,26,42-tri-tert-butyl 1-methyl 9,18,23,28-tetraoxo-2,5,11,14-tetraoxa-8,17,22,27-tetraazadotetracontane-1,21,26,42-tetracarboxylate 4c. LCMS (ESI) calc'd for $C_{51}H_{92}N_4O_{16}$ $[M+H]^+$: 1017.7, found 1017.6. $^1H$ NMR (300 MHz, $CD_3OD$): δ 4.31-4.23 (m, 2H), 4.18 (s, 2H), 4.02 (s, 2H), 3.74 (s, 3H), 3.73-3.63 (m, 8H), 3.62-3.53 (m, 4H), 3.48-3.36 (m, 4H), 2.43-2.06 (m, 11H), 1.97-1.79 (m, 1H), 1.70-1.52 (m, 4H), 1.51-1.42 (m, 27H), 1.37-1.28 (m, 20H).

Step D: (22S,27S)-22,27-bis(tert-butoxycarbonyl)-46,46-dimethyl-10,19,24,29,44-pentaoxo-3,6,12,15,45-pentaoxa-9,18,23,28-tetraazaheptatetracontan-1-oic acid 4d To a stirred solution of (21S,26S)-21,26,42-tri-tert-butyl 1-methyl 9,18,23,28-tetraoxo-2,5,11,14-tetraoxa-8,17,22,27-tetraazadotetracontane-1,21,26,42-tetracarboxylate 4c (930 mg, 0.91 mmol) in THF (10 mL) was added 1 M LiOH (1.83 mL, 1.83 mmol) at 0° C. The reaction mixture was stirred at 0° C. for 1 h. The resulting solution was quenched with 1 M HCl (1.83 mL) and purified by Flash (Column: Flash $C^{18}$ 120 g; Mobile Phase A: water (0.05% TFA), Mobile Phase B: ACN; Flow rate: 70 mL/min; Gradient: 1% B to 75% B in 10 min, 75% B to 90% B in 20 min; Detector: UV 220 nm; Rt=25 min) to afford (22S,27S)-22,27-bis(tert-butoxycarbonyl)-46,46-dimethyl-10,19,24,29,44-pentaoxo-3,6,12,15,45-pentaoxa-9,18,23,28-tetraazaheptatetracontan-1-oic acid 4d. LCMS (ESI) calc'd for $C_{50}H_{90}N_4O_{16}$ $[M+H]^+$: 1003.6, found 1003.5. $^1H$ NMR (400 MHz, $CD_3OD$): δ 4.29 (dt, J=9.6, 4.7 Hz, 2H), 4.17 (S, 2H), 4.03 (s, 2H), 3.76-3.65 (m, 8H), 3.64-3.56 (m, 4H), 3.50-3.35 (m, 4H), 2.46-2.07 (m, 10H), 1.97-1.84 (m, 2H), 1.69-1.54 (m, 4H), 1.52-1.45 (m, 27H), 1.10-1.29 (m, 20H).

Step E: Synthesis of Intermediate 4e

To a stirred solution of (22S,27S)-22,27-bis(tert-butoxycarbonyl)-46,46-dimethyl-10,19,24,29,44-pentaoxo-3,6,12,15,45-pentaoxa-9,18,23,28-tetraazaheptatetracontan-1-oic acid 4d (200 mg, 0.20 mmol) in DMF (2 mL) and water (0.2 mL) were added 2-(2-aminoethoxy)-N-(2-(2-(2-methoxy-2-oxoethoxy)ethoxy)ethyl)-N,N-dimethylethanaminium chloride hydrochloride M (146 mg, 0.40 mmol), HATU (91 mg, 0.24 mmol) and DIEA (0.21 mL, 1.20 mmol) at 0° C. The reaction mixture was stirred at 0° C. for 1 h. The resulting solution was quenched with water (2 mL) and purified by Flash (Column: Flash $C^{18}$ 120 g; Mobile Phase A: water (0.05% TFA), Mobile Phase B: ACN; Flow rate: 80 mL/min; Gradient: 10% B to 30% B in 10 min, 30% B to 70% B in 20 min; Detector: UV 220 nm; Rt=25 min) to afford 4e. LCMS (ESI) calc'd for $C_{65}H_{117}F_3N_6O_{22}$ $[M-TFA^-]^+$: 1277.8, found 1277.8.

Step F: Synthesis of Intermediate 4f

To a stirred solution of 4e (270 mg, 0.19 mmol) in THF (3 mL) was added 1 M LiOH (0.39 mL, 0.39 mmol) at 0° C. The reaction mixture was stirred at 0° C. for 1 h. The resulting solution was quenched with 1 M HCl (0.39 mL) and purified by Flash (Column: Flash $C^{18}$ 80 g; Mobile Phase A: water, Mobile Phase B: ACN; Flow rate: 60 mL/min; Gradient: 1% B to 30% B in 10 min, 30% B to 60% B in 15 min; Detector: UV 220 nm; Rt=23 min). The fractions containing desired product were combined and concentrated. The residue was re-dissolved in ACN (3 mL) and water (5 mL), and added 1 N HCl (0.15 mL) at 0° C. The solution was lyophilized to afford 4f. LCMS (ESI) calc'd for $C_{62}H_{115}ClN_6O_{20}$ $[M-Cl^-]^+$: 1263.8, found 1263.7. $^1H$ NMR (400 MHz, $CD_3OD$): δ 4.30 (dt, J=11.7, 5.4 Hz, 2H), 4.19-4.12 (m, 2H), 4.07-3.99 (m, 4H), 3.80-3.39 (m, 32H), 3.26 (s, 6H), 2.45-2.13 (m, 10H), 1.98-1.80 (m, 2H), 1.70-1.56 (m, 4H), 1.54-1.44 (m, 27H), 1.10-1.29 (m, 20H).

Step G: Synthesis of 4g

To a solution of D (15.0 mg, 10.7 μmol) in DMF (300 μL) and water (30 μL) was added 4f (19.6 mg, 0.015 mmol) at room temperature. After cooling to −20° C., HATU (8.17 mg, 0.021 mmol) and DIEA (15 μL, 0.086 mmol) were added to the mixture at −20° C. The mixture was stirred at 0° C. for 0.5 h. The reaction solution was quenched with water (100 μL) and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 20% B to 60% B in 20 min; Detector: UV 254/210 nm; Rt=20 min). The fractions containing desired product were combined and concentrated under reduced pressure. The residue was re-dissolved in ACN (5 mL) and water (5 mL), lyophilized to afford 4g. LCMS (ESI) calc'd for $C_{136}H_{202}F_4N_{20}O_{33}$ $[(M\text{-}TFA^-+H)/2]^+$: 1303.7, found 1303.3.

Step H: Synthesis of 4h

To a solution of 4g (25.0 mg, 9.19 μmol) in DCM (5 mL) was added TFA (6.2 mL, 80 mmol) at −20° C. The reaction mixture was stirred at room temperature for 1 h. The reaction solution was concentrated under reduced pressure and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 20% B to 60% B in 20 min; Detector: UV 254/210 nm; Rt=16 min). The fractions containing desired product were combined and concentrated under reduced pressure. The residue was re-dissolved in ACN (5 mL) and water (5 mL), lyophilized to afford 4h. LCMS (ESI) calc'd for $C_{124}H_{176}F_4N_{20}O_{33}$ $[(M\text{-}TFA^-+H)/2]^+$: 1218.6, found 1219.5.

Step I: Synthesis of Example 4

5 g of AG MP-1 Resin (cat #141-1841 BIO-RAD) was packed in column. The column was washed with water (2×10 mL), followed by 20% ACN in water (2×10 mL). A solution of 4h (18.0 mg, 7.06 μmol) in 60% ACN in water (20 mL) was loaded onto the resin column, and the column was eluted with 60% ACN in water (4×20 mL). The eluents were combined, water (5×4 mL) added, lyophilized to afford Example 4. LCMS (ESI) calc'd for $C_{122}H_{176}ClFN_{20}O_{31}$ $[M\text{-}Cl^-]^+$: 2436.3, found 2436.3; $[(M\text{-}Cl^-+H)/2]^+$: 1218.6, found 1219.2.

Preparation of Example 5

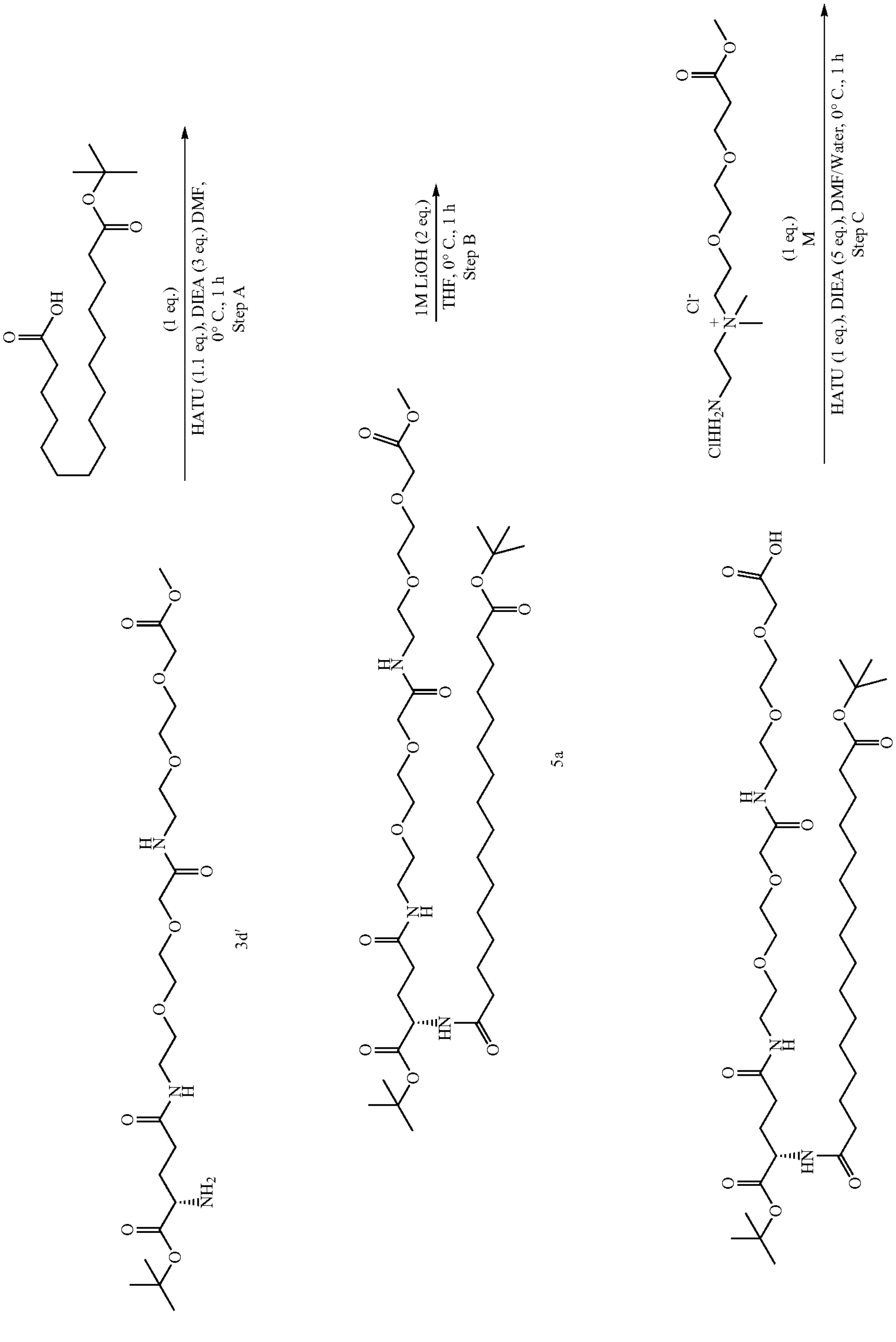
3d′
5a
5b

-continued
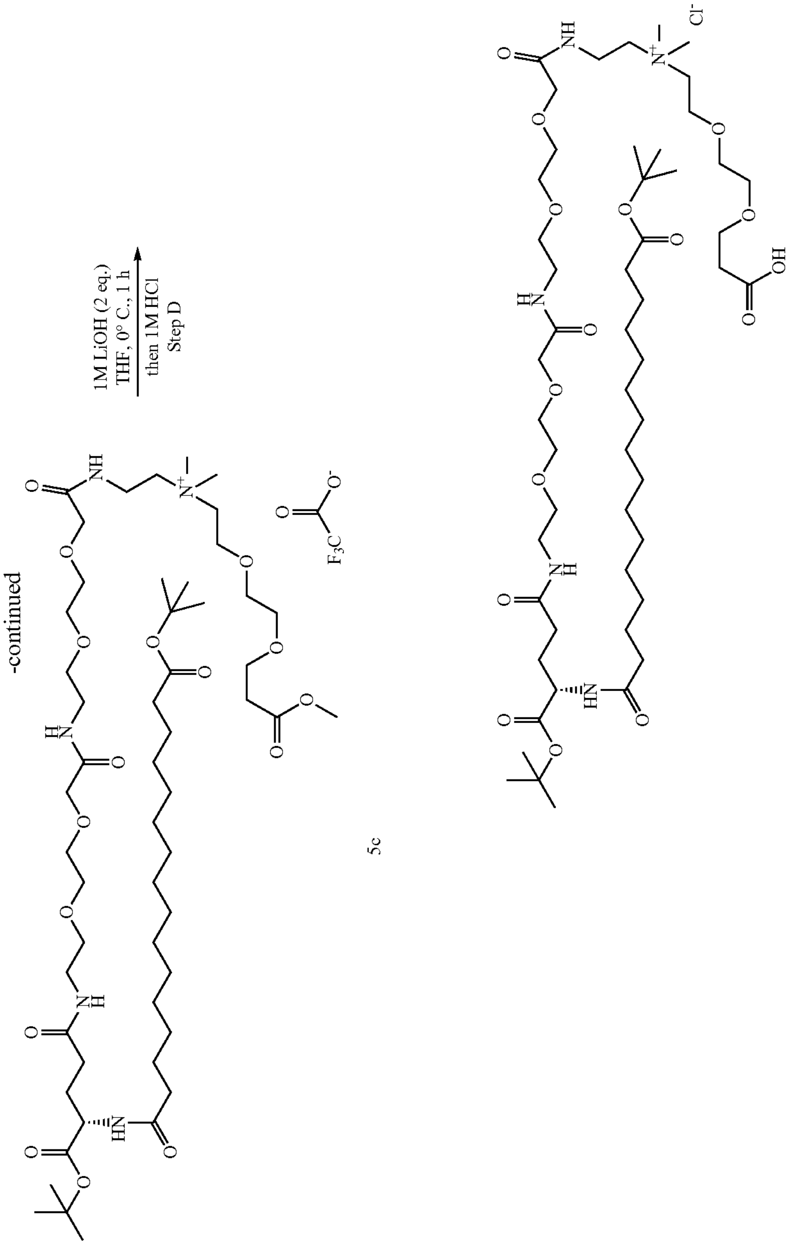
5c
5d

-continued
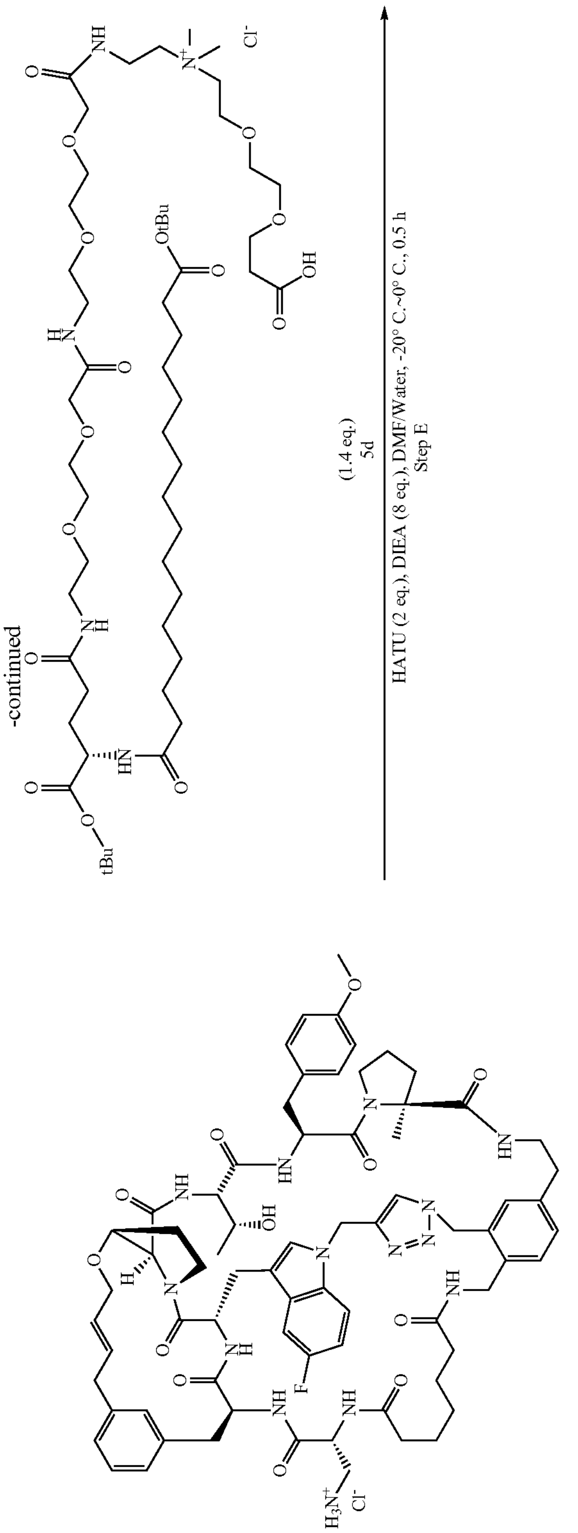
D

-continued
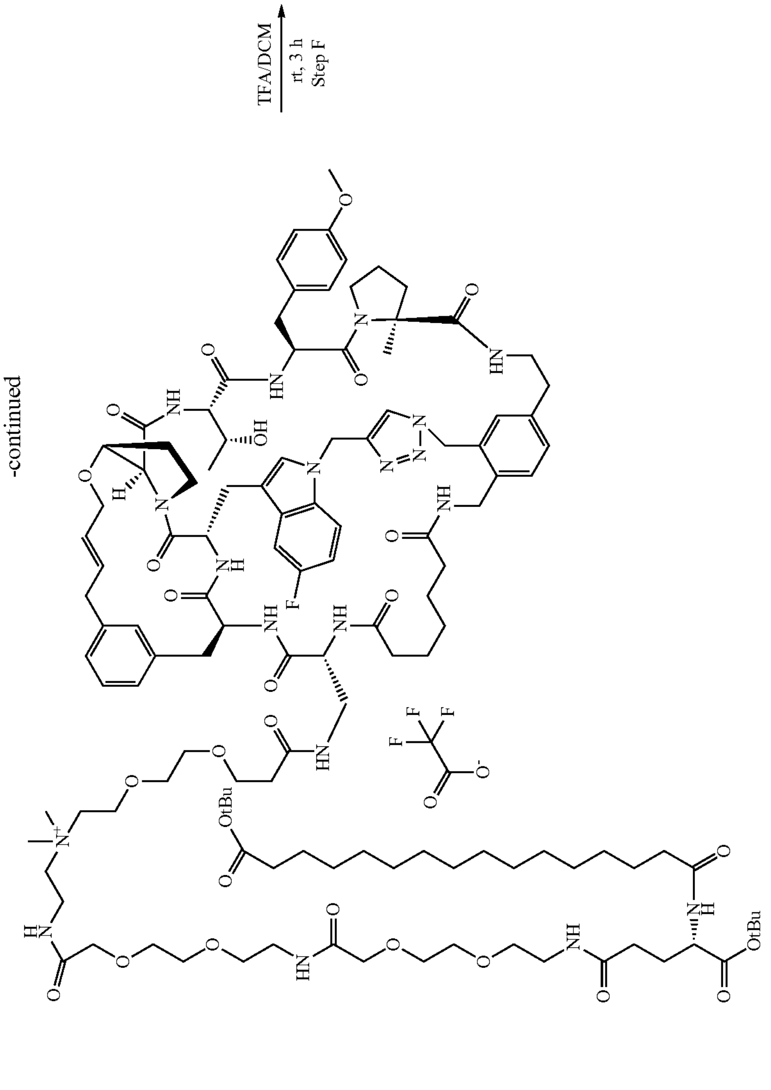
5e

-continued
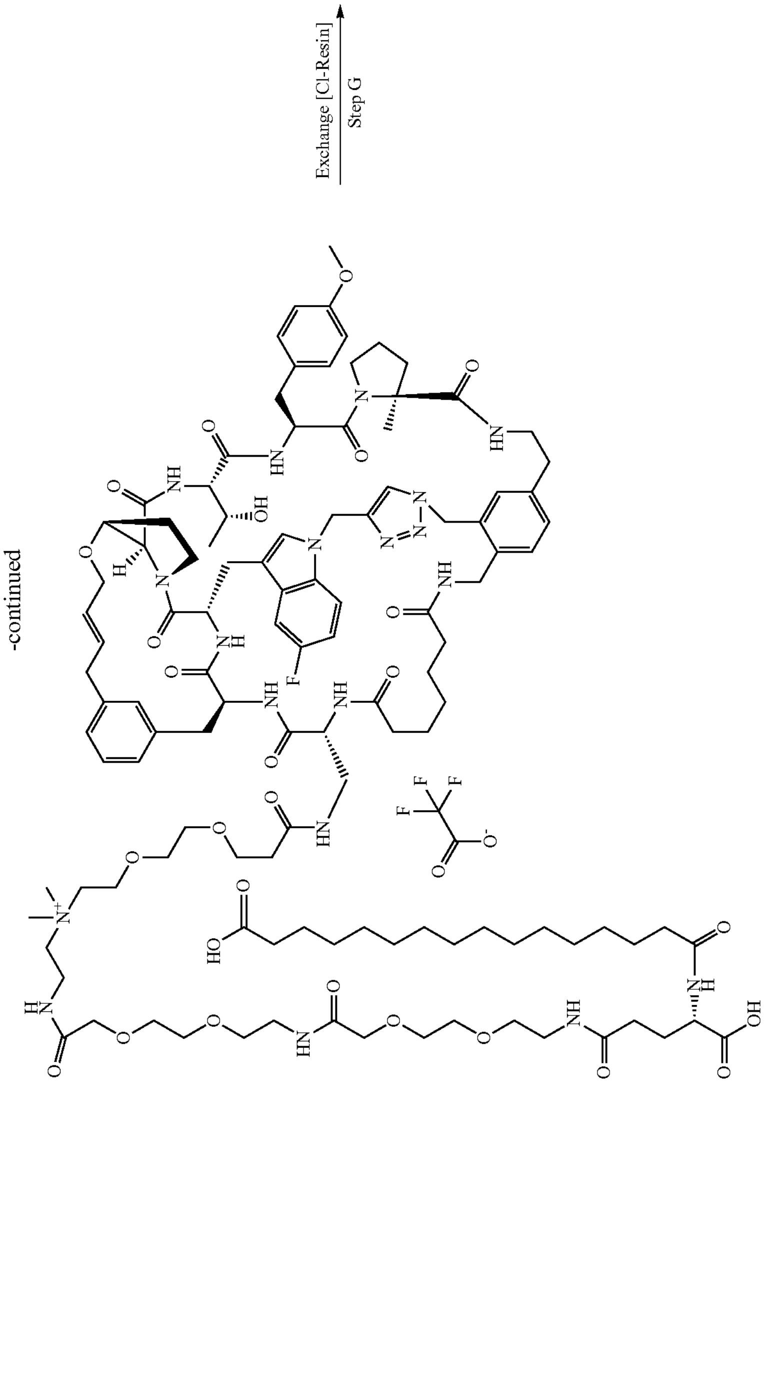
5f

-continued
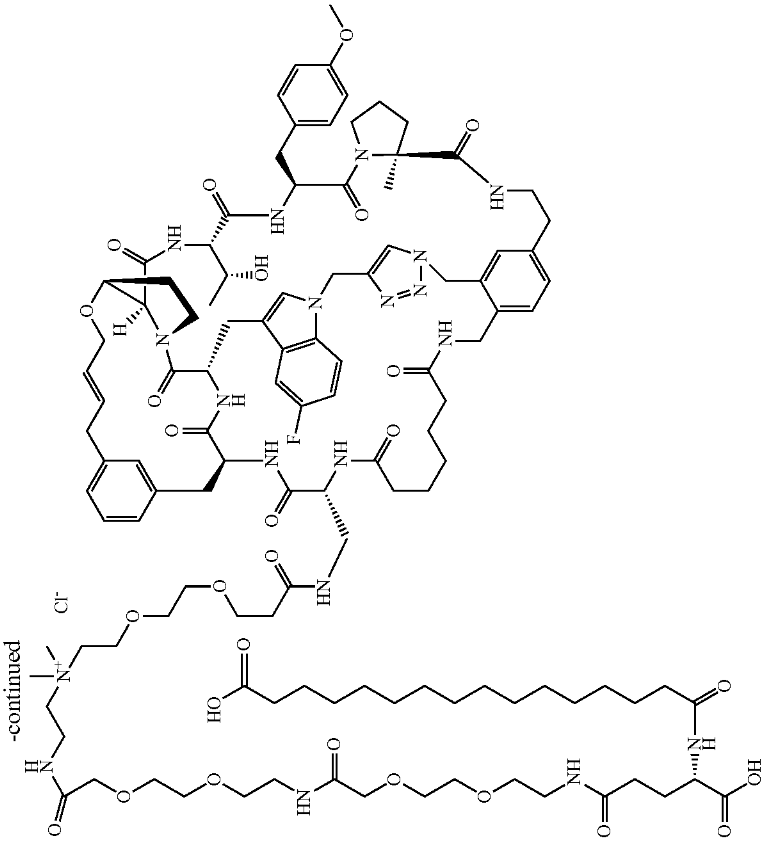
Example 5

Step A: (S)-21,37-di-tert-butyl 1-methyl 9,18,23-trioxo-2,5,11,14-tetraoxa-8,17,22-triazaheptatriacontane-1,21,37-tricarboxylate 5a To a solution of (S)-23-tert-butyl 1-methyl 22-amino-10,19-dioxo-3,6,12,15-tetraoxa-9,18-diazatricosane-1,23-dioate 3d' (510 mg, 1.005 mmol) in DMF (5 mL) were added 16-(tert-butoxy)-16-oxohexadecanoic acid (344 mg, 1.005 mmol), HATU (382 mg, 1.005 mmol) and DIEA (0.526 mL, 3.01 mmol) at 0° C. The mixture was stirred at 0° C. for 1 h. The reaction solution was quenched with water (1 mL) and purified by Flash (Column: Flash $C^{18}$ 80 g; Mobile Phase A: water (0.05% TFA), Mobile Phase B: ACN; Flow rate: 60 mL/min; Gradient: 10% B to 10% B in 5 min, 35% B to 90% B in 25 min; Detector: UV 220 nm; Rt=28 in) to afford the (S)-21,37-di-tert-butyl 1-methyl 9,18,23-trioxo-2,5,11,14-tetraoxa-8,17,22-triazaheptatriacontane-1,21,37-tricarboxylate 5a. LCMS (ESI) calc'd for $C_{42}H_{77}N_3O_{13}$ $[M+H]^+$: 832.6, found 832.6; $^1$H NMR (300 MHz, $CDCl_3$) δ 4.41 (td, J=8.5, 4.1 Hz, 1H), 4.15 (s, 2H), 4.03 (s, 2H), 3.75 (s, 3H), 3.74-3.41 (m, 16H), 2.41-2.07 (m, 7H), 2.02-1.82 (m, 1H), 1.70-1.52 (m, 4H), 1.46 (s, 9H), 1.44 (s, 9H), 1.33-1.22 (m, 20H).

Step B: (S)-22-(tert-butoxycarbonyl)-41,41-dimethyl-10,19,24,39-tetraoxo-3,6,12,15,40-pentaoxa-9,18,23-triazadotetracontan-1-oic acid 5b To a solution of (S)-21,37-di-tert-butyl 1-methyl 9,18,23-trioxo-2,5,11,14-tetraoxa-8,17,22-triazaheptatriacontane-1,21,37-tricarboxylate 5a (490 mg, 0.589 mmol) in THF (5 mL) was added 1 M lithium hydroxide (1.178 mL, 1.178 mmol) at 0° C. The mixture was stirred at 0° C. for 1 h. The reaction solution was quenched with 1 M HCl (1.2 mL) and purified by Flash (Column: Flash $C^{18}$ 80 g; Mobile Phase A: water, Mobile Phase B: ACN; Flow rate: 60 mL/min; Gradient: 10% B to 10% B in 10 min, 30% B to 90% B in 25 min; Detector: UV 220 nm; Rt=25 min). The fractions containing desired product were combined and concentrated. The residue was lyophilized to afford (S)-22-(tert-butoxycarbonyl)-41,41-dimethyl-10,19,24,39-tetraoxo-3,6,12,15,40-pentaoxa-9,18,23-triazadotetracontan-1-oic acid 5b. LCMS (ESI) calc'd for $C_{41}H_{75}N_3O_{13}$ [M+H]f: 818.5, found 818.6; $^1$H NMR (300 MHz, $CD_3OD$) δ 4.26 (dd, J=9.0, 5.0 Hz, 1H), 4.13 (s, 2H), 4.01 (s, 2H), 3.80-3.53 (m, 12H), 3.51-3.36 (m, 4H), 2.43-2.14 (m, 6H), 2.16-2.05 (m, 1H), 1.91 (dq, J=15.9, 8.0 Hz, 1H), 1.75-1.51 (m, 4H), 1.47 (s, 9H), 1.45 (s 9H), 1.32 (d, J=8.7 Hz, 20H).

Step C: Synthesis of Intermediate 5c

To a solution of (S)-22-(tert-butoxycarbonyl)-41,41-dimethyl-10,19,24,39-tetraoxo-3,6,12,15,40-pentaoxa-9,18,23-triazadotetracontan-1-oic acid 5b (250 mg, 0.306 mmol) in DMF (2 mL) and water (0.2 mL) were added 2-amino-N-(2-(2-(3-methoxy-3-oxopropoxy)ethoxy)ethyl)-N,N-dimethylethanaminium chloride hydrochloride M (102 mg, 0.306 mmol), HATU (116 mg, 0.306 mmol) and DIEA (0.267 mL, 1.528 mmol) at 0° C. The mixture was stirred at 0° C. for 1 h. The reaction solution was quenched with water (500 μL) and purified by Flash (Column: Flash $C^{18}$ 40 g; Mobile Phase A: water (0.05% TFA), Mobile Phase B: ACN; Flow rate: 45 mL/min; Gradient: 1% B to 1% B in 5 min, 30% B to 65% B in 20 min; Detector: UV 220 nm; Rt=24 min). The fractions containing desired product were combined and concentrated. The residue was re-dissolved in ACN (10 mL) and water (10 mL), and lyophilized to afford 5c. LCMS (ESI) calc'd for $C_{55}H_{100}F_3N_5O_{18}$ $[M-TFA^-]^+$: 1062.7, found 1062.7. $^1$H NMR (300 MHz, $CD_3OD$) δ 4.26 (dd, J=9.1, 5.2 Hz, 1H), 4.04 (s, 2H), 4.01 (s, 2H), 3.96 (s, 2H), 3.81-3.52 (m, 27H), 3.47 (t, J=5.6 Hz, 2H), 3.39 (t, J=5.6 Hz, 2H), 3.23 (s, 6H), 2.60 (t, J=6.0 Hz, 2H), 2.26 (dt, J=25.1, 7.5 Hz, 6H), 2.10 (dt, J=13.3, 7.1 Hz, 1H), 2.00-1.83 (m, 1H), 1.71-1.51 (m, 4H), 1.47 (s, 9H), 1.45 (s, 9H), 1.41-1.22 (d, J=10.5 Hz, 20H).

Step D: Synthesis of Intermediate 5d

To a solution of 5c (240 mg, 0.204 mmol) in THF (2.5 mL) was added 1 M LiOH (0.408 mL, 0.408 mmol) at 0° C. The mixture was stirred at 0° C. for 1 h. The reaction solution was quenched with 1 M HCl (0.41 mL) and purified by Flash (Column: Flash $C^8$ 40 g; Mobile Phase A: water, Mobile Phase B: ACN; Flow rate: 45 mL/min; Gradient: 1% B to 1% B in 5 min, 35% B to 70% B in 20 min; Detector: UV 220 nm; Rt=24 min). The fractions containing desired product were combined and concentrated. The residue was re-dissolved in ACN (5 mL) and water (5 mL), and added 1 N HCl (0.22 mL) at 0° C. and lyophilized to afford 5d. LCMS (ESI) calc'd for $Cs_2H_{98}ClN_5O_{16}$ $[M-Cl^-]^+$: 1048.7, found 1048.7. $^1$H NMR (300 MHz, $CD_3OD$): δ 4.26 (dd, J=9.1, 5.1 Hz, 1H), 4.05 (s, 2H), 4.02 (s, 2H), 3.96 (s, 2H), 3.83-3.51 (m, 24H), 3.47 (t, J=5.5 Hz, 2H), 3.39 (t, J=5.6 Hz, 3H), 3.22 (s, 6H), 2.42 (t, J=6.1 Hz, 2H), 2.30 (t, J=7.9 Hz, 2H), 2.21 (t, J=7.6 Hz, 4H), 2.18-2.02 (m, 1H), 1.91 (dd, J=14.2, 8.5 Hz, 1H), 1.59 (dd, J=15.7, 8.0 Hz, 5H), 1.47 (s, 9H), 1.45 (s, 9H), 1.31 (s, 20H).

Step E: Synthesis of 5e

To a solution of D (20 mg, 0.014 mmol) in DMF (200 μL) and water (20 μL) were added 5d (21.76 mg, 0.020 mmol), HATU (10.9 mg, 0.029 mmol) and DIEA (14.8 mg, 0.115 mmol) at −20° C. The mixture was stirred at −20° C. for 0.5 h. The reaction solution was quenched with water (50 μL) and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 30% B to 60% B in 15 min; Detector: UV 220 nm; Rt=13 min) to afford 5e. LCMS (ESI) calc'd for $C_{126}H_{183}F_4N_{19}O_{29}$ $[(M-TFA^-/2)]^+$: 1194.7, found 1195.9.

Step F: Synthesis of 5f

To a solution of 5e (27 mg, 10.78 μmol) in DCM (10 mL) was added TFA (12.5 mL) at −10° C. The mixture was stirred at RT for 3 h. The resulting mixture was concentrated under reduced pressure and the residue was and purified by Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 30% B to 60% B in 15 min; Detector: UV 220 nm; Rt=12 min) to 5f LCMS (ESI) calc'd for $C_{118}H_{167}F_4N_{19}O_{29}$ $[(M-TFA^-/2)]^+$: 1138.6, found 1140.0.

Step G: Synthesis of Example 5

6 g of AG MP-1 Resin (cat #141-1841 BIO-RAD) was packed in column. The column was washed with water (2×10 mL), followed by 20% ACN in water (2×10 mL). A solution of 5f (18 mg, 7.53 μmol) in 65% ACN in water (2 mL×2) was loaded onto the resin column, then the column was eluted with 65% ACN in water (80 mL). The eluents were combined and lyophilized to give Example 5. LCMS (ESI) calc'd for $C_{116}H_{167}ClFN_{19}O_{27}$ $[M-Cl^-]^+$: 2277.2, found 2277.2.

Preparation of Example 6
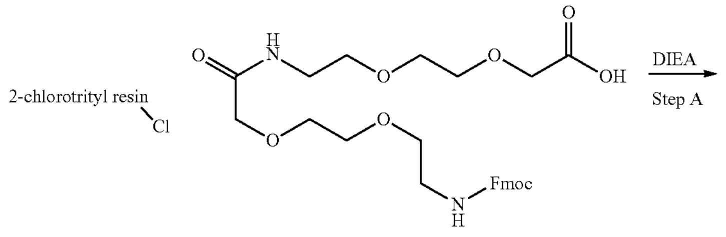
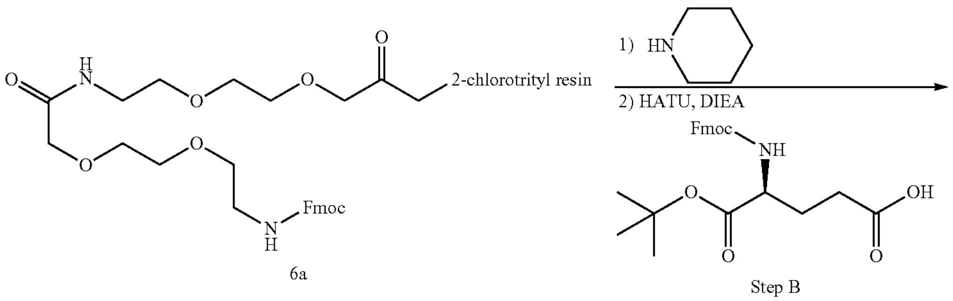
Step B
6a
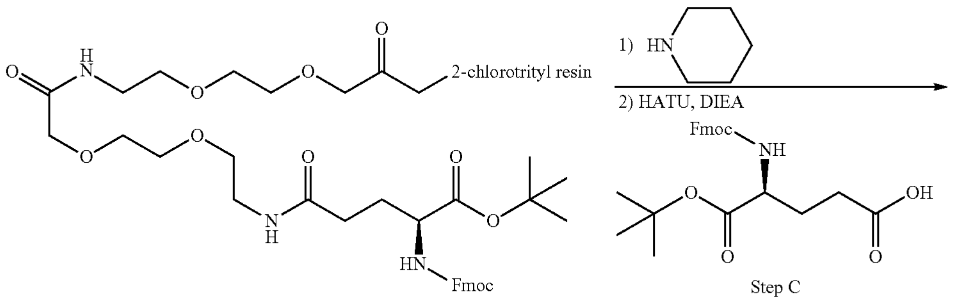
6b
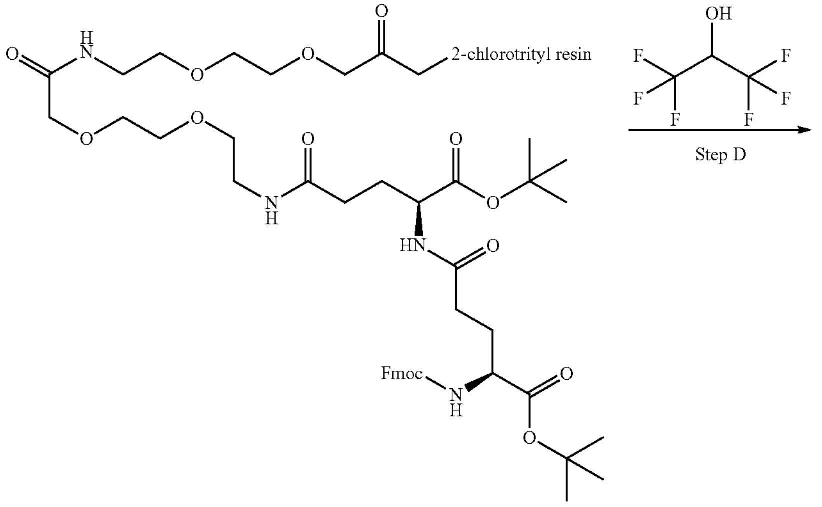
6c -continued
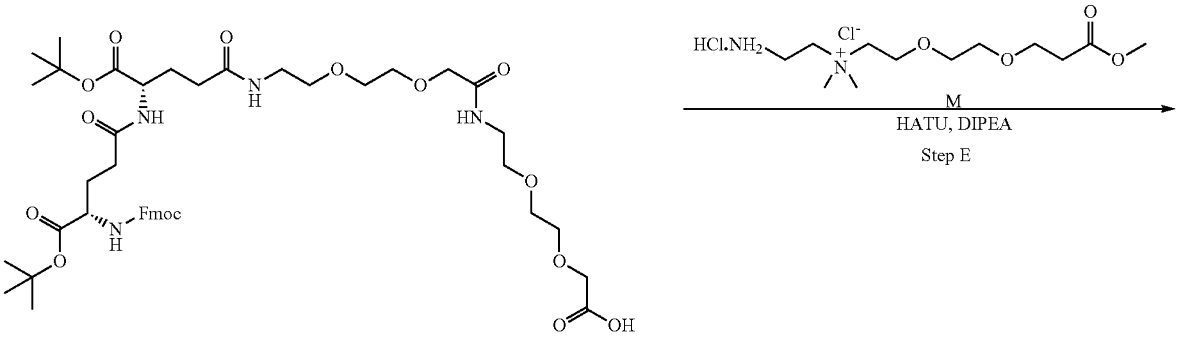
6d
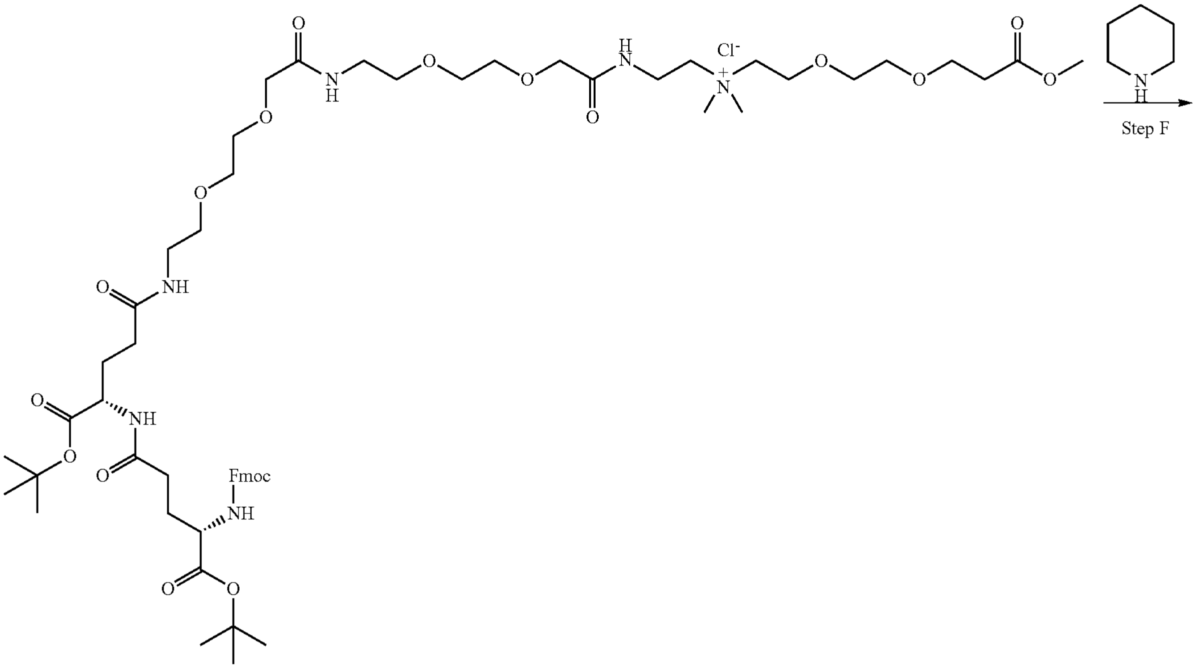
6e
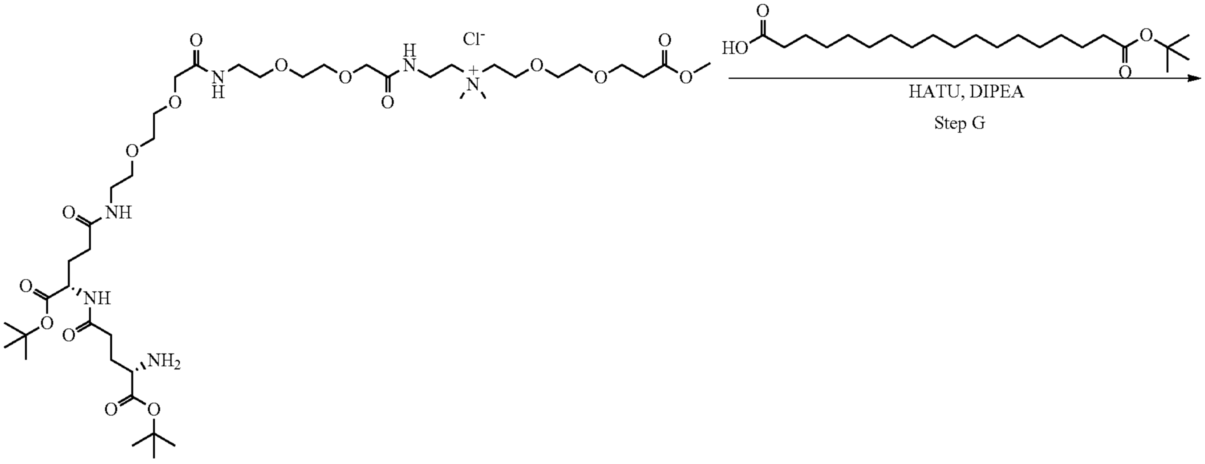
6f -continued
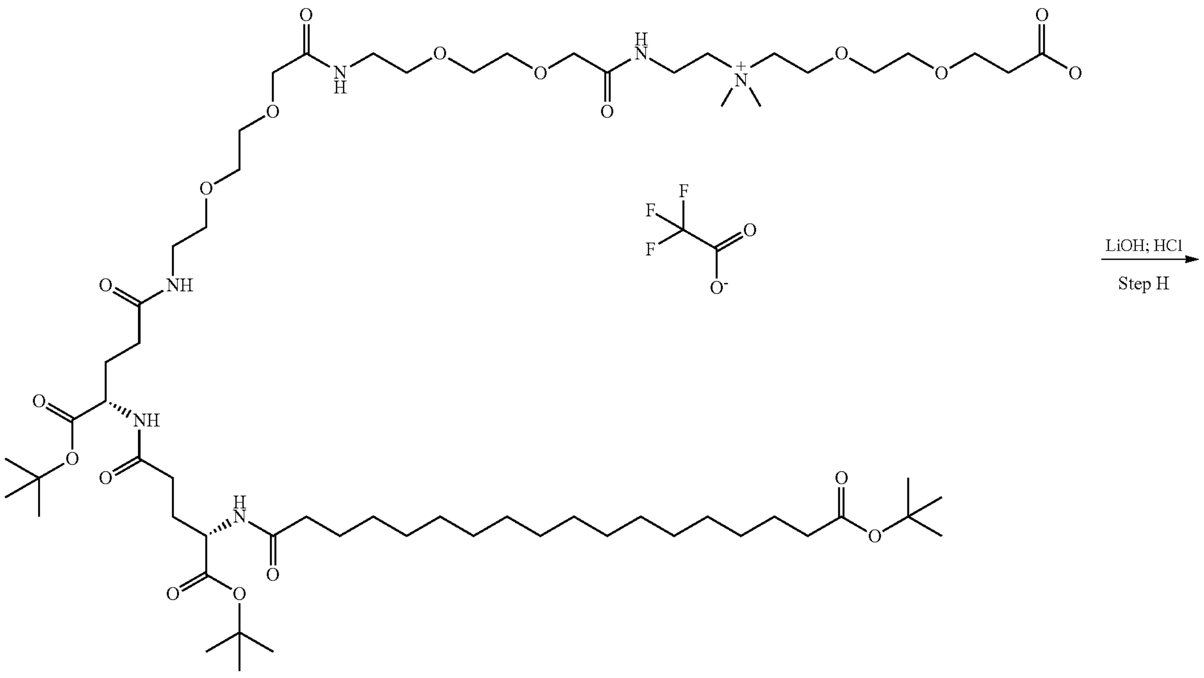
6g
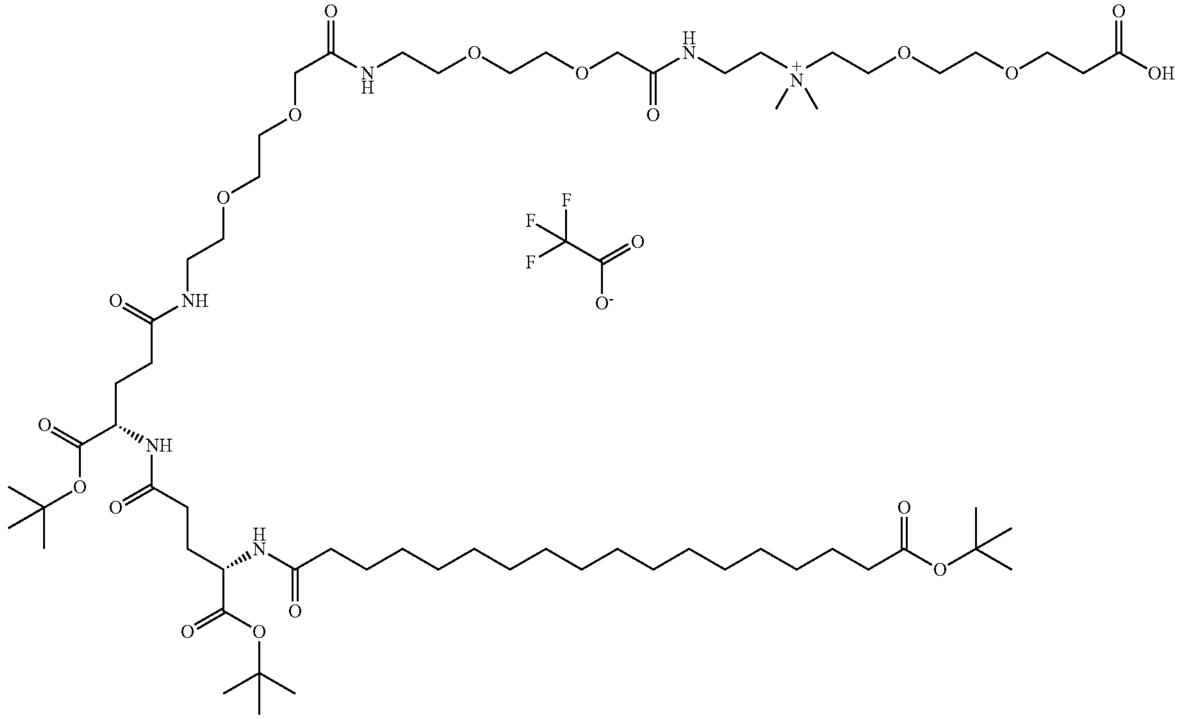
6h -continued
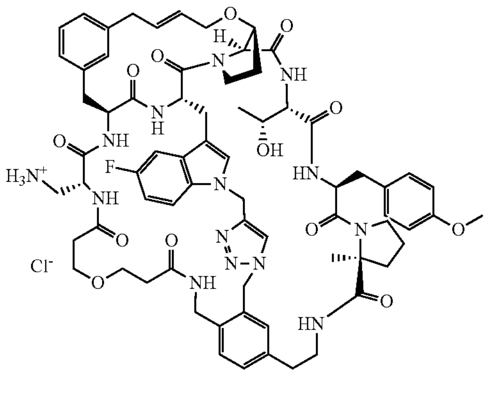
D
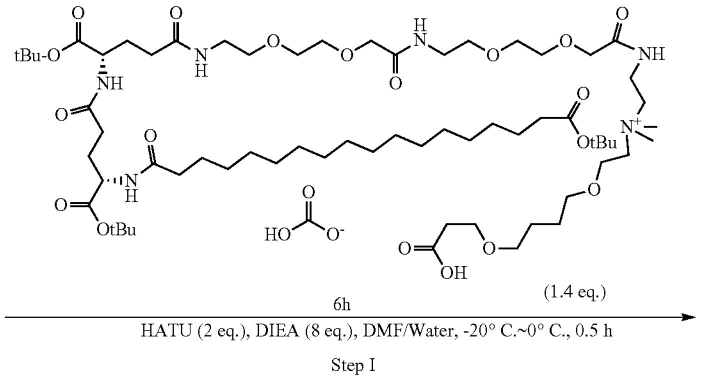
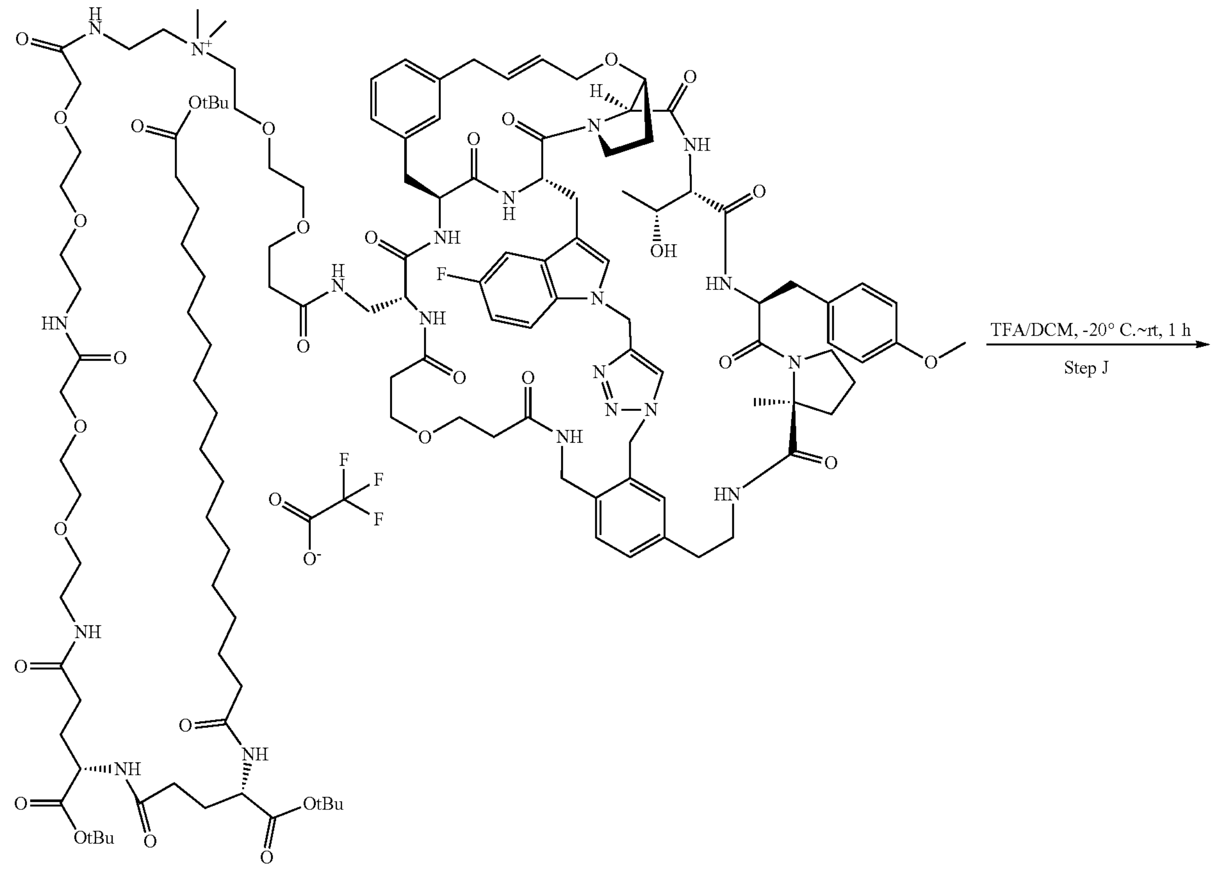
6i -continued
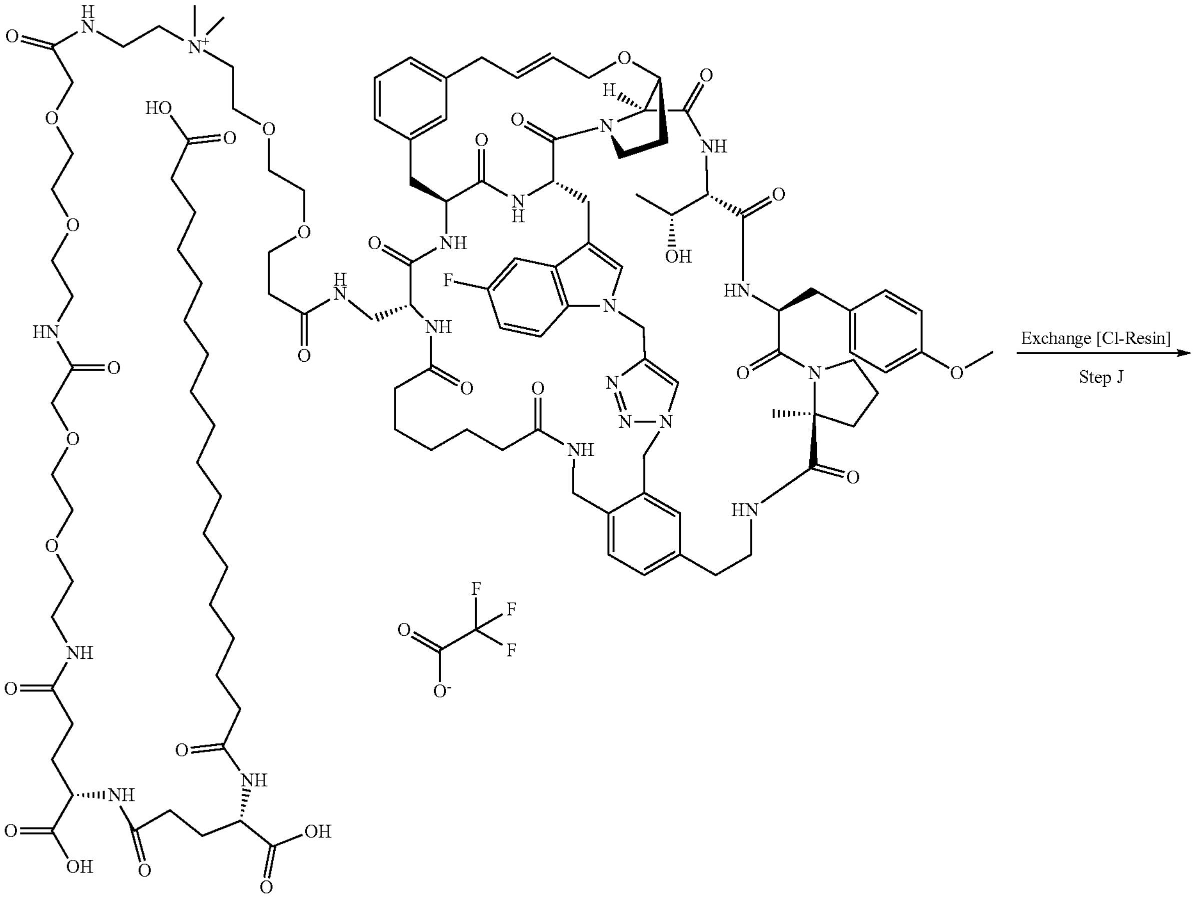
6j -continued

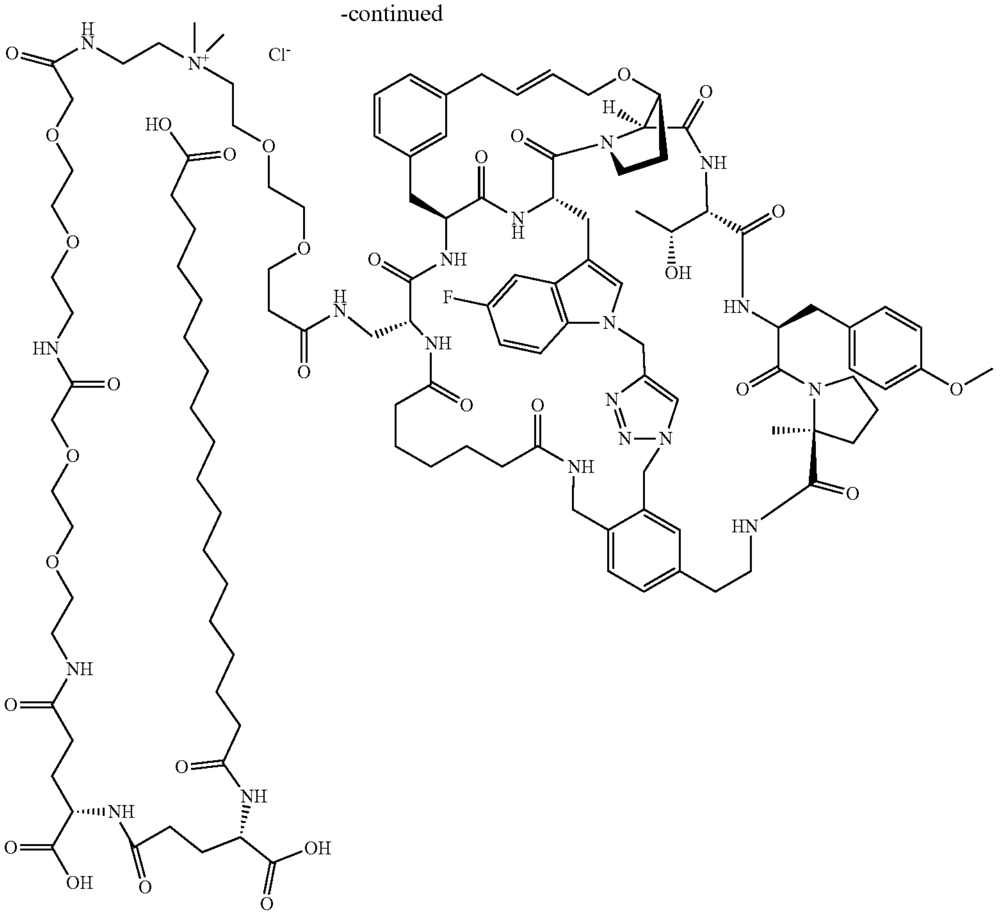

Example 6

Step A—Synthesis of Intermediate 6a

To 2-chlorotrityl chloride resin (0.5 g, about 1 mmol/g) was added dry DCM (3 mL) and the resin was allowed to stand at RT for 20 min. A solution of 17-(9-fluorenylmethyloxycarbonyl-amino)-9-aza-3,6,12,15-tetraoxa-10-on-heptadecanoic acid, CAS 560088-89-3 (332 mg, 0.625 mmol) and DIPLA (0.109 mL, 0.625 mmol) in DCM (1.5 mL) was added slowly, followed by more DIPLA (0.25 mL). The resin was shaken at RT for 2 h then filtered and rinsed with DCM three times. The resin was then quenched with 500 DIPLA and 10% MeOH in DCM (5 mL) and shaken for 2 h at RT. The resin was filtered, rinsed with DCM three times, DMF three times, DCM three times then dried under vacuum to give resin 6a.

Step B—Synthesis of Intermediate 6b

Resin 6a, from step A, was treated with 200% piperidine in DMF (4 mL), shaken for 30 min at RT, filtered and rinsed with DMF three times, DCM three times, and DMF three times. The resin was then treated with a solution of Fmoc-L-Glu-OtBu (0.851 g, 2.00 mmol), HATU (0.760 g, 2.00 mmol) and DIPLA (0.699 mL, 4.00 mmol) in DMF (5 mL) and shaken for 75 min at RT. The resin was filtered and rinsed with DMF three times, DCM three times, and DMF three times to afford resin S-2 which was used as is in the next step.

Step C—Synthesis of Intermediate 6c

Resin 6b, from Step B, was treated with 200% piperidine in DMF (4 mL), shaken for 30 min at RT, filtered and rinsed with DMF three times, DCM three times, and DMF three times. The resin was then treated with a solution of Fmoc-L-Glu-OtBu (0.851 g, 2.00 mmol), HATU (0.760 g, 2.00 mmol) and DIPLA (0.699 mL, 4.00 mmol) in DMF (5 mL) and shaken for 75 min at RT. The resin was filtered and rinsed with DMF three times, DCM three times, DMF three times, and DCM three times to afford resin 6c.

Step D—Synthesis of Intermediate 6d

Resin 6c, from Step C, was treated with 25% hexafluoroisopropanol in DCM (5 mL), shaken for 75 min at RT then filtered. The filtrate was concentrated under vacuum to provide intermediate 6d. LC/MS: $[M+H]^+=901.0$. $^1H$ NMR (400 MHz, DMSO-$d_6$): δ 8.14 (m, 1H), 7.90 (m, 2H), 7.70-7.75 (m, 2H), 7.64 (m, 1H), 7.40-7.45 (m, 2H), 7.30-7.35 (m, 2H), 4.32 (m, 1H), 4.20-4.28 (m, 2H), 4.05 (m, 1H), 3.99 (s, 2H), 3.90 (m, 1H), 3.98 (s, 2H), 3.50-3.60 (m, 6H), 3.37-3.45 (m, 4H), 3.24-3.35 (m, 6H), 3.17-3.22 (m, 2H), 2.22 (m, 2H), 2.15 (m, 2H), 1.85-1.98 (m, 2H), 1.70-1.82 (m, 2H), 1.39 (s, 18H).

Step E—Synthesis of Intermediate 6e

To a solution of intermediate 6d (300 mg, 0.333 mmol) and intermediate M (169 mg, 0.400 mmol) in DMF (4 ml)

at RT were added HATU (146 mg, 0.383 mmol) and DIEA (0.465 ml, 2.66 mmol) and the solution was stirred at RT for 2h. The final mixture was purified by reverse phase MPLC over C18 (eluting with a gradient of acetonitrile (+0.05% TFA) in water (+0.05% TFA)) to give 6e. LC/MS: $[M]^+$=1145.4.

Step B—Synthesis of Intermediate 6f

To a solution of 6e (327 mg, 0.285 mmol) in acetonitrile (5 ml) was added piperidine (0.085 ml, 0.856 mmol) and the solution was stirred at RT for 3 h. The final mixture was concentrated, the residue was dissolved in acetonitrile/water 2:1 (20 mL) then lyophilized to give 6f. LC/MS: $[M]^+$=923.3.

Step C—Synthesis of Intermediate 6g

To a solution of 6f (132 mg, 0.143 mmol) in DMF (4 ml) were added 18-(tert-butoxy)-18-oxooctadecanoic acid (74.1 mg, 0.200 mmol), HATU (76 mg, 0.200 mmol), and DIEA (0.100 ml, 0.571 mmol) and the solution was stirred at RT for 1 h. The final mixture was purified by reverse phase MPLC over C18 (eluting with a gradient of acetonitrile (+0.05% TFA) in water (+0.05% TFA)) to give 6g. LC/MS: $[M]^+$=1275.6.

Step D—Synthesis of Intermediate 6h

To a solution of 6g (161 mg, 0.117 mmol) in THF (2.5 ml) at 0° C. was added LiOH (0.135 ml, 0.135 mmol) then the solution was stirred at RT for 2 h. The final mixture was quenched at 0° C. with 1 N HCl (100 uL), concentrated and the residue was purified by reverse phase MPLC over C18 (eluting with a gradient of acetonitrile (+0.05% TFA) in water (+0.05% TFA)) to provide 6h. LC/MS: $[M]^+$=1261.5. $^1$H NMR (500 MHz, $CD_3OD$): δ 4.29-4.23 (m, 2H), 4.05 (s, 2H), 4.01 (s, 2H), 3.98-3.93 (m, 2H), 3.78-3.53 (m, 24H), 3.46 (t, J=5.6 Hz, 2H), 3.39 (td, J=5.6, 4.0 Hz, 2H), 3.21 (s, 6H), 2.40 (t, J=6.1 Hz, 2H), 2.37-2.09 (m, 10H), 1.93-1.82 (m, 2H), 1.68-1.51 (m, 4H), 1.469 (s, 9H), 1.467 (s, 9H), 1.44 (s, 9H), 1.36-1.26 (m, 24H).

Step I: Synthesis of 6i

To a solution of D (20.0 mg, 0.014 mmol) in DMF (200 μL) and water (20 μL) was added 6h (26.5 mg, 0.020 mmol) at room temperature. After cooling to −20° C., HATU (10.9 mg, 0.029 mmol) and DIEA (20 μL, 0.115 mmol) were added to the mixture. The mixture was stirred at 0° C. for 0.5 h. The reaction solution was quenched with water (100 μL) and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 20% B to 80% B in 30 min; Detector: UV 254/210 nm; Rt=30 min). The fractions containing desired product were combined and concentrated under reduced pressure. The residue was re-dissolved in ACN (5 mL) and water (5 mL), lyophilized to afford 6i. LCMS (ESI) calc'd for $C_{137}H_{202}F_4N_{20}O_{32}$ $[(M-TFA^-+H)/2]$f: 1301.8, found 1302.8.

Step J: Synthesis of 6j

To a solution of 6i (26.0 mg, 9.57 μmol) in DCM (5.2 mL) was added TFA (6.5 mL, 84 mmol) at −20° C. The reaction mixture was stirred at room temperature for 1 h. The reaction solution was concentrated under reduced pressure and purified by Flash (Column: Flash $C^{18}$ 40 g; Mobile Phase A: water (0.1% TFA), Mobile Phase B: ACN; Flow rate: 45 mL/min; Gradient: 2% B to 2% B in 5 min, 20% B to 60% B in 20 min; Detector: UV 254/210 nm; Rt=18 min). The fractions containing desired product were combined and concentrated under reduced pressure. The residue was re-dissolved in ACN (5 mL) and water (5 mL), lyophilized to afford 6j. LCMS (ESI) calc'd for $C_{125}H_{178}F_4N_{20}O_{32}$ $[(M-TFA^-+H)/2]$f: 1217.7, found 1218.6.

Step K: Synthesis of Example 6

5 g of AG MP-1 Resin (cat #141-1841 BIO-RAD) was packed in column. The column was washed with water (2×10 mL), followed by 20% ACN in water (2×10 mL). A solution of 6j (18.0 mg, 7.06 μmol) in 60% ACN in water (20 mL) was loaded onto the resin column, and the column was eluted with 60% ACN in water (4×20 mL). The eluents were combined, water (5×4 mL) added, lyophilized to afford Example 6. LCMS (ESI) calc'd for $C_{123}H_{178}ClFN_{20}O_{30}$ $[M-Cl^-]^+$: 2434.3, found 2434.3; $[(M-Cl^-+H)/2]^+$: 1217.7, found 1218.2.

Preparation of Example 7

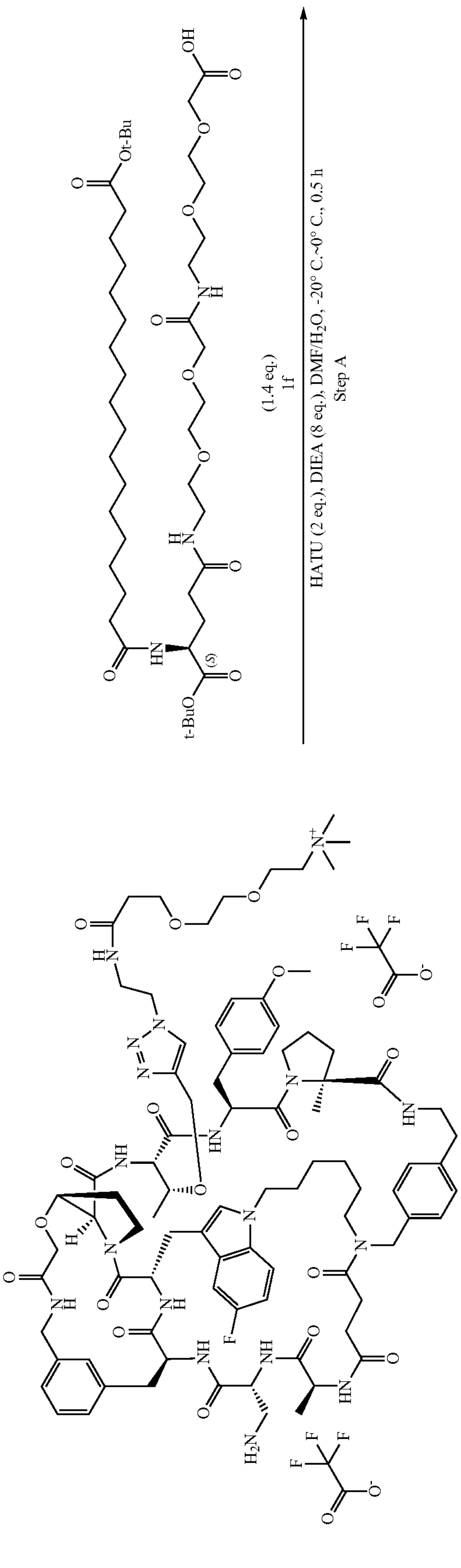
J

-continued
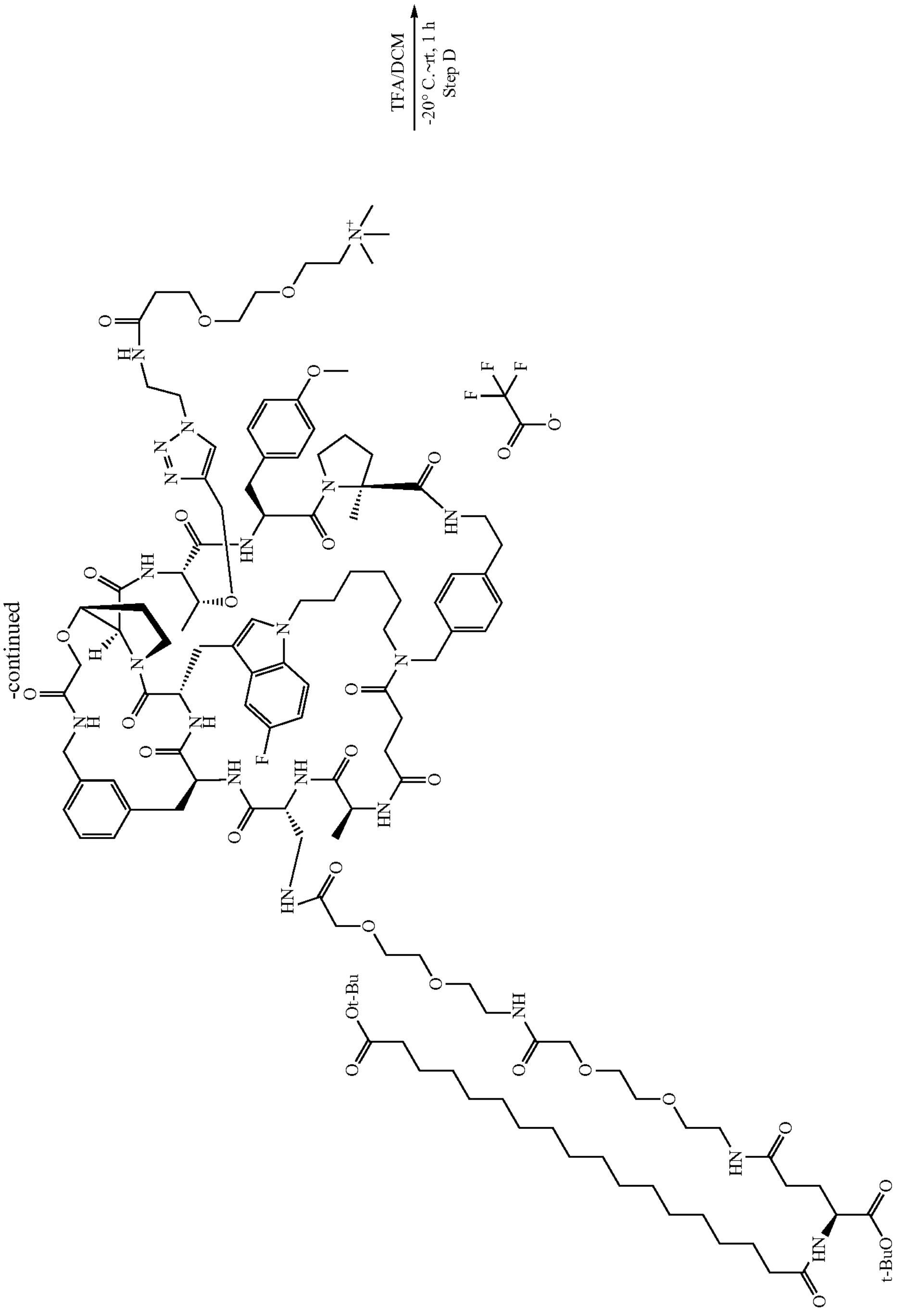
7a

-continued
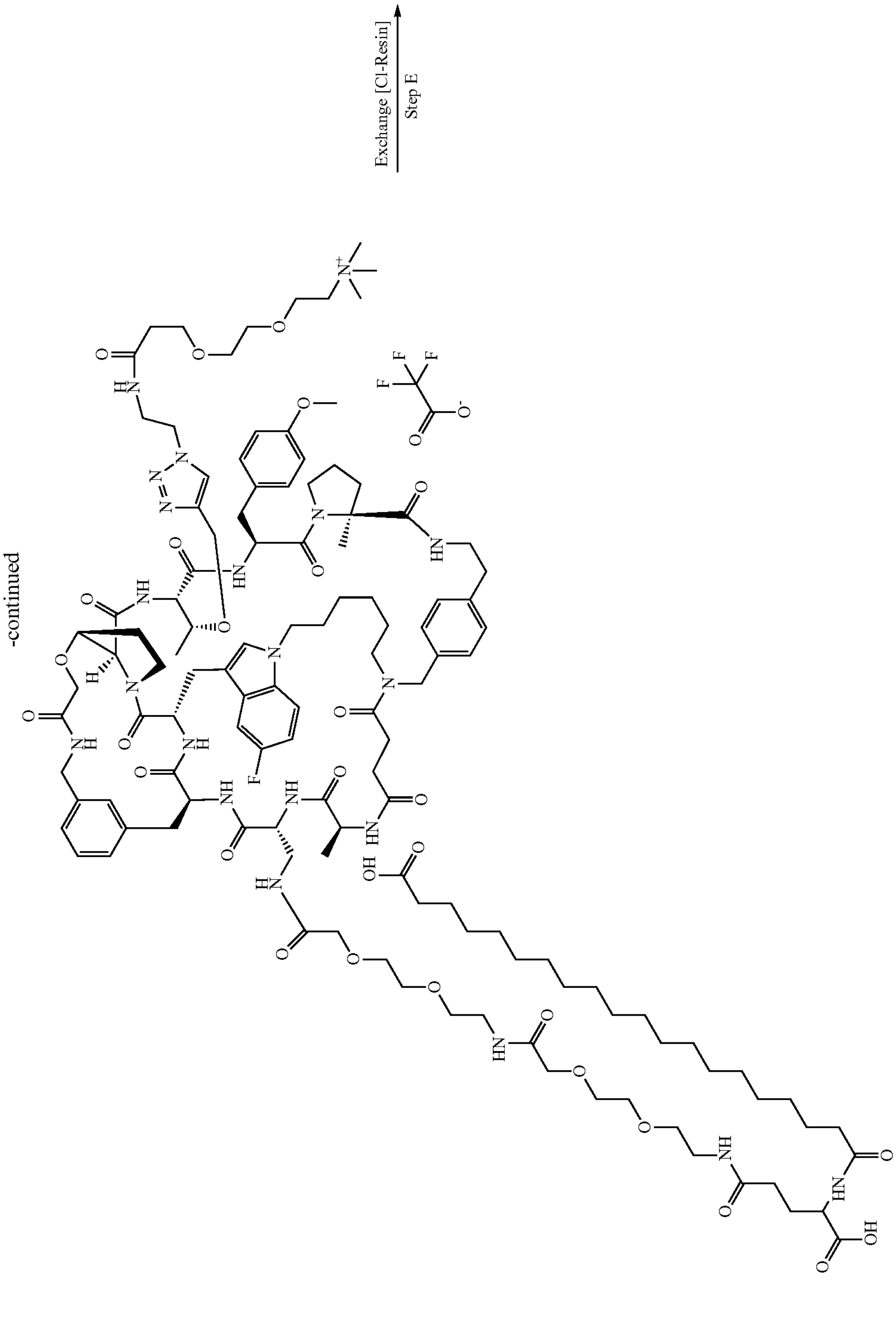
7b

-continued
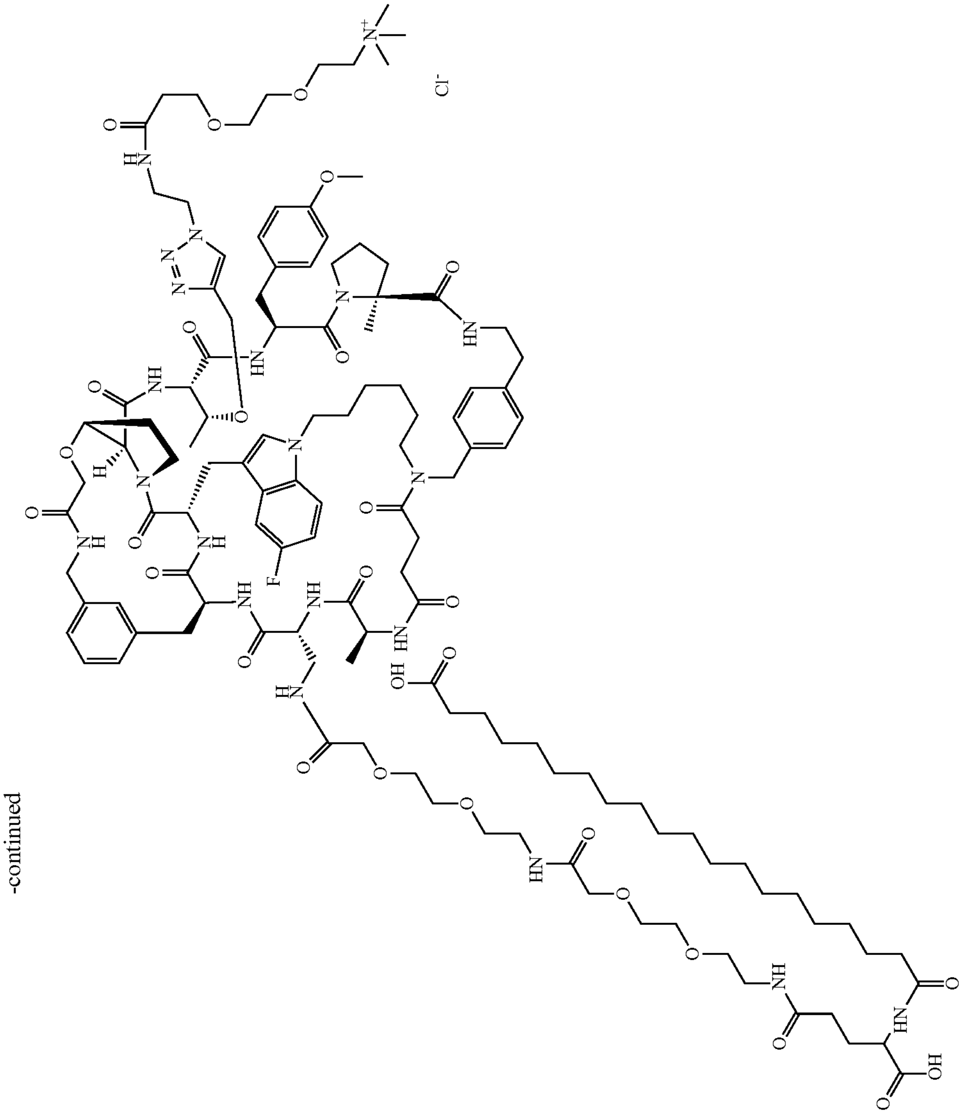
Example 7

Step A: Synthesis of 7a

To a solution of J (14.5 mg, 7.44 μmol) in DMF (200 μL) and water (20 μL) were added (S)-22-(tert-butoxycarbonyl)-43,43-dimethyl-10,19,24,41-tetraoxo-3,6,12,15,42-pentaoxa-9,18,23-triazatetratetracontan-1-oic acid if (8.82 mg, 10.4 μmol), HATU (5.66 mg, 0.015 mmol) and DIEA (10.4 μL, 0.060 mmol) at −20° C. The mixture was stirred at 0° C. for 0.5 h. The reaction solution was quenched with water (100 μL) and purified Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 40% B to 80% B in 20 min; Detector: UV 254/210 nm; Rt=20 min). The fractions containing desired product were combined and concentrated under reduced pressure. The residue was re-dissolved in ACN (5 mL) and water (5 mL), lyophilized to afford 7a. LCMS (ESI) calc'd for $C_{134}H_{193}F_4N_{21}O_{33}$ [(M-TFA$^-$+H)/2]$^+$: 1274.2, found 1275.1.

Step B: Synthesis of 7b

To a solution of 7a (13.0 mg, 4.81 μmol) in DCM (2.6 mL) was added TFA (3.2 mL, 41.5 mmol) at −20° C. The reaction mixture was stirred at room temperature for 1 h. The resulting solution was concentrated under reduced pressure and the residue was purified by Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 20% B to 50% B in 20 min; Detector: UV 254/210 nm; Rt=18 min). The fractions containing desired product were combined and concentrated under reduced pressure. The residue was re-dissolved in ACN (5 mL) and water (5 mL), and lyophilized to afford 7b. LCMS (ESI) calc'd for $C_{125}H_{181}F_4N_{21}O_{31}$ [(M-TFA$^-$+H)/2]$^+$: 1218.2, found 1219.1.

Step C: Synthesis of Example 7

5 g of AG MP-1 Resin (cat #141-1841 BIO-RAD) was packed in column. The column was washed with water (2×10 mL), followed by 20% ACN in water (2×10 mL). A solution of 7b (11 mg, 4.31 μmol) in 50% ACN in water (20 mL) was loaded onto the resin column, and the column was eluted with 50% ACN in water (4×20 mL). The eluents were combined and lyophilized to afford Example 7. LCMS (ESI) calc'd for $C_{123}H_{181}ClFN_{21}O_{29}$ [M-Cl]$^+$: 2435.3, found 2435.3; [(M-Cl+H)/2]$^+$: 1218.2, found 1218.7.

Preparation of Example 8

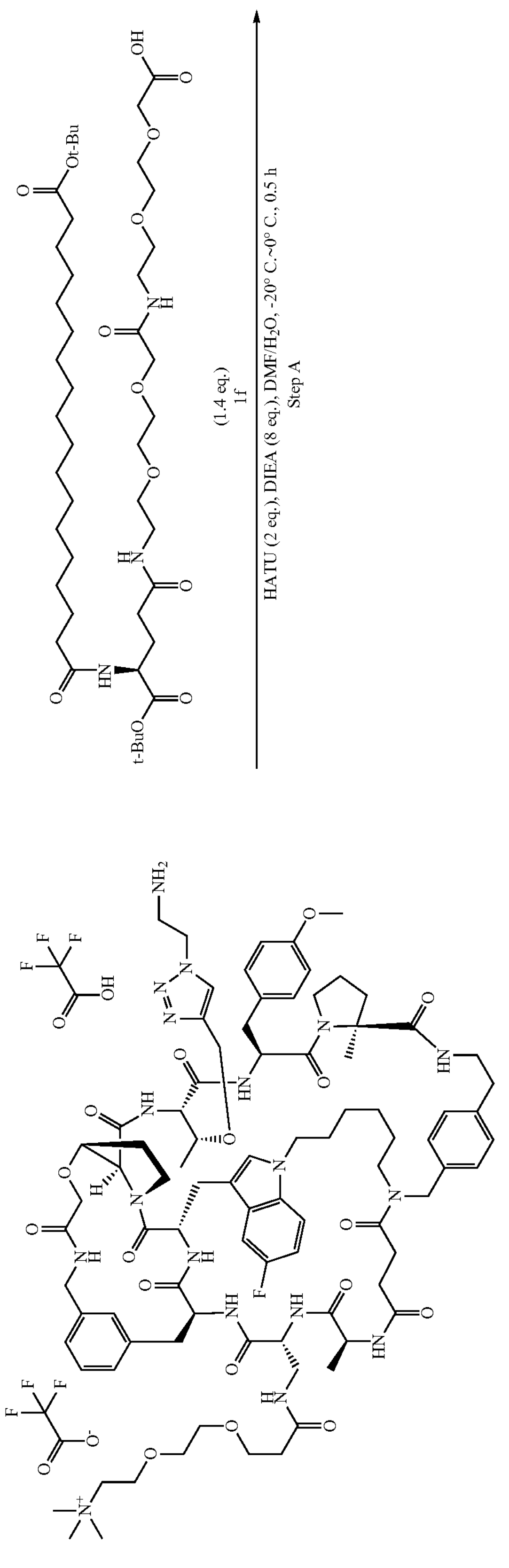
I

-continued
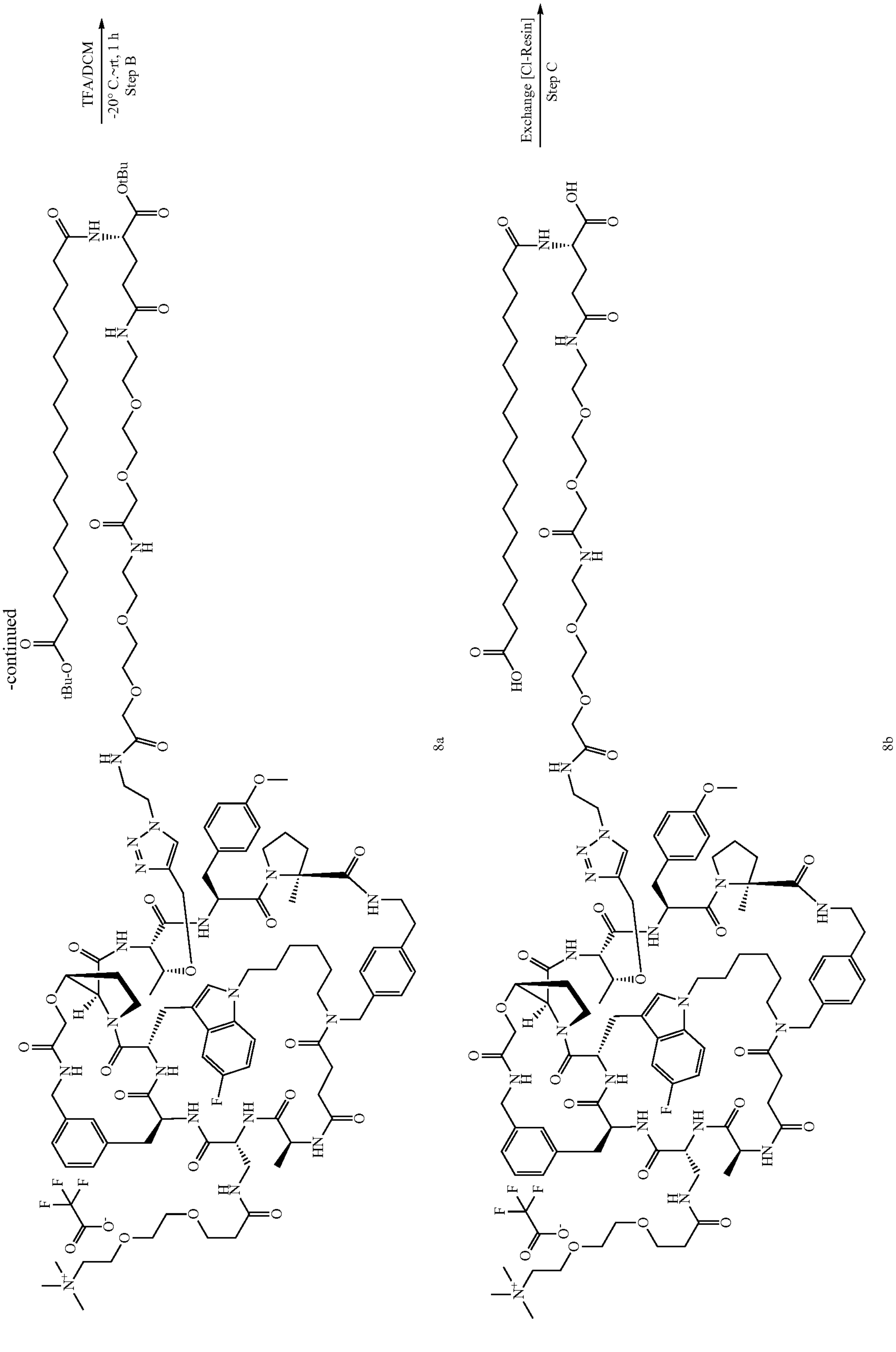
8a
8b

-continued
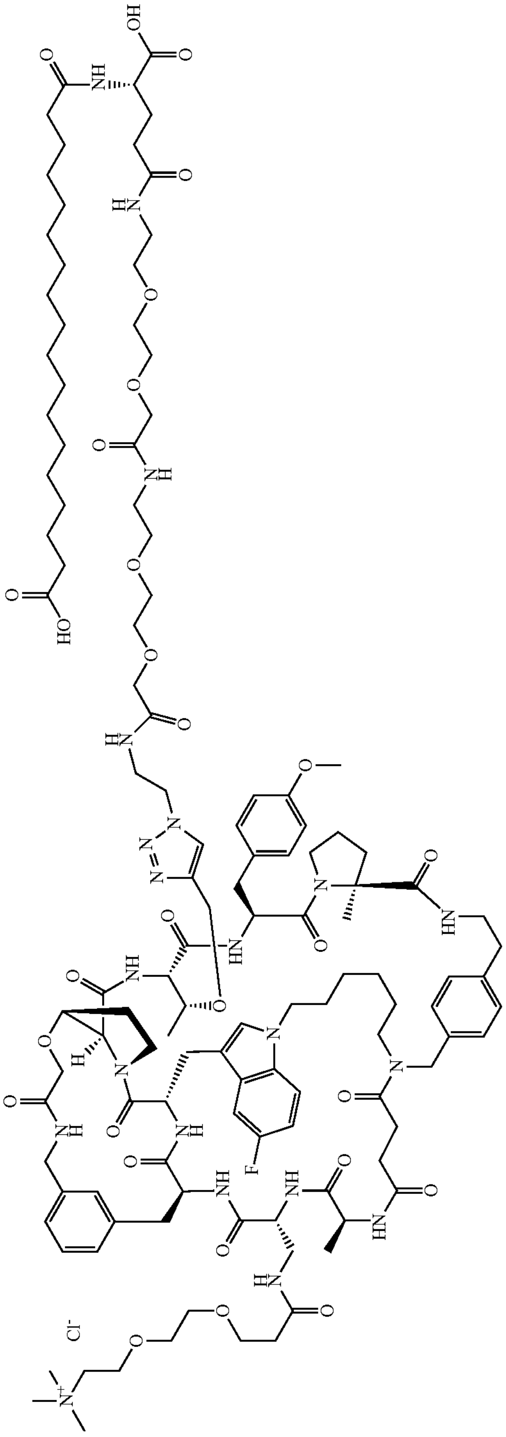
Example 8

Step A: Synthesis of 8a

To a solution of I (15.0 mg, 7.70 mol) in DMF (200 μL) and water (20 μL) were added (S)-22-(tert-butoxycarbonyl)-43,43-dimethyl-10,19,24,41-tetraoxo-3,6,12,15,42-pentaoxa-9,18,23-triazatetratetracontan-1-oic acid if (9.12 mg, 10.78 μmol), HATU (5.86 mg, 0.015 mmol) and DIEA (10.8 μL, 0.062 mmol) at −20° C. The mixture was stirred at 0° C. for 0.5 h. The reaction solution was quenched with water (50 μL) and purified Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 30% B to 70% B in 20 min; Detector: UV 254/210 nm; Rt=22 min). The fractions containing desired product were combined and concentrated under reduced pressure. The residue was re-dissolved in ACN (5 mL) and water (5 mL), lyophilized to afford 8a. LCMS (ESI) calc'd for $C_{133}H_{197}F_4N_{21}O_{31}$ [(M-$TFA^-$+H)/2]: 1274.2, found 1275.0.

Step B: Synthesis of 8b

To a solution of 8b (10.0 mg, 3.76 μmol) in DCM (1.4 mL) was added TFA (1.7 mL, 22.1 mmol) at −20° C. The reaction mixture was stirred at room temperature for 1 h. The resulting solution was concentrated under reduced pressure and the residue was purified by Flash (Column: Flash $C^{18}$ 20 g; Mobile Phase A: water (0.1% TFA), Mobile Phase B: ACN; Flow rate: 30 mL/min; Gradient: 2% B to 2% B in 5 min, 20% B to 50% B in 15 min; Detector: UV 254/210 nm; Rt=18 min). The fractions containing desired product were combined and concentrated under reduced pressure. The residue was re-dissolved in ACN (3 mL) and water (3 mL), and lyophilized to 8b. LCMS (ESI) calc'd for $C_{125}H_{181}F_4N_{21}O_{31}$ $[(M\text{-}TFA^-+H)/2]^+$: 1218.2, found 1218.7.

Step C: Synthesis of Example 8

5 g of AG MP-1 Resin (cat #141-1841 BIO-RAD) was packed in column. The column was washed with water (2×10 mL), followed by 20% ACN in water (2×10 mL). A solution of 8b (9 mg, 3.53 μmol) in 50% ACN in water (20 mL) was loaded onto the resin column, and the column was eluted with 50% ACN in water (4×20 mL). The eluents were combined and lyophilized to afford 6.9 mg Example 8. LCMS (ESI) calc'd for $C_{123}H_{181}ClFN_{21}O_{29}$ $[M\text{-}Cl^-]^+$: 2435.3, found 2435.3; $[(M\text{-}Cl^-+H)/2]^+$: 1218.2, found 1218.8.

Preparation of Example 9

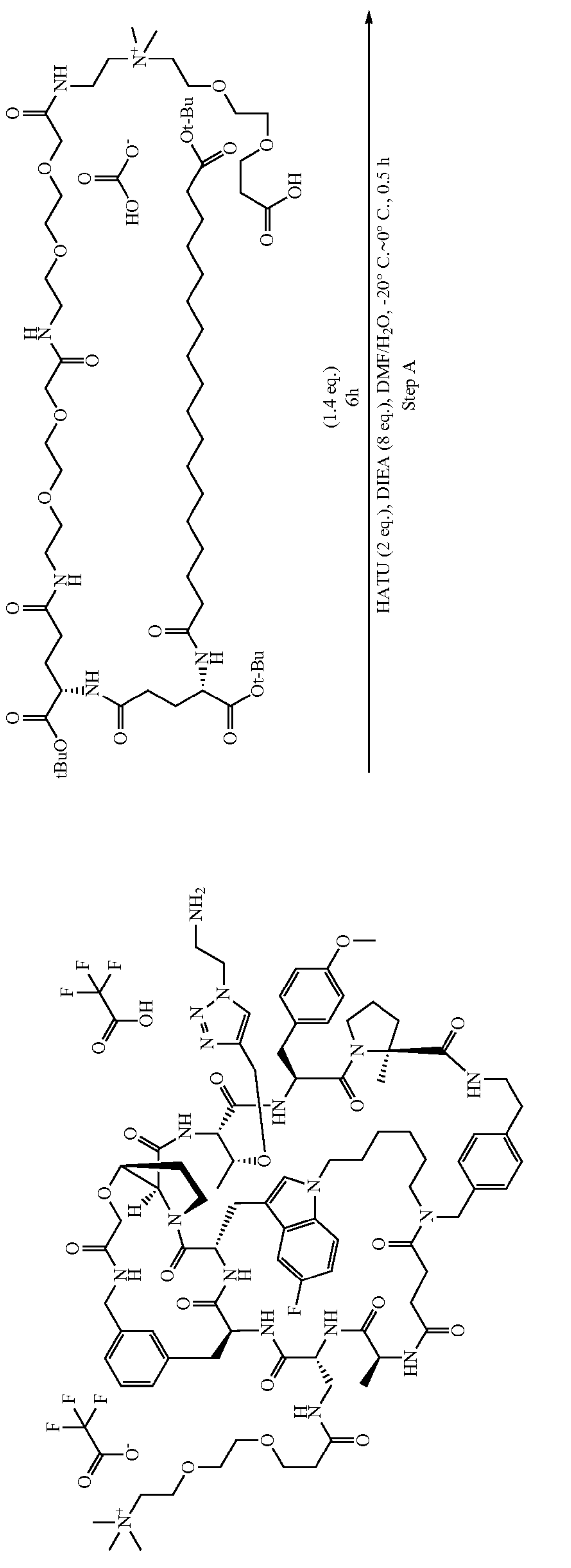
I

-continued
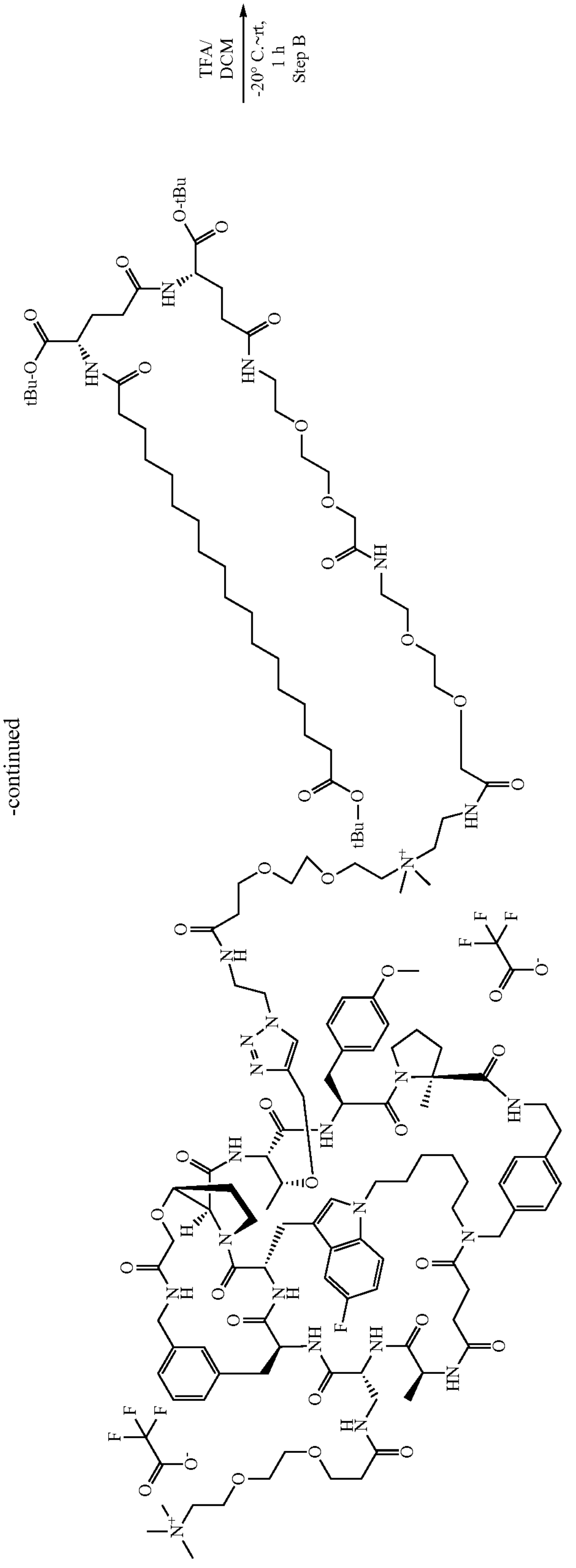
9a

-continued
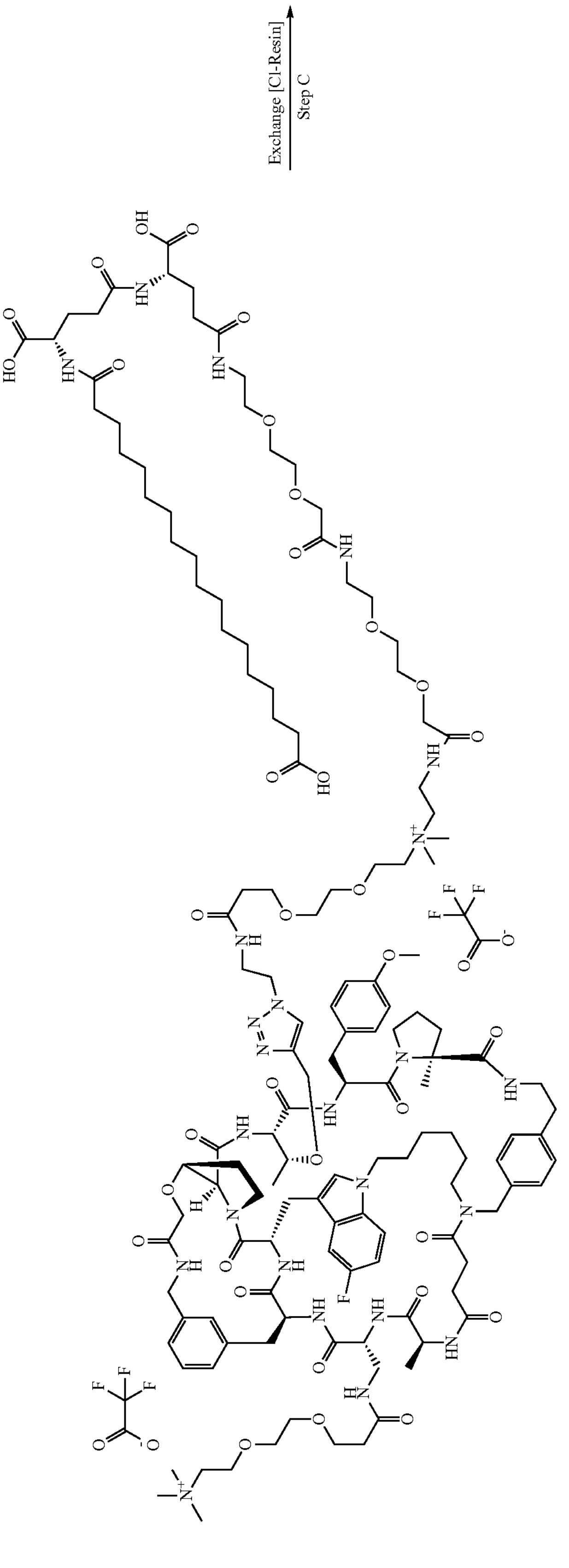
9b

-continued
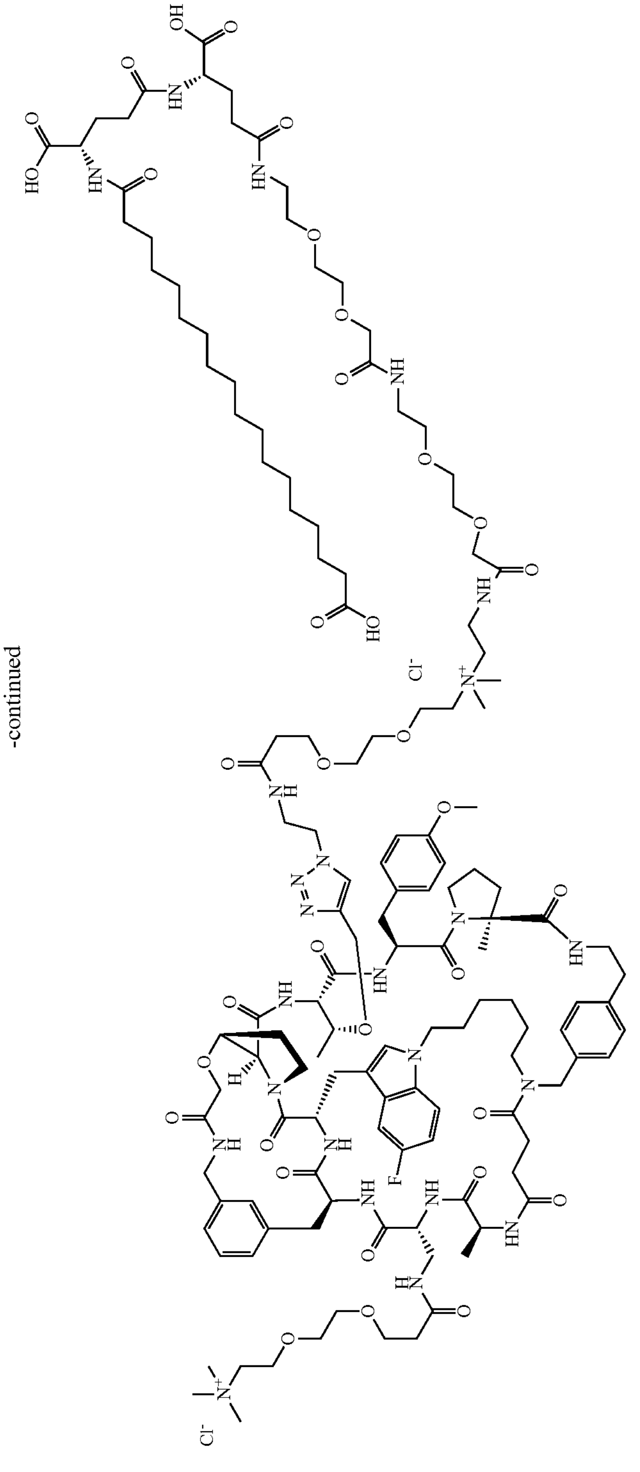
Example 9

Step A: Synthesis of 9a

To a solution of I (20.0 mg, 10.27 μmol) in DMF (200 μL) and water (20 μL) were added (25S,30S)-25,30-bis(tert-butoxycarbonyl)-N-(2-(2-(2-carboxyethoxy)ethoxy)ethyl)-N,N,51,51-tetramethyl-4,13,22,27,32,49-hexaoxo-6,9,15,18,50-pentaoxa-3,12,21,26,31-pentaazadopentacontan-1-aminium hydrogencarbonate 6h (19.0 mg, 0.014 mmol), HATU (7.81 mg, 0.021 mmol) and DIEA (14.3 μL, 0.082 mmol) at −20° C. The mixture was stirred at 0° C. for 0.5 h. The reaction solution was quenched with water (50 μL) and purified Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 20% B to 60% B in 20 min; Detector: UV 254/210 nm; Rt=23 min). The fractions containing desired product were combined and concentrated under reduced pressure. The residue was re-dissolved in ACN (5 mL) and water (5 mL), lyophilized to afford 9a. LCMS (ESI) calc'd for $C_{155}H_{235}F_7N_{24}O_{39}$ $[(M-2TFA^-)/2]^+$: 1481.9, found 1482.4.

Step B: Synthesis of 9b

To a solution of 9a (22.0 mg, 6.89 μmol) in DCM (4.4 mL) was added TFA (5.5 mL, 71.4 mmol) at −20° C. The reaction mixture was stirred at room temperature for 1 h. The resulting solution was concentrated under reduced pressure and the residue was purified by Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 20% B to 50% B in 15 min; Detector: UV 254/210 nm; Rt=18 min). The fractions containing desired product were combined and concentrated under reduced pressure. The residue was re-dissolved in ACN (5 mL) and water (5 mL), and lyophilized to afford 9b. LCMS (ESI) calc'd for $C_{143}H_{211}F_7N_{24}O_{39}$ $[(M-2TFA^-)/2]^+$: 1397.8, found 1398.3.

Step C: Synthesis of Example 9

5 g of AG MP-1 Resin (cat #141-1841 BIO-RAD) was packed in column. The column was washed with water (2×10 mL), followed by 20% ACN in water (2×10 mL). A solution of 9b (16 mg, 5.29 μmol) in 50% ACN in water (20 mL) was loaded onto the resin column, and the column was eluted with 50% ACN in water (4×20 mL). The eluents were combined and lyophilized to afford Example 9. LCMS (ESI) calc'd for $C_{139}H_{211}C_2FN_{24}O_{35}$ $[M-Cl]^+$: 2794.5, found 2794.5; $[(M-Cl+H)/2]^+$: 1397.8, found 1398.5.

Preparation of Example 10

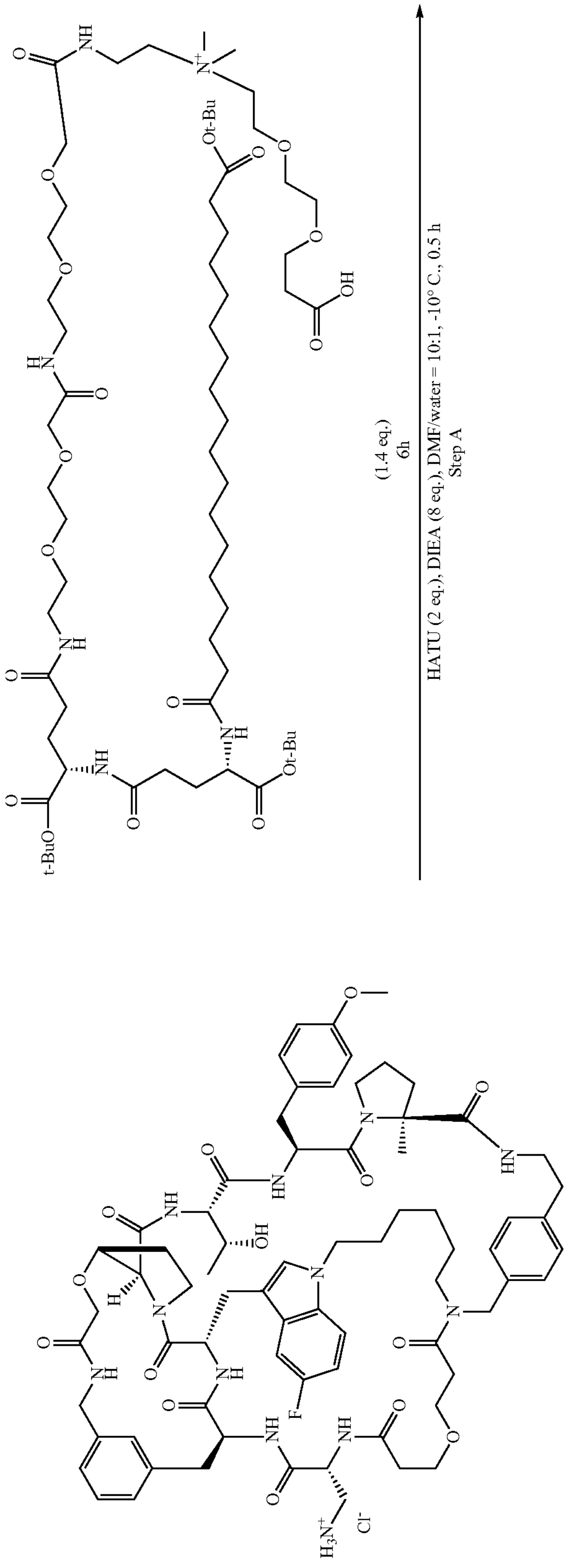
L

-continued
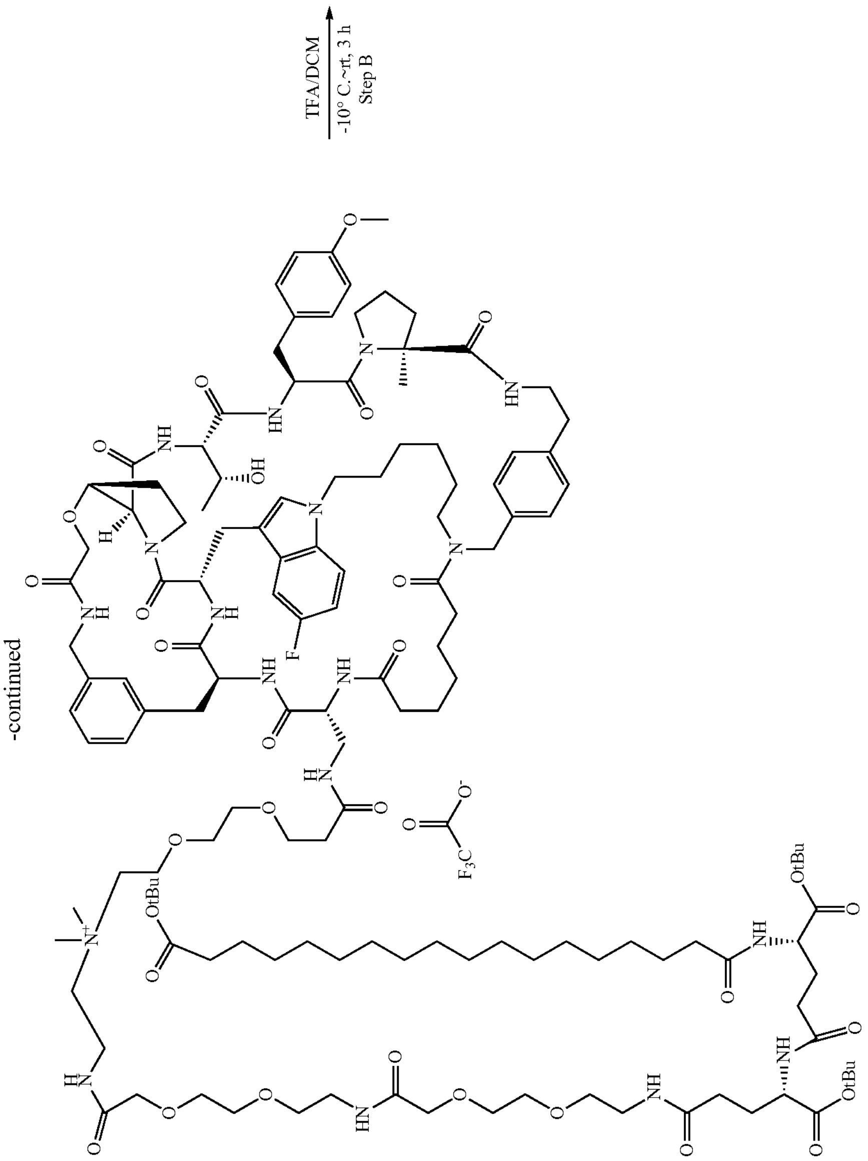
10a

-continued
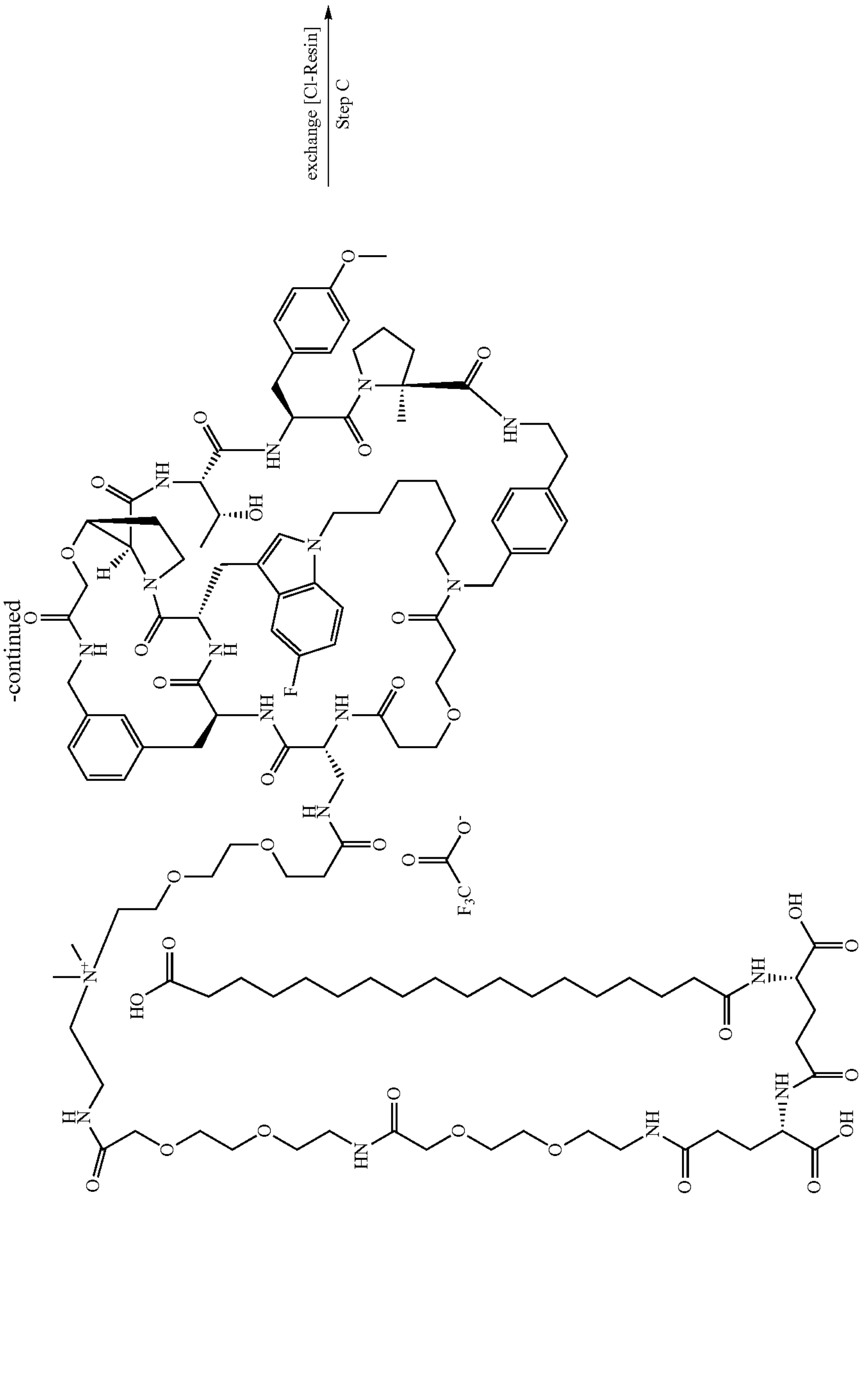
10b

-continued
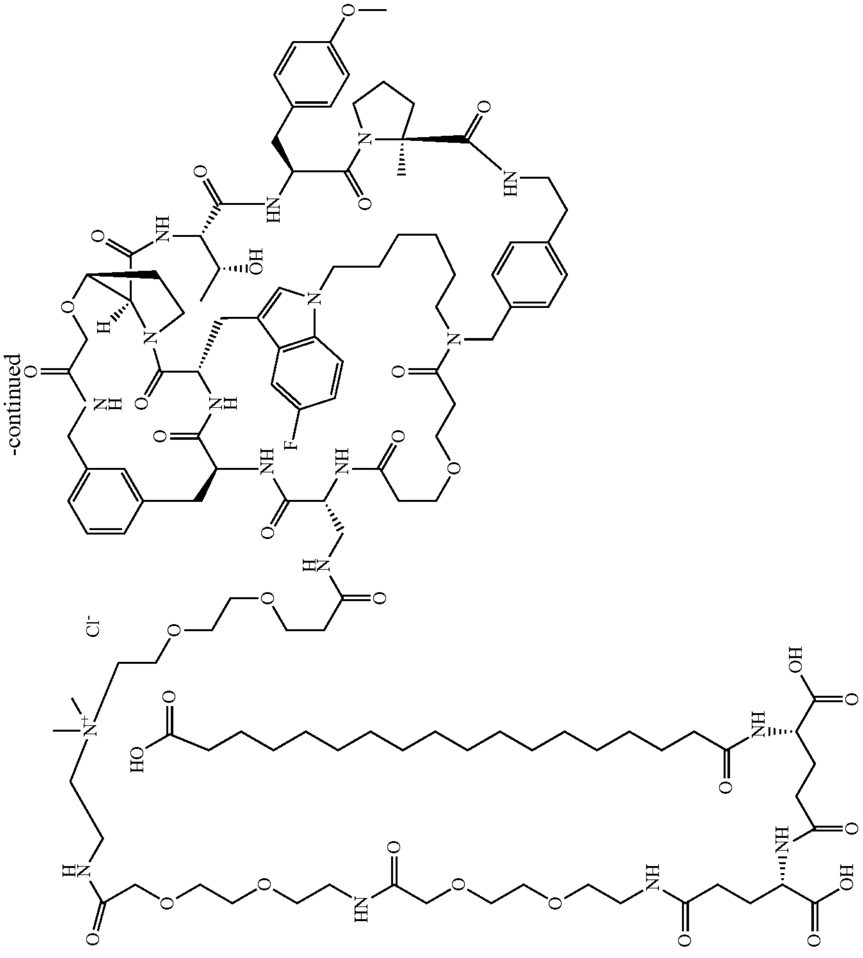
Example 10

Step A: Synthesis of 10a

To a solution of L (20.0 mg, 0.014 mmol) in DMF (200 μL) and water (20 μL) were added (25S,30S)-25,30-bis(tert-butoxycarbonyl)-N-(2-(2-(2-carboxyethoxy)ethoxy)ethyl)-N,N,51,51-tetramethyl-4,13,22,27,32,49-hexaoxo-6,9,15,18,50-pentaoxa-3,12,21,26,31-pentaazadopenta contan-1-aminium hydrogencarbonate 6h (26.4 mg, 0.020 mmol), HATU (10.8 mg, 0.028 mmol) and DIEA (14.7 mg, 0.114 mmol) at −10° C. The reaction mixture was stirred at −10° C. for 0.5 h. The resulting solution was quenched with water (50 μL) and purified by Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 30% B to 60% B in 15 min; Detector: UV 220 nm; Rt=18 min) to afford 10a. LCMS (ESI) calc'd for $C_{137}H_{206}F_4N_{18}O_{34}$ $[(M\text{-}TFA^-/2)]^+$: 1305.3, found 1306.7.

Step B: Synthesis of 10b

To a solution of 10a (28.0 mg, 10.27 μmol) in DCM (10 mL) was added TFA (12.5 mL) at −10° C. The mixture was stirred at room temperature for 3 h. The resulting mixture was concentrated under reduced pressure and the residue was and purified by Flash (Column: Flash $C^{18}$ 40 g; Mobile Phase A: water (0.1% TFA), Mobile Phase B: ACN; Flow rate: 50 mL/min; Gradient: 2% B to 2% B in 5 min, 30% B to 60% B in 15 min; Detector: UV 220 nm; Rt=12 min) to afford 10b. LCMS (ESI) calc'd for $C_{125}H_{182}F_4N_{18}O_{34}$ $[(M\text{-}TFA^-/2)]^+$: 1221.2, found 1222.2.

Step C: Synthesis of Example 10

6 g of AG MP-1 Resin (cat #141-1841 BIO-RAD) was packed in column. The column was washed with water (2×10 mL), followed by 20% ACN in water (2×10 mL). A solution of 10b (17 mg, 6.65 μmol) in 65% ACN in water (2 mL×2) was loaded onto the resin column, the column was eluted with 65% ACN in water (80 mL). The eluents were combined and lyophilized to give Example 10. LCMS (ESI) calc'd for $C_{123}H_{182}ClFN_{18}O_{32}$ $[M\text{-}Cl^-]^+$: 2442.3, found 2442.3.

Preparation of Example 11

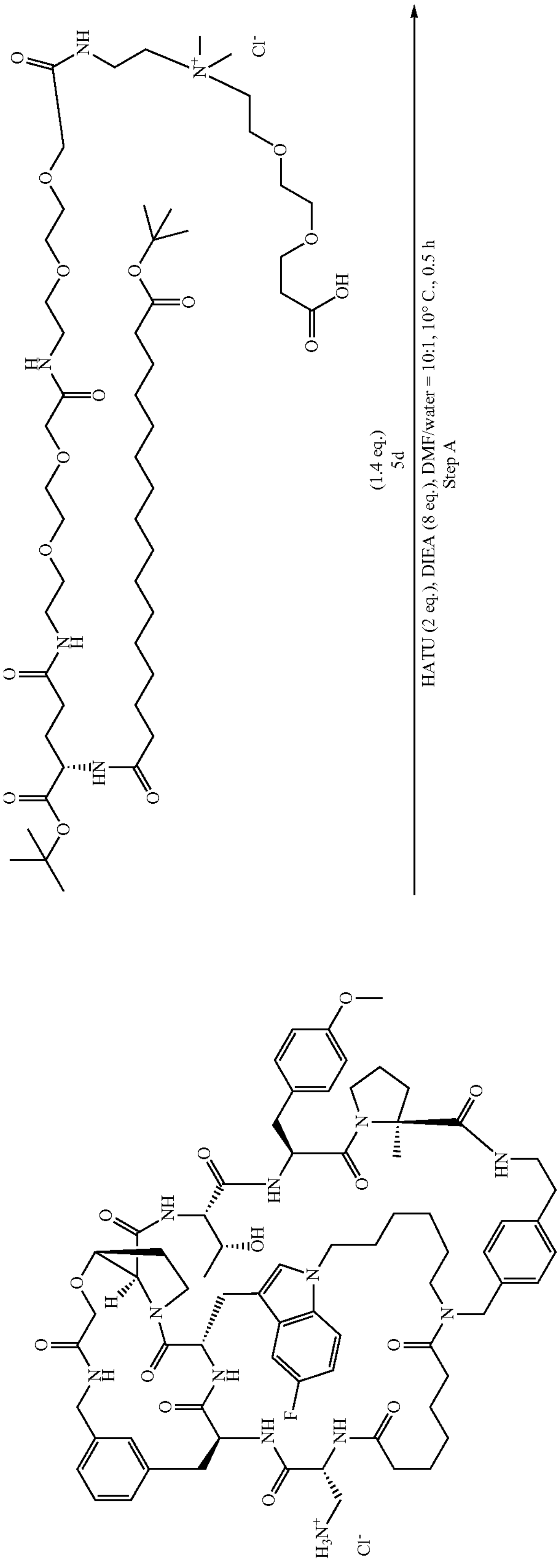
L

-continued
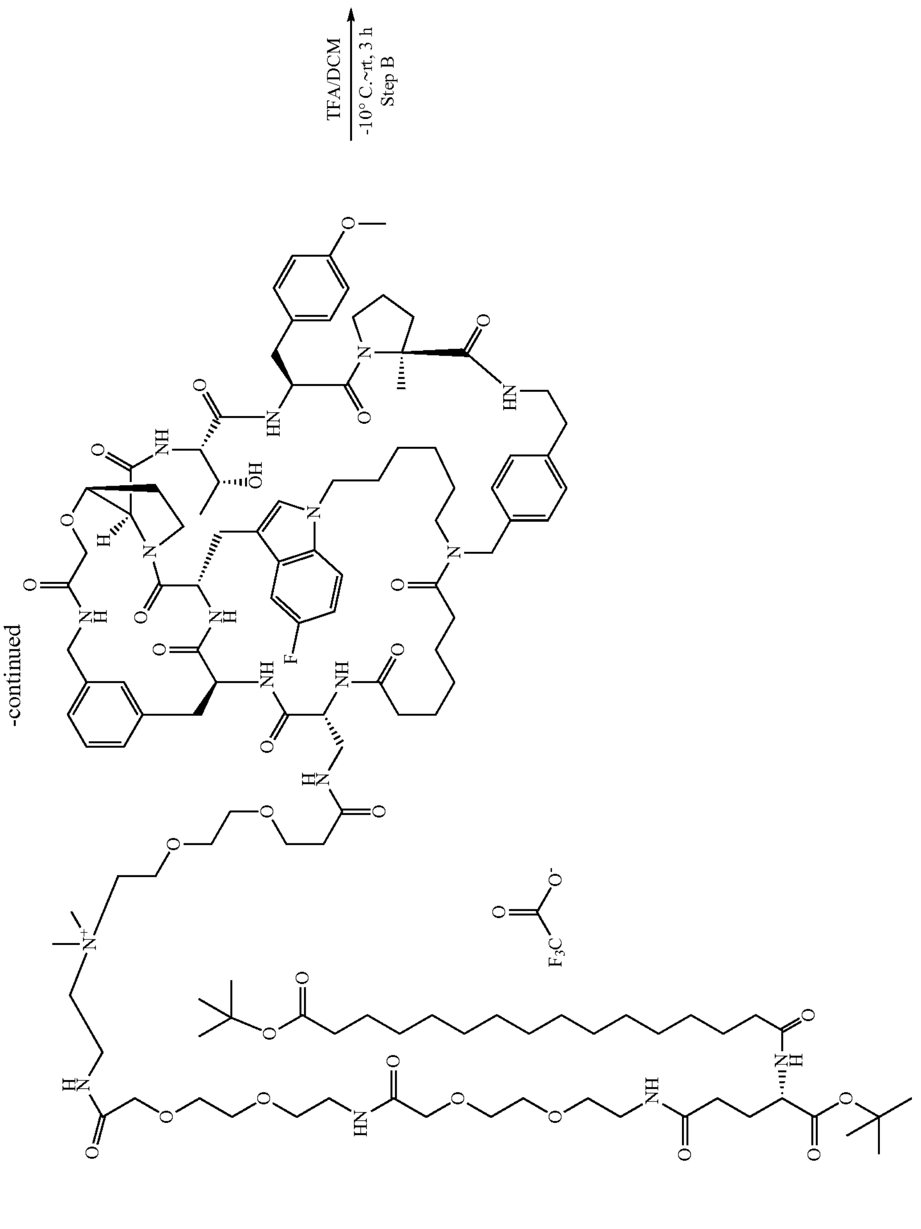
11a

-continued
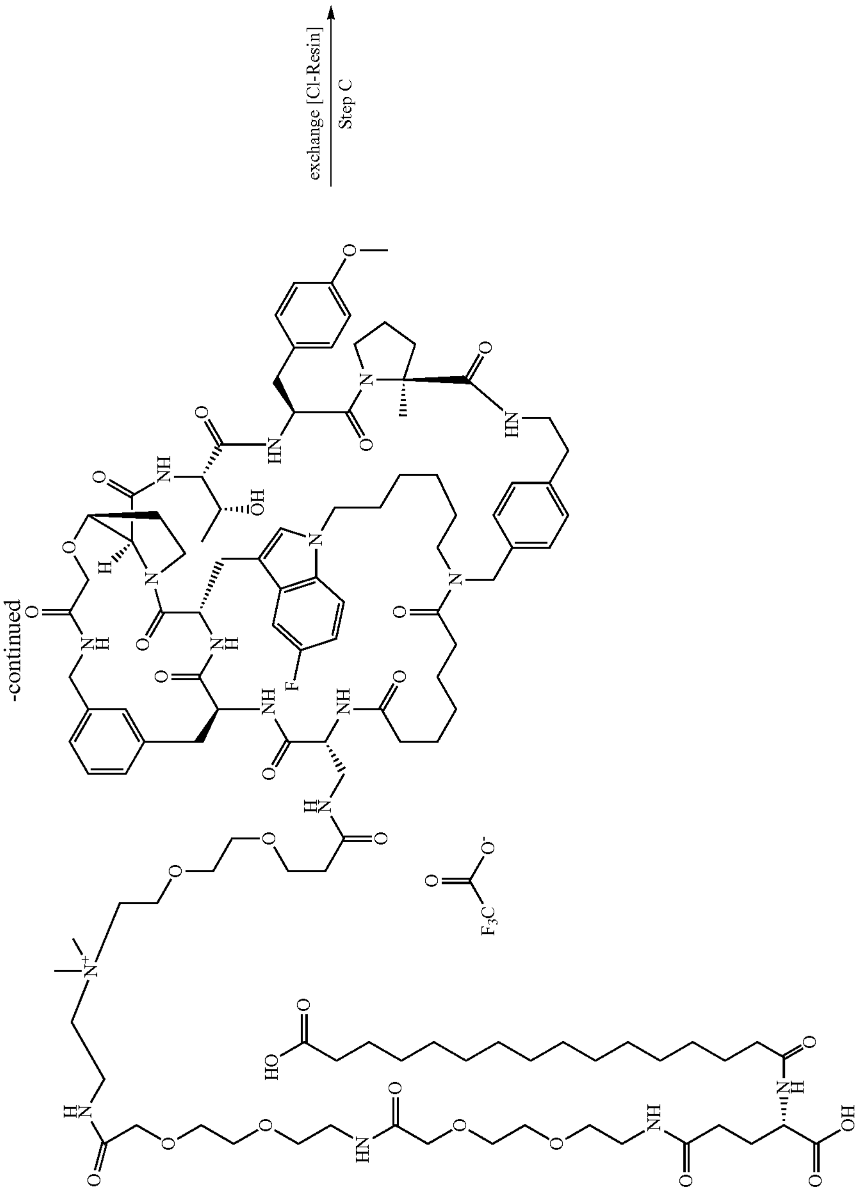
11b

-continued
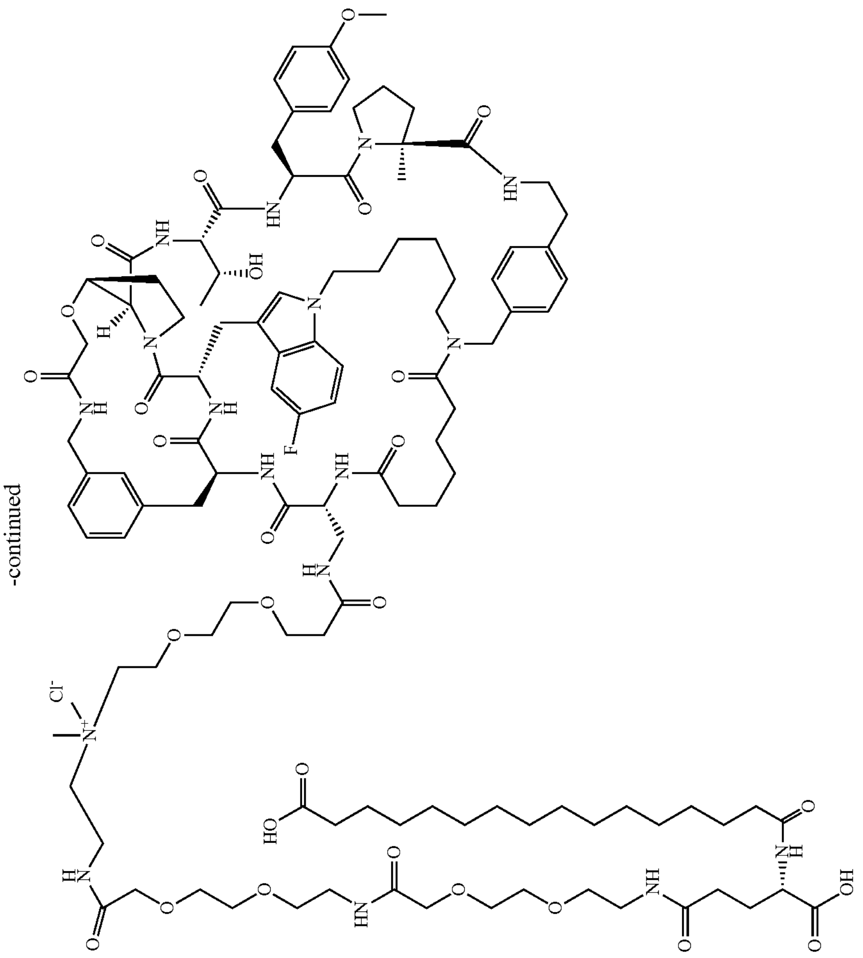
Example 11

Step A: Synthesis of 11a

To a solution of L (20.0 mg, 0.014 mmol) in DMF (200 μL) and water (20 μL) were added (S)-25-(tert-butoxycarbonyl)-N-(2-(2-(2-carboxyethoxy)ethoxy)ethyl)-N,N,44,44-tetramethyl-4,13,22,27,42-pentaoxo-6,9,15,18,43-pentaoxa-3,12,21,26-tetraazapentatetracontan-1-aminium chloride 5d (21.6 mg, 0.020 mmol), HATU (10.8 mg, 0.028 mmol) and DIEA (18.8 μL, 0.114 mmol) at −10° C. The reaction mixture was stirred at 0° C. for 0.5 h. The resulting solution was quenched with water (200 μL) and purified by Flash with the following condition: Column: Flash $C^{18}$ 40 g; Mobile Phase A: water (0.1% TFA), Mobile Phase B: ACN; Flow rate: 50 mL/min; Gradient: 2% B to 2% B in 5 min, 30% B to 65% B in 20 min; Detector: UV 210 nm; Rt=25 min to afford 11a. LCMS (ESI) calc'd for $C_{126}H_{187}F_4N_{17}O_{31}$ $[(M\text{-}TFA^-/2)]^+$: 1199.5, found 1200.0.

Step B: Synthesis of 11b

To a solution of 11a (27.0 mg, 10.75 μmol) in DCM (10 mL) was added TFA (12.5 mL) at −10° C. The reaction mixture was stirred at room temperature for 3 h. The reaction solution was concentrated under reduced pressure and purified by Flash: Column: Flash $C^{18}$ 40 g; Mobile Phase A: water (0.1% TFA), Mobile Phase B: ACN; Flow rate: 50 mL/min; Gradient: 2% B to 2% B in 5 min, 30% B to 60% B in 20 min; Detector: UV 210 nm; Rt=25 min to afford 11b. LCMS (ESI) calc'd for $C_{118}H_{171}F_4N_{17}O_{31}$ $[(M\text{-}TFA^-/2)]^+$: 1143.1, found 1143.7.

Step C: Synthesis of Example 11

5 g of AG MP-1 Resin (cat #141-1841 BIO-RAD) was packed in column. The column was washed with water (2×10 mL), followed by 20% ACN in water (2×10 mL). A solution of 11b (17 mg, 7.08 μmol) in 60% ACN in water (20 mL) was loaded onto the resin column, then the column was eluted with 60% ACN in water (4×20 mL). The eluents were combined, water (5×4 mL) added, lyophilized to afford Example 11. LCMS (ESI) calc'd for $C_{116}H_{171}ClFN_{17}O_{29}$ $[M-Cl^-]^+$: 2285.2, found 2285.2;

Preparation of Example 12

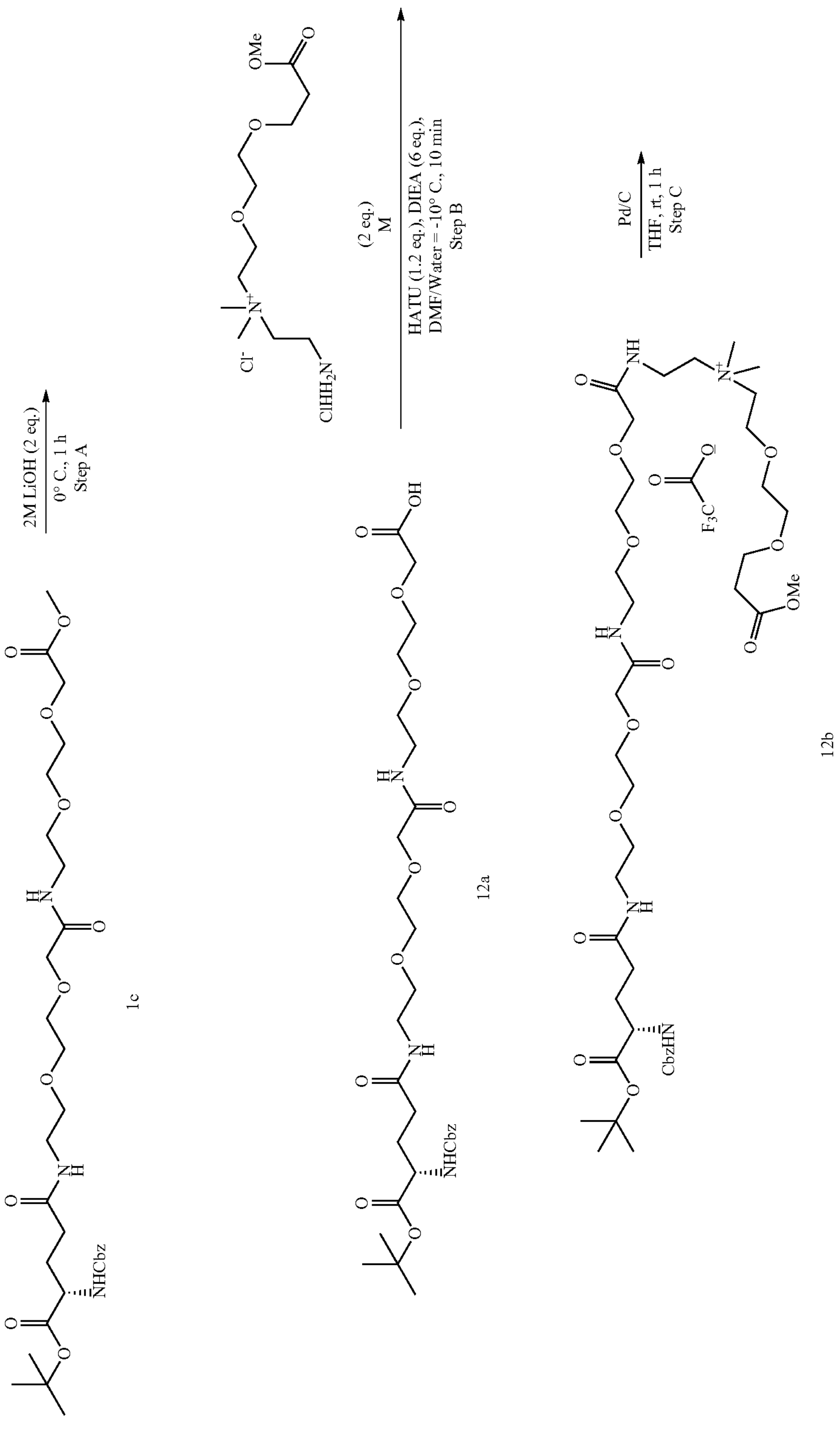
1c
12a
12b

-continued
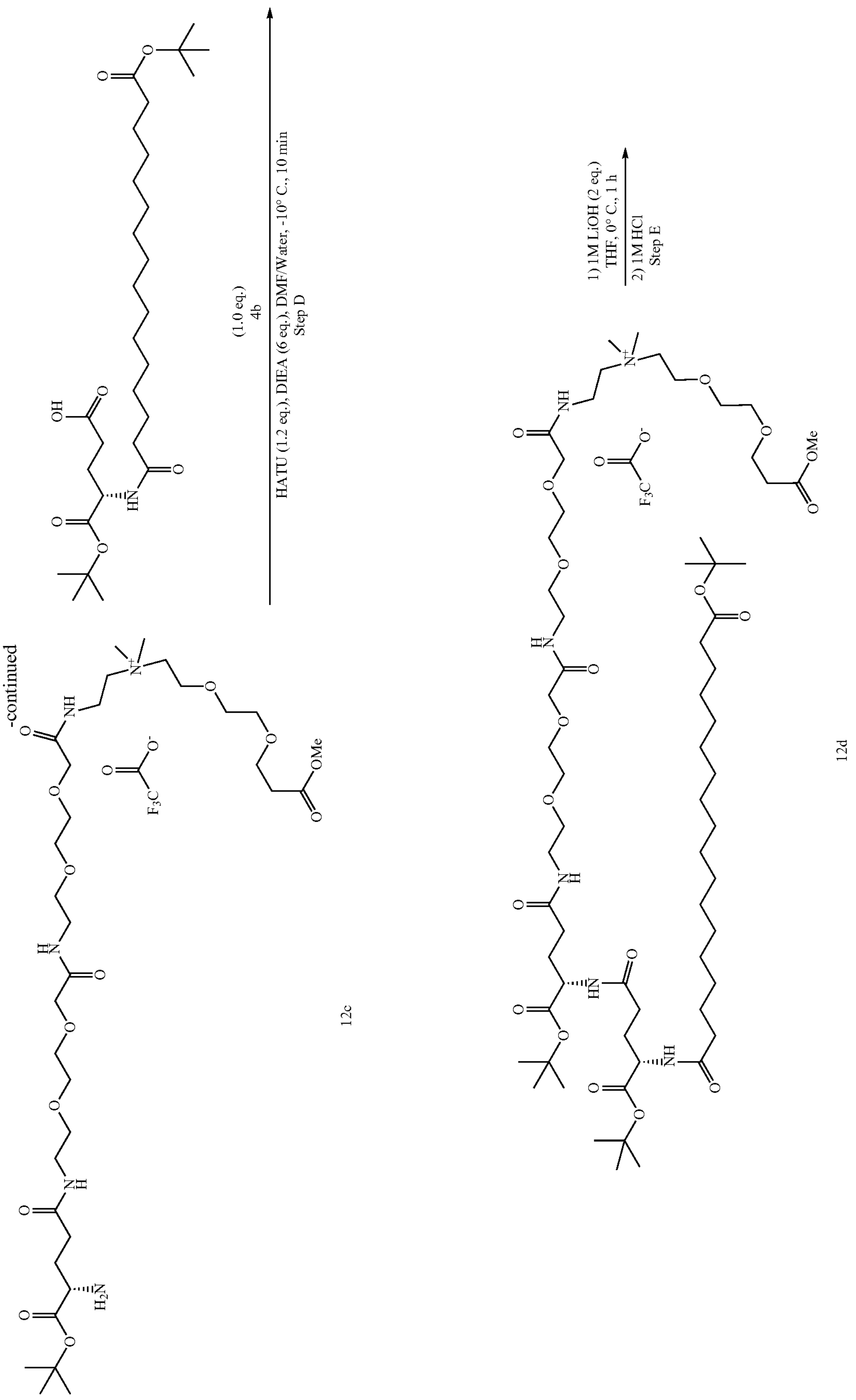
12c
12d

-continued
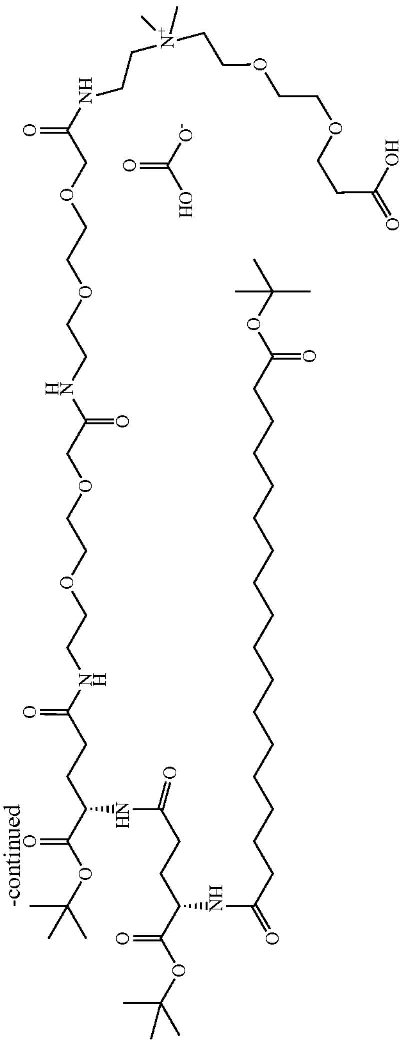
12e
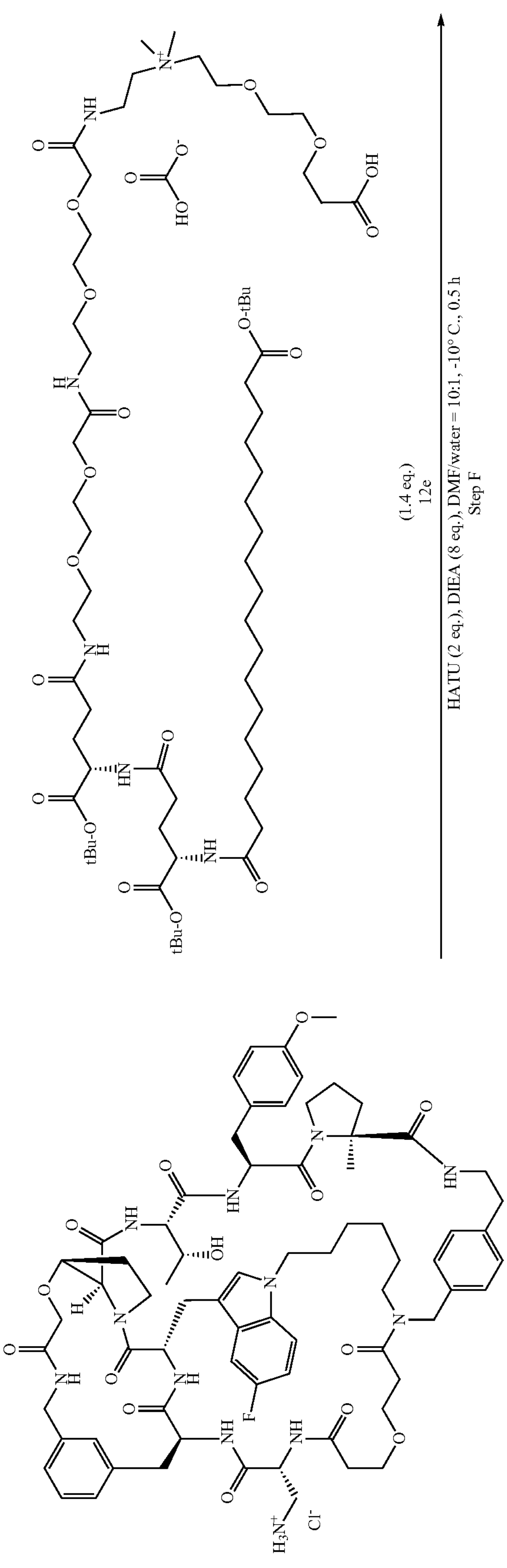
L

-continued
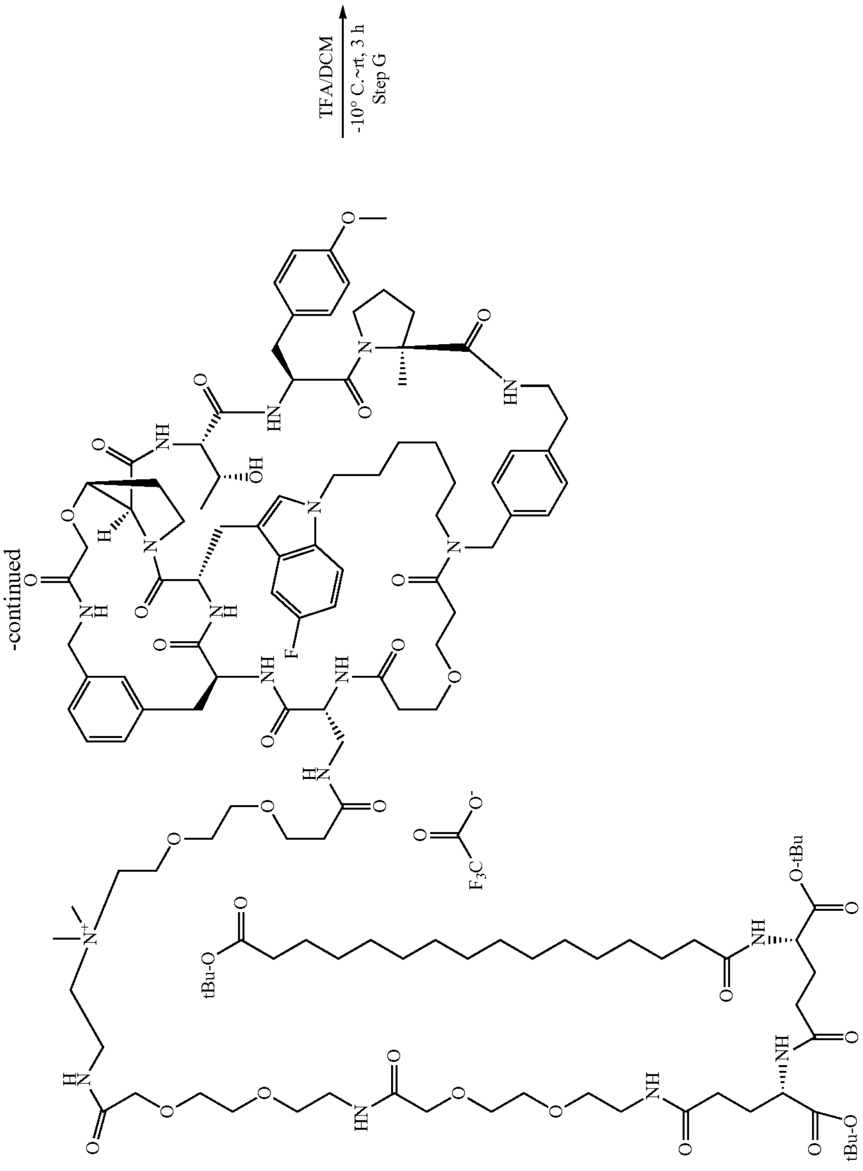
12f

-continued
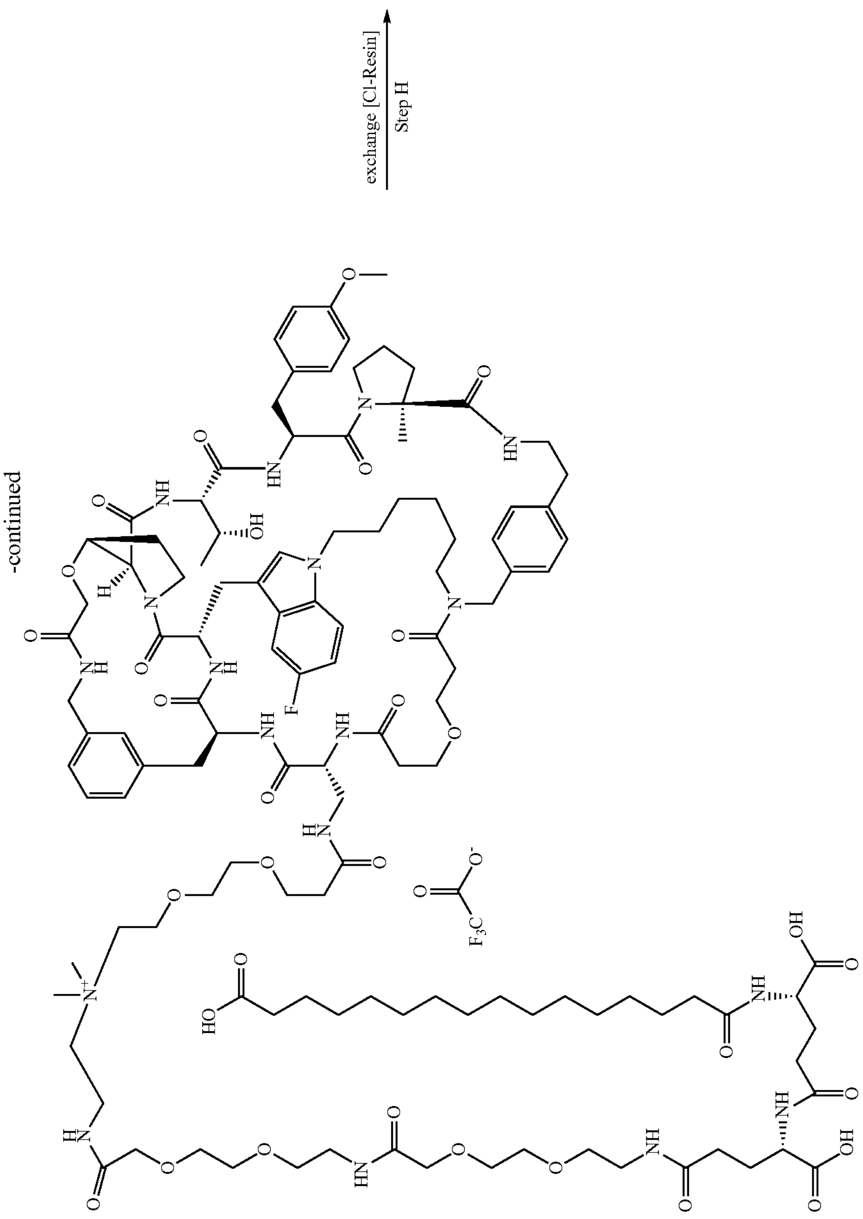
12g

-continued
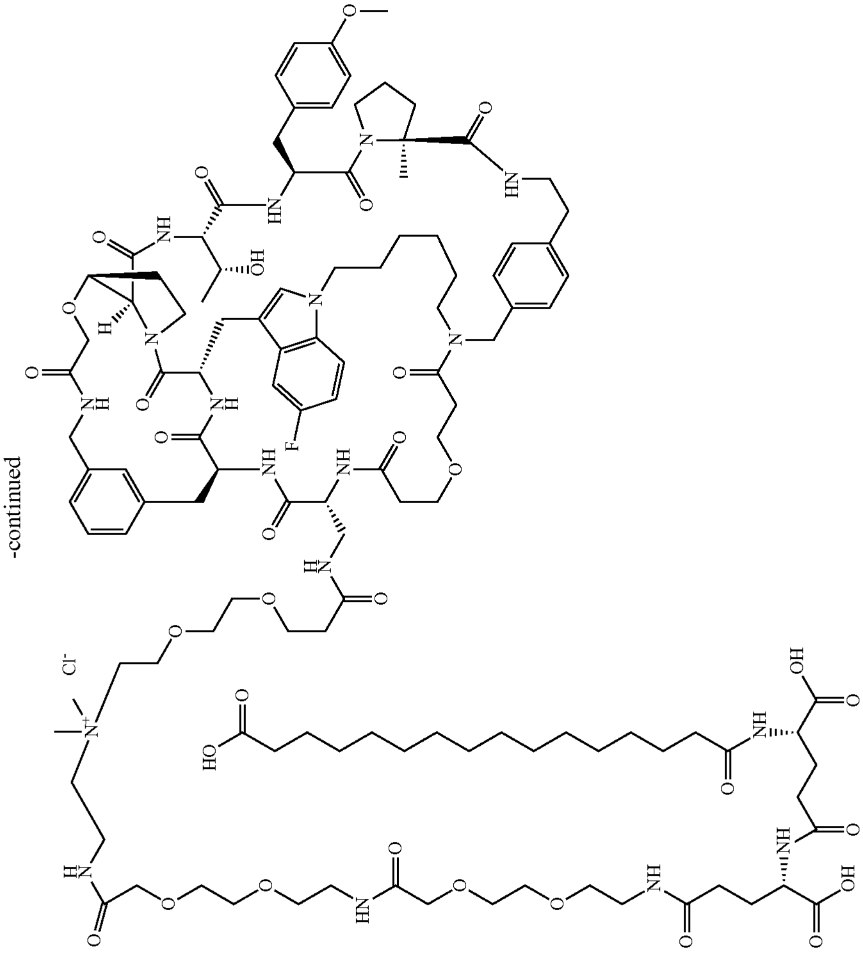
Example 12

Step A: (S)-5-(tert-butoxycarbonyl)-3,8,17-trioxo-1 phenyl-2,12,15,21,24 pentaoxa-4,9,18-triazahexacosan-26-oic acid 12a To a solution of (S)-23-tert-butyl 1-methyl 22-(((benzyloxy)carbonyl)amino)-10,19-dioxo-3,6,12,15-tetraoxa-9,18-diazatricosane-1,23-dioate 1c (2.00 g, 3.12 mmol) in THF (20 mL) was added 2 M LiOH (3.12 mL, 6.23 mmol) at 0° C. The mixture was stirred at 0° C. for 2 h. The reaction solution was quenched with 1 M HCl (6.3 mL) and purified by Flash (Column: Flash $C^{18}$ 120 g; Mobile Phase A: water, Mobile Phase B: Water; Flow rate: 60 mL/min; Gradient: 10% B to 10% B in 10 min, 35% B to 80% B in 20 min; Detector: UV 220 nm; RT=26 min). The fractions containing desired product were combined and concentrated. The residue was lyophilized to afford (S)-5-(tert-butoxycarbonyl)-3,8,17-trioxo-1-phenyl-2,12,15,21,24-pentaoxa-4,9,18-triazahexacosan-26-oic acid 12a. LCMS (ESI) calc'd for $C_{29}H_{45}N_3O_{12}$ $[M+H]^+$: 628.3, found 628.3. $^1H$ NMR (400 MHz, $CDCl_3$): δ 7.47-7.31 (m, 5H), 5.11 (s, 2H), 4.22 (br, 1H), 4.16 (s, 2H), 4.03 (s, 2H), 3.66 (tt, J=25.7, 4.5 Hz, 12H), 3.56-3.39 (m, 4H), 2.41-2.25 (m, 2H), 2.20 (dt, J=12.2, 5.8 Hz, 1H), 1.97 (dq, J=15.0, 7.7 Hz, 1H), 1.54-1.39 (m, 9H).

Step B: (S)-5-(tert-butoxycarbonyl)-N-(2-(2-(3-methoxy-3-oxopropoxy)ethoxy)ethyl)-N,N-dimethyl-3,8,17,26-tetraoxo-1-phenyl-2,12,15,21,24-pentaoxa-4,9,18,27-tetraazanonacosan-29-aminium 2,2,2-trifluoroacetate 12b To a mixture of (S)-5-(tert-butoxycarbonyl)-3,8,17-trioxo-1-phenyl-2,12,15,21,24-pentaoxa-4,9,18-triazahexacosan-26-oic acid 12a (200 mg, 0.319 mmol), HATU (145 mg, 0.382 mmol) and DIEA (247 mg, 1.912 mmol) in DMF (1 mL) was added a solution of 2-amino-N-(2-(2-(3-methoxy-3-oxopropoxy)ethoxy)ethyl)-N,N-dimethylethanaminium chloride hydrochloride M (214 mg, 0.637 mmol) in DMF (1 mL) and water (0.2 mL) at −10° C. The resulting mixture was stirred at −10° C. for 30 min. The reaction mixture was quenched by water (2 mL) and purified by RP Flash (Column: Flash $C^{18}$ 330 g; mobile phase: ACN in water (0.1% TFA), 30%-70% in 20 min; Detector, UV 210 nm. RT: 12 min). The collected fractions were combined and concentrated under reduced pressure to give (S)-5-(tert-butoxycarbonyl)-N-(2-(2-(3-methoxy-3-oxopropoxy)ethoxy)ethyl)-N,N-dimethyl-3,8,17,26-tetraoxo-1-phenyl-2,12,15,21,24-pentaoxa-4,9,18,27-tetraazanonacosan-29-aminium 2,2,2-trifluoroacetate 12b. LCMS (ESI) calc'd for $C_{43}H_{70}F_3N_5O_{17}$ [M-TFA-]$^+$: 873.0, found 873.0.

Step C: (S)-25-amino-N-(2-(2-(3-methoxy-3-oxopropoxy)ethoxy)ethyl)-N,N,28,28-tetramethyl-4,13,22,26-tetraoxo-6,9,15,18,27-pentaoxa-3,12,21-triazanonacosan-1-aminium 2,2,2-trifluoroacetate 12c To a solution of (S)-5-(tert-butoxycarbonyl)-N-(2-(2-(3-methoxy-3-oxopropoxy)ethoxy)ethyl)-N,N-dimethyl-3,8,17,26-tetraoxo-1-phenyl-2,12,15,21,24-pentaoxa-4,9,18,27-tetraazanonacosan-29-aminium 2,2,2-trifluoroacetate 12b (160 mg, 0.162 mmol) in THF (5 mL) was added Pd/C (dry, 10% wt) (34.5 mg, 0.032 mmol) under nitrogen atmosphere. The mixture was degassed with hydrogen for three times and stirred at room temperature for 2 h under hydrogen. The resulting mixture was filtered and the filtrate was concentrated under reduced pressure to afford (S)-25-amino-N-(2-(2-(3-methoxy-3-oxopropoxy)ethoxy)ethyl)-N,N,28,28-tetramethyl-4,13,22,26-tetraoxo-6,9,15,18,27-pentaoxa-3,12,21-triazanonacosan-1-aminium 2,2,2-trifluoroacetate 12c. LCMS (ESI) calc'd for $C_{35}H_{64}F_3N_5O_{15}$ $[M-TFA^-]^+$: 738.5, found 738.5.

Step D: Synthesis of 12d

To a mixture of (S)-5-(tert-butoxy)-4-(16-(tert-butoxy)-16-oxohexadecanamido)-5-oxopentanoic acid 4b (76 mg, 0.145 mmol), HATU (66.0 mg, 0.174 mmol) and DIEA (112 mg, 0.868 mmol) in DMF (0.7 mL) was added a solution of 12c (140 mg, 0.145 mmol) in DMF (0.7 mL) and water (0.14 mL) at −10° C. The resulting mixture was stirred for 30 min at −10° C. The reaction mixture was quenched by water (2 mL) and purified by RP Flash (Column: Flash $C^{18}$ 120 g; mobile phase: ACN in water (0.1% TFA), 30%-80% in 20 min; Detector, UV 210 nm. RT: 14 min). The collected fractions were combined and concentrated under reduced pressure to give 12d. LCMS (ESI) calc'd for $C_{64}H_{115}F_3N_6O_{21}$ $[M-TFA^-]^+$: 1247.8, found 1248.1.

Step E: Synthesis of 12e

To a mixture of 12d (140 mg, 0.103 mmol) in THF (3 mL) was added 1 M LiOH (0.206 mL, 0.206 mmol) at 0° C. The resulting mixture was stirred for 1 h at 0° C. The reaction mixture was quenched by 1 M HCl (0.2 mL) and purified by RP Flash (Column: Flash $C^{18}$ 120; mobile phase: ACN in water (0.10% $NH_4HCO_3$), 30%-80% in 20 min; Detector, UV 210 nm. RT: 15 min). The collected fractions were combined and concentrated under reduced pressure to give 12e. LCMS (ESI) calc'd for $C_{62}H_{114}N_6O_{22}$ $[M-HCO_3^-]^+$: 1233.8, found 1234.1. $^1H$ NMR (400 MHz, $CD_3OD$): δ 4.33-4.23 (m, 2H), 4.05 (d, J=15.2 Hz, 4H), 3.82-3.54 (m, 24H), 3.53-3.35 (m, 6H), 3.24 (s, 6H), 2.50-2.11 (m, 12H), 1.97-1.82 (m, 2H), 1.69-1.54 (m, 4H), 1.53-1.41 (m, 27H), 1.38-1.28 (m, 20H).

Step F: Synthesis of 12f

To a stirred solution of L (20 mg, 0.014 mmol) in DMF (0.2 mL) and water (0.02 mL) were added (25S,30S)-25,30-bis(tert-butoxycarbonyl)-N-(2-(2-(2-carboxyethoxy)ethoxy)ethyl)-N,N,49,49-tetramethyl-4,13,22,27,32,47-hexaoxo-6,9,15,18,48-pentaoxa-3,12,21,26,31-pentaazapentacontan-1-aminium hydrogencarbonate 12e (25.8 mg, 0.020 mmol), HATU (10.83 mg, 0.028 mmol) and DIEA (14.73 mg, 0.114 mmol) at −10° C. The resulting mixture was stirred at −10° C. for 30 min. The reaction mixture was quenched by water (1 mL) and purified by RP Flash (Column: Flash $C^{18}$ 40 g; mobile phase: ACN in water (0.1% TFA), 30%-70% in 25 min; Detector, UV 210 nm. RT: 15 min). The collected fractions were combined and concentrated under reduced pressure to give 12f. LCMS (ESI) calc'd for $C_{135}H_{202}F_4N_{18}O_{34}$ $[(M-TFA^-)/2]^+$: 1291.2, found 1292.7.

Step G: Synthesis of 12g

To a stirred solution of 12f (26 mg, 9.64 μmol) in DCM (5 mL) was added TFA (6.25 mL) at −10° C. The resulting mixture was stirred at room temperature for 3 h. The reaction mixture was concentrated under reduced pressure and the residue was purified by RP Flash (Column: Flash $C^{18}$ 40 g; mobile phase: acetonitrile in water (0.10% TFA), 30%-50% in 15 min; Detector, UV 210 nm. RT: 10 min). The collected fractions were combined and concentrated under reduced pressure to give 12g. LCMS (ESI) calc'd for $C_{123}H_{178}F_4N_{18}O_{34}$ $[(M\text{-}TFA^-)/2]^+$: 1207.1, found 1208.5.

Step H: Synthesis of Example 12

5 g of AG MP-1 Resin (cat #141-1841 BIO-RAD) was packed in column. The column was washed with water (2×10 mL), followed by 20% ACN in water (2×10 mL). A solution of 12g (18 mg, 7.12 μmol) in ACN and water (3:2, 20 mL) was loaded onto the resin column, then the column was eluted with 60% ACN in water (4×20 mL). The eluents were combined and lyophilized to afford Example 12. LCMS (ESI) calc'd for $C_{121}H_{178}ClFN_{18}O_{32}$ $[M-Cl^-]^+$: 2415.8, found 2415.3.

Preparation of Example 13

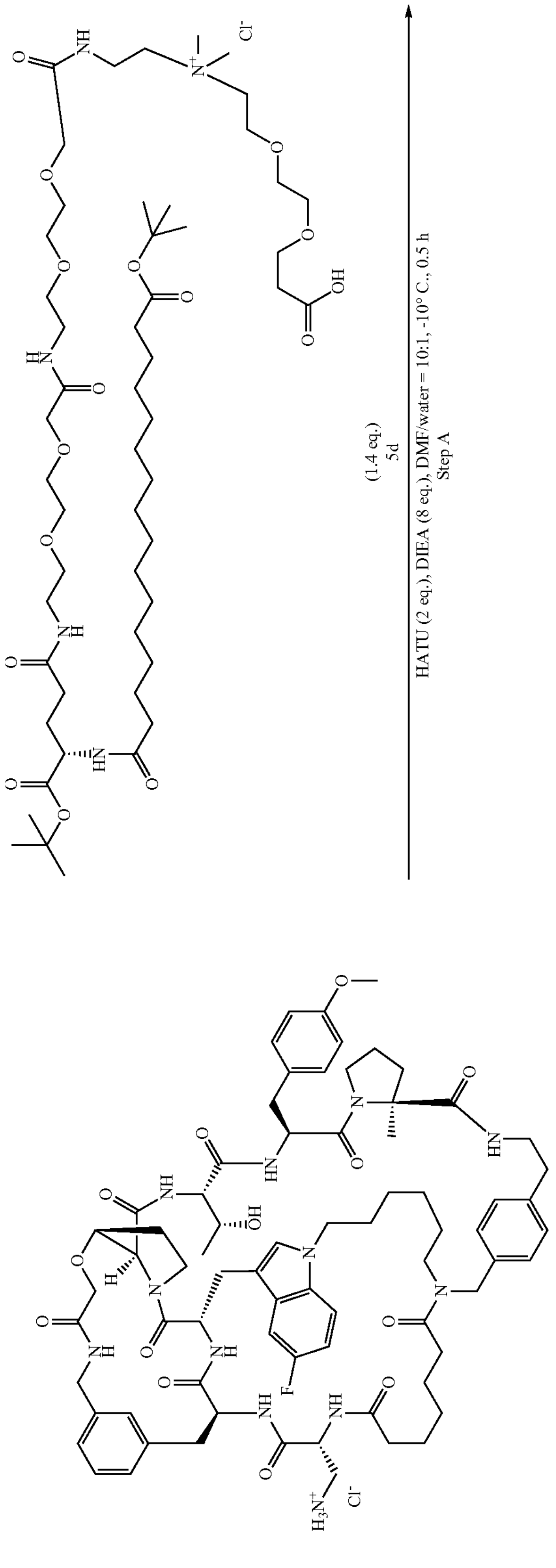
D

-continued
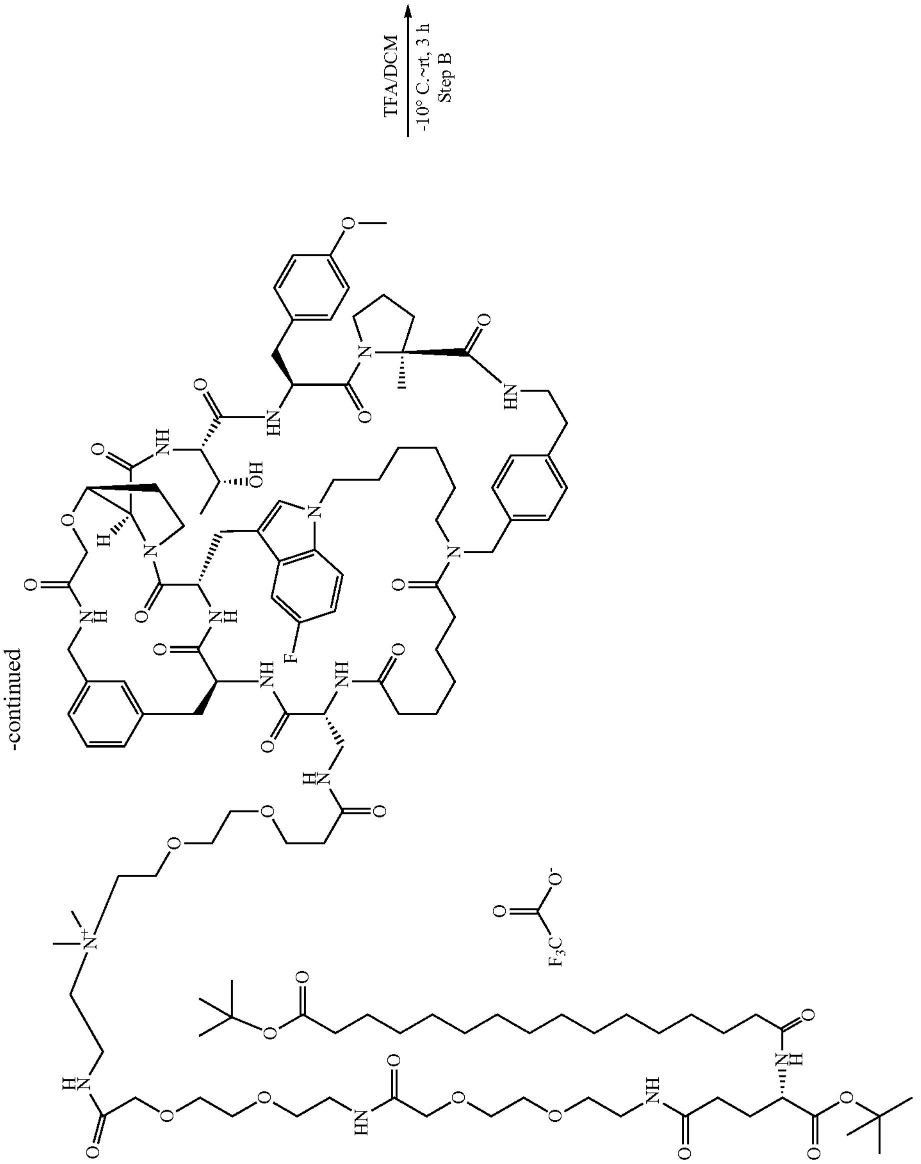
13a

-continued
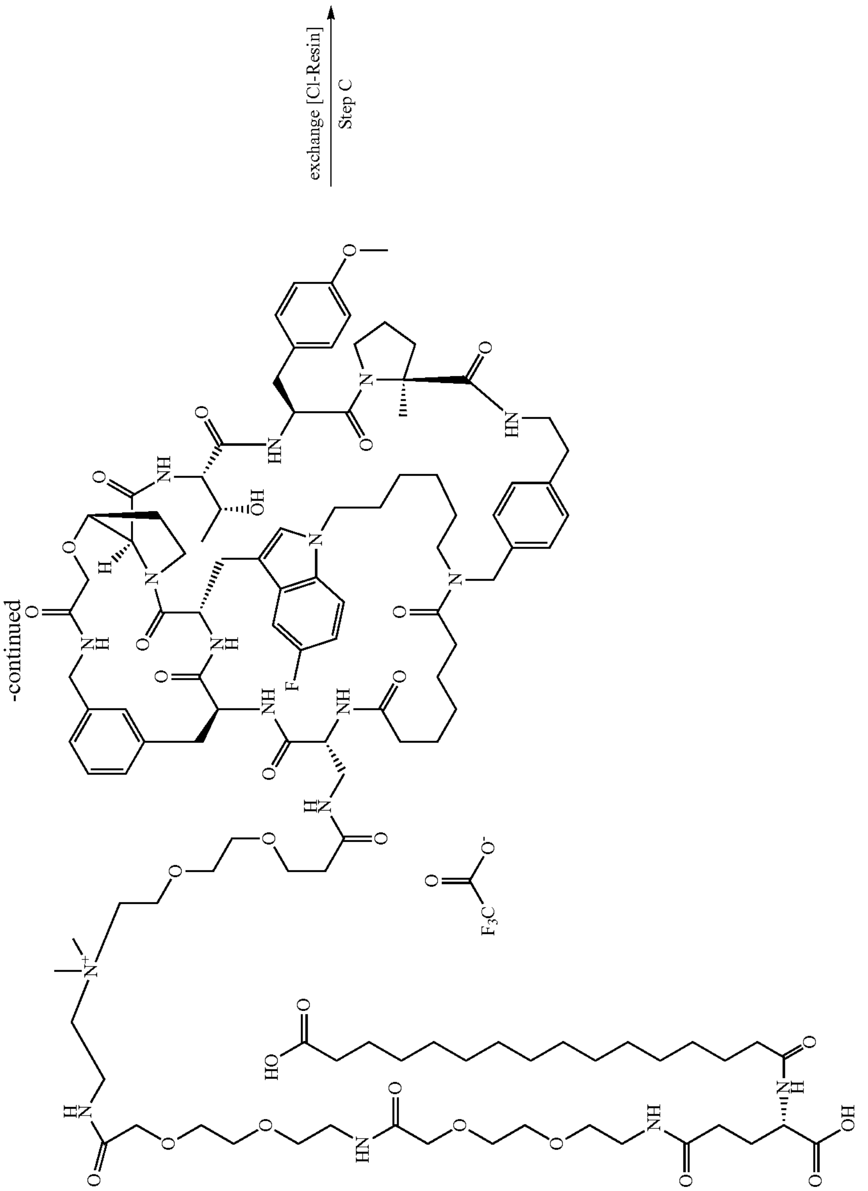
13b

-continued
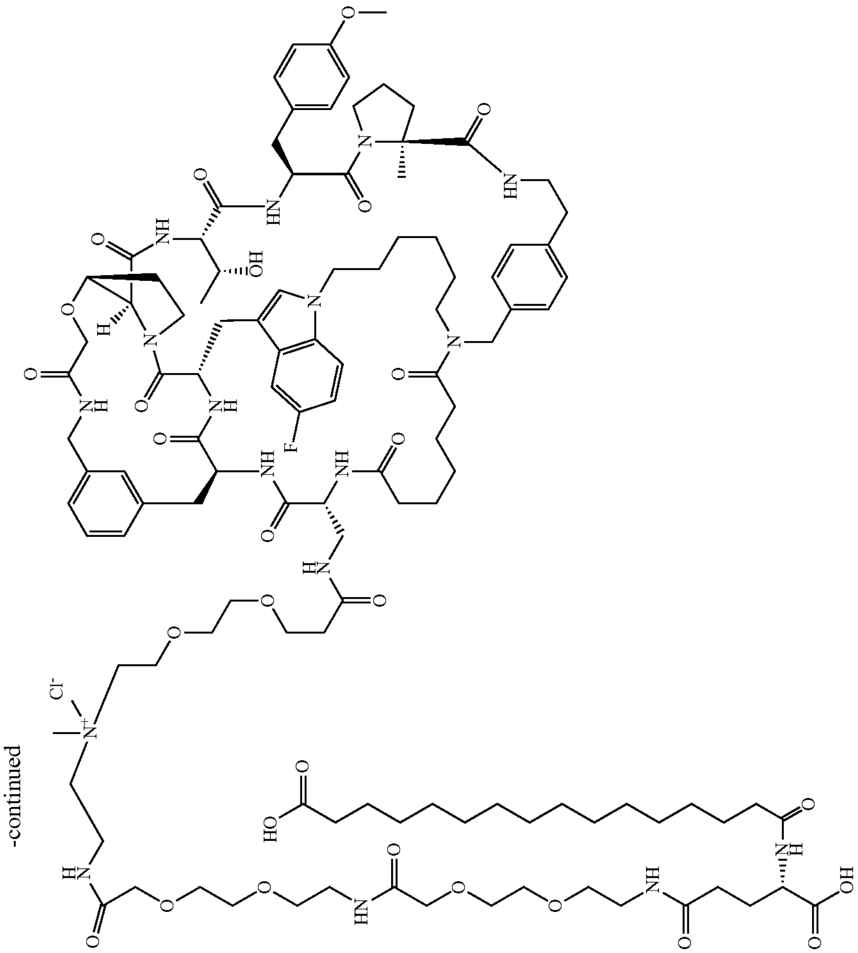
Example 13

Step A: Synthesis of 13a

To a solution of 5d (55.3 mg, 0.051 mmol) in acetonitrile (1 ml) and DMF (0.15 ml) were added D (55 mg, 0.039 mmol), HATU (17.15 mg, 0.045 mmol) and DIPEA (0.041 ml, 0.235 mmol), then the mixture was stirred for 30 min. The mixture was slowly dripped into a centrifuge tube filled with IPAc/cyclopentylmethyl ether 1:1 (30 ml) and the tube was completed to 35 ml. The tube was chilled at −78 C for 2 min then centrifuged at −10 C for 20 min. The solvent was decanted, IPAc/cyclopentylmethyl ether 1:1 (30 ml) was added, the tube shaken, chilled at −78 C for 2 min then centrifuged at −10° C. for 20 min. The solvent was decanted and the solid concentrated out of toluene/acetonitrile then DCM to provide 13a. LCMS (ESI) calc'd for $C_{125}H_{189}FN_{17}O_{28}Cl$ [(M−Cl$^-$/2)]$^+$: 1198.5, found 1198.5.

Step B: Synthesis of 13b

To a solution of 13a (73.5 mg, 30 μmol) in DCM (2 mL) was added TFA (1.8 mL) at −10° C. The reaction mixture was stirred at room temperature for 3 h. The reaction solution was concentrated under reduced pressure and purified by Flash: Column: Flash $C^{18}$ 40 g; Mobile Phase A: water (0.1% TFA), Mobile Phase B: ACN; Flow rate: 50 mL/min; Gradient: 2% B to 2% B in 5 min, 30% B to 60% B in 20 min; Detector: UV 210 nm; Rt=25 min to afford 13b. LCMS (ESI) calc'd for $C_{119}H_{173}F_4N_{17}O_{30}$ [(M-TFA$^-$/2)]$^+$: 1142.3, found 1142.6.

Step C: Synthesis of Example 13

5 g of AG MP-1 Resin (cat #141-1841 BIO-RAD) was packed in column. The column was washed with water (3×20 mL), followed by 20% ACN in water (3×20 mL). A solution of 13b (30 mg, 13 μmol) in 60% ACN in water (20 mL) was loaded onto the resin column, then the column was eluted with 60% ACN in water (4×20 mL). The eluents were combined, water (5×4 mL) added, lyophilized to afford Example 13. LCMS (ESI) calc'd for $C_{117}H_{173}ClFN_{17}O_{28}$ [M−Cl$^-$/2]$^+$: 1142.5, found 1142.5;

Activity Determination

Selected compounds of the invention were subjected to one or more of the following procedures to assay their activity for antagonism of PCSK9 activity.

The following is a description of the assays used to determine activity of compounds of the invention, and any comparator compounds reported, toward PCSK9 antagonism. Biotinylated PCSK9 was obtained commercially.

Alexa FRET Standard TR-FRET

The PCSK9 Alexa FRET Standard assay measures the interaction between PCSK9 and an AlexaFluor647 (AF) tagged cyclic peptide, Reagent A ($K_D$=83 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2), 0.01% BSA, and 0.01% Surfactant P20. A separate solution containing 40 nM of the AlexaFluor tagged cyclic peptide is made in the same buffer system. An Echo is used to transfer 0.750 ul of compound to an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 20 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the Ic50 and the $K_D$ of AF cyclic peptide. Counts (B-counts) of the europium-labeled PCSK9 are followed to observe if compounds are adversely PCSK9. A fall off of the B-counts likely indicates a false positive of inhibition. Data from this procedure is reported as "A='numerical value' (nanomolar)"

Reagent A was prepared in accordance with the following method:

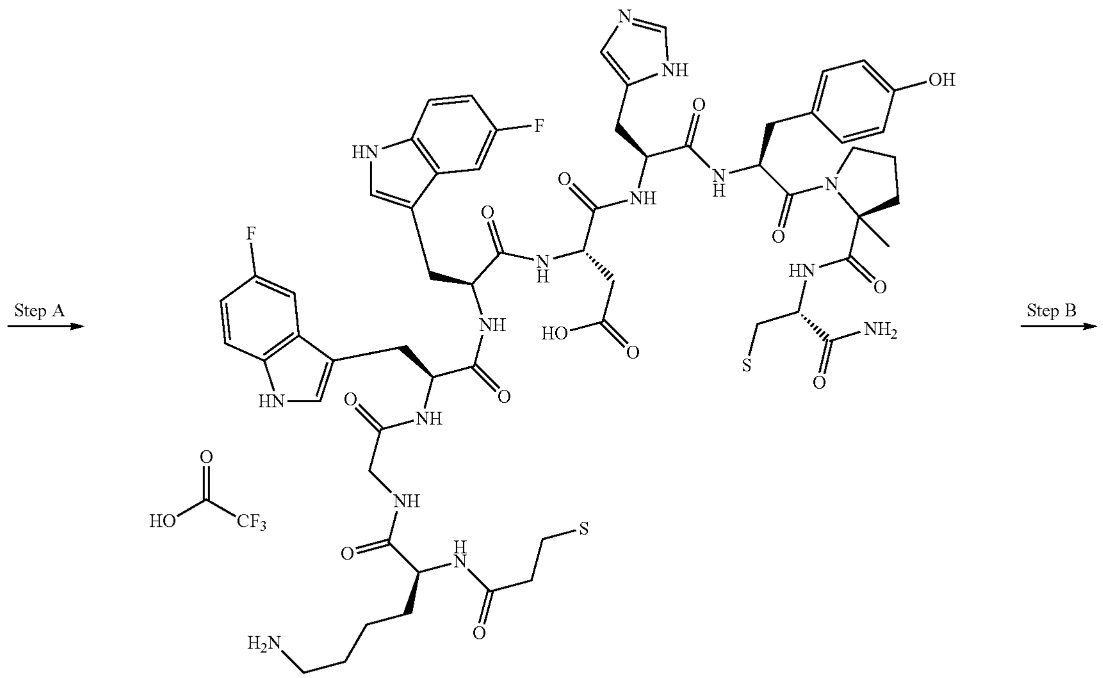

Int. A

-continued
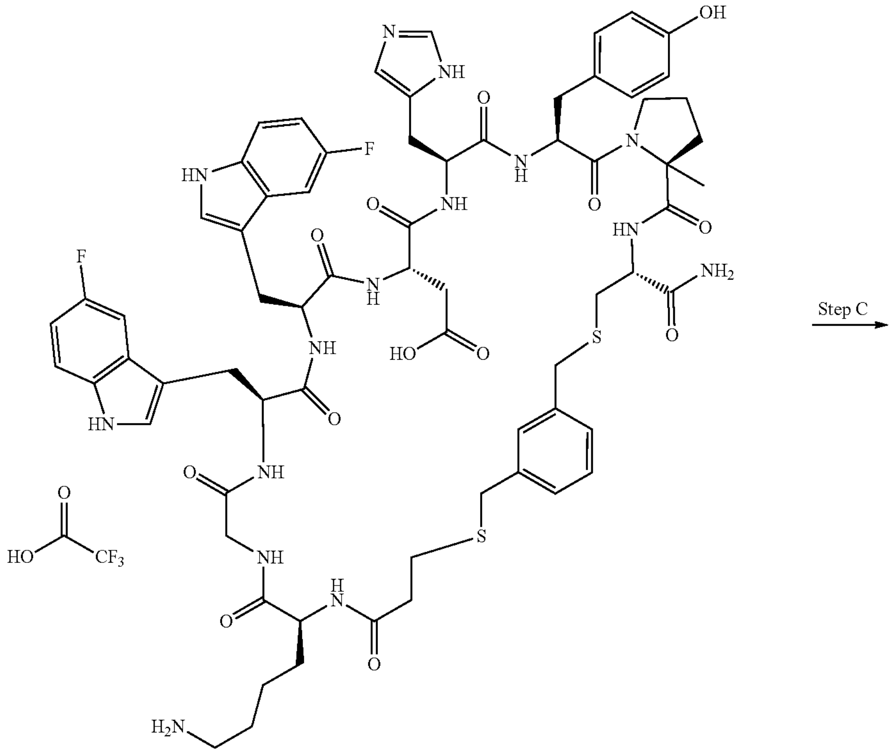
Int. B
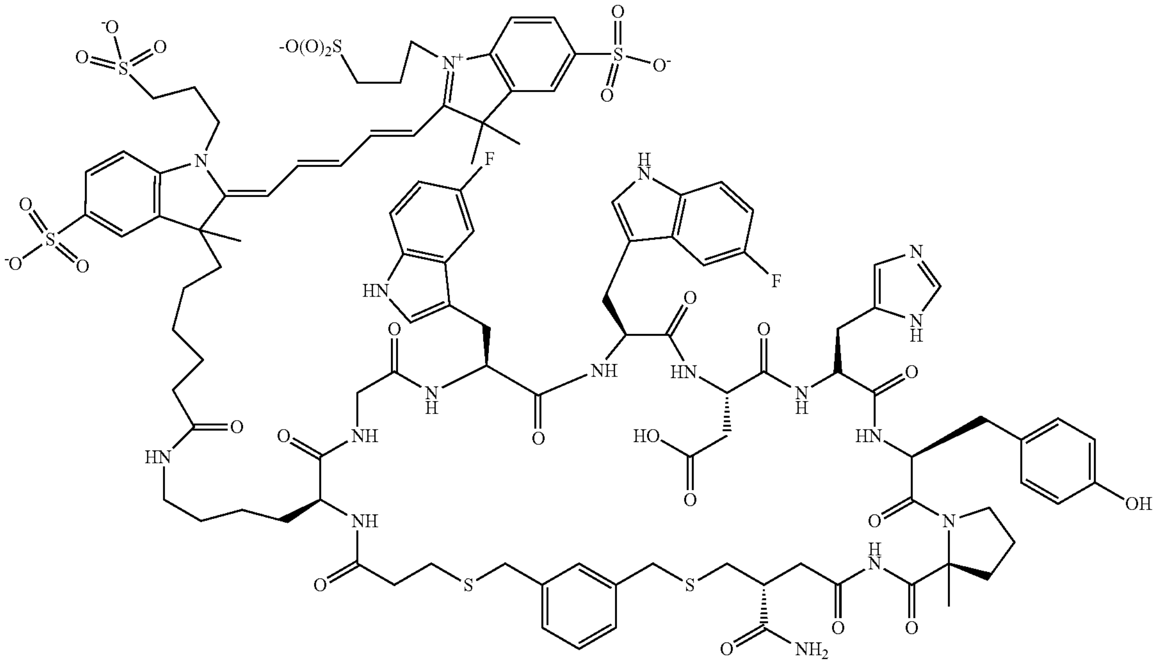
REAGENT A

Step A—Synthesis of Intermediate Compound Int-A

The peptide was synthesized on a 0.250 mmol scale on CEM Liberty Blue, Microwave synthesizer using Fmoc/tBu chemistry on PS Rink-Amide MBHA resin, 0.32 mmol $g^{-1}$. The assembly was performed using single-couplings using 4 eq of Fmoc protected amino acid 0.2M in DMF, 4 eq of 0.5M HATU in DMF, 4 eq of 2M DIPEA (double coupling for Tyr). Fmoc deprotection cycles were performed using 20% (V/V) piperidine in DMF.

The sequence of Fmoc protected amino acids and building blocks used are:

1. N-(((9H-fluoren-9-yl)methoxy)carbonyl)-S-trityl-L-cysteine
2. (S)-1((((9H-fluoren-9-yl)methoxy)carbonyl)amino)-2-methylpyrrolidine-2-carboxylic acid
3. (((9H-fluoren-9-yl)methoxy)carbonyl)-L-tyrosine
4. N-(((9H-fluoren-9-yl)methoxy)carbonyl)-N-trityl-L-histidine
5. (S)-2-((((9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)glycine
9. $N^2$-(((9H-fluoren-9-yl)methoxy)carbonyl)-$N^6$-(tert-butoxycarbonyl)-L-lysine
10. 3-(tritylthio)propanoic acid At the end of the assembly, the resin was washed with DMF, MeOH, DCM, $Et_2O$. The peptide was cleaved from solid support using 50 ml of TFA solution (v/v) (91% TFA, 5% $H_2O$, 4% TIPS) for approximately 1.5 hours, at room temperature. The resin was filtered, washed with TFA and solution concentrated to dryness and lyophilized. Lyophilization afforded Intermediate Compound Int. A (399 mg), which was used as crude in the next step. LCMS anal. calcd. C61H75F2N15O13S2: 1328.48, found: 1328.2 $(M+1)^+$ Step B—Synthesis of Intermediate Compound Int-B: As Described for Reagent B Purified by RP-HPLC (Waters Deltapak C4, double cartridge, 40×100 mm, 15 μm, 300 A; 15% to 35% ACN/water+0.1% TFA modifier over 20 min). Collected fractions lyophilized to afford 35 mg of Intermediate Compound Int-B. LCMS anal. calcd. for C69H81F2N15O13S2: 1430.62; found: 1430.9 $(M+1)^+$ Step C—Synthesis of Compound Reagent A: As Described for Reagent B LCMS anal. calcd. for $C105H122F2N17O26S6^{3-}$: 2268.58; 1135.8 $(M+2)^{2+}$ Alexa FRET Plus TR-FRET The PCSK9 Alexa FRET Plus assay measures the interaction between PCSK9 and an AlexaFluor647 (AF) tagged cyclic peptide, Reagent B ($K_D$=35 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2), 0.01% BSA, and 0.01% Surfactant P20. A separate solution containing 1920 nM of the AlexaFluor tagged cyclic peptide is made in the same buffer system. An Echo is used to transfer 0.075 ul of compound plus 0.675 ul of DMSO to each well of an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 960 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the Ic50 and the $K_D$ of AF cyclic peptide. Counts (B-counts) of the europium-labeled PCSK9 are followed to observe if compounds are adversely affecting PCSK9. A fall off of the B-counts is likely indicates a false positive of inhibition. Data from this procedure is reported as "P='numerical value' (nanomolar)"

Reagent B was prepared by the following procedure.

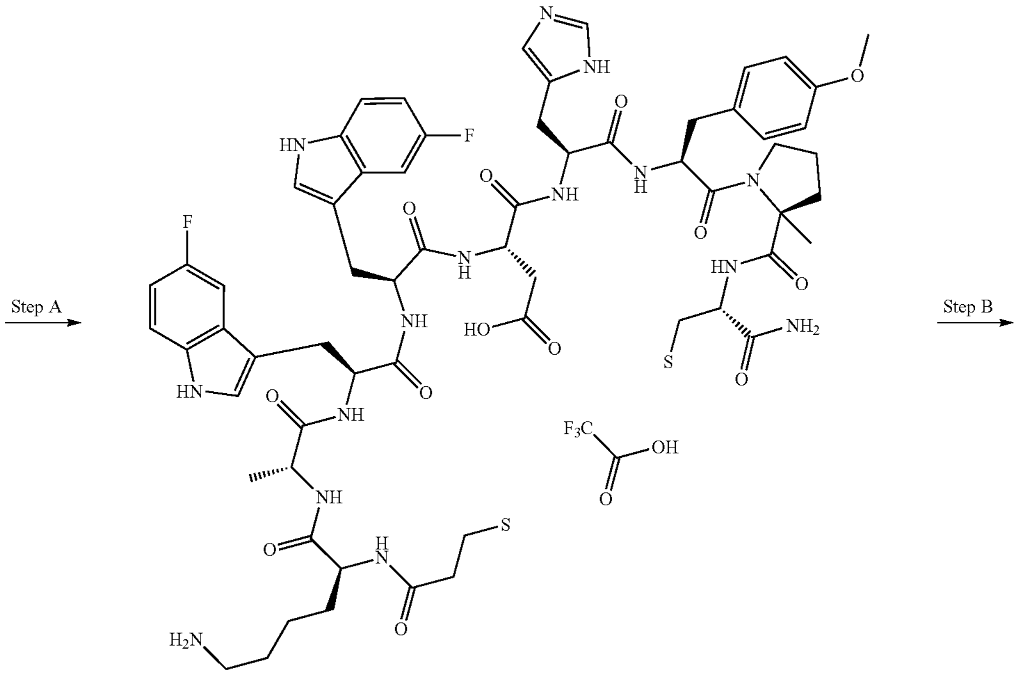

Int. A

-continued
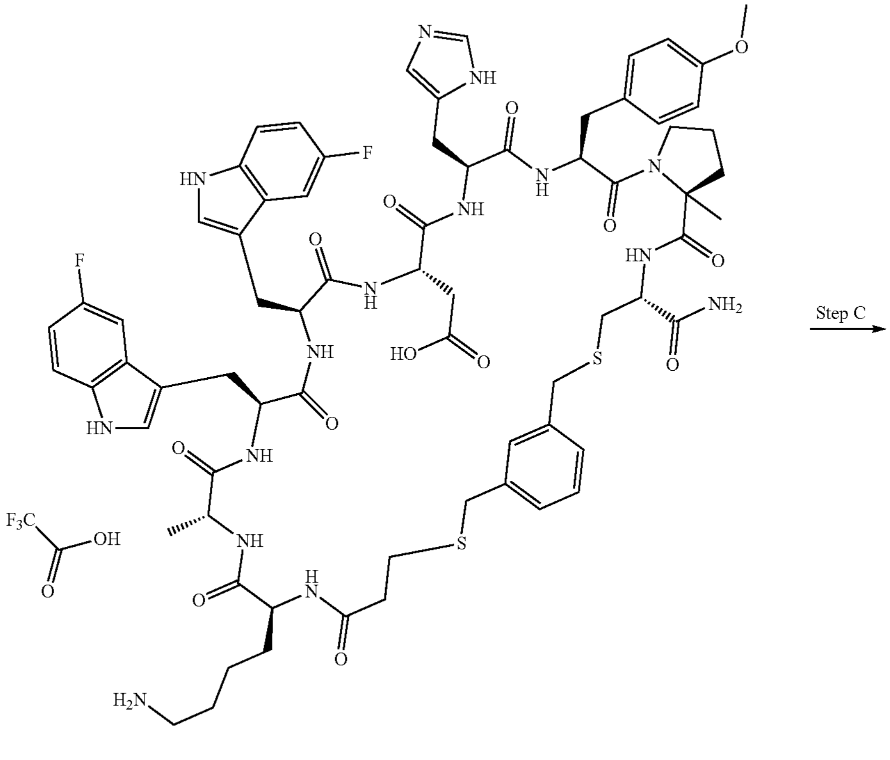
Int. B
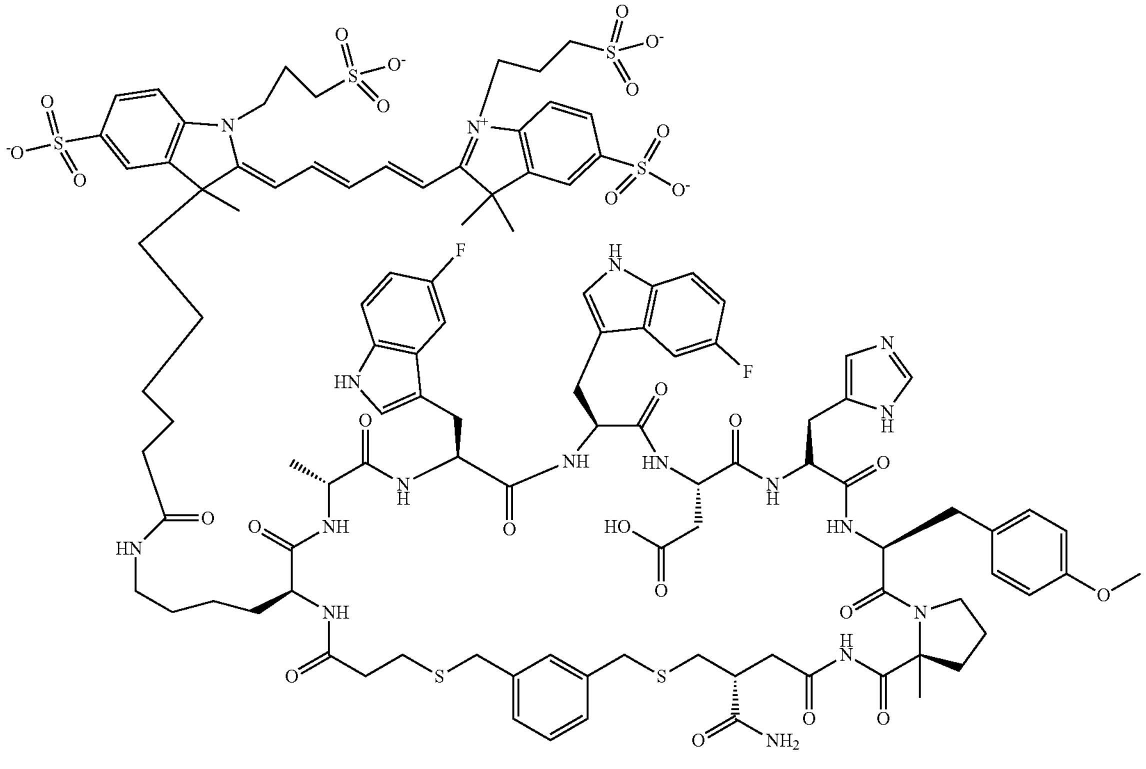
Reagent B

Step A—Synthesis of Intermediate Compound Int-A

The peptide was synthesized on a 0.250 mmol scale on CEM Liberty Blue, Microwave synthesizer using Fmoc/tBu chemistry on PS Rink-Amide MBHA resin, 0.32 mmol $g^{-1}$. The assembly was performed using single-couplings using 4 eq of Fmoc protected amino acid 0.2M in DMF, 4 eq of 1M Oxyma in DMF, 4 eq of 0.5M N,N-diisopropylcarbodiimide (DIC) (double coupling for Y01). Fmoc deprotection cycles were performed using 20% (V/V) piperidine in DMF.

The sequence of Fmoc protected amino acids and building blocks used are:

1. N-(((9H-fluoren-9-yl)methoxy)carbonyl)-S-trityl-L-cysteine
2. (S)-1((((9H-fluoren-9-yl)methoxy)carbonyl)amino)-2-methylpyrrolidine-2-carboxylic acid
3. (S)-2-((((9H-fluoren-9-yl)methoxy)carbonyl)amino)-3-(4-methoxyphenyl)propanoic acid
4. N-(((9H-fluoren-9-yl)methoxy)carbonyl)-N-trityl-L-histidine
5. (S)-2-((((9H-fluoren-9-yl)methoxy)carbonyl)amino)-4-(tert-butoxy)-4-oxobutanoic acid
6. (S)-2-((((9H-fluoren-9-yl)methoxy)carbonyl)amino)-3-(5-fluoro-1H-indol-3-yl)propanoic acid
7. (S)-2-((((9H-fluoren-9-yl)methoxy)carbonyl)amino)-3-(5-fluoro-1H-indol-3-yl)propanoic acid
8. (((9H-fluoren-9-yl)methoxy)carbonyl)-D-alanine
9. $N^2$-(((9H-fluoren-9-yl)methoxy)carbonyl)-$N^6$-(tert-butoxycarbonyl)-L-lysine
10. 3-(tritylthio)propanoic acid At the end of the assembly, the resin was washed with DMF, MeOH, DCM, $Et_2O$. The peptide was cleaved from solid support using 50 ml of TFA solution (v/v) (91% TFA, 5% $H_2O$, 4% TIPS) for approximately 1.5 hours, at room temperature. The resin was filtered, washed with TFA and solution concentrated to dryness and lyophilized. Lyophilization afforded Intermediate Compound Int. A (300 mg), which was used as crude in the next step. LCMS anal. calcd. C63H79F2N15O13S2: 1356.53, found: 1356.9 $(M+1)^+$ Step B—Synthesis of Intermediate Compound Int-B Crude Int-A (0.22 mmol) was dissolved in 24 ml of DMF. 6 ml of 1M aqueous solution of sodium bicarbonate was added to raise the pH to 7. Then 0.26 mmol of 1,3-bis (bromomethyl)benzene (0.1M in DMF) were added dropwise. Reaction was left under stirring at room temperature for 20 min, quenched with TFA (pH to 3-4) and then concentrated in vacuo to provide crude Int-B, which was purified by RP-HPLC (Waters XBridge, C18, 50×150 mm, 5 μm, 130 A; 25% to 40% ACN/water+0.1% TFA modifier over 20 min). Collected fractions were lyophilized to afford 35 mg of Intermediate Compound Int-B. LCMS anal. calcd. for C71H85F2N15O13S2: 1458.67; found: 1458.8 $(M+1)^+$ Step C—Synthesis of Compound Reagent B Intermediate Compound Int-B (15 mg) was dissolved in 0.2 ml of dry DMSO. Then 15 mg of ALEXAFLUOR 647NHS Ester (A37566, Life technology) dissolved in 1.5 ml of dry DMSO were added. 20 uL of dry DIPEA were added. Reaction was left under stirring at room temperature for 12h under Nitrogen atmosphere in the dark. Quenched with TFA (pH to 3-4) and purified by RP-HPLC (Dr Maish, Reprosil Gold C18, 250×20 mm, 120 Å, 10 μm; 20% to 35% of 0.1% TFA in ACN/0.1% TFA in $H_2O$, over 20 min, then 35% to 40% over 5 min at 20 mL/min flow rate). Collected fractions were lyophilized to afford 16.1 mg of Compound Reagent B. LCMS anal. for C107H126F2N17O26S6$^{3-}$: 2296.64; found: 1150.6 $(M+2)^{2+}$ Activity data obtained by one or both of the above-described procedures is reported for selected example compounds of the invention in the following format:

Example No.: A (standard TR Fret)='numerical value'; P (Alexa Fret plus standard TR Fret)='numerical value'/, note that all values reported are nanomolar.

Alexa FRET Ultra TR-FRET

The PCSK9 Alexa FRET Ultra assay measures the interaction between PCSK9 and an AlexaFluor647 (AF) tagged cyclic peptide, Reagent B ($K_D$=0.99 nM). A solution containing 1 nM biotinylated PCSK9+2.5 nM Lance Streptavidin Europium (Strep-Eu) is made in 50 mM HEPES pH 7.4, 0.15 M NaCl, 5 mM CaCl2), 0.01% BSA, and 0.01% Surfactant P20. A separate solution containing 1920 nM of the AlexaFluor tagged cyclic peptide is made in the same buffer system. An Echo is used to transfer 0.015 ul of compound plus 0.735 ul of DMSO to each well of an assay plate followed by the addition of 15 ul of PCSK9+Stept-Eu and 15 ul of AF peptide. The final assay volume is 30.750 ul containing 0.5 nM PCSK9, 1.25 nM Strep-Eu, and 960 nM AF cyclic peptide. The reaction is incubated at room temperature for at least two hours prior to fluorescence measurements using an Envision Multilabel Reader. IC50 values are determined by fitting data to a sigmoidal dose-response curve using nonlinear regression. Ki is then calculated from the Ic50 and the $K_D$ of AF cyclic peptide. Counts (B-counts) of the europium-labeled PCSK9 are followed to observe if compounds are adversely affecting PCSK9. A fall off of the B-counts is likely indicates a false positive of inhibition. Data from this procedure is reported as "Ki Ultra='numerical value' (data reported is nanomolar)"

The following compounds were assessed using the protocol described above and the results are shown in Table 2.

TABLE 2

Activity Data for Examples of the Invention.

| Example | Alexa FRET Stdt TR-FRET, nM | Alexa FRET Plus TR-FRET, nM | Alexa FRET Ultra TR-FRET, nM |
|---|---|---|---|
| 1 | <1.26 | 0.205 | 0.488 |
| 2 | <1.26 | 0.024 | 0.14 |
| 3 | <1.26 | 0.082 | 0.43 |
| 4 | <1.26 | 0.037 | 0.16 |
| 5 | <1.26 | 0.036 | 0.13 |
| 6 | <1.26 | 0.049 | 0.36 |
| 7 | <1.26 | <0.006 | 0.004 |
| 8 | <1.26 | <0.006 | 0.006 |
| 9 | <1.26 | <0.006 | 0.003 |
| 10 | <1.26 | <0.006 | 0.004 |
| 11 | <1.26 | <0.006 | 0.001 |
| 12 | <1.26 | <0.006 | 0.002 |
| 13 | <1.26 | <0.006 | 0.0008 |

What is claimed is:

1. A compound of Formula I

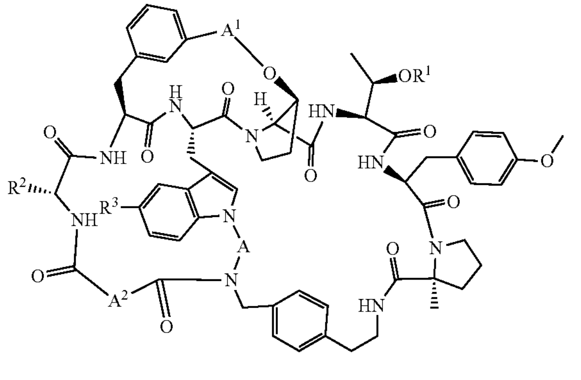

wherein:

A is $C_{2-6}$ alkyl;

$A^1$ is

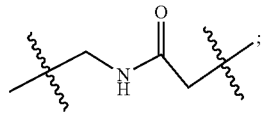

$A^2$ is $—(CR_2)_nX(CR_2)_n—$;

X is O or $CR_2$;

R is independently selected from H or $C_{1-6}$ alkyl;

$R^a$ is independently selected from H or $—C(O)OR^9$;

$R^b$ is independently selected from H, $C_{1-6}$ alkyl, or $C_{1-6}$ alkyl-$N^+(CH_3)_2$;

$R^d$ is independently selected from H or $—C(O)OR^9$;

$R^x$ is triazolyl;

$R^1$ is H;

$R^2$ is selected from $—(CR_2)_z—NR^b—C(O)R^{10}$;

$R^3$ is F;

$R^4$ is

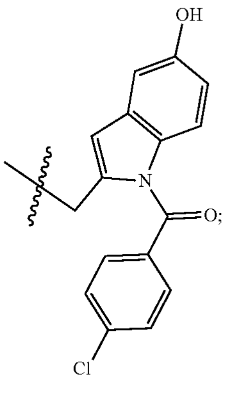 [SMILES: *Cc1cc2cc(O)ccc2n1C(=O)c1ccc(Cl)cc1]

$R^5$ is independently selected from $—(CR^a_2)_x—$, $—(CR^a_2)_x O(CR^a_2)_x—$, and $C_{1-8}$ alkyl;

$R^6$ is independently selected from $—(CR^a_2)_xNRC(O)—$, $—(CR_2)_xNRS(O)_2—$, and $—(CR^a_2)_nO(CR^a_2)_qNRC(O)—$;

$R^9$ is independently selected from H or $C_{1-6}$ alkyl;

$R^{10}$ is independently selected from:

a) $—(R^5—N^+(CH_3)_2—R^6)_u—(R^{20})_n—(R^6)_m—R^{12}$, b) $—(R^{20})_n—(R^6)_m—R^5—N^+(CH_3)_2—R^6—R^{12}$, c) $—(R^{20})_n—R^5—N^+(CH_3)_2—(R^{20})_s—(R^6)_q—R^{12}$, d) $—R^6—R^{20}—N^+(CH_3)_2—(R^{20})_n—(R^6)_m—R^{12}$, e) $—R^{20}—N^+(CH_3)_2—(R^6)_m—(R^{20})_n—(R^6)_q—R^{12}$, f) $—(R^{20})_n—(R^6)_m—R^{12}$, g) $—R^5—N^+(CH_3)_2—(R^{20})_n—(R^6)_m—R^5—[NRC(O)—R^5]_q$, h) $—R^{20}—N^+(CH_3)_2—(R^6)_m—R^5$, i) $—R^5—N^+(CH_3)_2—(R^{20})_n (R^6)_m—R^5$, j) $—R^5—N^+(CH_3)_2—(R^{20})_n—(R^6)_m—R^{12}$, k) $—(R^{20})_n—N^+(CH_3)_2—(R^{20})_n—(R^6)_q—R^{12}$, l) $—R^6—R^5—N^+(CH_3)_2—(R^{20})_n—(R^6)_q—R^{12}$, m) $—(R^{20})_n—N^+(CH_3)_2—(R^6)_q—R^{12}$, n) $—(R^{20})_n—(R^6)_m—R^{20}—N^+(CH_3)_2—(R^{20})_s—(R^6)_q—R^{12}$, o) $—R^{20}—N^+(CH_3)_2—(R^6)_m—R^4$, p) $—(R^{20})_n—N^+(CH_3)_2—(R^6)_q—(R^{20})_n—(R^6)_m—R^{12}$, q) $—R^{20}—N^+(CH_3)_2—(R^6)_m—(R^{20})_n —N^+(CH_3)_2—(R^{20})_n—(R^6)_q—R^{12}$, r) $—R^5—N^+(CH_3)_2—(R^6)_m—R^5—N^+(CH_3)_2—(R^{20})_n—(R^6)_q—R^{12}$, and s) $—CR^b_2—(R^{20})_n—(R^6)_m—R^{12}$;

$R^{12}$ is independently selected from $—C_{11-20}$ alkyl-$R^d$, $—(CR_2)_x—O—(CR_2)_x—R^d$, $—C_{11-20}$ alkyl-$C(O)NR—(CR^d_2)_2H$, and $C_{2-16}$ alkenyl;

$R^{20}$ is independently selected from a) $—(CR^a_2)_tO(CR^a_2)_qO—(CR^a_2)_t—$, b) $—(CR^a_2)_tO(CR^a_2)_qO—(CR^a_2)_t—NRC(O)—$, c) $—(CR^a_2)_tO(CR^a_2)_q—NRC(O)—(CR^a_2)_nO(CR^a_2)_nO—$, d) $—(CR^a_2)_t—NRC(O)—(CR^a_2)_qO(CR^a_2)_qO—(CR^a_2)_t—$, e) $—(CR^a_2)_tO(CR^a_2)_qO—(CR^a_2)_t—$, and f) $—(CR^a_2)_t—O—(CR^a_2)_qO(CR^a_2)_qO—(CR^a_2)_t—$;

m is independently selected from 0, 1, 2, 3 or 4;

n is independently selected from 1, 2 or 3;

q is independently selected from 1, 2, 3 or 4;

r is independently selected from 0, 1, 2, 3 or 4;

s is independently selected from 0, 1, 2 or 3;

t is independently selected from 0, 1, 2 or 3;

u is 1 or 2;

x is independently selected from 1, 2, 3, 4, 5, 6, 7, or 8;

z is independently selected from 1, 2, 3, 4, 5 or 6;

or a pharmaceutically acceptable salt of any thereof.

2. A compound of Formula I:

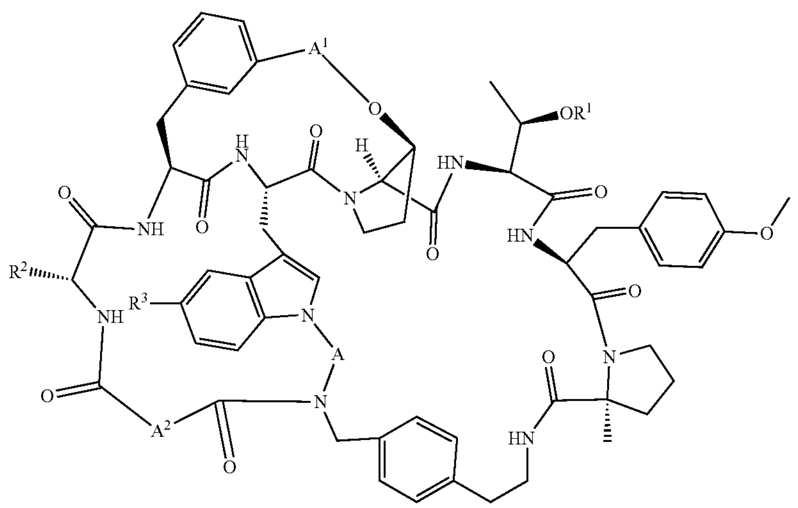

wherein:

A is selected from $C_{2-6}$ alkyl or $-(CR_2)_nR^x(CR_2)_n-$;

$A^1$ is

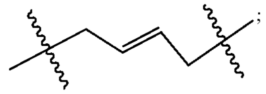

;

$A^2$ is $-(CR_2)_nX(CR_2)_n-$;

X is O or $CR_2$;

R is independently selected from H or $C_{1-6}$ alkyl;

Ra is independently selected from H or $-C(O)OR^9$;

$R^6$ is independently selected from H, $C_{1-6}$ alkyl, or $C_{1-6}$ alkyl-$N^+(CH_3)_2$;

$R^x$ is triazolyl;

$R^d$ is independently selected from H or $-C(O)OR^9$;

$R^1$ is H;

$R^2$ is selected from:

(a) $-(CR_2)_z-NR^b-C(O)R^{10}$, and (b) $-(CR_2)_z-NR-C(O)-(CR_2)_z[O(CR_2)_n]_r-N^+(CH_3)_3$;

$R^3$ is F;

$R^4$ is

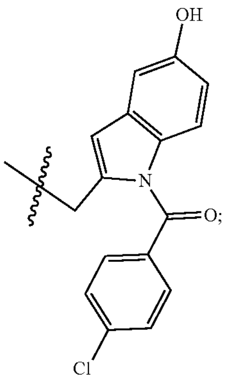 [SMILES: *Cc1cc2cc(O)ccc2n1C(=O)c1ccc(Cl)cc1]

$R^5$ is independently selected from $-(CR^a_2)_x-$, $-(CR^a_2)_xO(CR^a_2)_x-$, and $C_{1-8}$ alkyl;

$R^6$ is independently selected from $-(CR^a_2)_xNRC(O)-$, $-(CR_2)_xNRS(O)_2-$, and $-(CR^a_2)_nO(CR^a_2)_qNRC(O)-$;

$R^9$ is independently selected from H or $C_{1-6}$ alkyl;

$R^{10}$ is independently selected from:

a) $-(R^5-N^+(CH_3)_2-R^6)_u-(R^{20})_n-(R^6)_m-R^{12}$, b) $-(R^{20})_n-(R^6)_m-R^5-N^+(CH_3)_2-R^6-R^{12}$, c) $-(R^{20})_n-R^5-N^+(CH_3)_2-(R^{20}), -(R^6)_q-R^{12}$, d) $-R^6-R^{20}-N^+(CH_3)_2-(R^{20})_n (R^6)_m-R^{12}$, e) $-R^{20}-N^+(CH_3)_2-(R^6)_m-(R^{20})_n-(R^6)_q-R^{12}$, f) $-(R^{20})_n-(R^6)_m-R^{12}$, g) $-R^5-N^+(CH_3)_2-(R^{20})_n-(R^6)_m-R^5-[NRC(O)-R^5]_q$, h) $-R^{20}-N^+(CH_3)_2-(R^6)_m-R^5$, i) $-R^5-N^+(CH_3)_2-(R^{20})_n(R^6)_m-R^5$, j) $-R^5-N^+(CH_3)_2-(R^{20})_n-(R^6)_m-R^{12}$, k) $-(R^{20})_n-N^+(CH_3)_2-(R^{20})_n-(R^6)_q-R^{12}$, l) $-R^6-R^5-N^+(CH_3)_2-(R^{20})_n-(R^6)_q-R^{12}$, m) $-(R^{20})_n-N^+(CH_3)_2-(R^6)_q-R^{12}$, n) $-(R^{20})_n-(R^6)_m-R^{20}-N^+(CH_3)_2-(R^{20}), (R^6)_q-R^{12}$, o) $-R^{20}-N^+(CH_3)_2-(R^6)_m-R^4$, p) $-(R^{20})_n-N^+(CH_3)_2-(R^6)_q-(R^{20})_n-(R^6)_m-R^{12}$, q) $-R^{20}-N^+(CH_3)_2-(R^6)_m-(R^{20})_n-N^+(CH_3)_2-(R^{20})_n-(R^6)_q-R^{12}$, r) $-R^5-N^+(CH_3)_2-(R^6)_m-R^5-N^+(CH_3)_2-(R^{20})_n-(R^6)_q-R^{12}$, and s) $-CR^b_2-(R^{20})_n (R^6)_m-R^{12}$;

$R^{12}$ is independently selected from $-C_{11-20}$ alkyl-$R^d$, $-(CR_2)_x-O-(CR_2)_x-R^d$, $-C_{11-20}$ alkyl-$C(O)NR-(CR^d_2)_2H$, and $C_{2-16}$ alkenyl;

$R^{20}$ is independently selected from a) $-(CR^a_2)_tO(CR^a_2)_qO-(CR^a_2)_t-$, b) $-(CR^a_2)_tO(CR^a_2)_qO-(CR^a_2)_t-NRC(O)-$, c) $-(CR^a_2)_tO(CR^a_2)_q-NRC(O)-(CR^a_2)_nO(CR^a_2)_nO-$, d) $-(CR^a_2)_t-NRC(O)-(CR^a_2)_qO(CR^a_2)_qO-(CR^a_2)_t-$, e) $-(CR^a_2)_tO(CR^a_2)_qO-(CR^a_2)_t-$, and f) $-(CR^a_2)_t-O-(CR^a_2)_qO(CR^a_2)_qO-(CR^a_2)_t-$;

m is independently selected from 0, 1, 2, 3 or 4;
n is independently selected from 1, 2 or 3;
q is independently selected from 1, 2, 3 or 4;
r is independently selected from 0, 1, 2, 3 or 4;
s is independently selected from 0, 1, 2 or 3;
t is independently selected from 0, 1, 2 or 3;
u is 1 or 2;
x is independently selected from 1, 2, 3, 4, 5, 6, 7, or 8;
z is independently selected from 1, 2, 3, 4, 5 or 6;
or a pharmaceutically acceptable salt of any thereof.

3. A compound of Formula I:

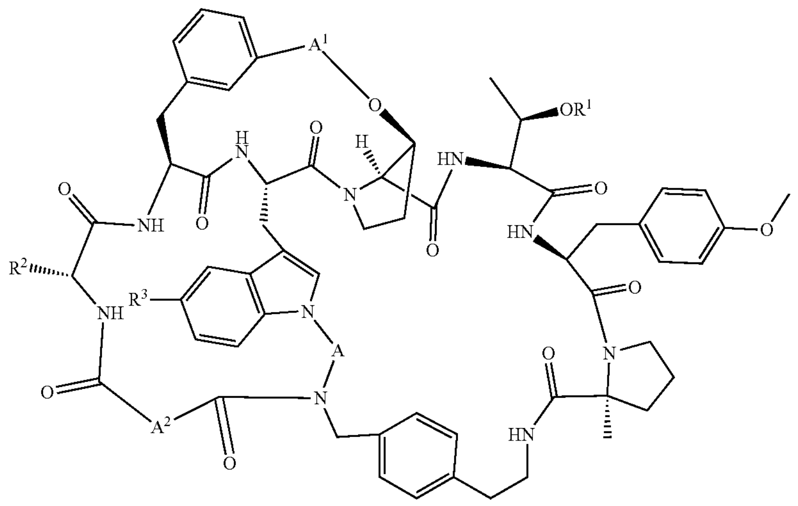

wherein:

A is $C_{2-6}$ alkyl;

$A^1$ is

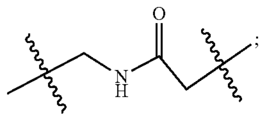

$A^2$ is $—(CR_2)_nNRC(O)(CR_2)_n—$;

R is independently selected from H or $C_{1-6}$ alkyl;

$R^a$ is independently selected from H or $—C(O)OR^9$;

$R^b$ is independently selected from H, $C_{1-6}$ alkyl, or $C_{1-6}$ alkyl-$N^+(CH_3)_2$;

$R^x$ is triazolyl;

$R^d$ is independently selected from H or $—C(O)OR^9$;

$R^1$ is selected from:

(a) $—(CR_2)_z—R^x—(CR_2)_zNR_2$, (b) $—(CR_2)_z—R^x—(CR_2)_z$ $NR—C(O)—(CR_2)_z[O(CR_2)_n]_r—N^+(CH_3)_3$, and (c) $—(CR_2)_z—R^x—(CR_2)_z—NR^b—C(O)R^{10}$;

$R^2$ is selected from:

(a) $—(CR_2)_z—NR^b—C(O)R^{10}$, and (b) $—(CR_2)_z—NR—C(O)—(CR_2)_z[O(CR_2)_n]_r—N^+(CH_3)_3$;

$R^3$ is F;

$R^4$ is

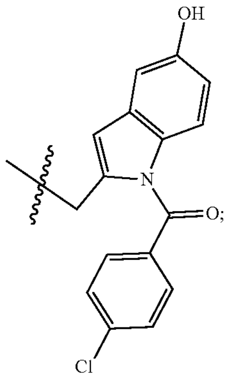 [SMILES: *Cc1cc2cc(O)ccc2n1C(=O)c1ccc(Cl)cc1]

$R^5$ is independently selected from $—(CR^a{}_2)_x—$, $—(CR^a{}_2)_xO(CR^a{}_2)_x—$, and $C_{1-8}$ alkyl;

$R^6$ is independently selected from $—(CR^a{}_2)_xNRC(O)—$, $—(CR_2)_xNRS(O)_2—$, and $—(CR^a{}_2)_nO(CR^a{}_2)_qNRC(O)—$;

$R^9$ is independently selected from H or $C_{1-6}$ alkyl;

$R^{10}$ is independently selected from:

a) $—(R^5—N^+(CH_3)_2—R^6)_u—(R^{20})_n—(R^6)_m—R^{12}$,
b) $—(R^{20})_n—(R^6)_m—R^5—N^+(CH_3)_2—R^6—R^{12}$,
c) $—(R^{20})_n—R^5—N^+(CH_3)_2—(R^{20})_s—(R^6)_q—R^{12}$
d) $—R^6—R^{20}—N^+(CH_3)_2—(R^{20})_n(R^6)_m—R^{12}$,
e) $—R^{20}—N^+(CH_3)_2—(R^6)_m—(R^{20})_n—(R^6)_q—R^{12}$,
f) $—(R^{20})_n—(R^6)_m—R^{12}$,
g) $—R^5—N^+(CH_3)_2—(R^{20})_n—(R^6)_m—R^5—[NRC(O)—R^5]_q$,
h) $—R^{20}—N^+(CH_3)_2—(R^6)_m—R^5$, i) $-R^5-N^+(CH_3)_2-(R^{20})_n-(R^6)_m-R^5$, j) $-R^5-N^+(CH_3)_2-(R^{20})_n-(R^6)_m-R^{12}$, k) $-(R^{20})_n-N^+(CH_3)_2-(R^{20})_n-(R^6)_q-R^{12}$ l) $-R^6-R^5-N^+(CH_3)_2-(R^{20})_n-(R^6)_q-R^{12}$ m) $-(R^{20})_n-N^+(CH_3)_2-(R^6)_q-R^{12}$, n) $-(R^{20})_n-(R^6)_m-R^{20}-N^+(CH_3)_2-(R^{20})_s-(R^6)_q-R^{12}$ o) $-R^{20}-N^+(CH_3)_2-(R^6)_m-R^4$, p) $-(R^{20})_n-N^+(CH_3)_2-(R^6)_q-(R^{20})_n (R^6)_m-R^{12}$, q) $-R^{20}-N^+(CH_3)_2-(R^6)_m-(R^{20})_n-N^+(CH_3)_2-(R^{20})_n-(R^6)_q-R^{12}$, r) $-R^5-N^+(CH_3)_2-(R^6)_m-R^5-N^+(CH_3)_2-(R^{20})_n-(R^6)_q-R^{12}$, and s) $-CR^b{}_2-(R^{20})_n (R^6)_m-R^{12}$;

$R^{12}$ is independently selected from $-C_{11-20}$ alkyl-$R^d$, $-(CR_2)_x-O-(CR_2)_x-R^d$, $-C_{11-20}$ alkyl-C(O)NR$-(CR^d{}_2)_2$H, and $C_{2-16}$ alkenyl;

$R^{20}$ is independently selected from a) $-(CR^a{}_2)_tO(CR^a{}_2)_qO-(CR^a{}_2)_t-$, b) $-(CR^a{}_2)_tO(CR^a{}_2)_qO-(CR^a{}_2)_t-NRC(O)-$, c) $-(CR^a{}_2)_tO(CR^a{}_2)_q-NRC(O)-(CR^a{}_2)_nO(CR^a{}_2)_nO-$, d) $-(CR^a{}_2)_t-NRC(O)-(CR^a{}_2)_qO(CR^a{}_2)_qO-(CR^a{}_2)_t-$, e) $-(CR^a{}_2)_tO(CR^a{}_2)_qO-(CR^a{}_2)_t-$, and f) $-(CR^a{}_2)_t-O-(CR^a{}_2)_qO(CR^a{}_2)_qO-(CR^a{}_2)_t-$;

m is independently selected from 0, 1, 2, 3 or 4;

n is independently selected from 1, 2 or 3;

q is independently selected from 1, 2, 3 or 4;

r is independently selected from 0, 1, 2, 3 or 4;

s is independently selected from 0, 1, 2 or 3;

t is independently selected from 0, 1, 2 or 3;

u is 1 or 2;

x is independently selected from 1, 2, 3, 4, 5, 6, 7, or 8;

z is independently selected from 1, 2, 3, 4, 5 or 6;

or a pharmaceutically acceptable salt of any thereof.

4. A compound selected from the group consisting of:

1*

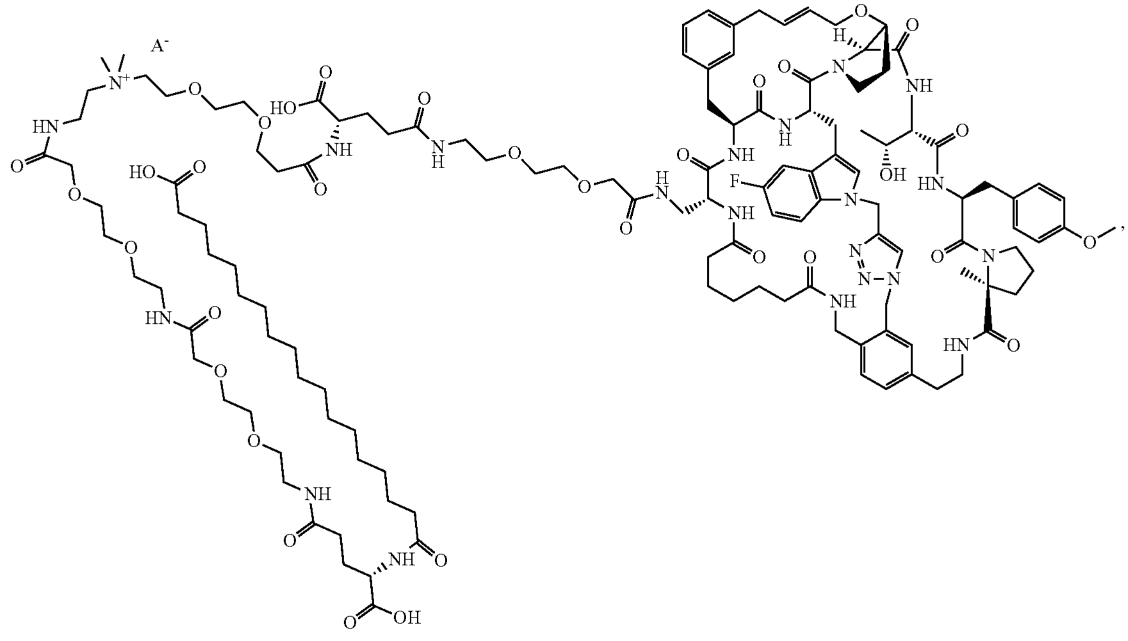

,

-continued
2*
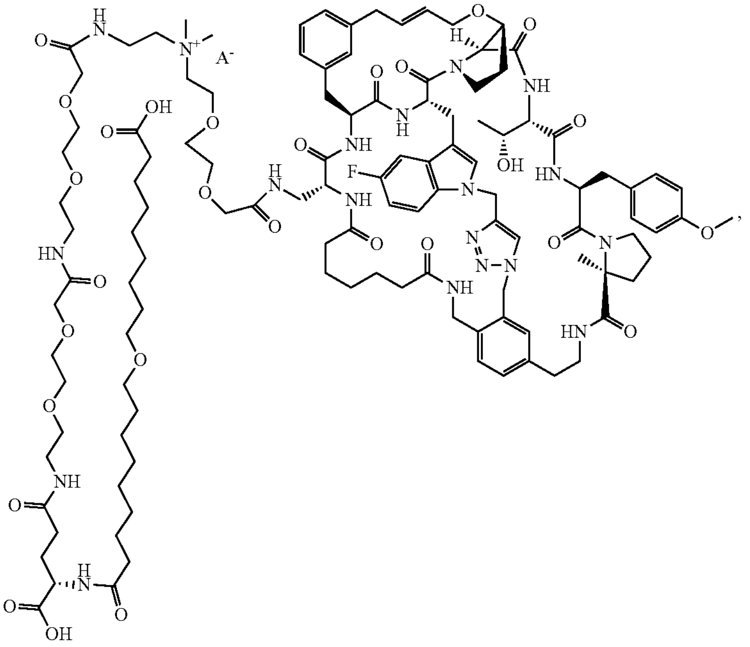
3*
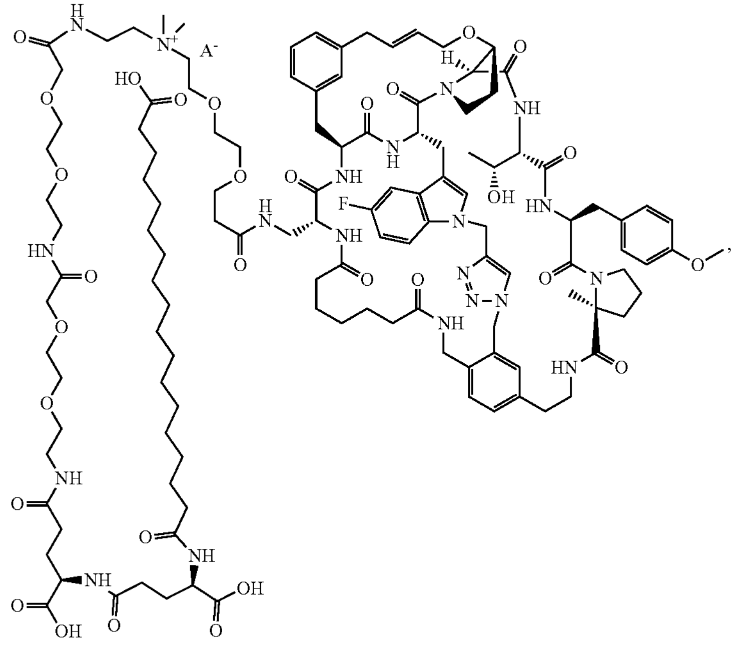

-continued
4*
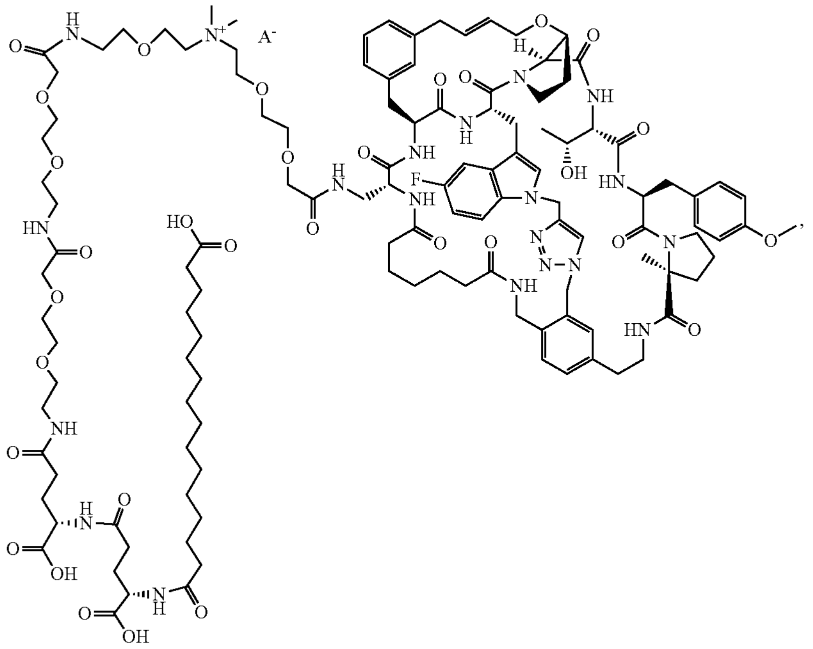
5*
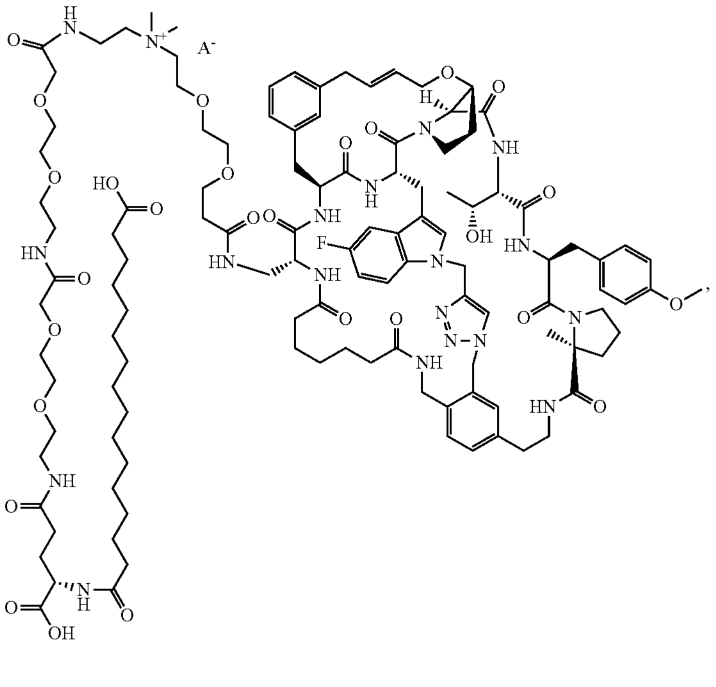

-continued
6*
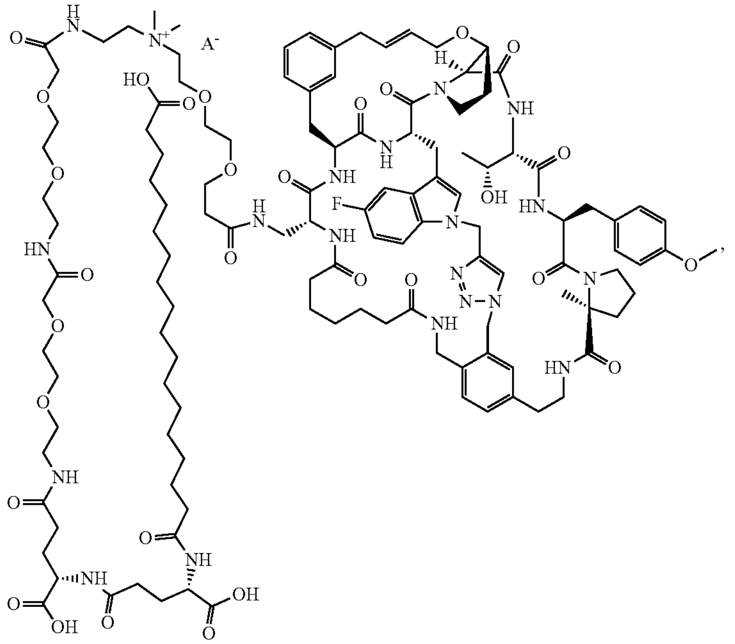
7*
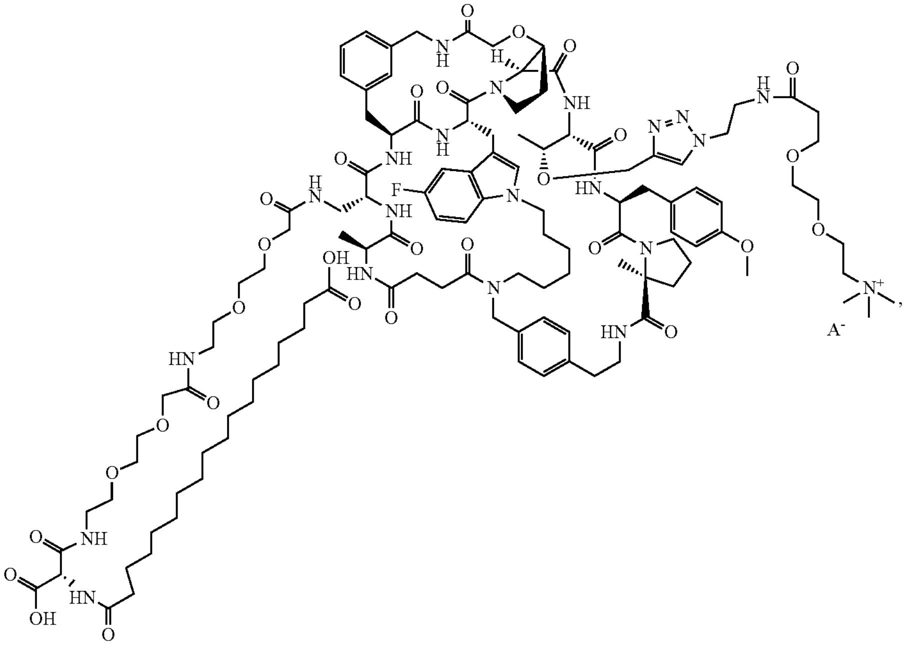

-continued
8*
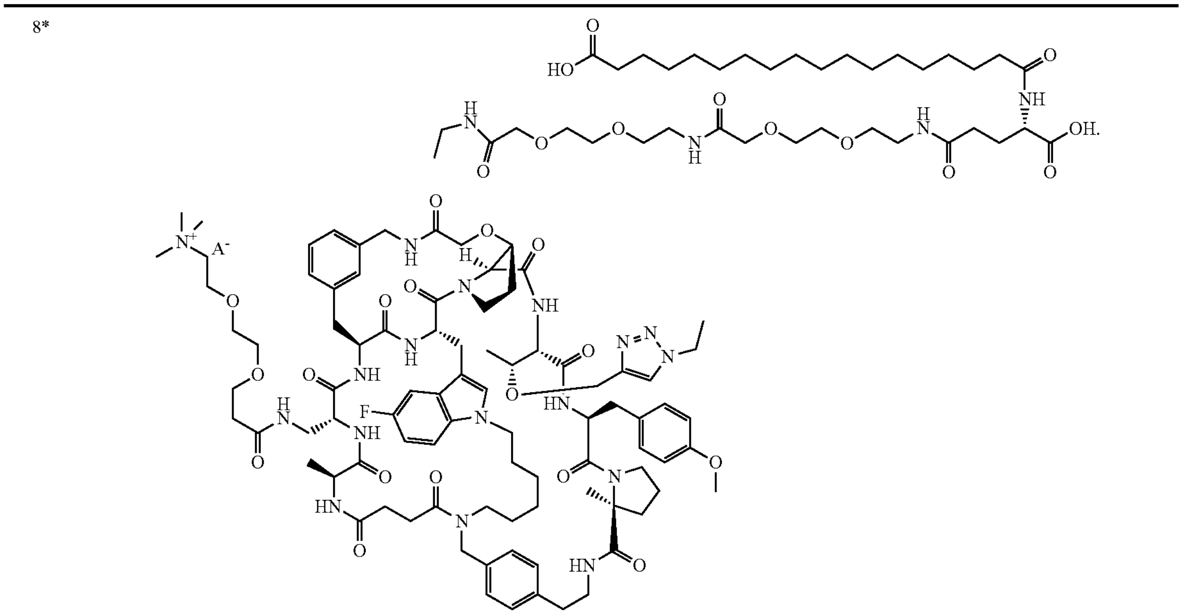
9*
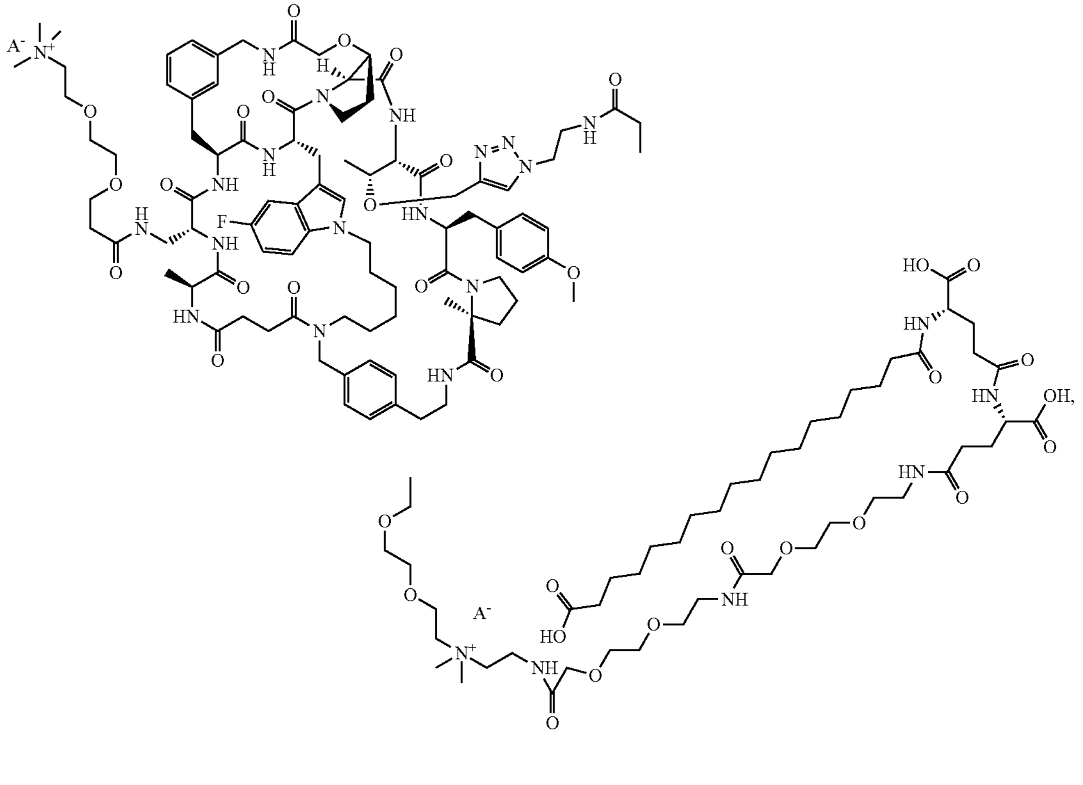

-continued
10*
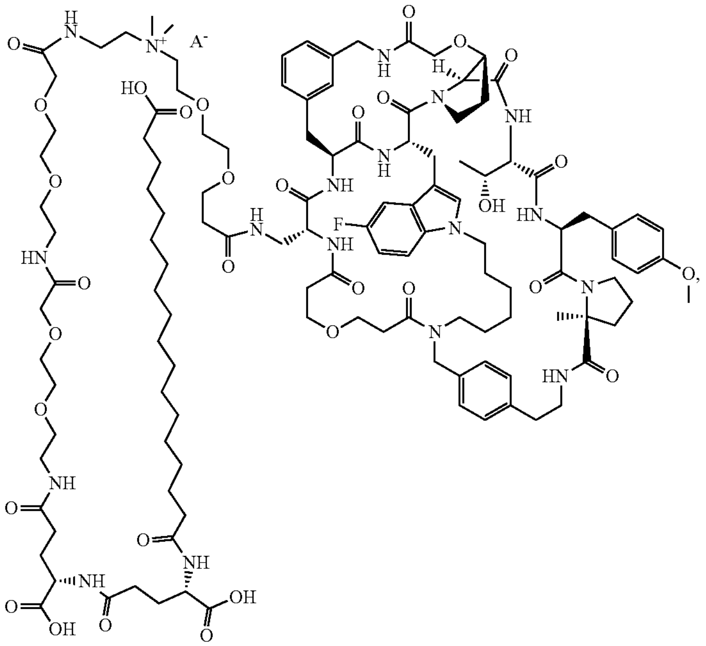
11*
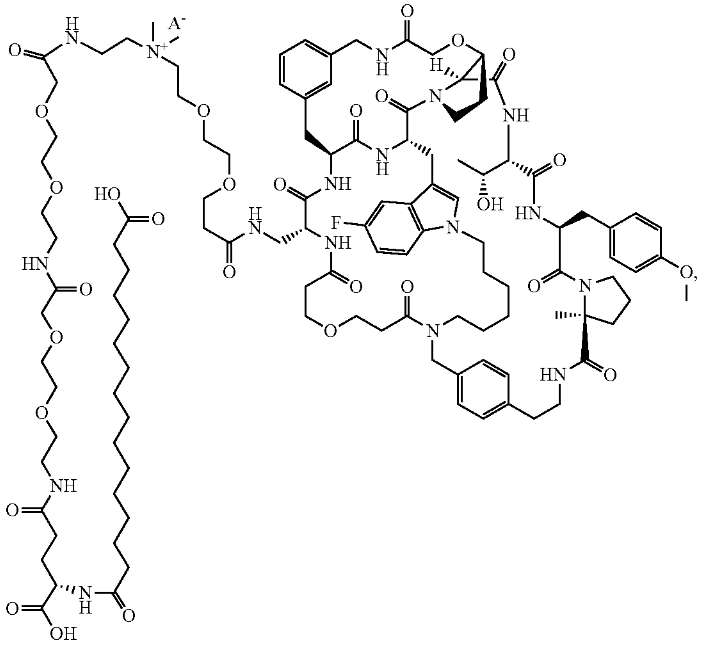

-continued
12*
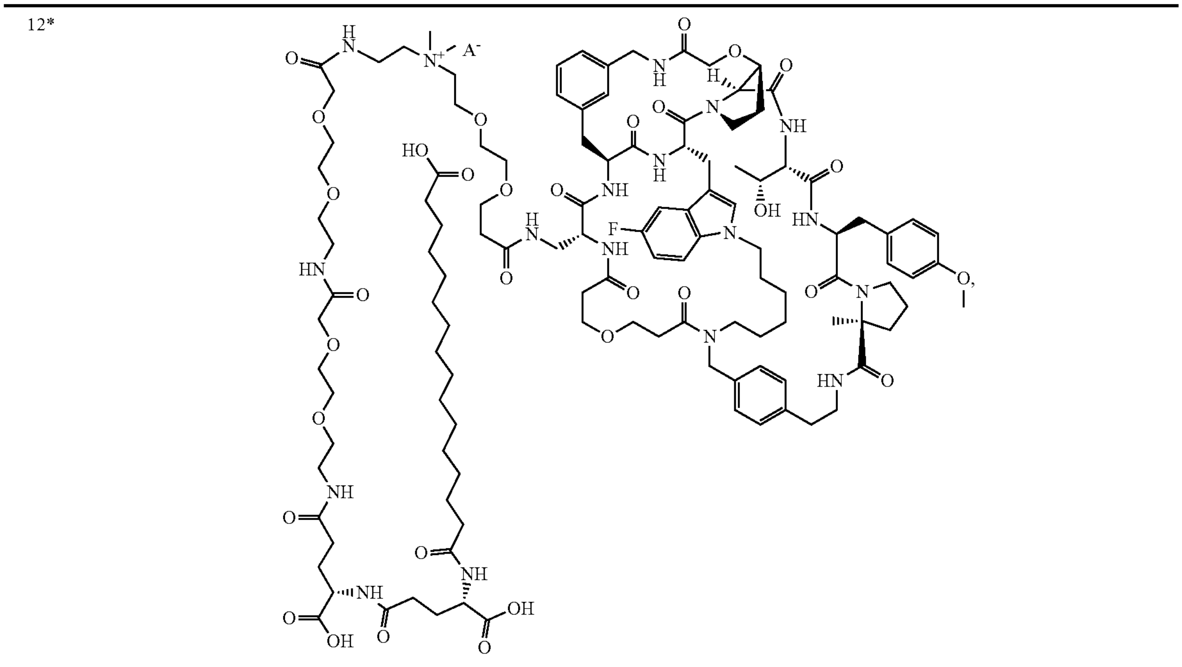
and
13*
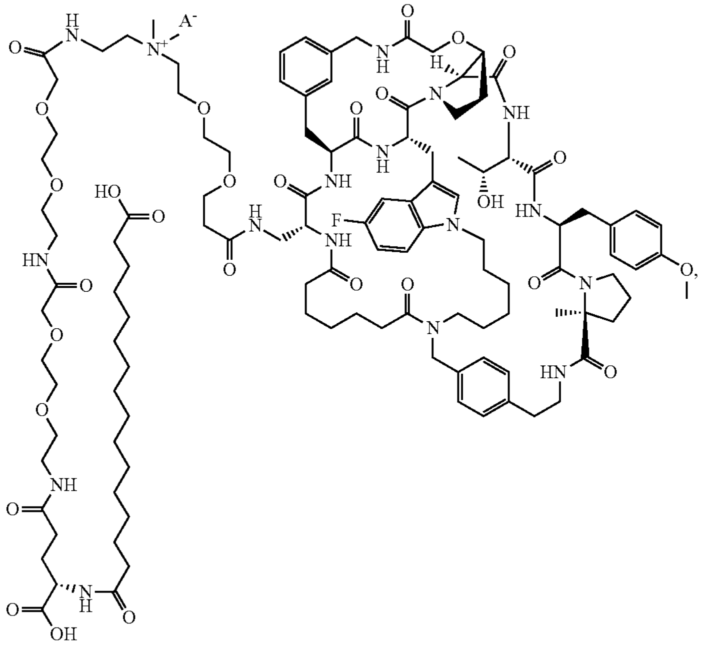
wherein $A^-$ is a pharmaceutically acceptable counter ion, or a pharmaceutically acceptable salt thereof.

5. The compound of claim 4, selected from the group consisting of:
1
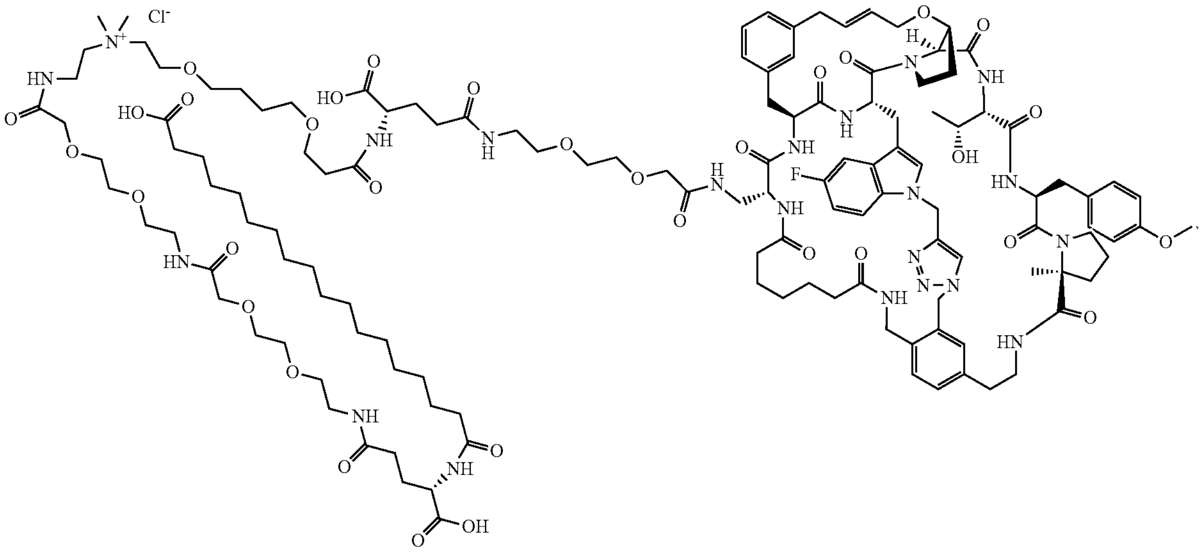
2
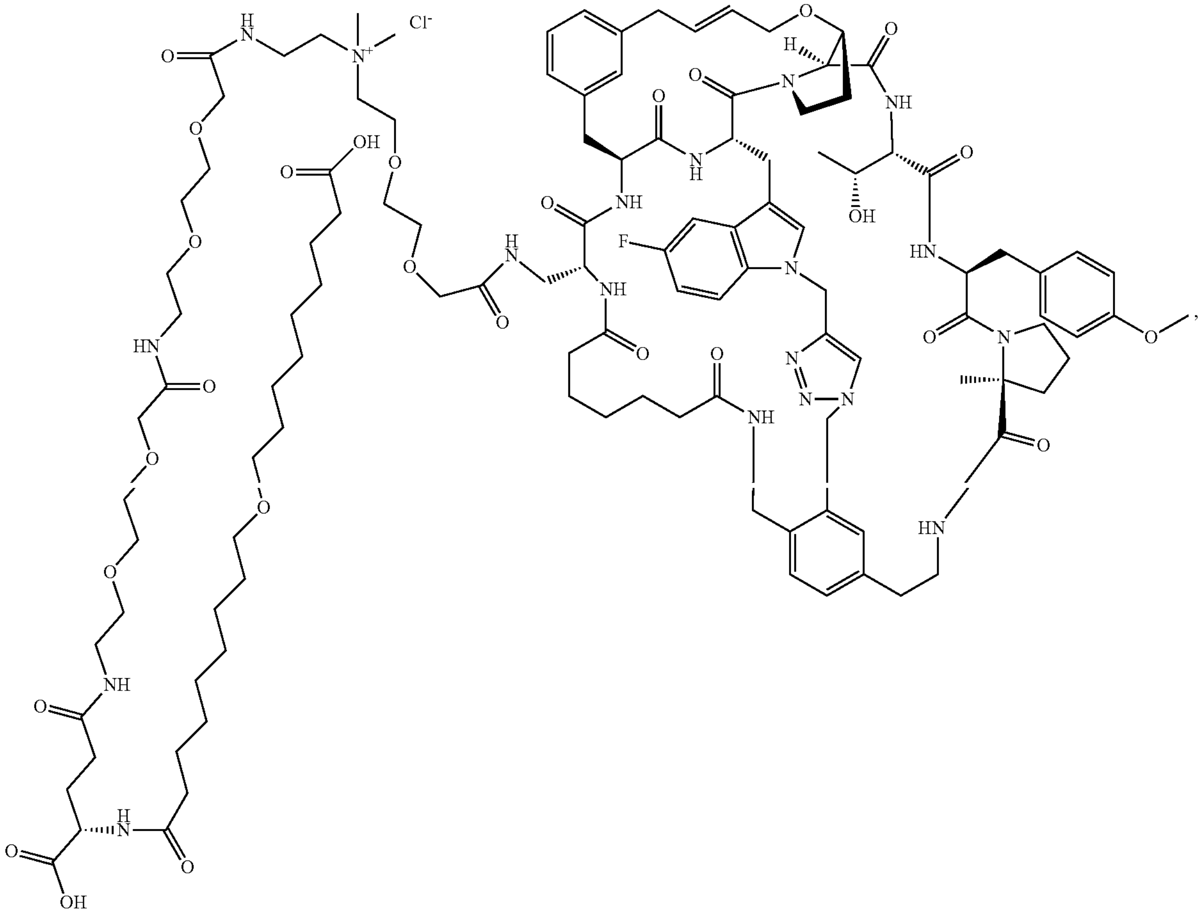

-continued
3
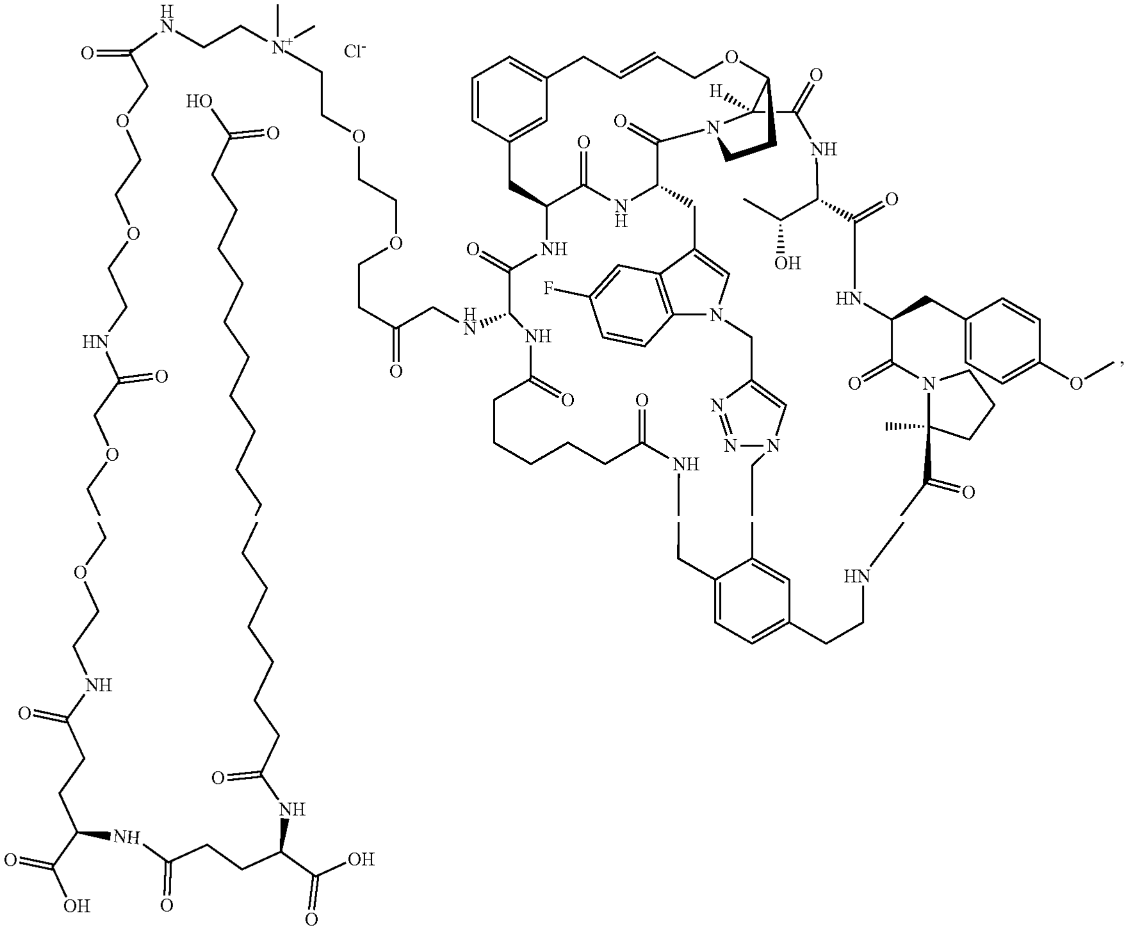
4
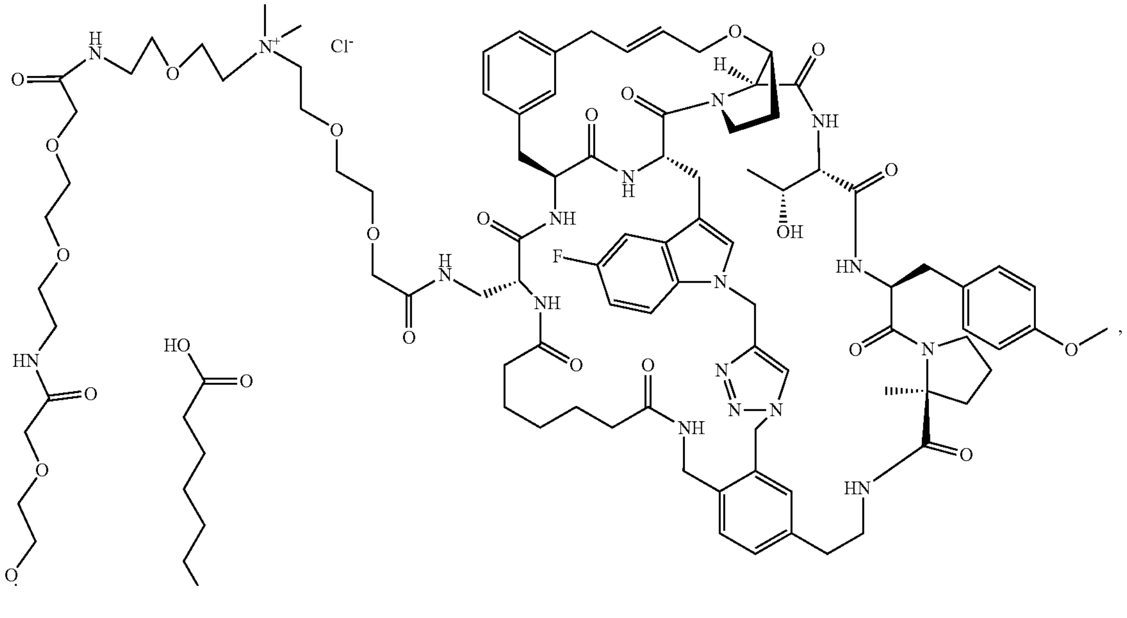

-continued
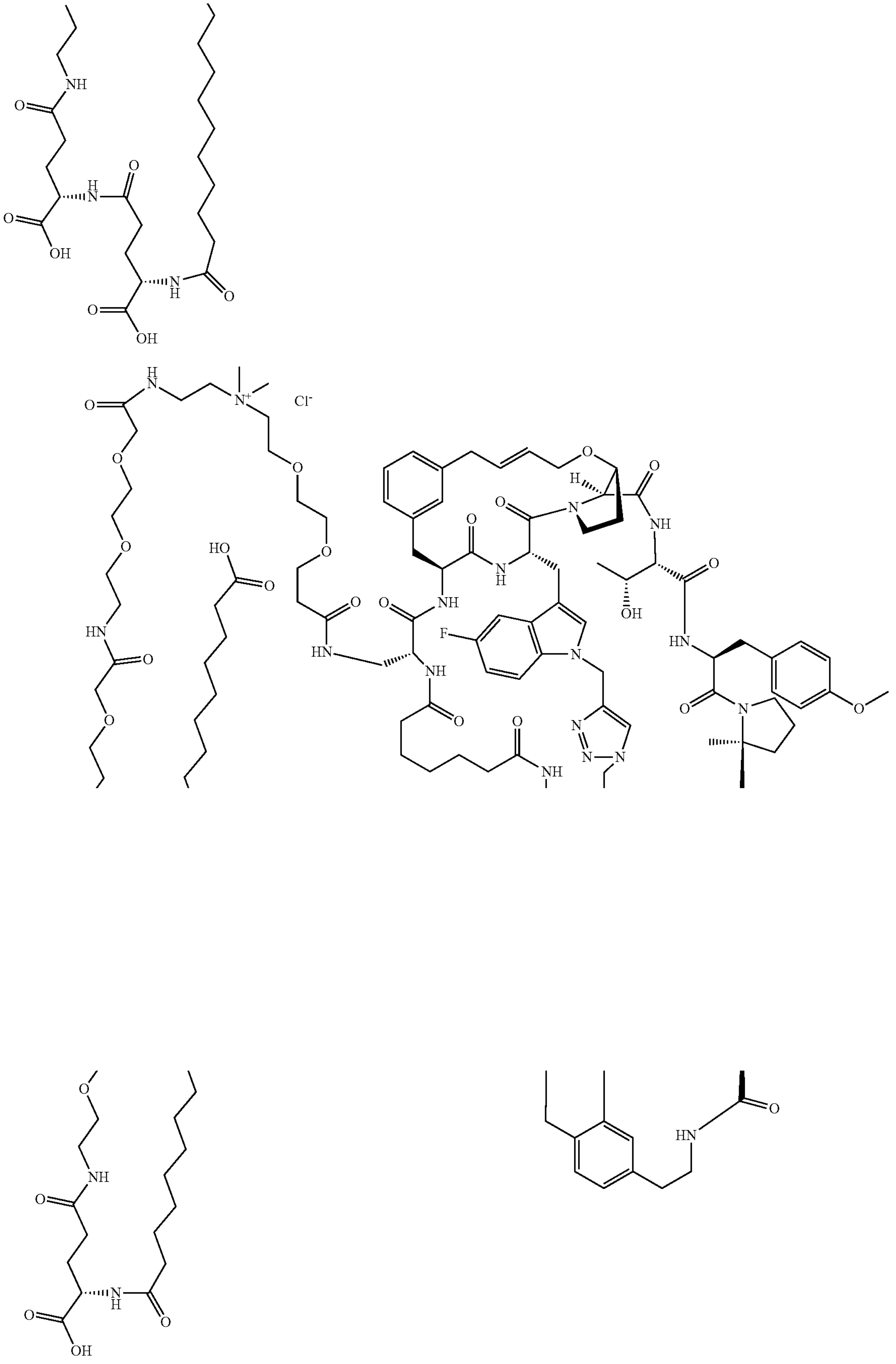
,

-continued
6
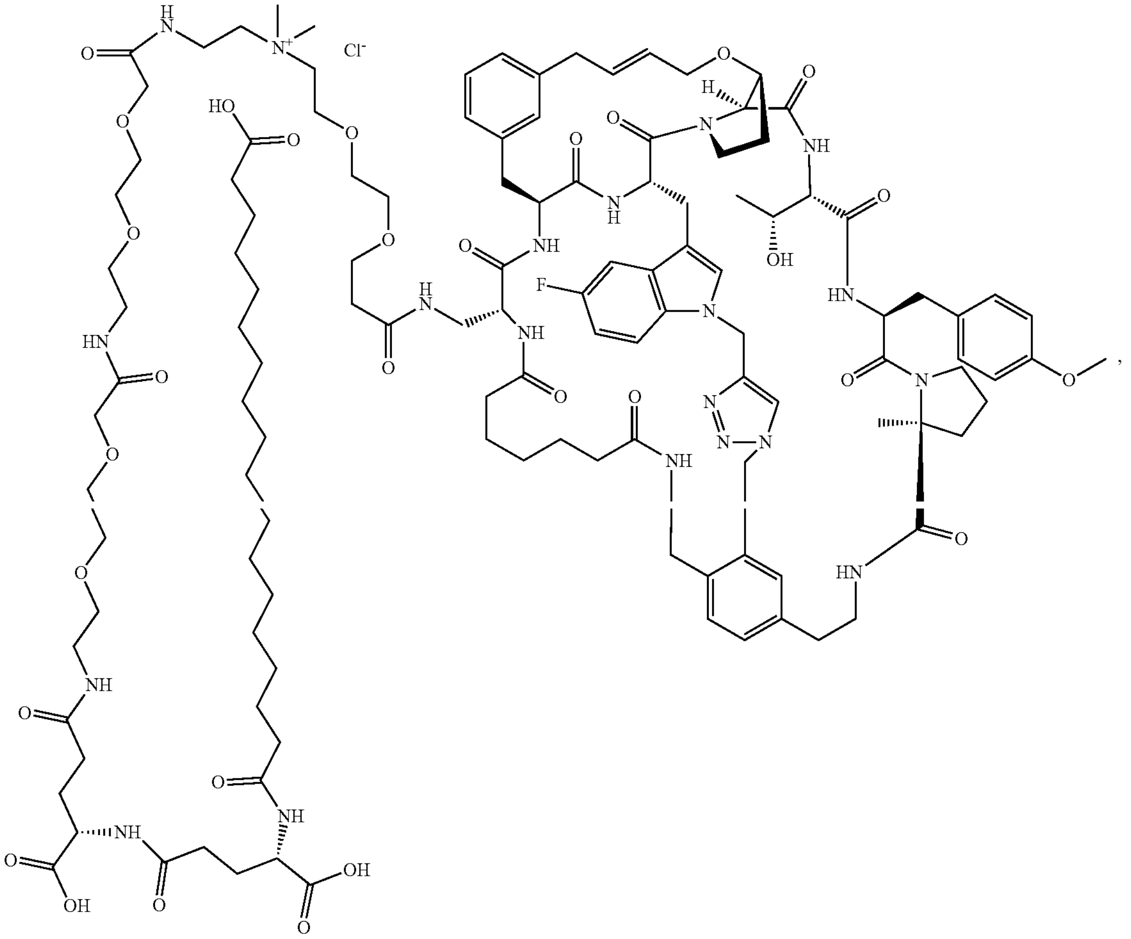
7
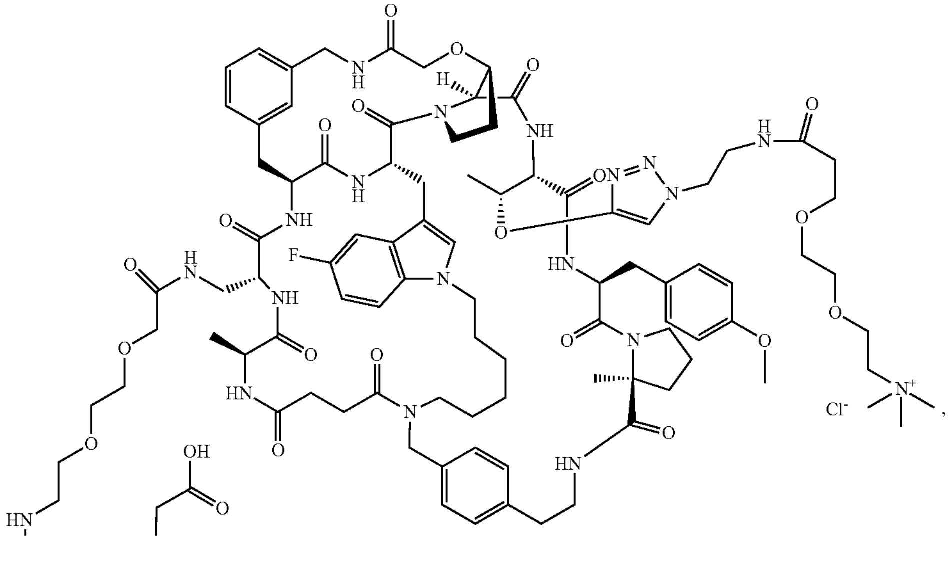

-continued
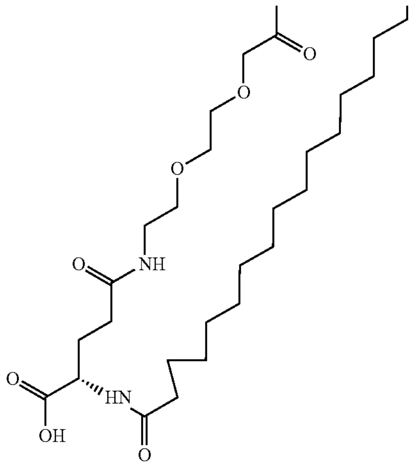
8
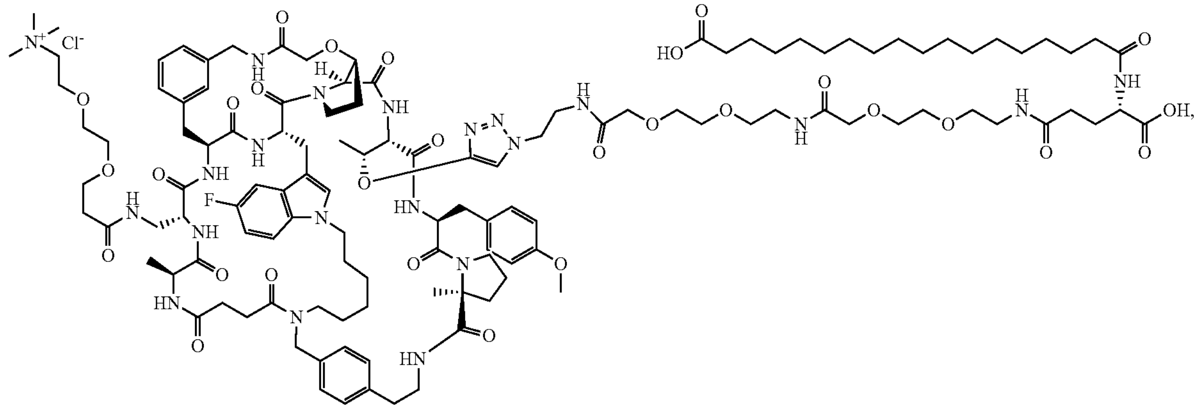
9
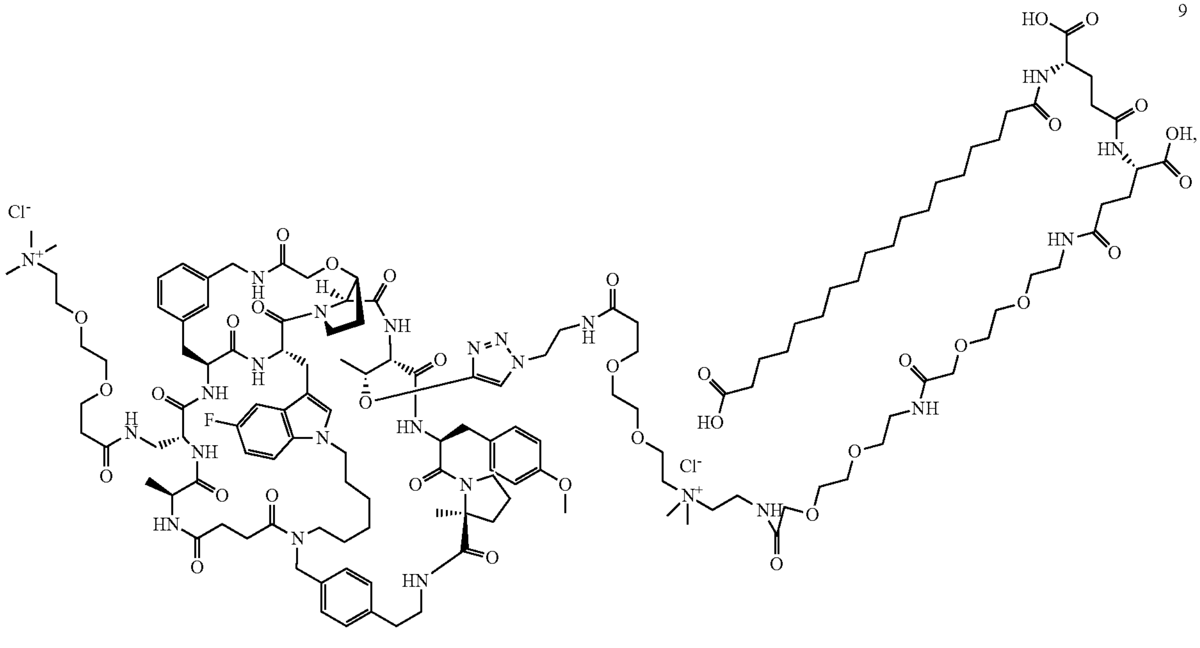

-continued
10
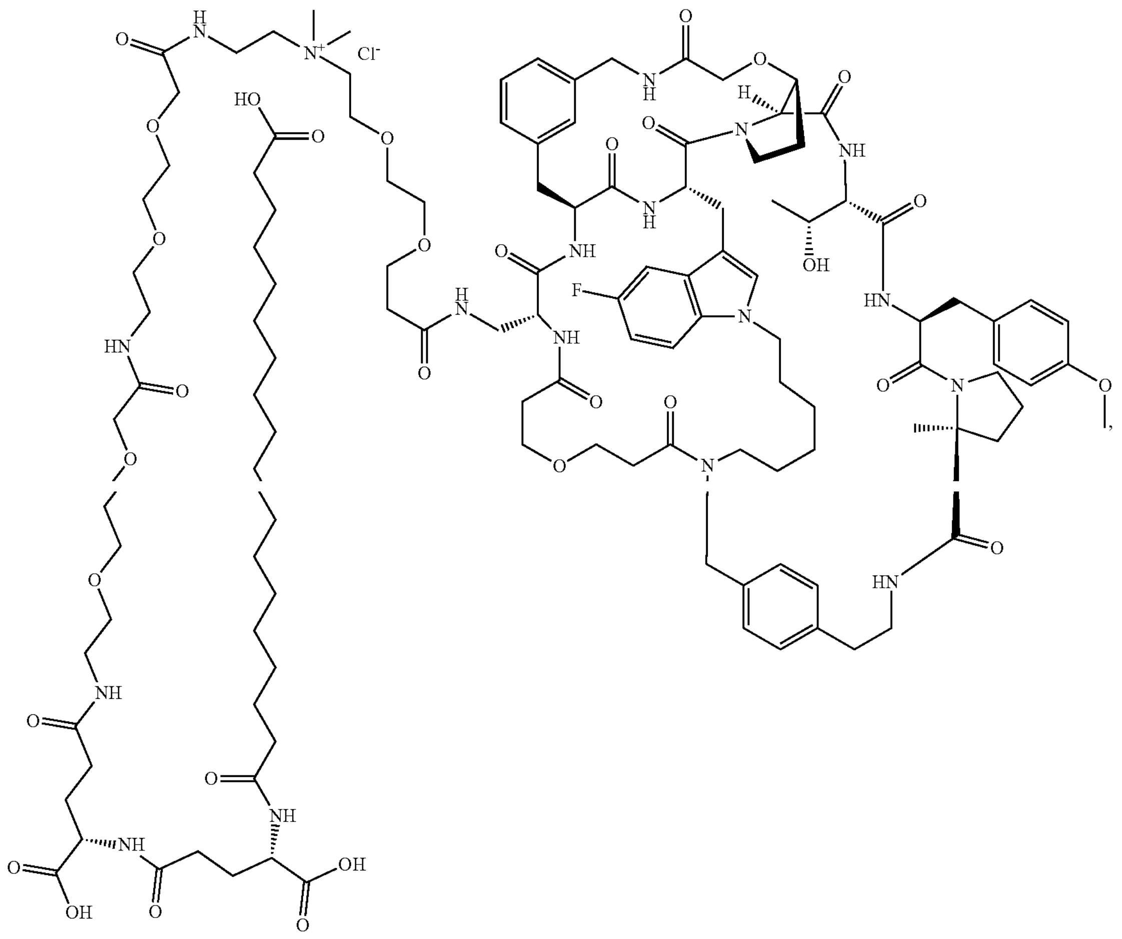
11
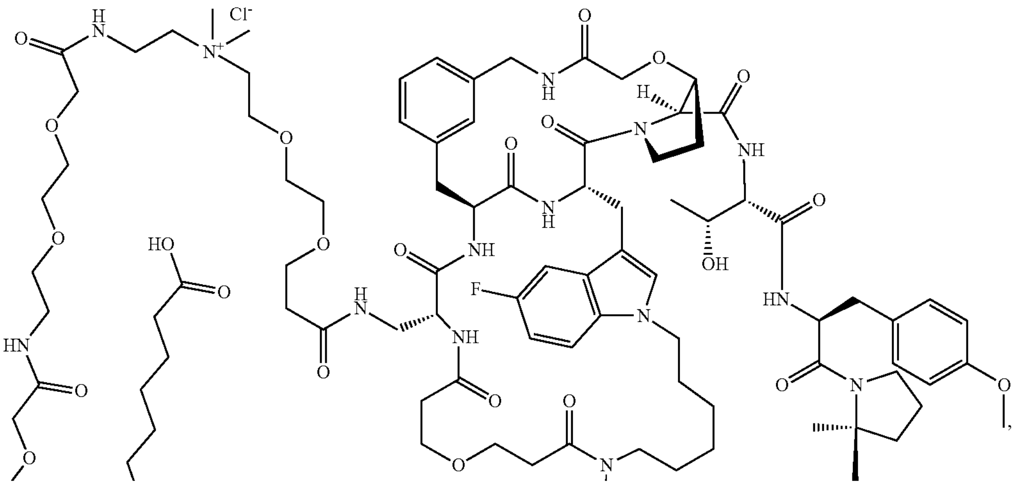

-continued
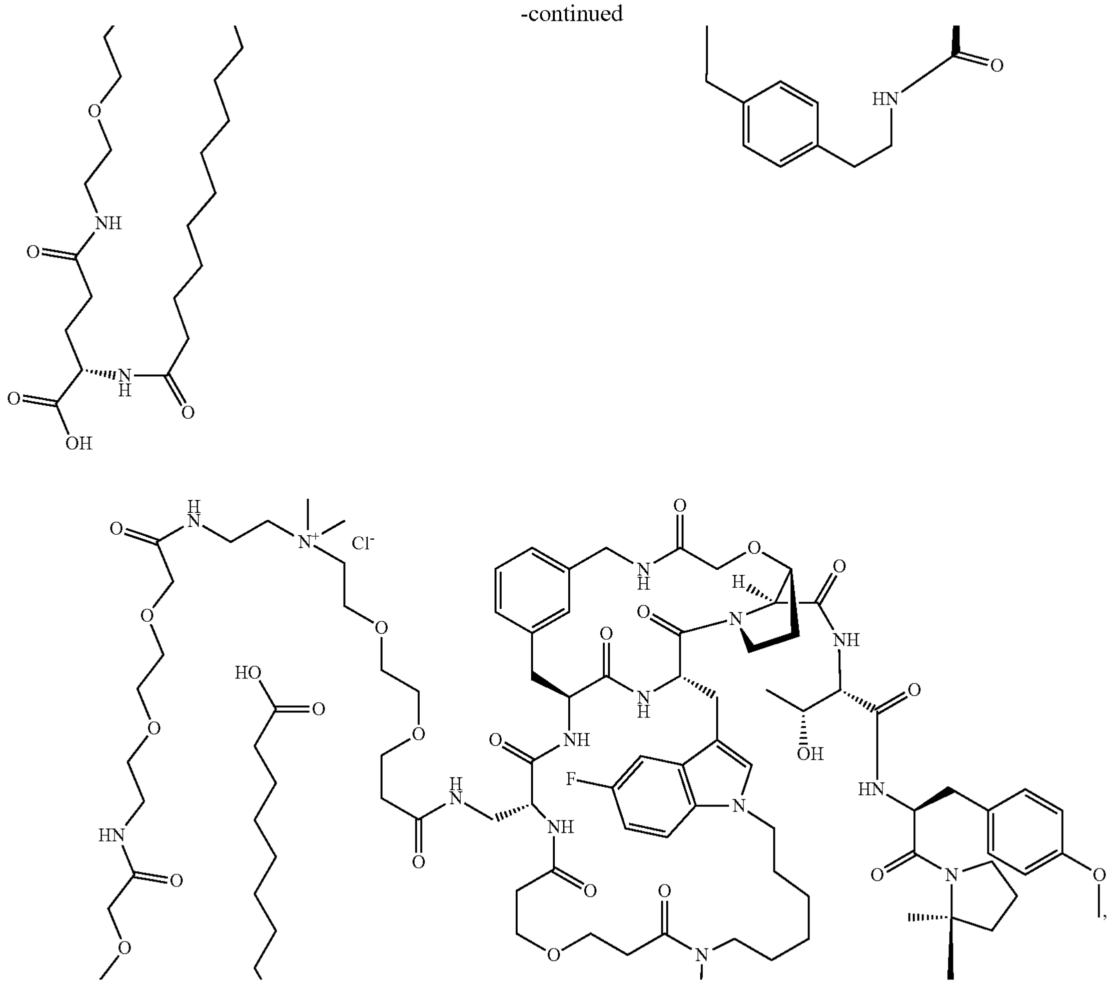
12
, and
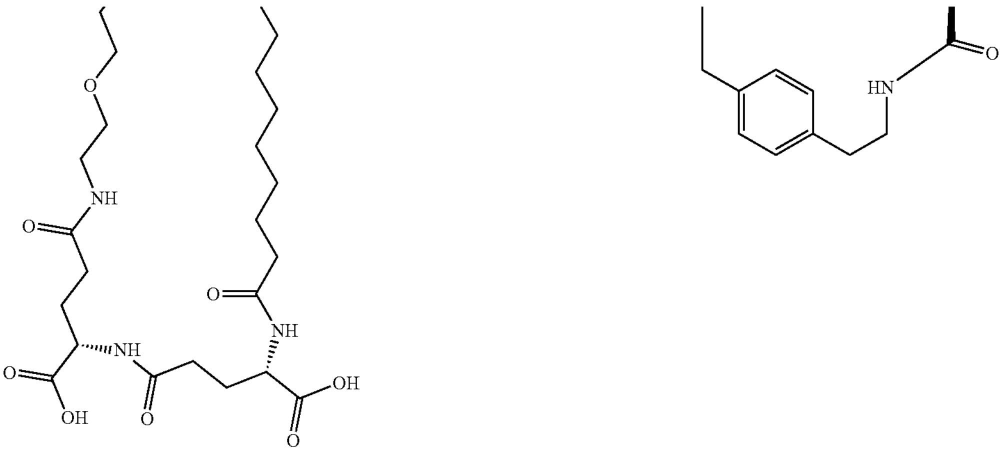

-continued
13
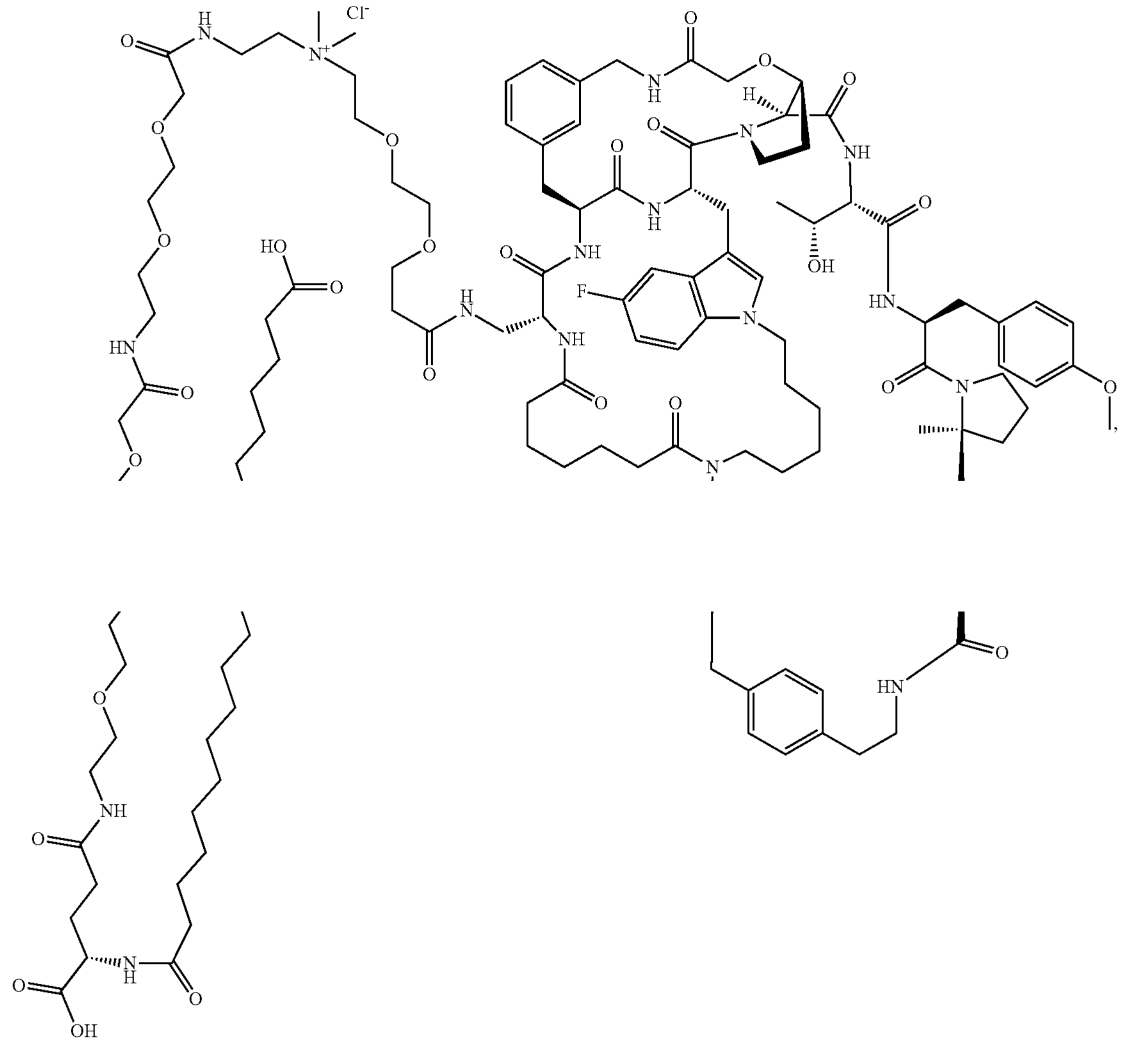
or any other pharmaceutically acceptable salt thereof.
6. The compound of claim 5, selected from the group consisting of:
7
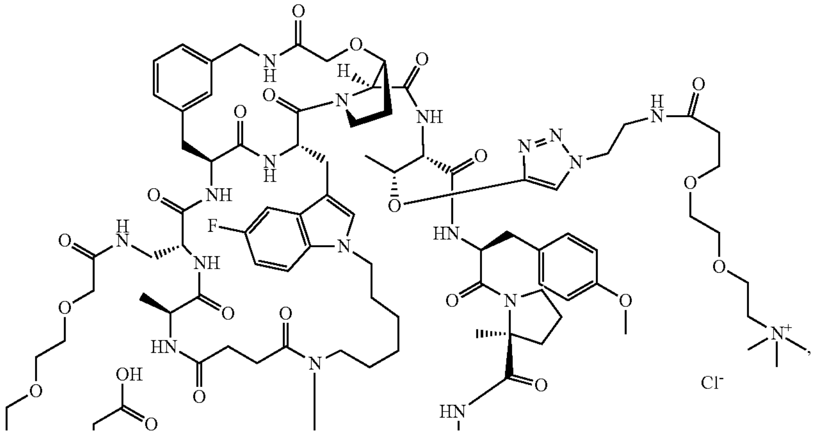
, -continued
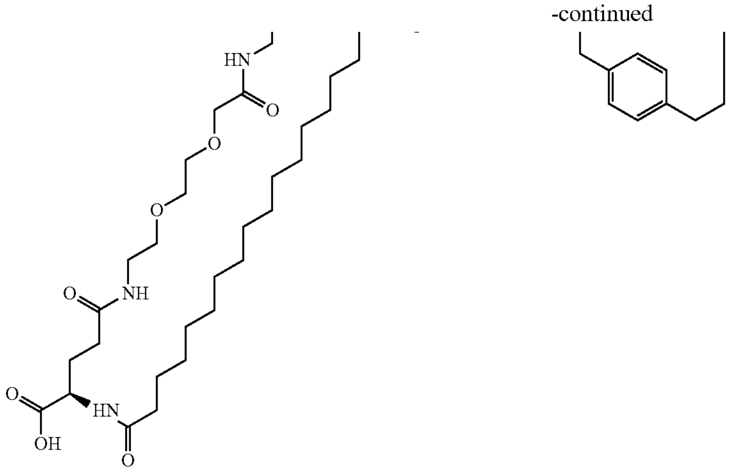
9
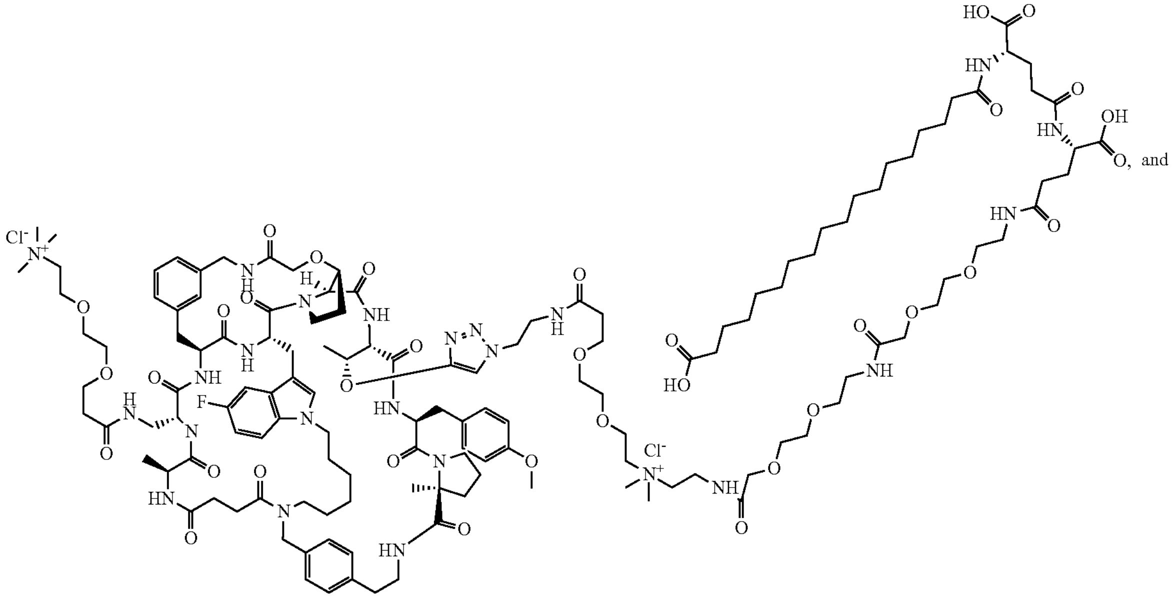
and
11
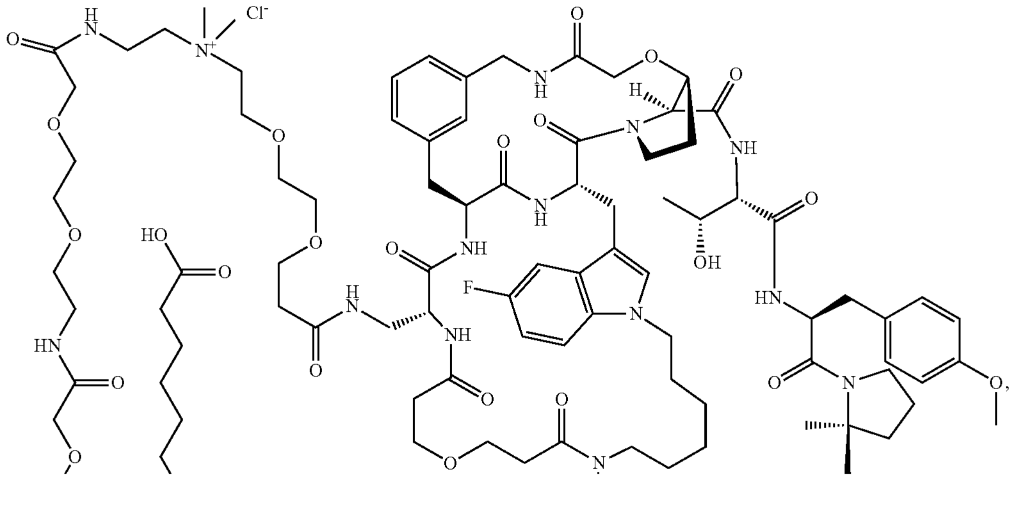

-continued
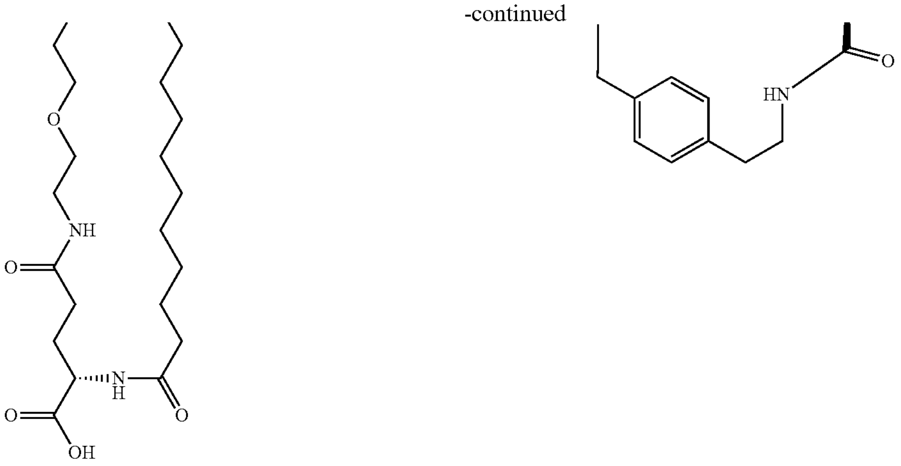
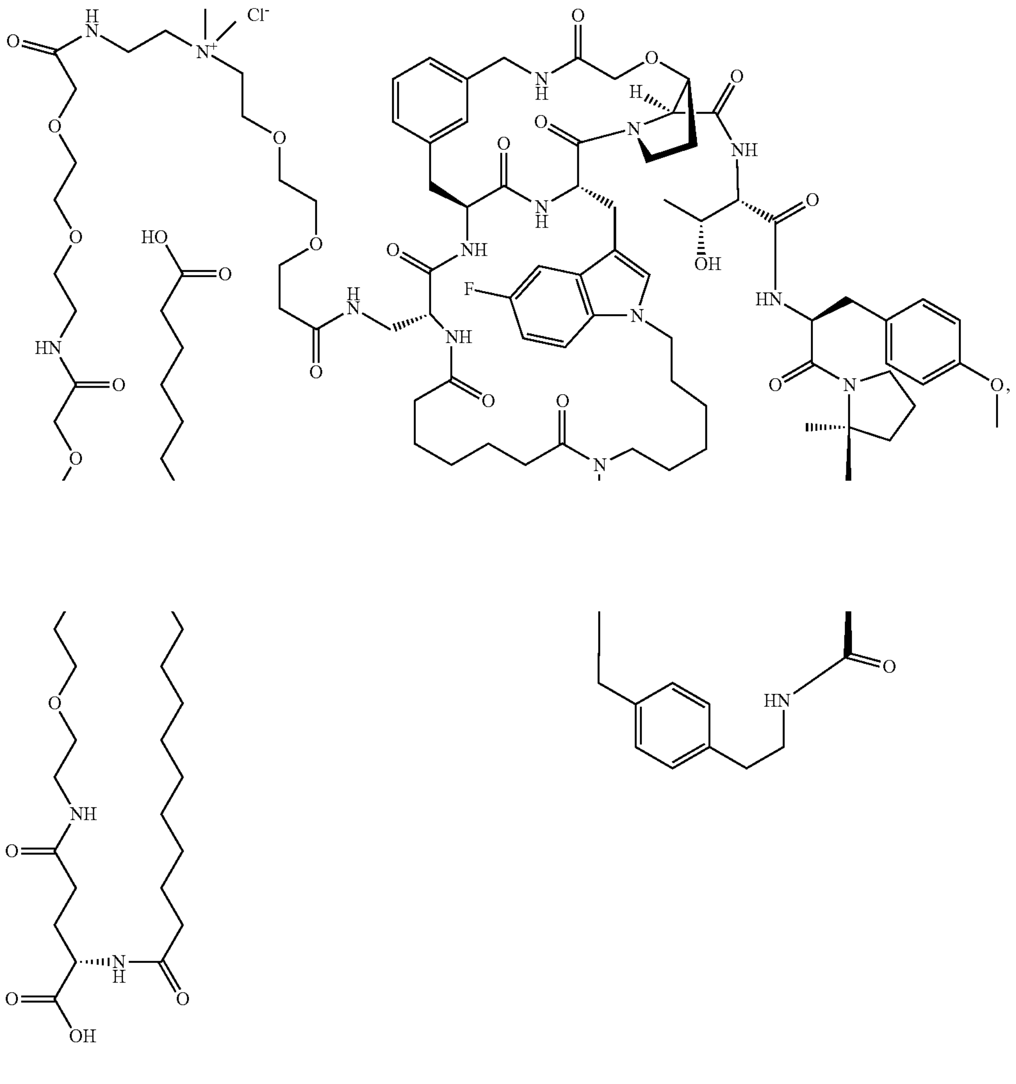
13
or any other pharmaceutically acceptable salt thereof.

7. The compound of claim 4, which is selected from the group consisting of:
Ex-7*
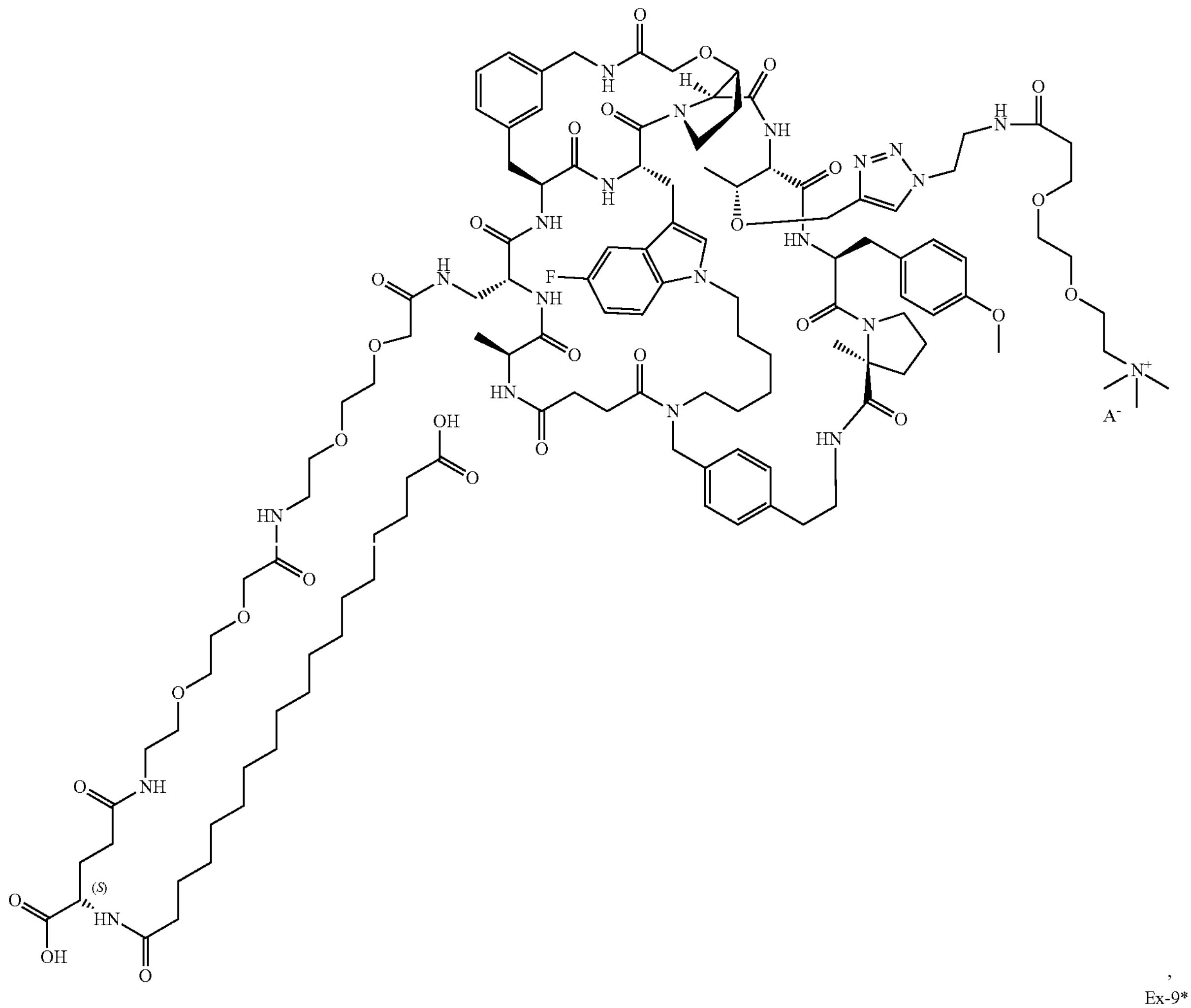
,
Ex-9*
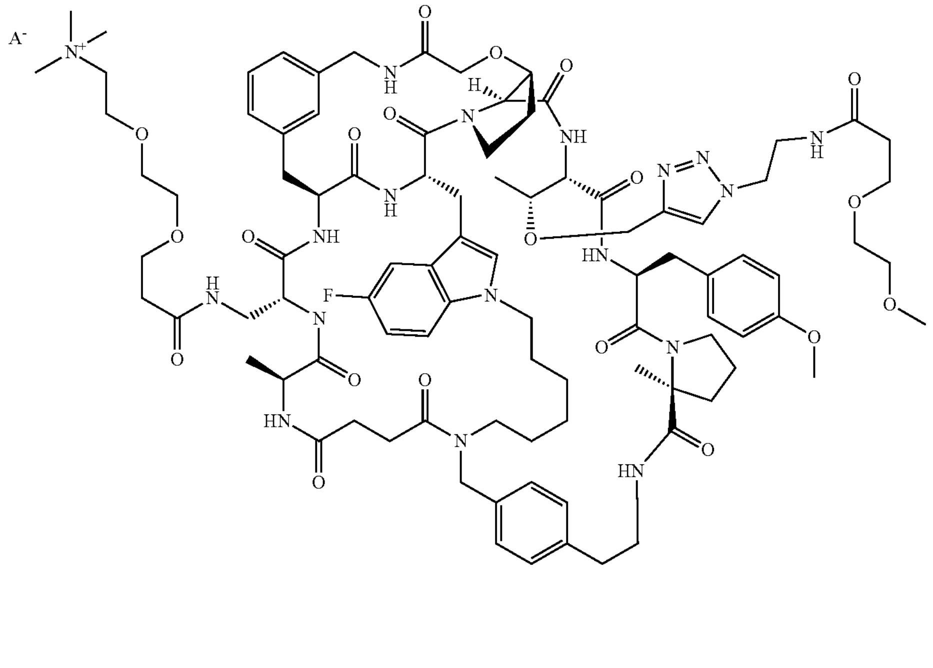

-continued
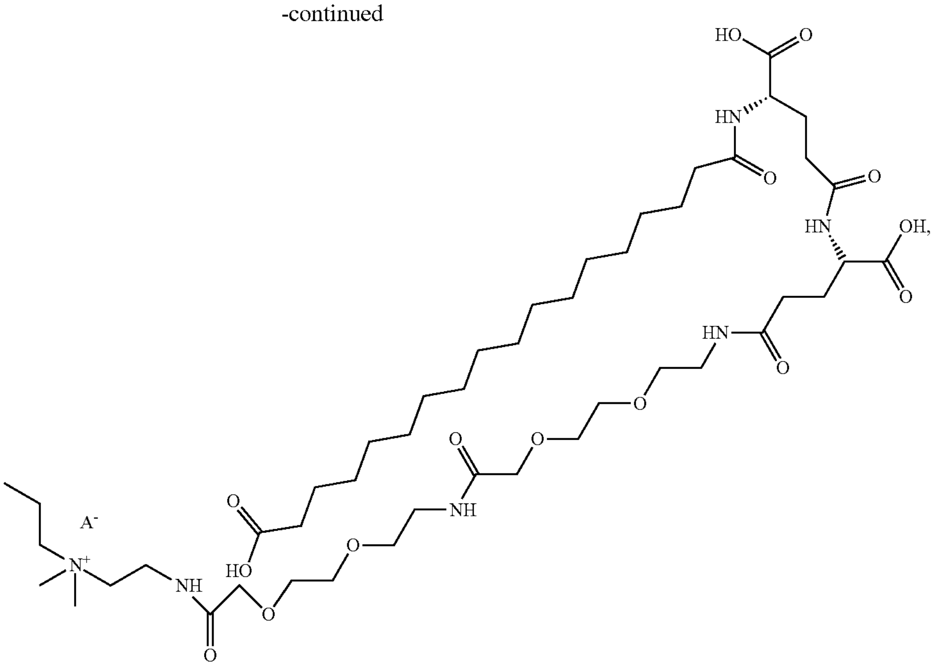
Ex-11*
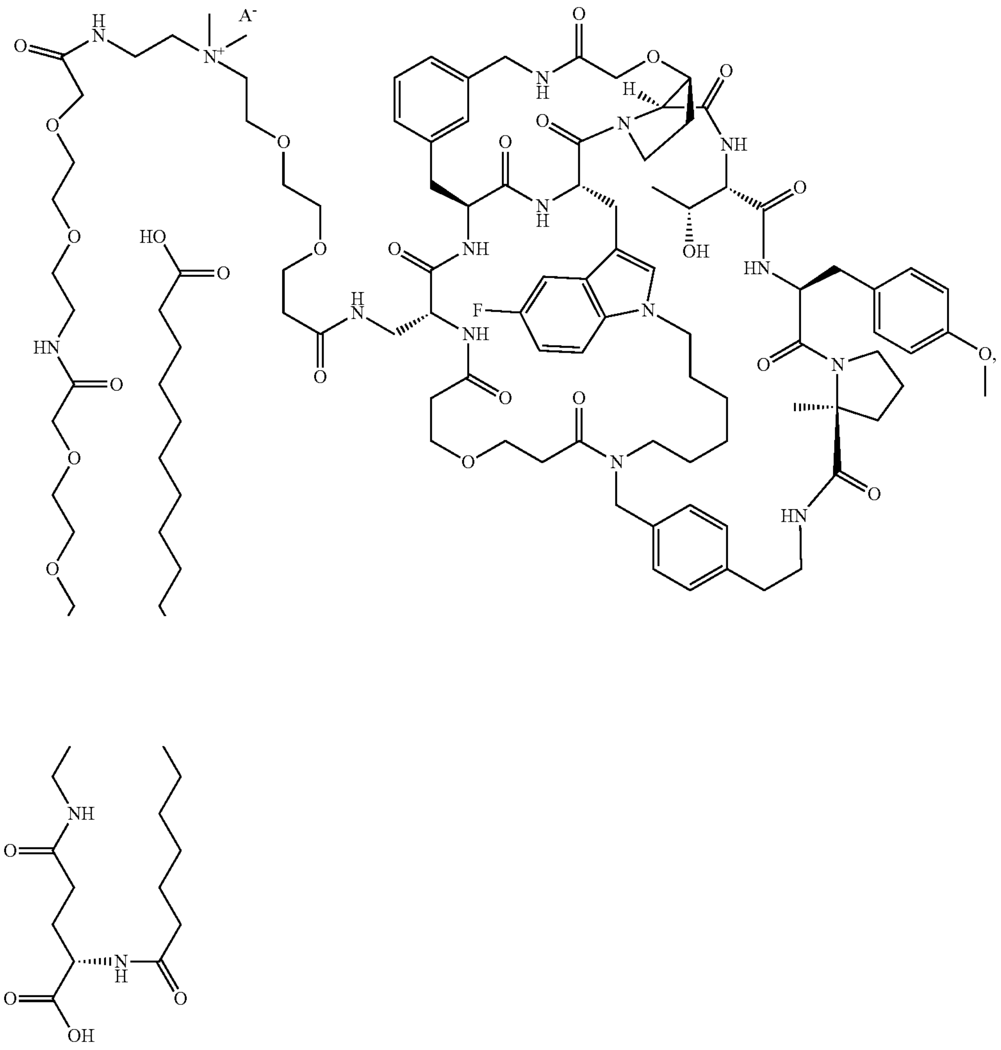
and

-continued

Ex-13*

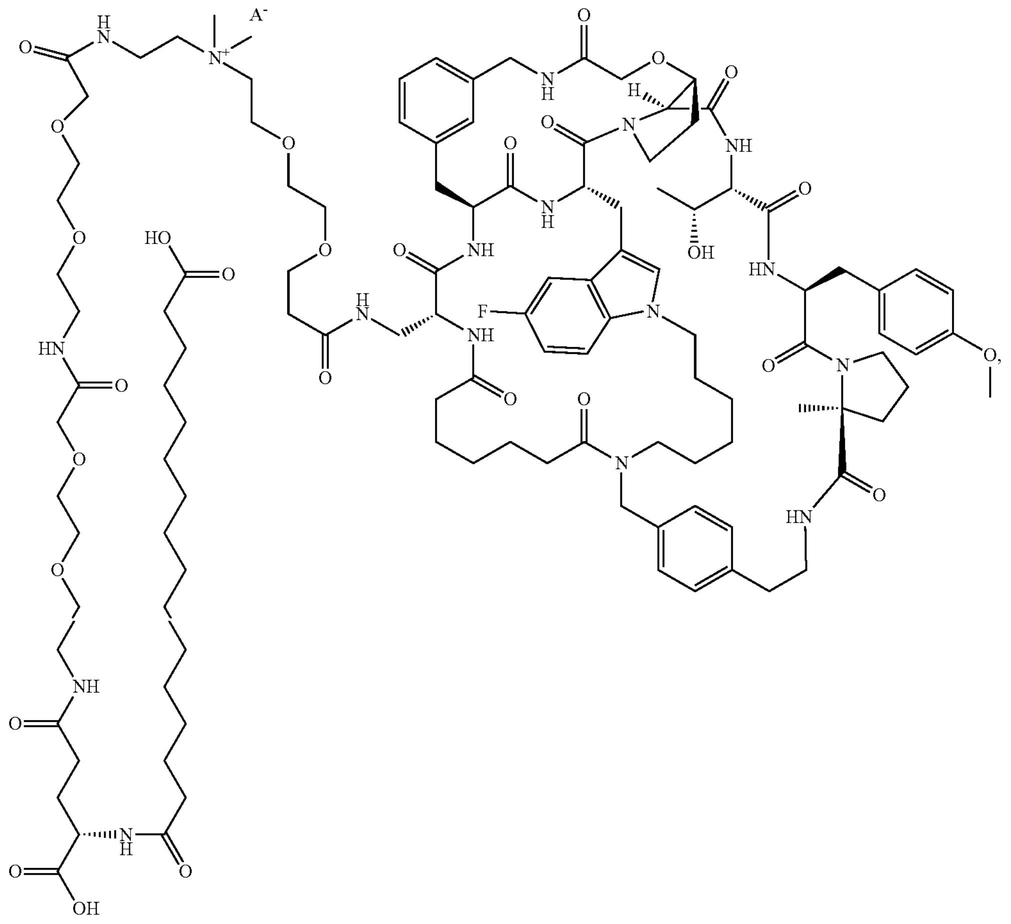

wherein $A^-$ is a pharmaceutically acceptable counter ion, or a pharmaceutically acceptable salt thereof.

8. A composition comprising at least one compound of claim 1, or a pharmaceutically acceptable salt thereof, and at least one pharmaceutically acceptable excipient.

9. A method of treating hypercholesterolemia, comprising administering to a patient in need thereof a therapeutically effective amount of a composition of claim 8.

10. A method of treating hypercholesterolemia, comprising administering to a patient in need thereof a therapeutically effective amount of a compound of claim 1.

11. A composition comprising at least one compound of claim 4, or a pharmaceutically acceptable salt thereof, and at least one pharmaceutically acceptable excipient.

12. A method of treating hypercholesterolemia, comprising administering to a patient in need thereof a therapeutically effective amount of a composition of claim 11.

13. A method of treating hypercholesterolemia, comprising administering to a patient in need thereof a therapeutically effective amount of a compound of claim 4.

14. A composition comprising at least one compound of claim 2, or a pharmaceutically acceptable salt thereof, and at least one pharmaceutically acceptable excipient.

15. A method of treating hypercholesterolemia, comprising administering to a patient in need thereof a therapeutically effective amount of a composition of claim 14.

16. A method of treating hypercholesterolemia, comprising administering to a patient in need thereof a therapeutically effective amount of a compound of claim 2.

17. A composition comprising at least one compound of claim 3, or a pharmaceutically acceptable salt thereof, and at least one pharmaceutically acceptable excipient.

18. A method of treating hypercholesterolemia, comprising administering to a patient in need thereof a therapeutically effective amount of a composition of claim 17.

19. A method of treating hypercholesterolemia, comprising administering to a patient in need thereof a therapeutically effective amount of a compound of claim 3.

* * * * *